(12) United States Patent
Bender et al.

(10) Patent No.: US 8,618,153 B2
(45) Date of Patent: Dec. 31, 2013

(54) HEPATITIS C VIRUS INHIBITORS

(75) Inventors: John A. Bender, Middletown, CT (US); Makonen Belema, North Haven, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/611,708

(22) Filed: Sep. 12, 2012

(65) Prior Publication Data

US 2013/0012540 A1 Jan. 10, 2013

Related U.S. Application Data

(62) Division of application No. 12/942,183, filed on Nov. 9, 2010, now abandoned.

(60) Provisional application No. 61/260,569, filed on Nov. 12, 2009.

(51) Int. Cl.
*A01N 43/50* (2006.01)
*A61K 31/415* (2006.01)
*C07D 403/02* (2006.01)

(52) U.S. Cl.
USPC .................. 514/397; 514/396; 548/314.7

(58) Field of Classification Search
None
See application file for complete search history.

(56) References Cited

U.S. PATENT DOCUMENTS

| | | | |
|---|---|---|---|
| 5,654,451 A | 8/1997 | Kari | |
| 7,894,996 B2 | 2/2011 | Rice et al. | |
| 8,088,368 B2 * | 1/2012 | Guo et al. | 424/85.4 |
| 2010/0158862 A1 | 6/2010 | Kim et al. | |
| 2011/0092415 A1 | 4/2011 | DeGoey et al. | |
| 2011/0195044 A1 | 8/2011 | Romine | |
| 2011/0237636 A1 | 9/2011 | Belema et al. | |
| 2012/0195857 A1 | 8/2012 | Belema et al. | |
| 2012/0196794 A1 | 8/2012 | Gao et al. | |

FOREIGN PATENT DOCUMENTS

| | | |
|---|---|---|
| WO | WO 94/15909 | 7/1994 |
| WO | WO 2004/005264 | 1/2004 |
| WO | WO 2006/022442 | 3/2006 |
| WO | WO 2006/093867 | 9/2006 |
| WO | WO 2006/133326 | 12/2006 |
| WO | WO 2007/031791 | 3/2007 |
| WO | WO 2007/058384 | 5/2007 |
| WO | WO 2007/076034 | 7/2007 |
| WO | WO 2007/077186 | 7/2007 |
| WO | WO 2007/081517 | 7/2007 |
| WO | WO 2007/138242 | 12/2007 |
| WO | WO 2008/014430 | 1/2008 |
| WO | WO 2008/021927 | 2/2008 |
| WO | WO 2008/021928 | 2/2008 |
| WO | WO 2008/021936 | 2/2008 |
| WO | WO 2008/070447 | 6/2008 |
| WO | WO 2008/133753 | 11/2008 |
| WO | WO 2009/020825 | 2/2009 |
| WO | WO 2009/020828 | 2/2009 |
| WO | WO 2009/102318 | 8/2009 |
| WO | WO 2009/102325 | 8/2009 |
| WO | WO 2009/102568 | 8/2009 |
| WO | WO 2009/102633 | 8/2009 |
| WO | WO 2009/102694 | 8/2009 |
| WO | WO 2010/017401 | 2/2010 |
| WO | WO 2010/039793 | 4/2010 |
| WO | WO 2010/062821 | 6/2010 |
| WO | WO 2010/065668 | 6/2010 |
| WO | WO 2010/065674 | 6/2010 |
| WO | WO 2010/065681 | 6/2010 |
| WO | WO 2010065668 A1 * | 6/2010 |
| WO | WO 2010/075376 | 7/2010 |
| WO | WO 2010/091413 | 8/2010 |
| WO | WO 2010/094977 | 8/2010 |
| WO | WO 2010/096302 | 8/2010 |
| WO | WO 2010/096462 | 8/2010 |
| WO | WO 2010/096777 | 8/2010 |
| WO | WO 2010/099527 | 9/2010 |
| WO | WO 2010/111483 | 9/2010 |
| WO | WO 2010/111534 | 9/2010 |
| WO | WO 2010/111673 | 9/2010 |

(Continued)

OTHER PUBLICATIONS

Fridell, R.A. et al., "Resistance Analysis of the Hepatitis C Virus NS5A Inhibitor BMS-790052 in an In Vitro Replicon System", Antimicrobial Agents and Chemotherapy, vol. 54, No. 9, pp. 3641-3650 (2010).

(Continued)

*Primary Examiner* — Jeffrey S. Lundgren
*Assistant Examiner* — Michael Schmitt
(74) *Attorney, Agent, or Firm* — Pamela A. Mingo

(57) ABSTRACT

This disclosure concerns novel compounds of Formula (I) or as defined in the specification and compositions comprising such novel compounds. These compounds are useful antiviral agents, especially in inhibiting the function of the NS5A protein encoded by Hepatitis C virus (HCV). Thus, the disclosure also concerns a method of treating HCV related diseases or conditions by use of these novel compounds or a composition comprising such novel compounds.

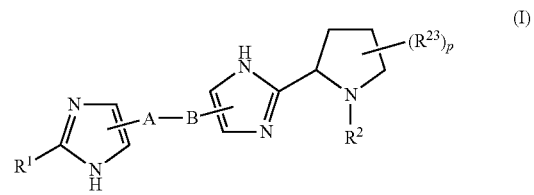

6 Claims, No Drawings

(56) References Cited

FOREIGN PATENT DOCUMENTS

| | | |
|---|---|---|
| WO | WO 2010/117635 | 10/2010 |
| WO | WO 2010/117704 | 10/2010 |
| WO | WO 2010/117977 | 10/2010 |
| WO | WO 2010/120621 | 10/2010 |
| WO | WO 2010/120935 | 10/2010 |
| WO | WO 2010/122162 | 10/2010 |
| WO | WO 2010/132538 | 11/2010 |
| WO | WO 2010/132601 | 11/2010 |
| WO | WO 2010/138368 | 12/2010 |
| WO | WO 2010/138488 | 12/2010 |
| WO | WO 2010/138790 | 12/2010 |
| WO | WO 2010/138791 | 12/2010 |
| WO | WO 2010/144646 | 12/2010 |
| WO | WO 2010/148006 | 12/2010 |
| WO | WO 2011/004276 | 1/2011 |
| WO | WO 2011/009084 | 1/2011 |
| WO | WO 2011/015657 | 2/2011 |
| WO | WO 2011/015658 | 2/2011 |
| WO | WO 2011/026920 | 3/2011 |
| WO | WO 2011/028596 | 3/2011 |
| WO | WO 2011/031904 | 3/2011 |
| WO | WO 2011/031934 | 3/2011 |
| WO | WO 2011/046811 | 4/2011 |
| WO | WO 2011/050146 | 4/2011 |
| WO | WO 2011/054834 | 5/2011 |
| WO | WO 2011/059850 | 5/2011 |
| WO | WO 2011/059887 | 5/2011 |
| WO | WO 2011/066241 | 6/2011 |
| WO | WO 2011/068941 | 6/2011 |
| WO | WO 2011/075439 | 6/2011 |
| WO | WO 2011/075607 | 6/2011 |
| WO | WO 2011/075615 | 6/2011 |
| WO | WO 2011/079327 | 6/2011 |
| WO | WO 2011/081918 | 7/2011 |
| WO | WO 2011/082077 | 7/2011 |
| WO | WO 2011/087740 | 7/2011 |
| WO | WO 2011/091417 | 7/2011 |
| WO | WO 2011/091446 | 7/2011 |
| WO | WO 2011/091532 | 8/2011 |

OTHER PUBLICATIONS

Gao, M. et al., "Chemical genetics strategy identifies an HCV NS5A inhibitor with a potent clinical effect", Nature, vol. 465, pp. 96-100 (2010).

Lemm, J.A. et al., "Identification of Hepatitis C Virus NS5A inhibitors", Journal of Virology, vol. 84, No. 1, pp. 482-491 (2010).

Romine, J.L. et al., "Inhibitors of HCV NS5A: From Iminothiazolidinones to Symmetrical Stilbenes", ACS Medicinal Chemistry Letters, vol. 2, pp. 224-229 (2011).

* cited by examiner

HEPATITIS C VIRUS INHIBITORS

CROSS-REFERENCE TO RELATED APPLICATIONS

This Divisional application claims the benefit of U.S. Ser. No. 12/942,183 filed Nov. 9, 2010 which claims the benefit of U.S. Provisional Application U.S. Ser. No. 61/260,569 filed Nov. 12, 2009.

FIELD OF THE DISCLOSURE

The present disclosure is generally directed to antiviral compounds, and more specifically directed to compounds which can inhibit the function of the NS5A protein encoded by Hepatitis C virus (HCV), compositions comprising such compounds, and methods for inhibiting the function of the NS5A protein.

BACKGROUND OF THE DISCLOSURE

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma. The current standard of care for HCV, which employs a combination of pegylated-interferon and ribavirin, has a non-optimal success rate in achieving sustained viral response and causes numerous side effects. Thus, there is a clear and long-felt need to develop effective therapies to address this undermet medical need. HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome due to the high error rate of the encoded RNA dependent RNA polymerase which lacks a proof-reading capability. At least six major genotypes have been characterized, and more than 50 subtypes have been described with distribution worldwide. The clinical significance of the genetic heterogeneity of HCV has demonstrated a propensity for mutations to arise during monotherapy treatment, thus additional treatment options for use are desired. The possible modulator effect of genotypes on pathogenesis and therapy remains elusive. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions by both acting as a cofactor for the NS3 protease and assisting in the membrane localization of NS3 and other viral replicase components. The formation of a NS3-NS4A complex is necessary for proper protease activity resulting in increased proteolytic efficiency of the cleavage events. The NS3 protein also exhibits nucleoside triphosphatase and RNA helicase activities. NS5B (also referred to herein as HCV polymerase) is a RNA-dependent RNA polymerase that is involved in the replication of HCV with other HCV proteins, including NS5A, in a replicase complex.

Compounds useful for treating HCV-infected patients are desired which selectively inhibit HCV viral replication. In particular, compounds which are effective to inhibit the function of the NS5A protein are desired. The HCV NS5A protein is described, for example, in Tan, S.-L. et al., *Virology*, 284: 1-12 (2001); and in Park, K.-J. et al., *J. Biol. Chem.*, 30711-30718 (2003); Tellinghuisen, T. L. et al., *Nature*, 435:374 (2005); Love, R. A. et al., *J. Virol.*, 83:4395 (2009); Appel, N. et al., *J. Biol. Chem.*, 281:9833 (2006); Huang, L., *J. Biol. Chem.*, 280:36417 (2005); Rice, C. et al., PCT Publication No. WO 2006/093867, Sep. 8, 2006.

SUMMARY OF THE DISCLOSURE

The present disclosure provides compounds which selectively inhibit HCV viral replication, as characterized by Formula (I):

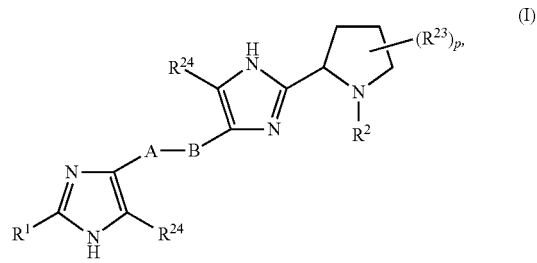

or a pharmaceutically acceptable salt thereof, wherein:

A and B are independently selected from

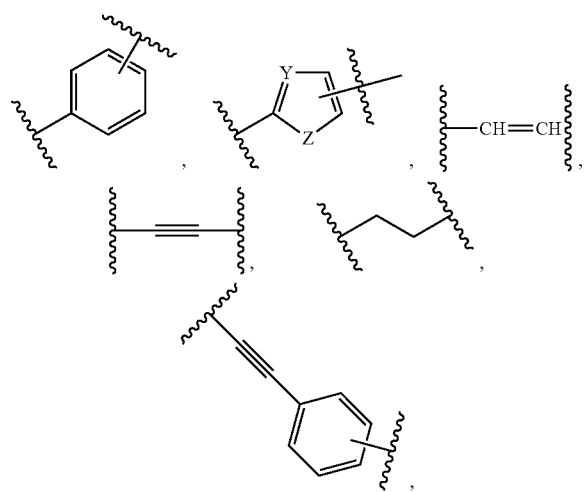

-continued

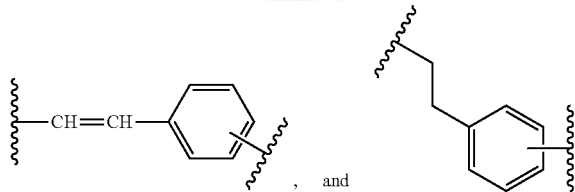
, and provided that at least one of A and B is other than phenyl and provided that A-B is other than

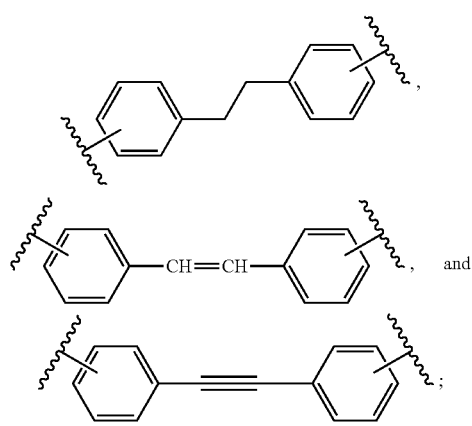

Y is nitrogen (N) or CH;
Z is oxygen (O) or sulfur (S);
each $R^{24}$ is independently selected from hydrogen and halo;
$R^1$ is selected from

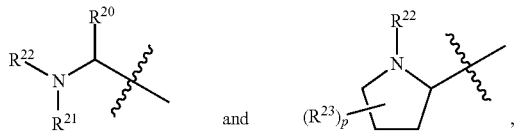

wherein p is 0 or 1;
$R^{20}$ is selected from hydrogen and alkyl;
$R^{21}$ is selected from hydrogen and alkyl;
$R^{22}$ is hydrogen or —C(O)R$^x$; and
$R^{23}$ is selected from hydrogen and alkyl, wherein the alkyl can optionally form a fused three- to six-membered ring with an adjacent carbon atom, wherein the three- to six-membered ring is optionally substituted with one or two alkyl groups;
$R^2$ is hydrogen or —C(O)R$^y$;
$R^x$ and $R^y$ are each independently selected from cycloalkyl, heteroaryl, heterocyclyl, alkoxy, and alkyl, said alkyl being substituted by one or more substituents independently selected from aryl, alkenyl, cycloalkyl, heterocyclyl, heteroaryl, —OR$^3$, —NR$^a$R$^b$, and —C(O)NR$^c$R$^d$,
wherein any said aryl and heteroaryl may optionally be substituted with one or more substituents independently selected from alkenyl, alkyl, haloalkyl, arylalkyl, heterocyclyl, heterocyclylalkyl, halogen, cyano, nitro, —C(O)OR$^4$, OR$^5$, —NR$^a$R$^b$, (NR$^a$R$^b$)alkyl, and (MeO)(HO)P(O)O—, and
wherein any said cycloalkyl and heterocyclyl may optionally be fused onto an aromatic ring and may optionally be substituted with one or more substituents independently selected from alkoxy, alkyl, hydroxyl, halogen, aryl, —NR$^a$R$^b$, oxo, and —C(O)OR$^4$;
$R^3$ is hydrogen, alkyl, or arylalkyl;
$R^4$ is selected from alkyl and arylalkyl;
$R^5$ is hydrogen, alkyl, or arylalkyl;
$R^a$ and $R^b$ are independently selected from hydrogen, alkyl, cycloalkyl, arylalkyl, heteroaryl, —C(O)R$^6$, —C(O)OR$^7$, —C(O)NR$^c$R$^d$, and (NR$^c$R$^d$)alkyl, or alternatively, $R^a$ and $R^b$, together with the nitrogen atom to which they are attached, form a five- or six-membered ring or bridged bicyclic ring structure, wherein said five- or six-membered ring or bridged bicyclic ring structure optionally may contain one or two additional heteroatoms independently selected from nitrogen, oxygen, and sulfur and may contain one, two, or three substituents independently selected from $C_1$ to $C_6$ alkyl, $C_1$ to $C_4$ haloalkyl, aryl, hydroxyl, $C_1$ to $C_6$ alkoxy, $C_1$ to $C_4$ haloalkoxy, and halogen;
$R^6$ is alkyl;
$R^7$ is alkyl, cycloalkyl, arylalkyl, or haloalkyl; and
$R^c$ and $R^d$ are independently selected from hydrogen, alkyl, arylalkyl, and cycloalkyl.

In a first embodiment of the first aspect, the present disclosure provides a compound of Formula (I), or a pharmaceutically acceptable salt thereof, wherein Y is CH and Z is sulfur.

In a second embodiment of the first aspect, the present disclosure provides a compound of Formula (I), or a pharmaceutically acceptable salt thereof, wherein Y is nitrogen and Z is sulfur.

In a third embodiment of the first aspect, the present disclosure provides a compound of Formula (I), or a pharmaceutically acceptable salt thereof, wherein one of A and B is

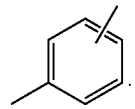

In a fourth embodiment of the first aspect, the present disclosure provides a compound of Formula (I), or a pharmaceutically acceptable salt thereof, wherein:
$R^1$ is

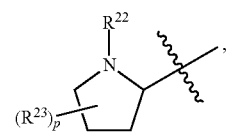

wherein $R^{22}$ is —C(O)R$^x$;
$R^2$ is —C(O)R$^y$; and
$R^x$ and $R^y$ are independently alkyl substituted by at least one —NR$^a$R$^b$, characterized by Formula (A):

(A)

wherein:

m is 0 or 1;

$R^8$ is hydrogen or alkyl;

$R^9$ is selected from hydrogen, cycloalkyl, aryl, heteroaryl, heterocyclyl, and alkyl optionally substituted with a substituent selected from aryl, alkenyl, cycloalkyl, heterocyclyl, heteroaryl, heterobicyclyl, —$OR^3$, —$C(O)OR^4$, —$NR^aR^b$, and —$C(O)NR^cR^d$, wherein aryl and heteroaryl may optionally be substituted with one or more substituents independently selected from alkenyl, alkyl, haloalkyl, arylalkyl, heterocyclyl, heterocyclylalkyl, halogen, cyano, nitro, —$C(O)OR^4$, $OR^5$, —$NR^aR^b$, ($NR^aR^b$)alkyl, and (MeO)(HO)P(O)O—, and wherein cycloalkyl and heterocyclyl may optionally be fused onto an aromatic ring and may optionally be substituted with one or more substituents independently selected from alkoxy, alkyl, hydroxyl, halogen, aryl, —$NR^aR^b$, oxo, and —$C(O)OR^4$; and $R^3$, $R^4$, $R^5$, $R^a$, $R^b$, $R^c$, and $R^d$ are defined as above.

In a fifth embodiment of the first aspect, the present disclosure provides a compound of Formula (I), or a pharmaceutically acceptable salt thereof, wherein:

$R^1$ is

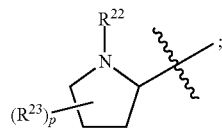

wherein $R^{22}$ is —$C(O)R^x$;

$R^2$ is —$C(O)R^y$; and $R^x$ and $R^y$ are independently alkyl substituted by at least one —$NR^aR^b$, characterized by Formula (A):

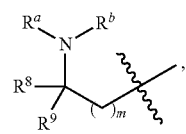

wherein:

m is 0;

$R^8$ is hydrogen; and $R^9$ is selected from hydrogen, cycloalkyl, aryl, and alkyl optionally substituted with one —$OR^3$ substituent and $R^3$, $R^4$, $R^5$, $R^a$, $R^b$, $R^c$, and $R^d$ are defined as above.

In a sixth embodiment of the first aspect, the present disclosure provides a compound of Formula (I), or a pharmaceutically acceptable salt thereof, wherein $R^1$ is

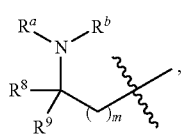

$R^2$ is —$C(O)R^y$;
$R^{20}$ is alkyl;
$R^{21}$ is hydrogen;
$R^{22}$ is —$C(O)R^x$;

$R^x$ and $R^y$ are independently alkyl substituted by at least one —$NR^aR^b$, characterized by Formula (A):

(A)

$R^a\diagdown N\diagup R^b$
$R^8$—
$R^9$ $(\phantom{)}_m$ wherein:

m is 0 or 1;

$R^8$ is hydrogen or alkyl;

$R^9$ is selected from hydrogen, cycloalkyl, aryl, heteroaryl, heterocyclyl, and alkyl optionally substituted with a substituent selected from aryl, alkenyl, cycloalkyl, heterocyclyl, heteroaryl, heterobicyclyl, —$OR^3$, —$C(O)OR^4$, —$NR^aR^b$, and —$C(O)NR^cR^d$, wherein aryl and heteroaryl may optionally be substituted with one or more substituents independently selected from alkenyl, alkyl, haloalkyl, arylalkyl, heterocyclyl, heterocyclylalkyl, halogen, cyano, nitro, —$C(O)OR^4$, $OR^5$, —$NR^aR^b$, ($NR^aR^b$)alkyl, and (MeO)(HO)P(O)O—, and wherein cycloalkyl and heterocyclyl may optionally be fused onto an aromatic ring and may optionally be substituted with one or more substituents independently selected from alkoxy, alkyl, hydroxyl, halogen, aryl, —$NR^aR^b$, oxo, and —$C(O)OR^4$; and $R^3$, $R^4$, $R^5$, $R^a$, $R^b$, $R^c$, and $R^d$ are defined as in claim 1.

In a seventh embodiment of the first aspect, the present disclosure provides a compound of Formula (I), or a pharmaceutically acceptable salt thereof, wherein $R^1$ is

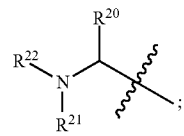

$R^2$ is —$C(O)R^y$;
$R^{20}$ is alkyl;
$R^{21}$ is hydrogen;
$R^{22}$ is —$C(O)R^x$;

$R^x$ and $R^y$ are independently alkyl substituted by at least one —$NR^aR^b$, characterized by Formula (A):

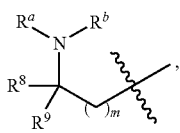

wherein:

m is 0;

$R^8$ is hydrogen; and $R^9$ is selected from hydrogen, cycloalkyl, aryl, and alkyl optionally substituted with one —$OR^3$ substituent.

In an eighth embodiment of the first aspect the present disclosure provides a compound of Formula (I), or a pharmaceutically acceptable salt thereof, wherein $R^2$ and $R^{22}$ are both hydrogen.

In a ninth embodiment of the first aspect the present disclosure provides a compound of Formula (I), or a pharmaceutically acceptable salt thereof, wherein at least one of A and B is

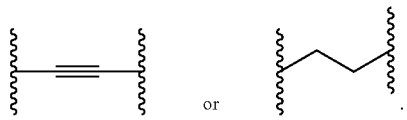

In a second aspect the present disclosure provides a composition comprising a compound of Formula (I)

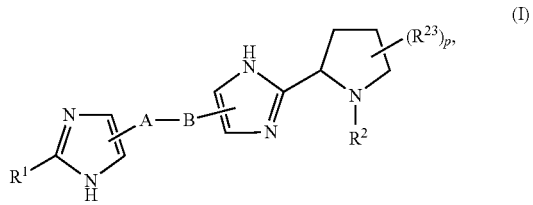

or a pharmaceutically acceptable salt thereof, and a pharmaceutically acceptable carrier, wherein Formula (I) is defined according to any of the embodiments described above in the first aspect of the present disclosure.

In a first embodiment of the second aspect the composition further comprises at least one additional compound having anti-HCV activity.

In a second embodiment of the second aspect at least one of the additional compounds is an interferon or a ribavirin.

In a third embodiment of the second aspect the interferon is selected from interferon alpha 2B, pegylated interferon alpha, consensus interferon, interferon alpha 2A, and lymphoblastoid interferon tau.

In a fourth embodiment of the second aspect the present disclosure provides a composition comprising a compound of Formula (I), or a pharmaceutically acceptable salt thereof, a pharmaceutically acceptable carrier, and at least one additional compound having anti-HCV activity, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the second aspect the present disclosure provides a composition comprising a compound of Formula (I), or a pharmaceutically acceptable salt thereof, a pharmaceutically acceptable carrier, and at least one additional compound having anti-HCV activity, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a third aspect the present disclosure provides a method of treating an HCV infection in a patient, comprising administering to the patient a therapeutically effective amount of a compound of Formula (I):

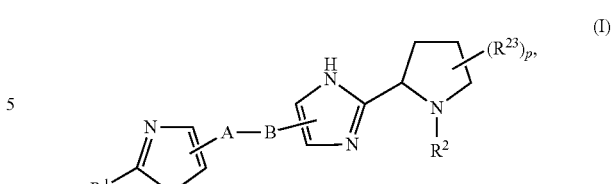

or a pharmaceutically acceptable salt thereof, wherein Formula (I) is defined according to any of the embodiments described above in the first aspect of the present disclosure.

In a first embodiment of the third aspect the method further comprises administering at least one additional compound having anti-HCV activity prior to, after or simultaneously with the compound of Formula (I), or a pharmaceutically acceptable salt thereof.

In a second embodiment of the third aspect at least one of the additional compounds is an interferon or a ribavirin.

In a third embodiment of the third aspect the interferon is selected from interferon alpha 2B, pegylated interferon alpha, consensus interferon, interferon alpha 2A, and lymphoblastoid interferon tau.

In a fourth embodiment of the third aspect the present disclosure provides a method of treating an HCV infection in a patient, comprising administering to the patient a therapeutically effective amount of a compound of Formula (I), or a pharmaceutically acceptable salt thereof, and at least one additional compound having anti-HCV activity prior to, after or simultaneously with the compound of Formula (I), or a pharmaceutically acceptable salt thereof, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the third aspect the present disclosure provides a method of treating an HCV infection in a patient, comprising administering to the patient a therapeutically effective amount of a compound of Formula (I), or a pharmaceutically acceptable salt thereof, and at least one additional compound having anti-HCV activity prior to, after or simultaneously with the compound of Formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order to accommodate a substituent at any given location.

Certain features of substructures of Formula (I) are further illustrated below:

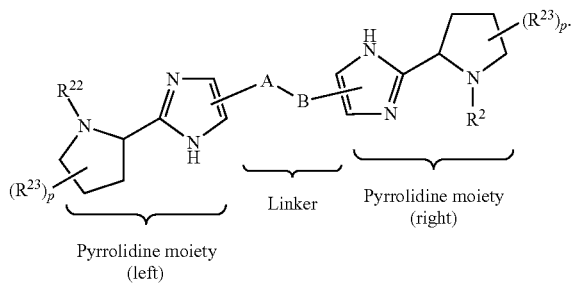

In the formula as depicted above (compounds of Formula (I) wherein $R^1$ is a pyrrolidine moiety), the "pyrrolidine moiety" on the left side of the "linker" is independent from the "pyrrolidine moiety" on the right side of the linker in respect of, e.g., (1) substituent on the pyrrolidine nitrogen ($R^{22}$ or $R^2$), and (2) stereochemistry of the pyrrolidine ring. However, in some circumstances $R^{22}$ and $R^2$ are preferably the same, and/or the stereochemistry of the two pyrrolidine rings is preferably the same. It should be understood that the depiction of a pyrrolidine moiety on the "left" side or on the "right" side is for illustration purpose only, which does not in any way limit the scope of the disclosure.

In a pyrrolidine moiety on either side of the molecule, the stereogenic carbon center on the pyrrolidine ring can take either (R)- or (S)-configuration as illustrated below:

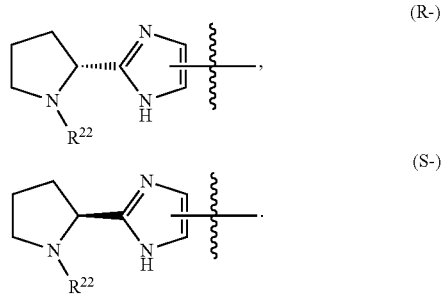

Thus, this disclosure is intended to cover all possible stereoisomers even when a single stereoisomer, or no stereochemistry, is described in a structure. The same principle also applies to the $R^2$ groups.

In Formula (I), the linkage between the linker group and the imidazole group of either left or right "pyrrolidine moiety" can take place at either the C-4 or the C-5 position on the imidazole ring. As a person of ordinary skill in the art would understand, due to tautomerization of the imidazole ring, a bonding at the C-4 position may be construed to be equivalent to a bonding at the C-5 position, as illustrated in the following equation:

Thus, this disclosure is intended to cover all possible tautomers even when a structure depicts only one of them.

In this disclosure, a floating bond (e.g.,

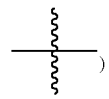

)

or a floating substituent (e.g., —$R^{23}$) on a structure indicates that the bond or substituent can attach to any available position of the structure by removal of a hydrogen from the available position. It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, for substituent $(R^{23})_p$, when p is 2, each of the two $R^{23}$ groups may be the same or different.

All patents, patent applications, and literature references cited in the specification are herein incorporated by reference in their entirety. In the case of inconsistencies, the present disclosure, including definitions, will prevail.

DEFINITIONS

Definitions have been provided above for each of the groups defined. In addition, the following definitions shall be used.

As used herein, the singular forms "a", "an", and "the" include plural reference unless the context clearly dictates otherwise.

Unless stated otherwise, all aryl, cycloalkyl, heteroaryl, and heterocyclyl groups of the present disclosure may be substituted as described in each of their respective definitions. For example, the aryl part of an arylalkyl group may be substituted as described in the definition of the term "aryl."

The term "acetyl," as used herein, refers to —C(O)CH$_3$.

The term "alkenyl," as used herein, refers to a monovalent, straight or branched hydrocarbon chain having one or more, preferably one to two, double bonds therein. The double bond of an alkenyl group can be unconjugated or conjugated to another unsaturated group. Suitable alkenyl groups include, but are not limited to, $C_2$ to $C_{10}$ alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

The term "alkoxy," as used herein, refers to an alkyl group attached to the parent molecular moiety through an oxygen atom. Representative examples of alkoxy group include, but are not limited to, methoxy (CH$_3$O—), ethoxy (CH$_3$CH$_2$O—), and t-butoxy ((CH$_3$)$_3$CO—).

The term "alkyl," as used herein, refers to a group derived from a straight or branched chain saturated hydrocarbon by

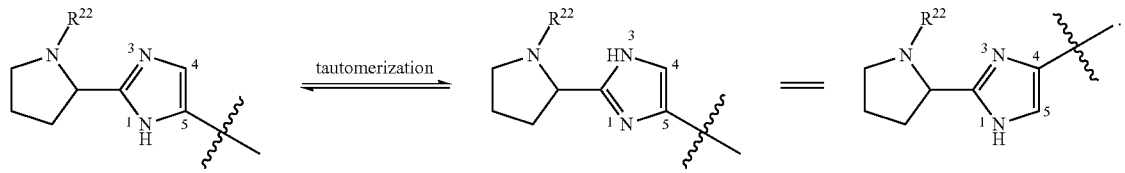

removal of a hydrogen from one of the saturated carbons. The alkyl group preferably contains from one to ten carbon atoms. Representative examples of alkyl group include, but are not limited to, methyl, ethyl, isopropyl, and tert-butyl.

The term "alkylcarbonyl," as used herein, refers to an alkyl group attached to the parent molecular moiety through a carbonyl group. Representative examples of alkylcarbonyl group include, but are not limited to, acetyl (—C(O)CH$_3$), propanoyl (—C(O)CH$_2$CH$_3$), n-butyryl (—C(O)CH$_2$CH$_2$CH$_3$), and 2,2-dimethylpropanoyl or pivaloyl (—C(O)C(CH$_3$)$_3$).

The term "allyl," as used herein, refers to the —CH$_2$CH=CH$_2$ group.

The term "aryl," as used herein, refers to a group derived from an aromatic carbocycle by removal of a hydrogen atom from an aromatic ring. The aryl group can be monocyclic, bicyclic or polycyclic, wherein in bicyclic or polycyclic aryl group, the aromatic carbocycle can be fused onto another four- to six-membered aromatic or non-aromatic carbocycle. Representative examples of aryl groups include, but are not limited to, phenyl, indanyl, indenyl, naphthyl, and 1,2,3,4-tetrahydronaphth-5-yl.

The term "arylalkyl," as used herein, refers to an alkyl group substituted with one, two, or three aryl groups, wherein aryl part of the arylalkyl group may optionally be substituted by one to five substituents independently selected from C$_1$ to C$_6$ alkyl, C$_1$ to C$_4$ haloalkyl, C$_1$ to C$_6$ alkoxy, halogen, cyano, and nitro groups. Represented examples of arylalkyl include, but are not limited to, benzyl, 2-phenyl-1-ethyl (PhCH$_2$CH$_2$—), (naphth-1-yl)methyl, and (naphth-2-yl)methyl.

The term "benzyl," as used herein, refers to a methyl group on which one of the hydrogen atoms is replaced by a phenyl group, wherein said phenyl group may optionally be substituted by one to five substituents independently selected from methyl, trifluoromethyl (—CF$_3$), methoxy (—OCH$_3$), halogen, and nitro (—NO$_2$). Representative examples of benzyl group include, but are not limited to, PhCH$_2$—, 4-MeO—C$_6$H$_4$—CH$_2$—, and 2,4,6-tri-methyl-C$_6$H$_4$—CH$_2$—.

The term "bridged bicyclic ring," as used herein, refers to a ring structure comprising a bridgehead between two of the ring members, wherein the ring and the bridgehead optionally may independently comprise one or more, preferably one to two, heteroatoms independently selected from nitrogen, oxygen, and sulfur. Illustrated examples of a bridged bicyclic ring structure include, but are not limited to:

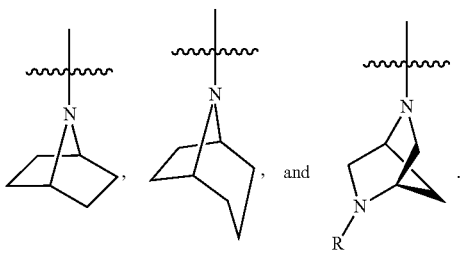

The terms "Cap" and "cap," as used herein, refer to the group which is placed on the nitrogen atom of the pyrrolidine ring in the compounds of Formula (I). It should be understood that "Cap" or "cap" can also refer to the reagent which is a precursor to the final "cap" in compounds of Formula (I) and is used as one of the starting materials in the reaction to append a group on the pyrrolidine nitrogen that results in the final product, a compound which contains the functionalized pyrrolidine that will be present in the compound of Formula (I).

The term "carbonyl," as used herein, refers to —C(O)—.
The term "carboxyl," as used herein, refers to —CO$_2$H.
The term "cyano," as used herein, refers to —CN.
The term "cycloalkyl," as used herein, refers to a group derived from a saturated carbocycle, having preferably three to eight carbon atoms, by removal of a hydrogen atom from the saturated carbocycle, wherein the saturated carbocycle can optionally be fused onto one or two other aromatic or nonaromatic carbocycles. Representative examples of cycloalkyl groups include, but are not limited to, cyclopropyl, cyclopentyl, cyclohexyl, and 1,2,3,4-tetrahydronaphth-1-yl.

The term "formyl," as used herein, refers to —CHO.
The terms "halo" and "halogen," as used herein, refer to F, Cl, Br, or I.
The term "haloalkoxy," as used herein, refers to a haloalkyl group attached to the parent molecular moiety through an oxygen atom.

The term "haloalkyl," as used herein, refers to an alkyl group substituted by at least one halogen atom. The haloalkyl group can be an alkyl group of which all hydrogen atoms are substituted by halogens. Representative examples of haloalkyl include, but are not limited to, trifluoromethyl (CF$_3$—), 1-chloroethyl (ClCH$_2$CH$_2$—), and 2,2,2-trifluoroethyl (CF$_3$CH$_2$—).

The term "heteroaryl," as used herein, refers to group derived from a monocyclic, bicyclic, or polycyclic compound comprising at least one aromatic ring comprising one or more, preferably one to three, heteroatoms independently selected from nitrogen, oxygen, and sulfur, by removal of a hydrogen atom from an aromatic ring thereof. As is well known to those skilled in the art, heteroaryl rings have less aromatic character than their all-carbon counterparts. Thus, for the purposes of the disclosure, a heteroaryl group need only have some degree of aromatic character. Illustrative examples of heteroaryl groups include, but are not limited to, pyridyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, isoxazolyl, oxazolyl, indolyl, quinolinyl, isoquinolinyl, benzisoxazolyl, benzothiazolyl, benzothienyl, and pyrrolopyridinyl.

The term "heteroarylalkyl," as used herein, refers to an alkyl group substituted with one, two, or three heteroaryl groups.

The term "heterobicyclyl," as used herein, refers to a ring structure comprising two fused, spiro, or bridged rings that include carbon and one or more, preferably one to three, heteroatoms independently selected from nitrogen, oxygen, and sulfur. The heterobicyclic ring structure is a subset of heterocyclic ring and can be saturated or unsaturated. Examples of heterobicyclic ring structures include, but are not limited to, tropane, quinuclidine, 6-oxaspiro[2.5]octane, and 7-azabicyclo[2.2.1]heptane.

The term "heterocyclyl," as used herein, refers to a group derived from a monocyclic, bicyclic, or polycyclic compound comprising at least one nonaromatic ring comprising one or more, preferably one to three, heteroatoms independently selected from nitrogen, oxygen, and sulfur, by removal of a hydrogen atom from the nonaromatic ring. The heterocyclyl group encompasses the heterobicyclyl group. The heterocyclyl groups of the present disclosure can be attached to the parent molecular moiety through a carbon atom or a nitrogen atom in the group. Examples of heterocyclyl groups include, but are not limited to, morpholinyl, oxazolidinyl, piperazinyl, piperidinyl, pyrrolidinyl, tetrahydrofuryl, thiomorpholinyl, and indolinyl.

The term "heterocyclylalkyl," as used herein, refers to an alkyl group substituted with one, two, or three heterocyclyl groups.

The terms "hydroxy" or "hydroxyl," as used herein, refer to —OH.

The term "nitro," as used herein, refers to —NO$_2$.

The term "—NR$^a$R$^b$," as used herein, refers to two groups, R$^a$ and R$^b$, which are attached to the parent molecular moiety through a nitrogen atom, or alternatively R$^a$ and R$^b$, together with the nitrogen atom to which they are attached, form a 5- or 6-membered ring or a fused- or bridged-bicyclic ring structure optionally containing one, two, or three additional heteroatom independently selected from nitrogen, oxygen, and sulfur. The term "—NR$^c$R$^d$" is defined similarly.

The term "(NR$^a$R$^b$)alkyl," as used herein, refers to an alkyl group substituted with one, two, or three —NR$^a$R$^b$ groups. The term "(NR$^c$R$^d$)alkyl" is defined similarly.

The term "oxo," as used herein, refers to =O.

The term "sulfonyl," as used herein, refers to —SO$_2$—.

Asymmetric centers exist in the compounds of the present disclosure. These centers are designated by the symbols "R" or "S", depending on the configuration of substituents around the chiral carbon atom. It should be understood that the disclosure encompasses all stereochemical isomeric forms, or mixtures thereof, which possess the ability to inhibit NS5A. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof. The term "compounds of the present disclosure", and equivalent expressions, are meant to embrace compounds of Formula (I), and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric. Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of a compound of Formula (I) as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of Formula (I) or pharmaceutically acceptable salts thereof, and one or more, preferably one to three, pharmaceutically acceptable carriers, diluents, or excipients. The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of Formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of Formula (I), or a pharmaceutically acceptable salt thereof, with one or more, preferably one to three, pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of Formula (I) and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research*, 3(6):318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base. Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals. The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

The compounds of the present disclosure can also be administered with a cyclosporin, for example, cyclosporin A. Cyclosporin A has been shown to be active against HCV in clinical trials (*Hepatology*, 38:1282 (2003); *Biochem. Biophys. Res. Commun.*, 313:42 (2004); *J. Gastroenterol.*, 38:567 (2003)).

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
| --- | --- | --- | --- |
| NIM811 | | Cyclophilin inhibitors | Novartis |
| Debio-025 | | | Debiopharm |
| Zadaxin | | Immunomodulator | SciClone |
| Suvus | | Methylene blue | Bioenvision |
| Actilon (CPG10101) | | TLR9 agonist | Coley |
| Batabulin (T67) | Anticancer | β-Tubulin inhibitor | Tularik Inc., South San Francisco, CA |
| ISIS 14803 | Antiviral | Antisense | ISIS Pharmaceuticals Inc, Carlsbad, CA/ Elan Pharmaceuticals Inc., New York, NY |

TABLE 1-continued

| Brand Name | Physiological Class | Type of Inhibitor or Target | Source Company |
| --- | --- | --- | --- |
| Summetrel | Antiviral | Antiviral | Endo Pharmaceuticals Holdings Inc., Chadds Ford, PA |
| GS-9132 (ACH-806) | Antiviral | HCV inhibitor | Achillion/Gilead |
| Pyrazolopyrimidine compounds and salts From WO 2005/047288 May 26, 2005 | Antiviral | HCV inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | Monoclonal antibody | XTL Biopharmaceuticals Ltd., Rehovot, Israel |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B replicase inhibitor | Wyeth/Viropharma |
| NM-283 | Antiviral | NS5B replicase inhibitor | Idenix/Novartis |
| GL-59728 | Antiviral | NS5B replicase inhibitor | Gene Labs/Novartis |
| GL-60667 | Antiviral | NS5B replicase inhibitor | Gene Labs/Novartis |
| 2'C MeA | Antiviral | NS5B replicase inhibitor | Gilead |
| PSI 6130 | Antiviral | NS5B replicase inhibitor | Roche |
| R1626 | Antiviral | NS5B replicase inhibitor | Roche |
| 2'C Methyl adenosine | Antiviral | NS5B replicase inhibitor | Merck |
| JTK-003 | Antiviral | RdRp inhibitor | Japan Tobacco Inc., Tokyo, Japan |
| Levovirin | Antiviral | Ribavirin | ICN Pharmaceuticals, Costa Mesa, CA |
| Ribavirin | Antiviral | Ribavirin | Schering-Plough Corporation, Kenilworth, NJ |
| Viramidine | Antiviral | Ribavirin prodrug | Ribapharm Inc., Costa Mesa, CA |
| Heptazyme | Antiviral | Ribozyme | Ribozyme Pharmaceuticals Inc., Boulder, CO |
| BILN-2061 | Antiviral | Serine protease inhibitor | Boehringer Ingelheim Pharma KG, Ingelheim, Germany |
| SCH 503034 | Antiviral | Serine protease inhibitor | Schering-Plough |
| Zadazim | Immune modulator | Immune modulator | SciClone Pharmaceuticals Inc., San Mateo, CA |
| Ceplene | Immunomodulator | Immune modulator | Maxim Pharmaceuticals Inc., San Diego, CA |
| CELLCEPT ® | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon - α | Interferon | Albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |

TABLE 1-continued

| Brand Name | Physiological Class | Type of Inhibitor or Target | Source Company |
|---|---|---|---|
| REBIF ® | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | Lymphoblastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/Ribavirin | Interferon | PEGylated IFN-α2b/ribavirin | Schering-Plough Corporation, Kenilworth, NJ |
| IP-501 | Liver protection | Antifibrotic | Indevus Pharmaceuticals Inc., Lexington, MA |
| IDN-6556 | Liver protection | Caspase inhibitor | Idun Pharmaceuticals Inc., San Diego, CA |
| ITMN-191 (R-7227) | Antiviral | Serine protease inhibitor | InterMune Pharmaceuticals Inc., Brisbane, CA |
| GL-59728 | Antiviral | NS5B replicase inhibitor | Genelabs |
| ANA-971 | Antiviral | TLR-7 agonist | Anadys |
| Boceprevir | Antiviral | Serine protease inhibitor | Schering-Plough |
| TMS-435 | Antiviral | Serine protease inhibitor | Tibotec BVBA, Mechelen, Belgium |
| BI-201335 | Antiviral | Serine protease inhibitor | Boehringer Ingelheim Pharma KG, Ingelheim, Germany |
| MK-7009 | Antiviral | Serine protease inhibitor | Merck |
| PF-00868554 | Antiviral | Replicase inhibitor | Pfizer |
| ANA598 | Antiviral | Non-Nucleoside NS5B polymerase inhibitor | Anadys Pharmaceuticals, Inc., San Diego, CA, USA |
| IDX375 | Antiviral | Non-Nucleoside replicase inhibitor | Idenix Pharmaceuticals, Cambridge, MA, USA |
| BILB 1941 | Antiviral | NS5B polymerase inhibitor | Boehringer Ingelheim Canada Ltd R&D, Laval, QC, Canada |
| PSI-7851 | Antiviral | Nucleoside polymerase inhibitor | Pharmasset, Princeton, NJ, USA |

The compounds of the present disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition. The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials. This disclosure is intended to encompass compounds having Formula (I) when prepared by synthetic processes or by metabolic processes including those occurring in the human or animal body (in vivo) or processes occurring in vitro.

The abbreviations used in the present application, including particularly in the illustrative examples which follow, are well-known to those skilled in the art. Some of the abbreviations used are as follows:

| | |
|---|---|
| Me | methyl |
| Et | ethyl |
| t-Bu | tert-butyl |
| iPr | isopropyl |
| min | minutes |
| rt or RT | room temperature or retention time (context will dictate) |
| TFA | trifluoroacetic acid |
| h or hr | hours |
| DMSO | dimethylsulfoxide |
| DME | dimethyl ether |
| LDA | lithium diisopropylamide; |
| NBS | N-bromosuccinimide |
| SEM-Cl | 2-(trimethylsilyl)ethoxymethyl chloride; |
| TBAF | tetrabutylammonium fluoride |
| EEDQ | 2-ethoxy-1-ethoxycarbonyl-1,2-dihydroquinoline |
| HATU | O-(7-azabenzotriazol-1-yl)-N,N,N',N'-tetramethyluronium hexafluorophosphate |
| iPr$_2$EtN | diisopropylethylamine |
| DIEA | diisopropylethylamine |
| DIPEA | diisopropylethylamine |
| Hunig's | diisopropylethylamine |
| Boc or BOC | tert-butoxycarbonyl |
| DMAP | 4-dimethylaminopyridine |
| HCl | hydrochloric acid |
| Na$_2$SO$_4$ | sodium sulfate |
| MgSO$_4$ | magnesium sulfate |
| PdCl$_2$(PPh$_3$)$_2$ | bis(triphenylphosphine)palladium(II)dichloride; MCX cartridge Waters OASIS ® MCX LP extraction cartridge |

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

Starting materials can be obtained from commercial sources or prepared by well-established literature methods known to those of ordinary skill in the art.

EXAMPLES AND METHOD OF PREPARATION

Examples for the present disclosure could be prepared as outlined in the following synthetic schemes. Alternative regioisomers can be prepared using the appropriate starting materials.

Scheme 1

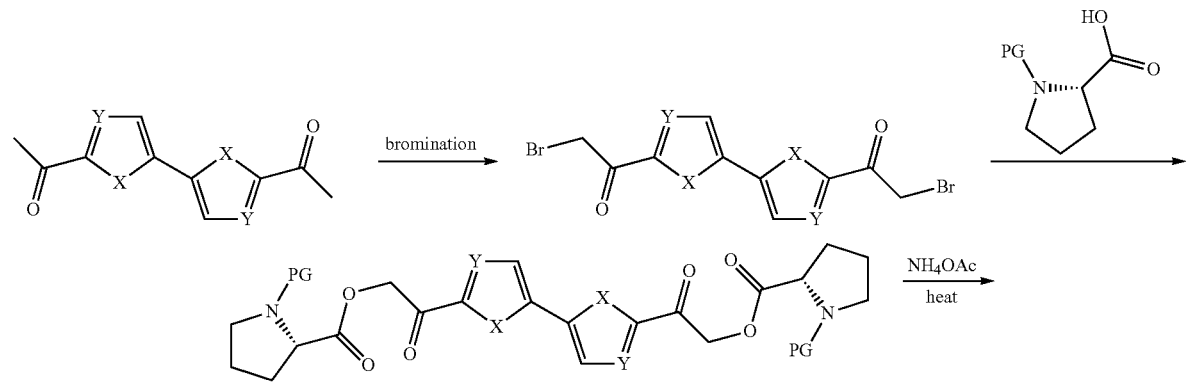

-continued

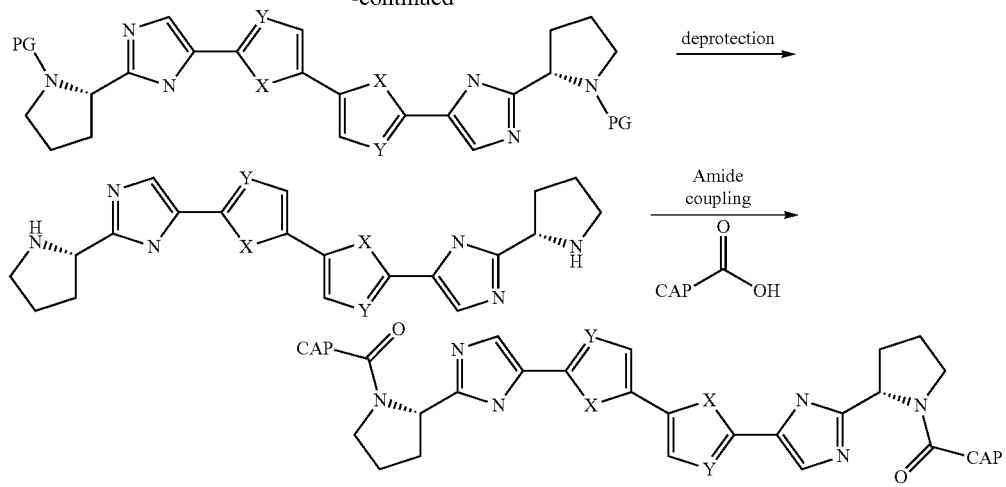

X = O, S
Y = CH, N

Bisbromination of 5,5'-diacetyl-2,2'-bithienyl (or bifuryl) (which could be prepared according to procedures outlined in Itahara, T. et al., *Synthesis*, 255-256 (1984)), 1,1'-(5,5'-bithiazole-2,2'-diyl)diethanone (which could be prepared according to analogous procedures outlined in Masui, K. et al., *J. Am. Chem. Soc*, 126(16):5074-5075 (2004)) or 1'-(5,5'-bisoxazole-2,2'-diyl)diethanone (which could be prepared according to analogous procedures outlined in Romero, F. A. et al., *J. Med. Chem.*, 50:1058-1068 (2007)) followed by esterification with protected (for example BOC or CBz) proline could form intermediate ketoesters. These intermediates could be cyclized to bisimidazoles with ammonium acetate at elevated temperatures. The final synthetic steps for preparing molecules in this disclosure could be deprotection under standard conditions followed by standard amide couplings (for example HATU, DEPBT, EDC or CDI) with known carboxylic acids.

Purity assessment and low resolution mass analysis were conducted on a Shimadzu LC system coupled with Waters MICROMASS® ZQ MS system.

The synthesis of key intermediates (i.e., intermediate-4, -9 and -16) is highlighted in Schemes 2 to 4, and the elaboration of these intermediates to Examples 1 to 20 is described in Scheme-5.

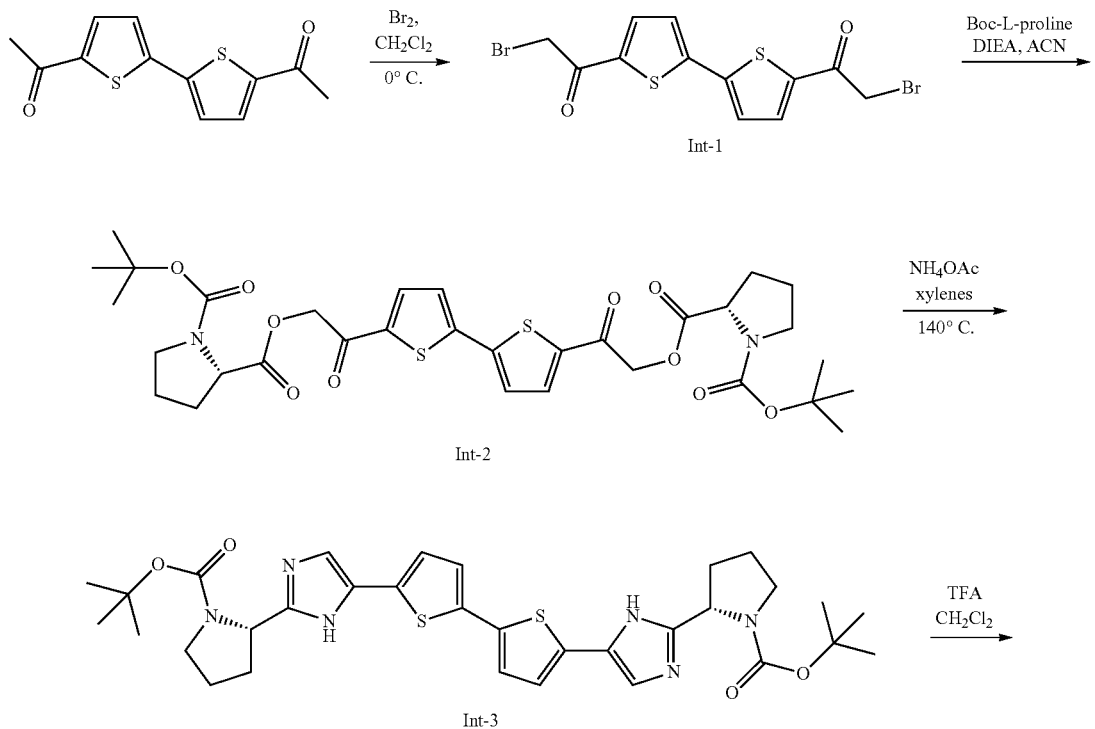

-continued
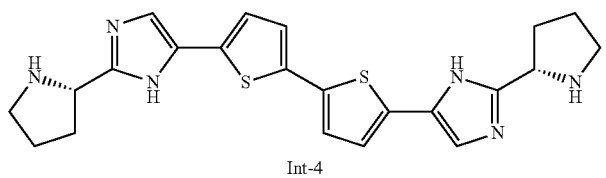
Int-4
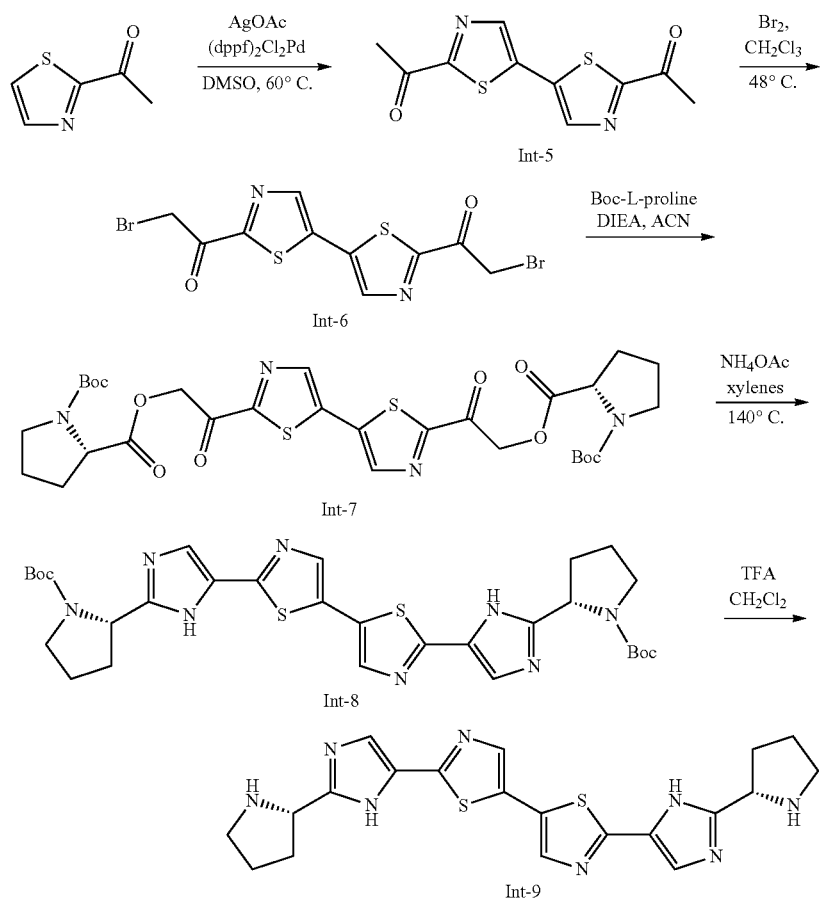
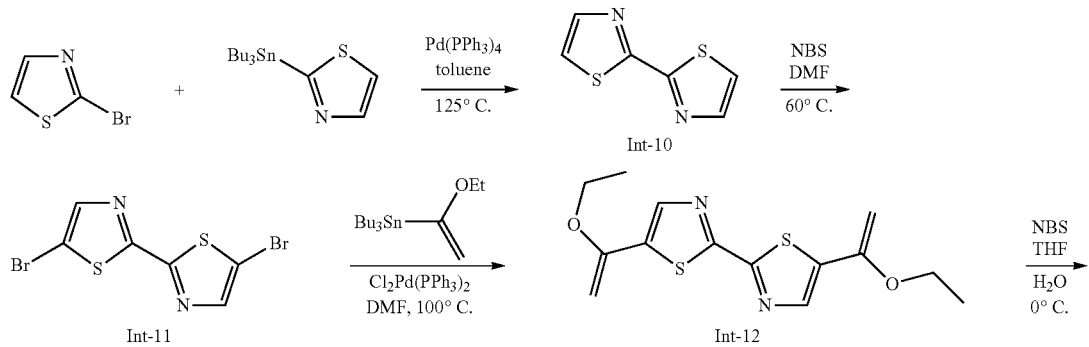

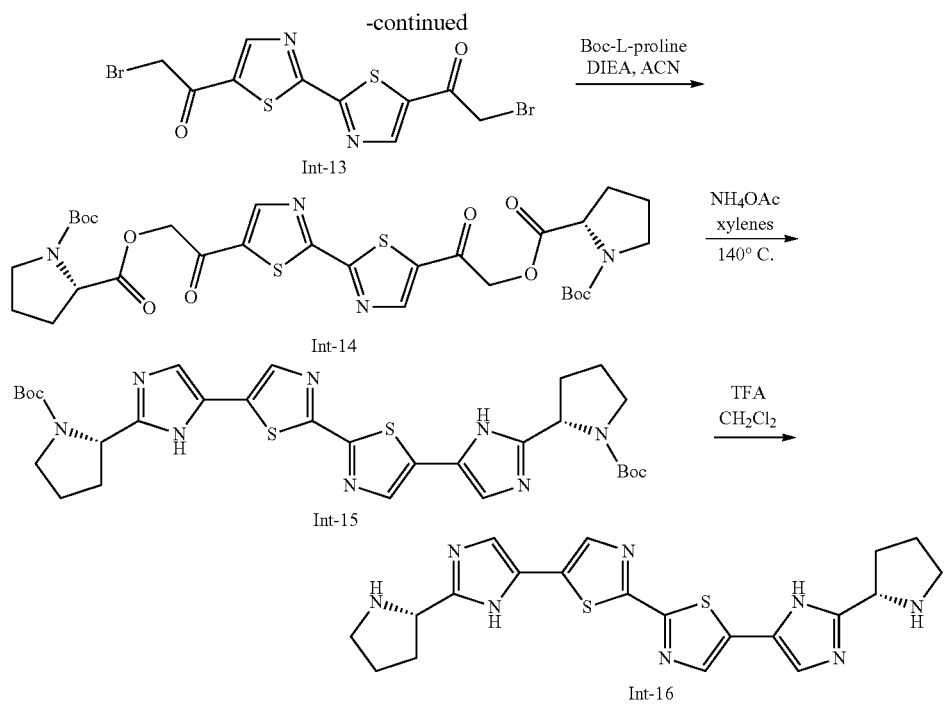

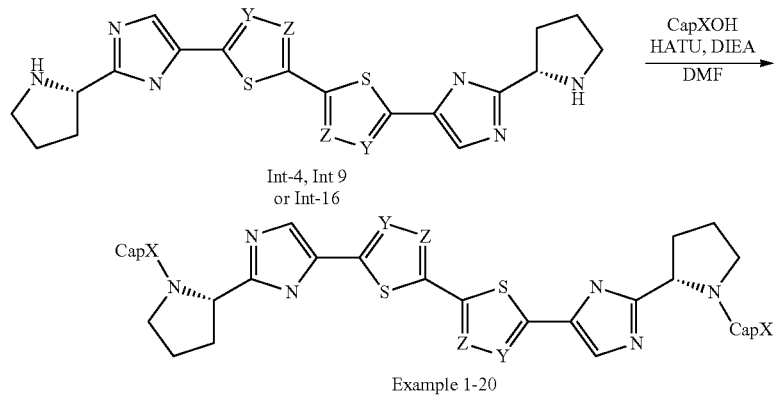

Intermediate 1

1,1'-(2,2'-Bithiophene-5,5'-diyl)bis(2-bromoethanone)

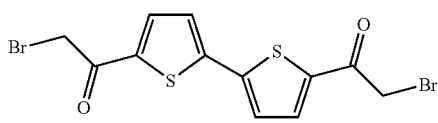

Bromine (0.270 mL, 5.23 mmol) was added dropwise to a stirred solution of 1,1'-(2,2'-bithiophene-5,5'-diyl)diethanone (1.31 g, 5.23 mmol) in ether (26.7 mL) and chloroform (10.7 mL) at 0° C. Once the addition was complete the reaction mixture was stirred at 0° C. for 5 min and then warmed up to room temperature and stirred 8 h. During the course of the reaction methanol was added to assist solubility. The reaction was concentrated to dryness and the major peaks, as noted by LCMS, corresponded to the starting material and a monobrominated product. The crude material was resubjected to the reaction conditions using dichloromethane (50 mL) as the only solvent. After 8 h at room temperature the reaction was diluted with tetrahydrofuran (100 mL) and concentrated. By LCMS, the crude bright yellow solid was found to be a mixture of 1,1'-(2,2'-bithiophene-5,5'-diyl)bis(2-bromoethanone) and tribrominated material (2.90 g). The material was taken into the next step without purification.

LC-MS retention time 2.88 min; m/z 409 (MH$^+$). LC data was recorded on a Shimadzu LC-10AS liquid chromatograph equipped with a PHENOMENEX® Luna 5 u C18 4.6×30 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% methanol/90% water/0.1% TFA and Solvent B was 90% methanol/10% water/0.1% TFA. MS data was determined using a MICROMASS® Platform for LC in electrospray mode.

Intermediate 2

(2S,2'S)-'2,2-2,2'-(2,2'-Bithiophene-5,5'-diyl)bis(2-oxoethane-2,1-diyl) 1-tert-butyl dipyrrolidine-1,2-dicarboxylate

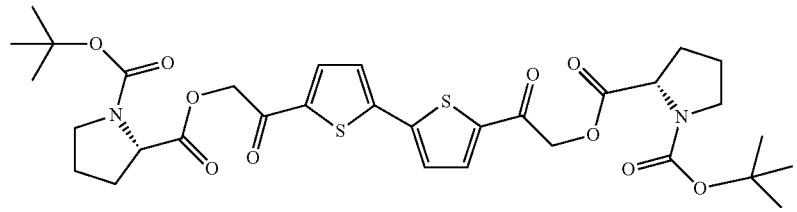 [SMILES: CC(C)(C)OC(=O)N1CCC[C@H]1C(=O)OCC(=O)c1ccc(-c2ccc(C(=O)COC(=O)[C@@H]3CCCN3C(=O)OC(C)(C)C)s2)s1]

DIEA (3.72 mL, 21.3 mmol) was added to a stirred slurry of crude 1,1'-(2,2'-bithiophene-5,5'-diyl)bis(2-bromoethanone) (contaminated with tribromo byproduct(s) from a previous reaction) (2.90 g, 7.11 mmol) and Boc-L-proline (3.82 g, 17.8 mmol) in acetonitrile (50 mL) at room temperature. The yellow/orange slurry was stirred 5 h at room temperature and the reaction mixture was concentrated to dryness in vacuo. The crude material was purified by column chromatography (0 to 5% methanol/dichloromethane). The fractions containing the desired product were collected and evaporated under vacuum to yield (2S,2'S)-'2,2-2,2'-(2,2'-bithiophene-5,5'-diyl)bis(2-oxoethane-2,1-diyl) 1-tert-butyl dipyrrolidine-1,2-dicarboxylate (5.09 g, 3.76 mmol, 52.9% yield, ~50% purity) as an orange foam. The material was used in the next step without further purification.

LC-MS retention time 2.53 min; m/z 699 (MNa+). LC data was recorded on a Shimadzu LC-10AS liquid chromatograph equipped with a PHENOMENEX® Luna 5 u C18 4.6×30 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% methanol/90% water/0.1% TFA and Solvent B was 90% methanol/10% water/0.1% TFA. MS data was determined using a MICROMASS® Platform for LC in electrospray mode.

Intermediate 3

(2S,2'S)-tert-Butyl 2,2'-(4,4'-(2,2'-bithiophene-5,5'-diyl)bis(1H-imidazole-4,2-diyl))dipyrrolidine-1-carboxylate

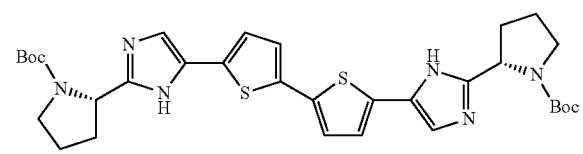 [SMILES: CC(C)(C)OC(=O)N1CCC[C@H]1c1ncc(-c2ccc(-c3ccc(-c4cnc([C@@H]5CCCN5C(=O)OC(C)(C)C)[nH]4)s3)s2)[nH]1]

A solution of (2S,2'S)-'2,2-2,2'-(2,2'-bithiophene-5,5'-diyl)bis(2-oxoethane-2,1-diyl) 1-tert-butyl dipyrrolidine-1,2-dicarboxylate (500 mg, 0.739 mmol, ~50% purity) and ammonium acetate (1.14 g, 14.8 mmol) in xylenes (10 mL) was heated to 140° C. for 2 h using microwave irradiation. The reaction mixture was concentrated, filtered and purified by preparative HPLC (Waters Sunfire C18 column 30×150 mm 5 u, eluted with a gradient of 15 to 90% acetonitrile/water/0.1% TFA) and the fractions shown (LCMS) to contain the desired product were filtered through a Strata XC MCX cartridge. The cartridge was washed with methanol and then the compound was release from the cartridge by flushing the column with a solution of 2M ammonia in methanol. The filtrate was concentrated to yield (2S,2'S)-tert-butyl 2,2'-(5,5'-(2,2'-bithiophene-5,5'-diyl)bis(1H-imidazole-5,2-diyl))dipyrrolidine-1-carboxylate (62.3 mg, 0.098 mmol, 13.2% yield over three steps) as a yellow oil.

LC-MS retention time 1.25 min; m/z 637.0 (MH+). LC data was recorded on a Shimadzu LC-10AS liquid chromatograph equipped with a PHENOMENEX® Luna C18 4.6×50 mm S10 column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (500 MHz, MeOD-$d_4$) δ ppm 7.21-7.34 (m, 2H), 7.13-7.21 (m, 2H), 7.10 (br s, 2H), 4.87 (br s, 2H), 3.60-3.72 (m, 2H), 3.48 (d, J=6.1 Hz, 2H), 2.36 (m, 2H), 1.88-2.08 (m, 6H), 1.46 (br s, 5H), 1.14-1.31 (m, 13H).

Intermediate 4

5'-(2,2'-Bithiene-5,5'-diyl)bis(2-((2S)-2-pyrrolidinyl)-1H-imidazole)

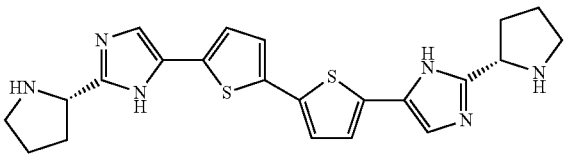 [SMILES: c1nc([C@@H]2CCCN2)[nH]c1-c1ccc(-c2ccc(-c3cnc([C@@H]4CCCN4)[nH]3)s2)s1]

TFA (1.0 mL, 13 mmol) was added to a stirred solution of (2S,2'S)-tert-butyl 2,2'-(5,5'-(2,2'-bithiophene-5,5'-diyl)bis(1H-imidazole-5,2-diyl))dipyrrolidine-1-carboxylate (110 mg, 0.173 mmol) in dichloromethane (5 mL) at room temperature. The reaction mixture was stirred for 2 h and concentrated. The residue was taken into methanol and filtered through a Strata XC MCX cartridge. The cartridge was washed with methanol. The compound was released from the cartridge by washing the column with a solution of 2 M ammonia in methanol. The filtrate was evaporated under reduced pressure to yield 5'-(2,2'-bithiene-5,5'-diyl)bis(2-((2S)-2-pyrrolidinyl)-1H-imidazole) (75 mg, 0.17 mmol, 99% yield) as an orange solid.

An aliquot of this material was purified by preparative HPLC (Waters Sunfire C18 column 30×150 mm 5 u, eluted with a gradient of 10 to 90% acetonitrile/water/10 mmol ammonium acetate) and the remaining material was purified by preparative HPLC (Waters Sunfire C18 column 30×150 mm 5 u, eluted with a gradient of 10 to 95% acetonitrile/water/0.1% TFA) to yield the TFA salt of the desired product.

LC-MS retention time 0.80 min; m/z 439.9 (MH$^+$). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (500 MHz, MeOD-d$_4$) δ ppm 7.36 (s, 2H), 7.20 (d, J=3.7 Hz, 2H), 7.13 (d, J=4.0 Hz, 2H), 4.61 (t, J=7.8 Hz, 2H), 3.34-3.42 (m, 2H), 3.24-3.30 (m, 2H), 2.36-2.46 (m, 2H), 2.11-2.28 (m, 4H), 1.99-2.11 (m, 2H).

Example 1

Methyl ((1S)-2-((2S)-2-(4-(5'-(2-((2S)-1-(N-(methoxycarbonyl)-L-alanyl)-2-pyrrolidinyl)-1H-imidazol-4-yl)-2,2'-bithiophen-5-yl)-1H-imidazol-2-yl)-1-pyrrolidinyl)-1-methyl-2-oxoethyl)carbamate

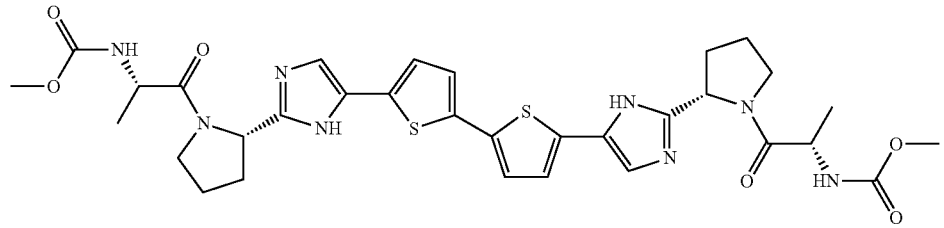

HATU (84 mg, 0.22 mmol) was added to a stirred solution of 5'-(2,2'-bithiene-5,5'-diyl)bis(2-((2S)-2-pyrrolidinyl)-1H-imidazole) (40 mg, 0.092 mmol), (S)-2-(methoxycarbonylamino)propanoic acid (34 mg, 0.23 mmol) and DIEA (0.16 mL, 0.92 mmol) in dimethylformamide (3 mL) at room temperature. The reaction was stirred for 16 h, diluted with methanol (2 mL) and water (2 mL) and stirred for 15 min. The reaction mixture was concentrated to dryness and purified by preparative HPLC (Waters Sunfire C18 column 30×150 mm 5 u, eluted with a gradient of 20 to 90% acetonitrile/water/ 0.1% TFA). Fractions containing the desired product were concentrated in vacuo and repurified by preparative HPLC (Waters Sunfire C18 column 30×150 mm 5 u, eluted with a gradient of 30 to 100% acetonitrile/water/10 mmol ammonium acetate) to yield the free base of the desired compound. A final preparative HPLC purification (Waters Sunfire C18 30×100 mm 5 u, eluted with a gradient of 10 to 100% methanol/water/0.1% TFA) was performed to yield a trifluoroacetate salt of methyl ((1S)-2-((2S)-2-(4-(5'-(2-((2S)-1-(N-(methoxycarbonyl)-L-alanyl)-2-pyrrolidinyl)-1H-imidazol-4-yl)-2,2'-bithiophen-5-yl)-1H-imidazol-2-yl)-1-pyrrolidinyl)-1-methyl-2-oxoethyl)carbamate (1.7 mg, 1.8 μmol, 2.0% yield) as a yellow solid.

LC-MS retention time 0.89 min; m/z 694.9 (MH$^+$). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (500 MHz, MeOD) δ ppm 7.72 (s, 2H), 7.42 (d, J=4.0 Hz, 2H), 7.36 (d, J=3.7 Hz, 2H), 5.22 (dd, J=8.1, 6.0 Hz, 2H), 4.47 (q, J=6.9 Hz, 2H), 4.01-3.94 (m, 2H), 3.81-3.87 (m, 2H), 3.65 (s, 6H), 2.48-2.56 (m, 2H), 2.26-2.12 (m, 6H), 1.32 (d, J=7.0, 6H).

Example 2

Methyl ((1S)-3-methoxy-1-(((2S)-2-(4-(5'-(2-((2S)-1-(N-(methoxycarbonyl)-O-methyl-L-homoseryl)-2-pyrrolidinyl)-1H-imidazol-4-yl)-2,2'-bithiophen-5-yl)-1H-imidazol-2-yl)-1-pyrrolidinyl)carbonyl)propyl)carbamate

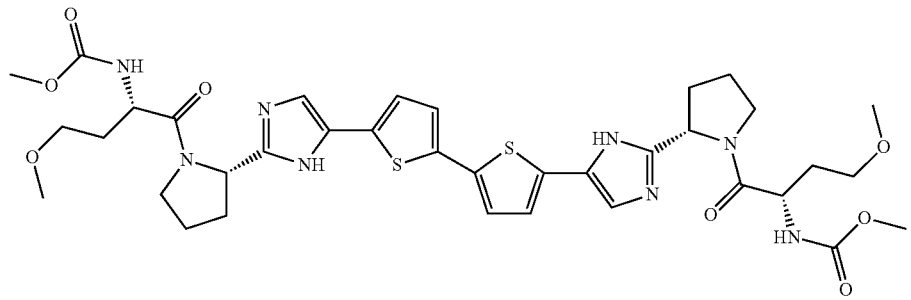

HATU (84 mg, 0.22 mmol) was added to a stirred solution of 5,5'-bis(2-((S)-pyrrolidin-2-yl)-1H-imidazol-4-yl)-2,2'-bithiophene (40 mg, 0.092 mmol), (S)-4-methoxy-2-(methoxycarbonylamino)butanoic acid (44 mg, 0.23 mmol) and DIEA (0.16 mL, 0.92 mmol) in dimethylformamide (3 mL) at room temperature. The reaction was stirred for 16 h, diluted with methanol (2 mL) and water (2 mL) and stirred for 15 min. The reaction mixture was concentrated to dryness in vacuo and purified by preparative HPLC (Waters Sunfire C18 column 30×150 mm 5 u, eluted with a gradient of 20 to 90% acetonitrile/water/0.1% TFA). Fractions containing the desired product were concentrated and repurified by preparative HPLC (Waters Sunfire C18 column 30×150 mm 5 u, eluted with a gradient of 30 to 100% acetonitrile/water/10 mmol ammonium acetate) to yield the free base of the desired compound. A final preparative HPLC (Waters Sunfire C18 30×100 mm 5 u, eluted with a gradient of 10 to 85% methanol/water/0.1% TFA) purification was performed to yield a trifluoroacetate salt of methyl ((1S)-3-methoxy-1-(((2S)-2-(4-(5'-(2-((2S)-1-(N-(methoxycarbonyl)-O-methyl-L-homoseryl)-2-pyrrolidinyl)-1H-imidazol-4-yl)-2,2'-bithiophen-5-yl)-1H-imidazol-2-yl)-1-pyrrolidinyl)carbonyl)propyl)carbamate (18 mg, 0.017 mmol, 19% yield) as a yellow solid.

LC-MS retention time 0.98 min; m/z 782.9 (MH$^+$). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (500 MHz, MeOD-d$_4$) δ ppm 7.70 (s, 2H), 7.41 (d, J=3.7 Hz, 2H), 7.34 (d, J=4.0 Hz, 2H), 5.27-5.21 (m, 2H), 4.57 (dd, J=8.9, 4.6 Hz, 2H), 3.92-4.06 (m, 2H), 3.90-3.82 (m, 2H), 3.70-3.60 (m, 6H), 3.57-3.35 (m, 8H), 2.58-2.45 (m, 2H), 2.40-1.75 (m, 12H).

Example 3

Methyl ((1R)-1-(((2S)-2-(4-(5'-(2-((2S)-1-((2R)-2-((methoxycarbonyl)amino)-3-methylbutanoyl)-2-pyrrolidinyl)-1H-imidazol-4-yl)-2,2'-bithiophen-5-yl)-1H-imidazol-2-yl)-1-pyrrolidinyl)carbonyl)-2-methylpropyl)carbamate HATU (84 mg, 0.22 mmol) was added to a stirred solution of 5'-(2,2'-bithiene-5,5'-diyl)bis(2-((2S)-2-pyrrolidinyl)-1H-imidazole) (40 mg, 0.092 mmol), (R)-2-(methoxycarbonylamino)-3-methylbutanoic acid (40 mg, 0.23 mmol) and DIEA (0.16 mL, 0.92 mmol) in dimethylformamide (3 mL) at room temperature. The reaction was stirred for 16 h, diluted with methanol (2 mL) and water (2 mL) and stirred for 15 min. The reaction mixture was concentrated to dryness and purified by preparative HPLC (Waters Sunfire C18 column 30×150 mm 5 u, eluted with a gradient of 20 to 90% acetonitrile/water/0.1% TFA). Fractions containing the desired product were concentrated and repurified by preparative HPLC (Waters Sunfire C18 column 30×150 mm 5 u, eluted with a gradient of 30 to 100% acetonitrile/water/10 mmol ammonium acetate) to yield the free base of the desired compound. A final preparative HPLC (Waters Sunfire C18 30×100 mm 5 u, eluted with a gradient of 10 to 85% methanol/water/0.1% TFA) purification was performed to yield a trifluoroacetate salt of methyl ((1R)-1-(((2S)-2-(4-(5'-(2-((2S)-1-(2R)-2-((methoxycarbonyl)amino)-3-methylbutanoyl)-2-pyrrolidinyl)-1H-imidazol-4-yl)-2,2'-bithiophen-5-yl)-1H-imidazol-2-yl)-1-pyrrolidinyl)carbonyl)-2-methylpropyl)carbamate (21 mg, 0.021 mmol, 23% yield) as an orange solid.

LC-MS retention time 1.18 min; m/z 751.0 (MH$^+$). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (500 MHz, MeOD-d$_4$) δ ppm 7.71 (s, 2H), 7.46 (d, J=4.0 Hz, 2H), 7.35 (d, J=4.0 Hz, 2H), 5.30-5.26 (m, 2H), 4.24 (d, J=7.2 Hz, 2H), 4.14-4.07 (m, 2H), 3.86-3.77 (m, 2H), 3.65 (s, 6H), 2.56-2.46 (m, 2H), 2.24-2.14 (m, 6H), 2.11-1.99 (m, 2H), 1.02 (t, J=7.5 Hz, 12H).

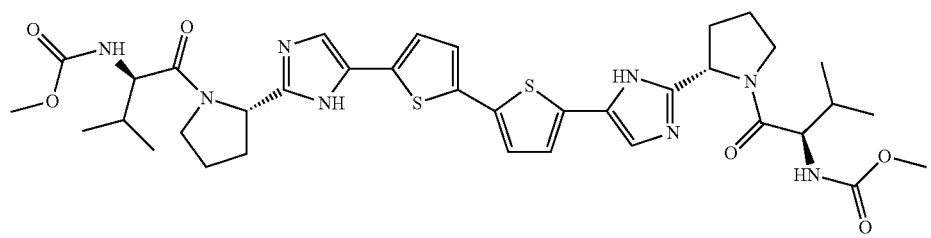

Example 4

Dimethyl (2,2'-bithiene-5,5'-diylbis(1H-imidazole-4,2-diyl(2S)-2,1-pyrrolidinediyl((1R)-2-oxo-1-phenyl-2,1-ethanediyl)))biscarbamate

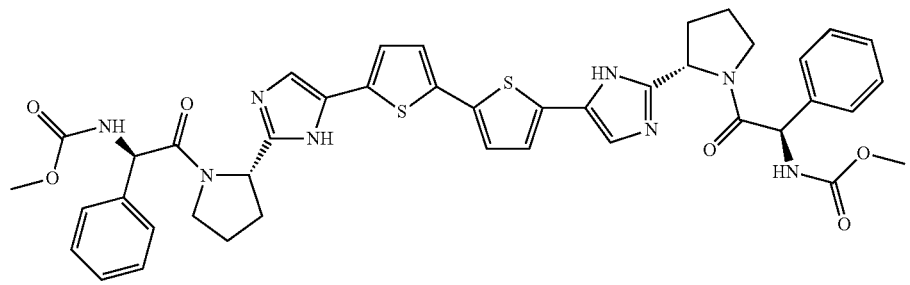

HATU (84 mg, 0.22 mmol) was added to a stirred solution of 5'-(2,2'-bithiene-5,5'-diyl)bis(2-((2S)-2-pyrrolidinyl)-1H-imidazole) (40 mg, 0.092 mmol), (R)-2-(methoxycarbonylamino)-2-phenylacetic acid (48 mg, 0.23 mmol) and DIEA (0.16 mL, 0.92 mmol) in dimethylformamide (3 mL) at room temperature. The reaction was stirred for 16 h, diluted with methanol (2 mL) and water (2 mL) and stirred for 15 min. The reaction mixture was concentrated to dryness in vacuo and purified by preparative HPLC (Waters Sunfire C18 column 30×150 mm 5 u, eluted with a gradient of 20 to 90% acetonitrile/water/0.1% TFA). Fractions containing the desired product were concentrated and repurified by preparative HPLC (Waters Sunfire C18 column 30×150 mm 5 u, eluted with a gradient of 30 to 100% acetonitrile/water/10 mmol ammonium acetate) to yield the free base of the desired compound. A final preparative HPLC (Waters Sunfire C18 30×100 mm 5 u, eluted with a gradient of 10 to 85% methanol/water/0.1% TFA) purification was performed to yield a trifluoroacetate salt of dimethyl (2,2'-bithiene-5,5'-diylbis(1H-imidazole-4,2-diyl(2S)-2,1-pyrrolidinediyl((1R)-2-oxo-1-phenyl-2,1-ethanediyl)))biscarbamate (20 mg, 0.019 mmol, 20% yield) as a yellow solid.

LC-MS retention time 1.28 min; m/z 818.9 (MH$^+$). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (500 MHz, MeOD-d$_4$) δ ppm 7.76 (s, 2H), 7.51 (d, J=3.7 Hz, 2H), 7.48-7.10 (m, 12H), 5.50 (s, 2H), 5.27 (dd, J=8.4, 3.8 Hz, 2H), 4.06-3.98 (m, 2H), 3.64 (s, 6H), 2.43-2.34 (m, 2H), 2.26-1.91 (m, 8H).

Example 5

(1R',1'R)-2,2'-(2,2'-Bithiene-5,5'-diylbis(1H-imidazole-4,2-diyl(2S)-2,1-pyrrolidinediyl))bis(N,N-dimethyl-2-oxo-1-phenylethanamine)

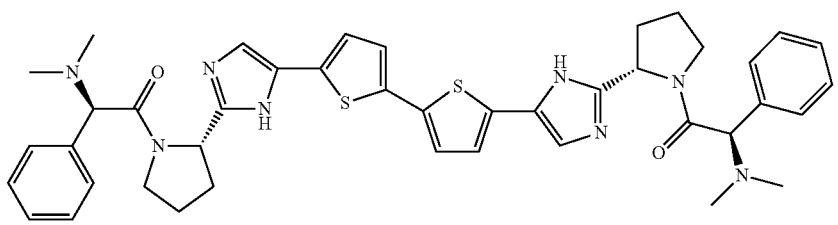 [SMILES: CN(C)[C@@H](C(=O)N1CCC[C@H]1c1ncc(-c2ccc(-c3ccc(-c4cnc([C@@H]5CCCN5C(=O)[C@@H](c5ccccc5)N(C)C)[nH]4)s3)s2)[nH]1)c1ccccc1]

HATU (84 mg, 0.22 mmol) was added to a stirred solution of 5'-(2,2'-bithiene-5,5'-diyl)bis(2-((2S)-2-pyrrolidinyl)-1H-imidazole) (40 mg, 0.092 mmol), (R)-2-(dimethylamino)-2-phenylacetic acid hydrochloride (49 mg, 0.23 mmol) and DIEA (0.16 mL, 0.92 mmol) in dimethylformamide (3 mL) at room temperature. The reaction was stirred for 16 h, diluted with methanol (2 mL) and water (2 mL) and stirred for 15 min. The reaction mixture was concentrated to dryness and purified by preparative HPLC (Waters Sunfire C18 column 30×150 mm 5 u, eluted with a gradient of 20 to 90% acetonitrile/water/0.1% TFA). Fractions containing the desired product were concentrated in vacuo and repurified by preparative HPLC (Waters Sunfire C18 column 30×150 mm 5 u, eluted with a gradient of 30 to 100% acetonitrile/water/10 mmol ammonium acetate) to yield the free base of the desired compound. A final preparative HPLC purification (Waters Sunfire C18 30×100 mm 5 u, eluted with a gradient of 10 to 85% methanol/water/0.1% TFA) was performed to yield a trifluoroacetate salt of (1R,1'R)-2,2'-(2,2'-bithiene-5,5'-diyl-bis(1H-imidazole-4,2-diyl(2S)-2,1-pyrrolidinediyl))bis(N,N-dimethyl-2-oxo-1-phenylethanamine) (14 mg, 0.011 mmol, 13% yield) as an orange solid.

LC-MS retention time 0.90 min; m/z 759.0 (MH$^+$). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. H NMR (500 MHz, MeOD-$d_4$) δ ppm 7.53-7.70 (m, 10H), 7.51 (s, 2H), 7.32 (d, J=4.0 Hz, 2H), 7.24 (d, J=3.7 Hz, 2H), 5.34-5.32 (m, 2H), 5.19 (dd, J=8.1, 4.1 Hz, 2H), 4.02-3.96 (m, 2H), 2.78 (br s, 12H), 2.58-2.03 (m, 8H), 1.95-1.87 (m, 2H).

Example 6

Methyl ((1S)-1-(((2S)-2-(4-(5'-(2-((2S)-1-((2S)-2-((methoxycarbonyl)amino)-3-methylbutanoyl)-2-pyrrolidinyl)-1H-imidazol-4-yl)-2,2'-bithiophen-5-yl)-1H-imidazol-2-yl)-1-pyrrolidinyl)carbonyl)-2-methylpropyl)carbamate

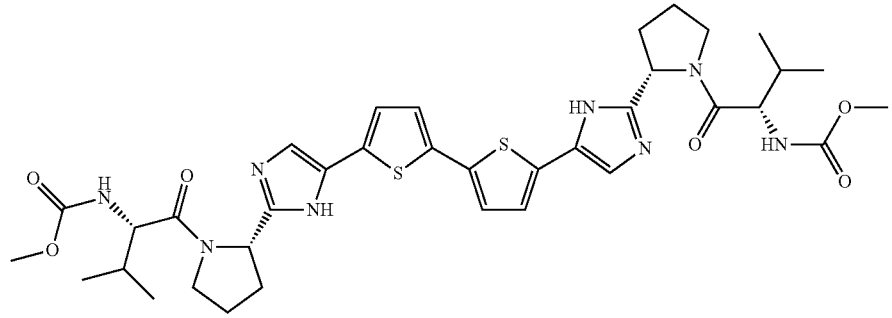

HATU (84 mg, 0.22 mmol) was added to a stirred solution of 5'-(2,2'-bithiene-5,5'-diyl)bis(2-((2S)-2-pyrrolidinyl)-1H-imidazole) (40 mg, 0.092 mmol), (S)-2-(methoxycarbonylamino)-3-methylbutanoic acid (40 mg, 0.23 mmol) and DIEA (0.16 mL, 0.92 mmol) in dimethylformamide (3 mL) at room temperature. The reaction was stirred for 16 h, diluted with methanol (2 mL) and water (2 mL) and stirred for 15 min. The reaction mixture was concentrated to dryness and purified by preparative HPLC (Waters Sunfire C18 column 30×150 mm 5 u, eluted with a gradient of 20 to 90% acetonitrile/water/0.1% TFA). Fractions containing the desired product were concentrated and repurified by preparative HPLC (Waters Sunfire C18 column 30×150 mm 5 u, eluted with a gradient of 30 to 100% acetonitrile/water/10 mmol ammonium acetate) to yield the free base of the desired compound. A final preparative HPLC purification (Waters Sunfire C18 30×100 mm 5 u, eluted with a gradient of 10 to 85% methanol/water/0.1% TFA) was performed to yield a trifluoroacetate salt of methyl ((1S)-1-(((2S)-2-(4-(5'-(2-((2S)-1-((2S)-2-((methoxycarbonyl)amino)-3-methylbutanoyl)-2-pyrrolidinyl)-1H-imidazol-4-yl)-2,2'-bithiophen-5-yl)-1H-imidazol-2-yl)-1-pyrrolidinyl)carbonyl)-2-methylpropyl)carbamate (13 mg, 0.012 mmol, 13% yield) as a yellow solid.

LC-MS retention time 1.10 min; m/z 751.0 (MH$^+$). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (500 MHz, MeOD-$d_4$) δ ppm 7.72 (s, 2H), 7.41 (d, J=4.0 Hz, 2H), 7.35 (d, J=4.0 Hz, 2H), 5.21-5.15 (m, 2H), 4.22 (d, J=7.3 Hz, 2H), 4.08 (br s, 2H), 3.88-3.80 (m, 2H), 3.66 (s, 6H), 3.37-3.33 (m, 2H), 2.32-2.22 (m, 2H), 2.20-1.98 (m, 6H), 1.00-0.85 (m, 12H).

Example 7

Dimethyl (2,2'-bithiene-5,5'-diylbis(1H-imidazole-4,2-diyl(2S)-2,1-pyrrolidinediyl((1S)-1-cyclopropyl-2-oxo-2,1-ethanediyl)))biscarbamate

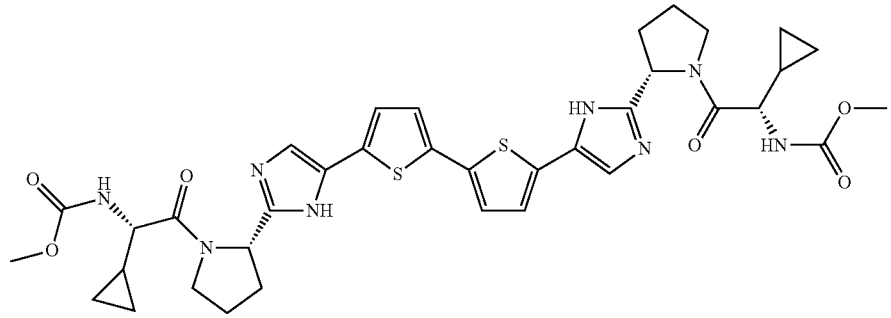

HATU (77 mg, 0.20 mmol) was added to a stirred solution of 5'-(2,2'-bithiene-5,5'-diyl)bis(2-((2S)-2-pyrrolidinyl)-1H-imidazole) (37 mg, 0.085 mmol), (S)-2-cyclopropyl-2-(methoxycarbonylamino)acetic acid (37 mg, 0.21 mmol) and DIEA (0.15 mL, 0.85 mmol) in dimethylformamide (3 mL) at room temperature. The reaction was stirred for 24 h, diluted with methanol (2 mL) and water (2 mL) and stirred for 15 min. The reaction mixture was concentrated to dryness in vacuo and purified by preparative HPLC (Waters Sunfire C18 column 30×150 mm 5 u, eluted with a gradient of 20 to 90% acetonitrile/water/0.1% TFA). Fractions containing the desired product were concentrated and repurified by preparative HPLC (Waters Sunfire C18 30×100 mm 5 u, eluted with a gradient of 10 to 85% methanol/water/0.1% TFA) to yield a trifluoroacetate salt of dimethyl (2,2'-bithiene-5,5'-diylbis (1H-imidazole-4,2-diyl(2S)-2,1-pyrrolidinediyl(((1S)-1-cyclopropyl-2-oxo-2,1-ethanediyl)))biscarbamate (4.0 mg, 0.0037 mmol, 4.4% yield) as an orange solid.

LC-MS retention time 1.02 min; m/z 747.0 (MH+). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (500 MHz, MeOD-d$_4$) δ ppm 7.74 (s, 2H), 7.44 (d, J=3.7 Hz, 2H), 7.37 (d, J=3.7 Hz, 2H), 5.24-5.19 (m, 2H), 4.06-3.98 (m, 2H), 3.87-3.78 (m, 4H), 3.66 (s, 6H), 2.57-2.47 (m, 2H), 2.29-2.05 (m, 6H), 1.17-1.05 (m, 2H), 0.63-0.29 (m, 8H).

Intermediate 5

1,1'-(5,5'-Bithiazole-2,2'-diyl)diethanone

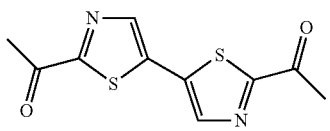 [SMILES: CC(=O)c1ncc(-c2cnc(C(C)=O)s2)s1]

Silver acetate (4.0 mL, 79 mmol) was added to a stirred solution of [1,1'-bis(diphenylphosphino)ferrocene]dichloropalladium(II) (0.970 g, 1.18 mmol), and 1-(thiazol-2-yl)ethanone (5.0 g, 39 mmol) in dimethylsulfoxide (235 mL). The reaction was purged with nitrogen and heated at 60° C. for 8 h. The reaction mixture was cooled, filtered through CELITE®, and washed with dichloromethane and water. The layers were separated and the organic was concentrated to dryness. The crude material was dry loaded onto silica gel and purified by flash chromatography (eluted with a gradient of 0 to 10% methanol in dichloromethane) to yield 1,1'-(5,5'-bithiazole-2,2'-diyl)diethanone (1.2 g) as a brown solid.

LC-MS retention time 1.54 min; m/z 252.8 (MH+). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (300 MHz, DMSO-d$_6$) δ ppm 8.62 (s, 2H), 2.66 (s, 6H).

Intermediate 6

1,1'-(5,5'-Bithiazole-2,2'-diyl)bis(2-bromoethanone)

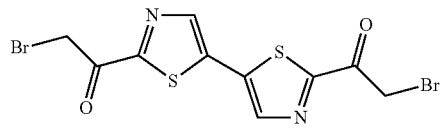 [SMILES: O=C(CBr)c1ncc(-c2cnc(C(=O)CBr)s2)s1]

Bromine (0.27 mL, 5.2 mmol) was added to s stirred solution of 1,1'-(5,5'-bithiazole-2,2'-diyl)diethanone (1.00 g, 3.96 mmol) in chloroform (40 mL) and the reaction was heated at 48° C. for 3 h. Additional bromine (2×200 mg, 2.50 mmol) was added at 1 h increments and then the reaction was stirred for 1 h at 48° C. (total reaction time=5 h). The reaction was concentrated to yield a crude mixture (showed a 1:2:1 ratio of mono:bis:tri-brominated products by LCMS) containing 1,1'-(5,5'-bithiazole-2,2'-diyl)bis(2-bromoethanone) (1.62 g) which was advanced into the next step without purification.

LC-MS retention time 1.90 min; m/z 409.0 (MH−). LC data was recorded on a Shimadzu LC-10AS liquid chromatograph equipped with a PHENOMENEX® Luna C18 4.6×50 mm S10 column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% acetonitrile/95% water/10 mM ammonium acetate and Solvent B was 95% acetonitrile/5% water/10 mM ammonium acetate. MS data was determined using a MICROMASS® Platform for LC in electrospray mode.

Intermediate 7

(2S,2'S)-'2,2-2,2'-(5,5'-Bithiazole-2,2'-diyl)bis(2-oxoethane-2,1-diyl) 1-tert-butyl dipyrrolidine-1,2-dicarboxylate

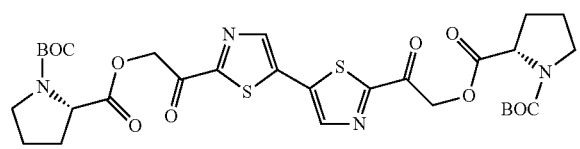 [SMILES: CC(C)(C)OC(=O)N1CCC[C@H]1C(=O)OCC(=O)c1ncc(-c2cnc(C(=O)COC(=O)[C@@H]3CCCN3C(=O)OC(C)(C)C)s2)s1]

DIEA (3.46 mL, 19.8 mmol) was added to a stirred solution of crude 1,1'-(5,5'-bithiazole-2,2'-diyl)bis(2-bromoethanone) (1.62 g) and Boc-L-proline (3.41 g, 15.8 mmol) in acetonitrile (10 mL) at room temperature. The black slurry was stirred for 6 h, concentrated to dryness in vacuo, and partitioned between ethyl acetate and sat aq. sodium bicarbonate. The organic layer was washed with 1M HCl and brine, dried over sodium sulfate, filtered and concentrated in vacuo to yield a crude mixture containing (2S,2'S)-'2,2-2,2'-(5,5'-bithiazole-2,2'-diyl)bis(2-oxoethane-2,1-diyl) 1-tertbutyl dipyrrolidine-1,2-dicarboxylate (1.71 g) as a brown solid. The material was used without further purification.

LC-MS retention time 2.78 min; m/z 701.0 (MNa+). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode.

Intermediate 8

Di-tert-butyl (2S,2'S)-2,2'-(5,5'-bi-1,3-thiazole-2,2'-diylbis(1H-imidazole-5,2-diyl))di(1-pyrrolidinecarboxylate)

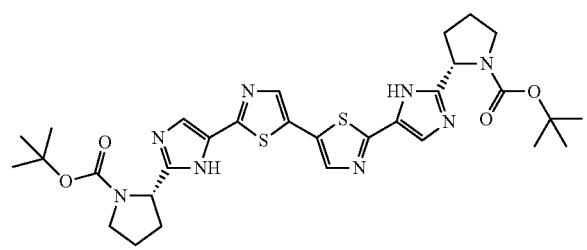 [SMILES: CC(C)(C)OC(=O)N1CCC[C@H]1c1ncc(-c2ncc(-c3cnc(-c4cnc([C@@H]5CCCN5C(=O)OC(C)(C)C)[nH]4)s3)s2)[nH]1]

A stirred solution of crude (2S,2'S)-'2,2-2,2'-(5,5'-bithiazole-2,2'-diyl)bis(2-oxoethane-2,1-diyl) 1-tert-butyl dipyrrolidine-1,2-dicarboxylate (500 mg) and ammonium acetate (1.14 g, 14.7 mmol) in xylenes (10 mL) was heated to 140° C. for 2 h using microwave irradiation. The reaction was concentrated and purified by column chromatography (0 to 70% acetone/hexanes). The fractions containing the desired product were collected and evaporated under vacuum to yield di-tert-butyl (2S,2'S)-2,2'-(5,5'-bi-1,3-thiazole-2,2'-diylbis (1H-imidazole-5,2-diyl))di(1-pyrrolidinecarboxylate) (377 mg, 0.590 mmol, 46.8% yield over three steps) as an orange solid.

LC-MS retention time 1.27 min; m/z 639.1 (MH$^+$). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (500 MHz, MeOD-d$_4$) δ ppm 8.12 (br s, 2H), 7.98 (br s, 2H), 5.11-4.97 (m, 2H), 3.72-3.63 (m, 2H), 3.60-3.50 (m, 2H), 2.55-2.41 (m, 2H), 2.16-1.97 (m, 6H), 1.47 (br s, 9H), 1.27 (br s, 9H).

Intermediate 9

2,2'-Bis(2-((2S)-2-pyrrolidinyl)-1H-imidazol-5-yl)-5,5'-bi-1,3-thiazole

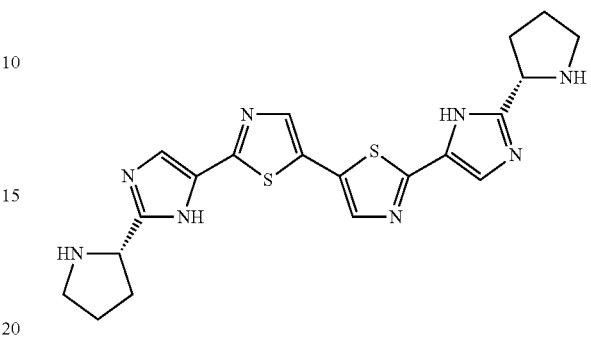

TFA (2 mL, 26.0 mmol) was added to a stirred solution of di-tert-butyl (2S,2'S)-2,2'-(5,5'-bi-1,3-thiazole-2,2'-diylbis (1H-imidazole-5,2-diyl))di(1-pyrrolidinecarboxylate) (450 mg, 0.704 mmol) in dichloromethane (15 mL) at room temperature. The reaction mixture was stirred for 2 h, additional TFA (2 mL, 26.0 mmol) was added and the mixture was stirred for an additional 2 h. The reaction was concentrated in vacuo and the residue was dissolved in methanol and filtered through a Strata XC MCX cartridge. The cartridge was washed with methanol and then the compound was released from the cartridge by washing with a solution of 2M ammonia in methanol. The filtrate was evaporated under reduced pressure to give 2,2'-bis(2-((2S)-2-pyrrolidinyl)-1H-imidazol-5-yl)-5,5'-bi-1,3-thiazole (181 mg) as an orange solid.

LC-MS retention time 0.66 min; m/z 439.1 (MH$^+$). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (500 MHz, MeOD-d$_4$) δ ppm 7.99 (s, 2H), 7.81 (s, 2H), 4.91-4.87 (m, 2H), 3.62-3.55 (m, 2H), 3.52-4.45 (m, 2H), 2.61-2.52 (m, 2H), 2.40-2.18 (m, 6H).

Example 8

(1R,1'R)-2,2'-(5,5'-Bi-1,3-thiazole-2,2'-diylbis(1H-imidazole-4,2-diyl(2S)-2,1-pyrrolidinediyl))bis(N,N-dimethyl-2-oxo-1-phenylethanamine)

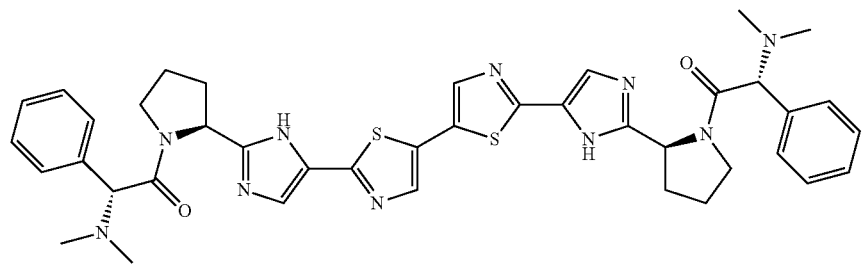 [SMILES: CN(C)[C@@H](C(=O)N1CCC[C@H]1c1ncc(-c2ncc(-c3cnc(-c4cnc([C@@H]5CCCN5C(=O)[C@@H](c5ccccc5)N(C)C)[nH]4)s3)s2)[nH]1)c1ccccc1]

HATU (66 mg, 0.17 mmol) was added to a stirred solution of a TFA salt of 2,2'-bis(2-((2S)-2-pyrrolidinyl)-1H-imidazol-5-yl)-5,5'-bi-1,3-thiazole (40 mg, 0.045 mmol), (R)-2-(dimethylamino)-2-phenylacetic acid hydrochloride (39 mg, 0.18 mmol) and DIEA (0.078 mL, 0.45 mmol) in dimethylformamide (2 mL) at room temperature. The reaction was stirred for 3 h, diluted with methanol (2 mL) and water (2 mL) and stirred for 15 min. The reaction mixture was concentrated in vacuo to dryness and purified by preparative HPLC (Waters Sunfire C18 column 30×150 mm 5 u, eluted with a gradient of 10 to 80% acetonitrile/water/0.1% TFA). Fractions containing the desired product were concentrated to yield a trifluoroacetate salt of (1R,1'R)-2,2'-(5,5'-Bi-1,3-thiazole-2,2'-diylbis(1H-imidazole-4,2-diyl(2S)-2,1-pyrrolidinediyl))bis(N,N-dimethyl-2-oxo-1-phenylethanamine) (18 mg, 0.015 mmol, 34% yield) as an orange solid.

LC-MS retention time 1.23 min; m/z 761.2 (MH+). LC data was recorded on a Shimadzu LC-10AS liquid chromatograph equipped with an X-bridge C18 4.6×30 mm 5 u column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 5% methanol/95% water/0.1% TFA and Solvent B was 95% methanol/5% water/0.1% TFA. MS data was determined using a MICROMASS® Platform for LC in electrospray mode. $^1$H NMR (500 MHz, MeOD-$d_4$) δ ppm 8.04-7.98 (m, 2H), 7.82-7.77 (m, 2H), 7.75-7.65 (m, 8H), 7.28-7.15 (m, 2H), 5.36 (s, 2H), 5.27-5.17 (m, 2H), 4.08-4.01 (m, 2H), 3.18-3.11 (m, 2H), 2.87 (br s, 12H), 2.27-2.02 (m, 6H), 1.95-1.87 (m, 2H).

Example 9

Dimethyl (5,5'-bi-1,3-thiazole-2,2'-diylbis(1H-imidazole-4,2-diyl(2S)-2,1-pyrrolidinediyl((1R)-2-oxo-1-phenyl-2,1-ethanediyl)))biscarbamate

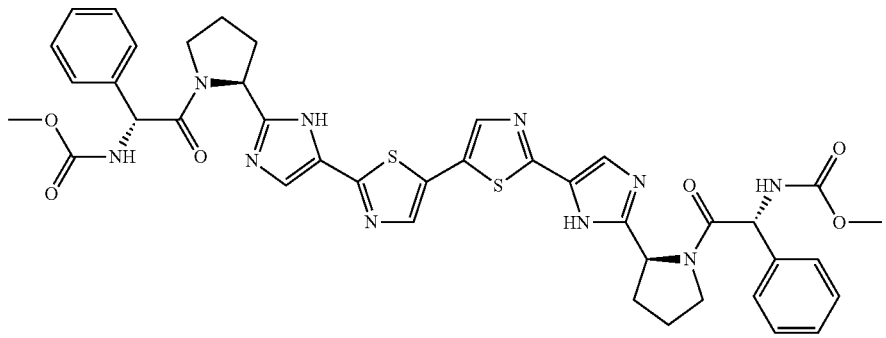

HATU (66 mg, 0.17 mmol) was added to a stirred solution of a TFA salt of 2,2'-bis(2-((2S)-2-pyrrolidinyl)-1H-imidazol-5-yl)-5,5'-bi-1,3-thiazole (40 mg, 0.045 mmol), (R)-2-(methoxycarbonylamino)-2-phenylacetic acid (37 mg, 0.18 mmol) and DIEA (0.078 mL, 0.45 mmol) in dimethylformamide (2 mL) at room temperature. The reaction was stirred for 3 h, diluted with methanol (2 mL) and water (2 mL) and stirred for 15 min. The reaction mixture was concentrated to dryness and purified by preparative HPLC (Waters Sunfire C18 column 30×150 mm 5 u, eluted with a gradient of 10 to 80% acetonitrile/water/0.1% TFA). Fractions containing the desired product were concentrated in vacuo and repurified by preparative HPLC (Waters Sunfire C18 column 30×100 mm 5 u, eluted with a gradient of 10 to 100% methanol/water/ 0.1% TFA) to yield a trifluoroacetate salt of dimethyl (5,5'-bi-1,3-thiazole-2,2'-diylbis(1H-imidazole-4,2-diyl(2S)-2,1-pyrrolidinediyl((1R)-2-oxo-1-phenyl-2,1-ethanediyl))) biscarbamate (16 mg, 0.015 mmol, 33% yield) as an orange solid.

LC-MS retention time 1.75 min; m/z 819.5 (MH+). LC data was recorded on a Shimadzu LC-10AS liquid chromatograph equipped with a PHENOMENEX® Luna C18 4.6×30 mm 10 u column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% acetonitrile/95% water/10 mM ammonium acetate and Solvent B was 95% acetonitrile/5% water/10 mM ammonium acetate. MS data was determined using a MICROMASS® Platform for LC in electrospray mode. $^1$H NMR (500 MHz, MeOD-$d_4$) δ ppm 8.21-8.08 (m, 2H), 7.98 (s, 2H), 7.51-7.31 (m, 10H), 7.16-6.99 (m, 2H), 5.52 (s, 2H), 5.25 (dd, J=8.1, 3.2 Hz, 2H), 4.06-3.99 (m, 2H), 3.66 (s, 6H), 2.38-2.21 (m, 2H), 2.21-2.07 (m, 4H), 2.02-1.82 (m, 2H).

Example 10

Methyl ((1S)-1-(((2S)-2-(4-(2'-(2-((2S)-1-((2S)-2-((methoxycarbonyl)amino)-3-methylbutanoyl)-2-pyrrolidinyl)-1H-imidazol-4-yl)-5,5'-bi-1,3-thiazol-2-yl)-1H-imidazol-2-yl)-1-pyrrolidinyl)carbonyl)-2-methylpropyl)carbamate

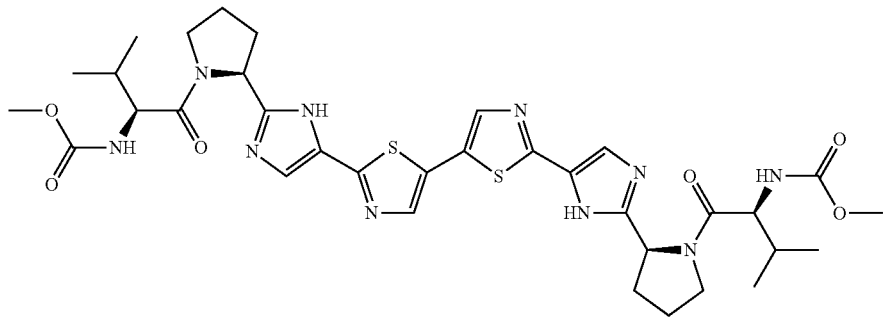

HATU (66 mg, 0.17 mmol) was added to a stirred solution of a TFA salt of 2,2'-bis(2-((2S)-2-pyrrolidinyl)-1H-imidazol-5-yl)-5,5'-bi-1,3-thiazole (40 mg, 0.045 mmol), (S)-2-(methoxycarbonylamino)-3-methylbutanoic acid (31 mg, 0.18 mmol) and DIEA (0.078 mL, 0.45 mmol) in dimethylformamide (2 mL) at room temperature. The reaction was stirred for 3 h, diluted with methanol (2 mL) and water (2 mL) and stirred for 15 min. The reaction mixture was concentrated to dryness in vacuo and purified by preparative HPLC (Waters Sunfire C18 column 30×150 mm 5 u, eluted with a gradient of 10 to 80% acetonitrile/water/0.1% TFA) to yield a trifluoroacetate salt of methyl ((1S)-1-(((2S)-2-(4-(2'-(2-((2S)-1-((2S)-2-((methoxycarbonyl)amino)-3-methylbutanoyl)-2-pyrrolidinyl)-1H-imidazol-4-yl)-5,5'-bi-1,3-thiazol-2-yl)-1H-imidazol-2-yl)-1-pyrrolidinyl)carbonyl)-2-methylpropyl)carbamate (23 mg, 0.023 mmol, 52% yield) as a yellow solid.

LC-MS retention time 1.85 min; m/z 753.5 (MH+). LC data was recorded on a Shimadzu LC-10AS liquid chromatograph equipped with an X-bridge C18 4.6×30 mm 5 u column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% methanol/95% water/0.1% TFA and Solvent B was 95% methanol/5% water/0.1% TFA. MS data was determined using a MICROMASS® Platform for LC in electrospray mode. $^1$H NMR (500 MHz, MeOD-$d_4$) δ ppm 8.08 (s, 2H), 7.93 (s, 2H), 5.22-5.17 (m, 2H), 4.23 (d, J=7.3 Hz, 2H), 4.09-4.01 (m, 2H), 3.91-3.82 (m, 2H), 3.66 (s, 6H), 2.52-2.41 (m, 2H), 2.33-2.23 (m, 2H), 2.22-2.09 (m, 4H), 2.08-1.99 (m, 2H), 0.95 (d, J=6.7 Hz, 6H), 0.91 (d, J=6.7 Hz, 6H).

Example 11

Methyl ((1R)-1-(((2S)-2-(4-(2'-(2-((2S)-1-((2R)-2-((methoxycarbonyl)amino)-3-methylbutanoyl)-2-pyrrolidinyl)-1H-imidazol-4-yl)-5,5'-bi-1,3-thiazol-2-yl)-1H-imidazol-2-yl)-1-pyrrolidinyl)carbonyl)-2-methylpropyl)carbamate

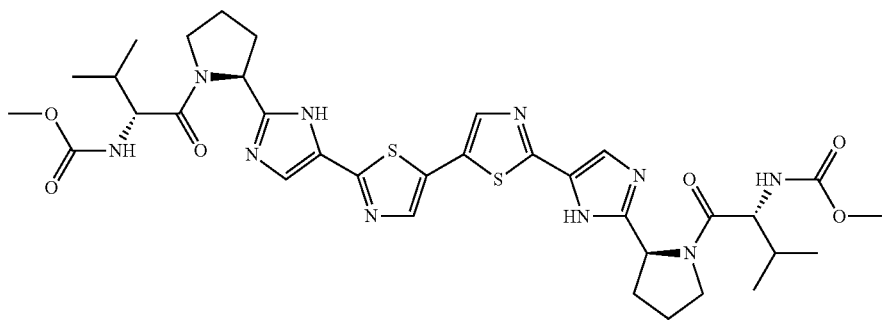

HATU (66 mg, 0.17 mmol) was added to a stirred solution of a TFA salt of 2,2'-bis(2-((2S)-2-pyrrolidinyl)-1H-imidazol-5-yl)-5,5'-bi-1,3-thiazole (40 mg, 0.045 mmol), (R)-2-(methoxycarbonylamino)-3-methylbutanoic acid (31.3 mg, 0.179 mmol) and DIEA (0.078 mL, 0.45 mmol) in dimethylformamide (2 mL) at room temperature. The reaction was stirred for 3 h, diluted with methanol (2 mL) and water (2 mL) and stirred for 15 min. The reaction mixture was concentrated to dryness in vacuo and purified by preparative HPLC (Waters Sunfire C18 column 30×150 mm 5 u, eluted with a gradient of 10 to 80% acetonitrile/water/0.1% TFA) to yield a trifluoroacetate salt of methyl ((1R)-1-(((2S)-2-(4-(2'-(2-((2S)-1-((2R)-2-((methoxycarbonyl)amino)-3-methylbutanoyl)-2-pyrrolidinyl)-1H-imidazol-4-yl)-5,5'-bi-1,3-thiazol-2-yl)-1H-imidazol-2-yl)-1-pyrrolidinyl)carbonyl)-2-methylpropyl)carbamate (16 mg, 0.016 mmol, 36% yield) as an orange solid.

LC-MS retention time 2.24 min; m/z 753.2 (MH+). LC data was recorded on a Shimadzu LC-10AS liquid chromatograph equipped with a PHENOMENEX® Luna C18 4.6×50 mm S10 column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% methanol/90% water/0.1% TFA and Solvent B was 90% methanol/10% water/0.1% TFA. MS data was determined using a MICROMASS® Platform for LC in electrospray mode. $^1$H NMR (500 MHz, MeOD-d$_4$) δ ppm 8.11 (s, 2H), 7.96 (s, 2H), 5.30-5.29 (m, 2H), 4.25 (d, J=7.3 Hz, 2H), 4.12-4.01 (m, 2H), 3.84-3.76 (m, 2H), 3.68 (s, 6H), 2.52-2.43 (m, 2H), 2.26-2.20 (m, 6H), 2.09-1.99 (m, 2H), 1.05-0.95 (m, 12H).

Example 12

Methyl ((1S,2R)-2-methoxy-1-(((2S)-2-(4-(2'-(2-((2S)-1-(N-(methoxycarbonyl)-O-methyl-L-threonyl)-2-pyrrolidinyl)-1H-imidazol-4-yl)-5,5'-bi-1,3-thiazol-2-yl)-1H-imidazol-2-yl)-1-pyrrolidinyl)carbonyl)propyl)carbamate

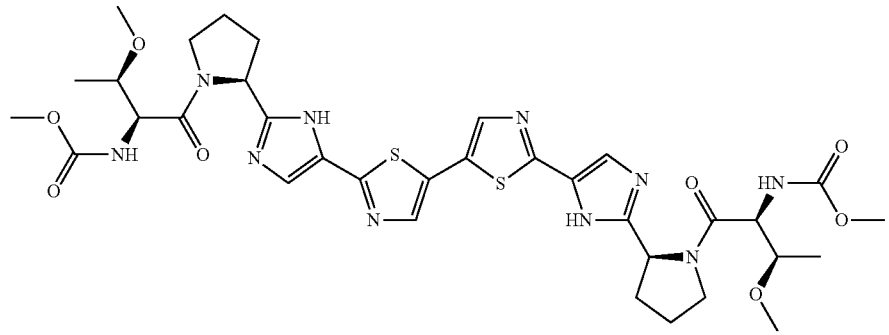

HATU (66 mg, 0.17 mmol) was added to a stirred solution of a TFA salt of 2,2'-bis(2-((2S)-2-pyrrolidinyl)-1H-imidazol-5-yl)-5,5'-bi-1,3-thiazole (40 mg, 0.045 mmol), (2S,3R)-3-methoxy-2-(methoxycarbonylamino)butanoic acid (34 mg, 0.18 mmol) and DIEA (0.078 mL, 0.45 mmol) in dimethylformamide (2 mL) at room temperature. The reaction was stirred for 3 h, diluted with methanol (2 mL) and water (2 mL) and stirred for 15 min. The reaction mixture was concentrated to dryness in vacuo and purified by preparative HPLC (Waters Sunfire C18 column 30×150 mm 5 u, eluted with a gradient of 10 to 80% acetonitrile/water/0.1% TFA) to yield a trifluoroacetate salt of methyl ((1S,2R)-2-methoxy-1-(((2S)-2-(4-(2'-(2-((2S)-1-(N-(methoxycarbonyl)-O-methyl-L-threonyl)-2-pyrrolidinyl)-1H-imidazol-4-yl)-5,5'-bi-1,3-thiazol-2-yl)-1H-imidazol-2-yl)-1-pyrrolidinyl)carbonyl)propyl)carbamate (17 mg, 0.017 mmol, 37% yield) as a yellow solid.

LC-MS retention time 1.51 min; m/z 785.3 (MH+). LC data was recorded on a Shimadzu LC-10AS liquid chromatograph equipped with a PHENOMENEX® Luna C18 4.6×50 mm S10 column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% methanol/90% water/0.1% TFA and Solvent B was 90% methanol/10% water/0.1% TFA. MS data was determined using a MICROMASS® Platform for LC in electrospray mode. $^1$H NMR (500 MHz, MeOD-d$_4$) δ ppm 8.14 (s, 2H), 8.04 (s, 2H), 5.27-5.21 (m, 2H), 4.49 (d, J=4.6 Hz, 2H), 4.07-4.00 (m, 2H), 3.94-3.84 (m, 4H), 3.66 (s, 12H), 2.56-2.46 (m, 2H), 2.33-2.09 (m, 6H), 1.14 (d, J=6.1 Hz, 6H).

Example 13

Methyl ((1S)-3-methoxy-1-(((2S)-2-(4-(2'-(2-((2S)-1-(N-(methoxycarbonyl)-O-methyl-L-homoseryl)-2-pyrrolidinyl)-1H-imidazol-4-yl)-5,5'-bi-1,3-thiazol-2-yl)-1H-imidazol-2-yl)-1-pyrrolidinyl)carbonyl)propyl)carbamate

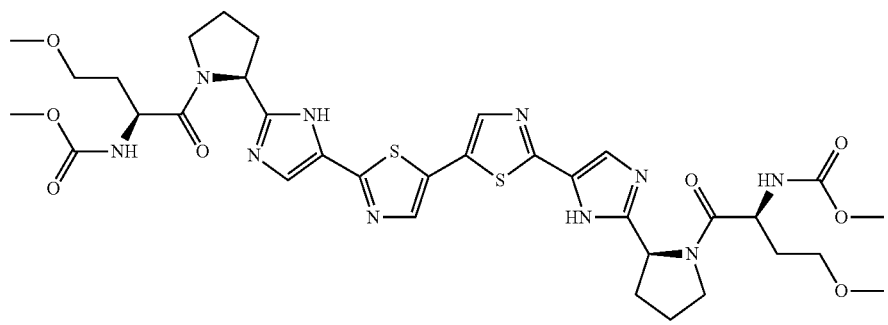

HATU (66 mg, 0.17 mmol) was added to a stirred solution of a TFA salt of 2,2'-bis(2-((2S)-2-pyrrolidinyl)-1H-imidazol-5-yl)-5,5'-bi-1,3-thiazole (40 mg, 0.045 mmol), (S)-4-methoxy-2-(methoxycarbonylamino)butanoic acid (34 mg, 0.18 mmol) and DIEA (0.078 mL, 0.45 mmol) in dimethylformamide (2 mL) at room temperature. The reaction was stirred for 5 h, diluted with methanol (2 mL) and water (2 mL) and stirred for 15 min. The reaction mixture was concentrated to dryness and purified by preparative HPLC (Waters Sunfire C18 column 30×150 mm 5 u, eluted with a gradient of 10 to 85% acetonitrile/water/0.1% TFA) to yield a trifluoroacetate salt of methyl ((1S)-3-methoxy-1-(((2S)-2-(4-(2'-(2-((2S)-1-(N-(methoxycarbonyl)-O-methyl-L-homoseryl)-2-pyrrolidinyl)-1H-imidazol-4-yl)-5,5'-bi-1,3-thiazol-2-yl)-1H-imidazol-2-yl)-1-pyrrolidinyl)carbonyl)propyl)carbamate (14 mg, 0.014 mmol, 31% yield) as a yellow solid.

LC-MS retention time 1.98 min; m/z 785.3 (MH$^+$). LC data was recorded on a Shimadzu LC-10AS liquid chromatograph equipped with a PHENOMENEX® Luna C18 4.6×50 mm S10 column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% methanol/90% water/0.1% TFA and Solvent B was 90% methanol/10% water/0.1% TFA. MS data was determined using a MICROMASS® Platform for LC in electrospray mode. $^1$H NMR (500 MHz, MeOD-d$_4$) δ ppm 8.09 (s, 2H), 7.94 (s, 2H), 5.23 (dd, J=7.6, 4.6 Hz, 2H), 4.58 (dd, J=8.4, 4.7 Hz, 2H), 4.02-3.95 (m, 2H), 3.94-3.86 (m, 2H), 3.65 (s, 6H), 3.55-3.44 (m, 6H), 3.35-3.32 (m, 4H), 2.52-2.40 (m, 2H), 2.31-2.02 (m, 8H), 1.91-1.78 (m, 2H).

Intermediate 10

2,2'-Bithiazole

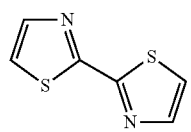

A solution of 2-bromothiazole (2.85 g, 17.4 mmol), 2-(tributylstannyl)thiazole (5.00 g, 13.4 mmol) and tetrakistriphenylphosphine palladium (0.77 g, 0.67 mmol) in toluene (120 mL) was degassed under vacuum for several minutes, backfilled with nitrogen and heated in a sealed pressure vessel at 125° C. for 48 h. The crude reaction mixture was concentrated and the residue was purified by column chromatography (0 to 30% ethyl acetate/hexanes) to yield 2,2'-bithiazole (2.21 g, 12.5 mmol, 93% yield) as a white solid.

LC-MS retention time 1.17 min; m/z 168.8 (MH$^+$). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (300 MHz, CDCl$_3$) δ ppm 7.90 (d, J=3.3 Hz, 2H), 7.45 (d, J=3.3 Hz, 2H).

Intermediate 11

5,5'-Dibromo-2,2'-bithiazole

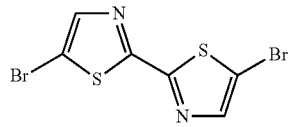 [SMILES: Brc1cnc(-c2ncc(Br)s2)s1]

A stirred solution of 2,2'-bithiazole (1.50 g, 8.92 mmol), N-bromosuccinimide (6.53 g, 35.7 mmol) and dimethylformamide (89 mL) was heated to 60° C. for 8 h. Additional N-bromosuccinimide (2.0 g, 11 mmol) was added and the mixture was stirred at 60° C. for 3 h. The reaction mixture was diluted with water (50 mL) and extracted with ethyl acetate (3×). The combined organic layers were dried over sodium sulfate, filtered and concentrated in vacuo. The crude product was triturated with methanol to yield 5,5'-dibromo-2,2'-bithiazole (1.93 g, 5.93 mmol, 66.5% yield) as a white solid.

LC-MS retention time 2.71 min; m/z 324.8, 326.8, 328.8 (1:2:1) (MH$^+$). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (500 MHz, DMSO-d$_6$) δ ppm 8.11 (s, 2H).

Intermediate 12

5,5'-Bis(1-ethoxyvinyl)-2,2'-bithiazole

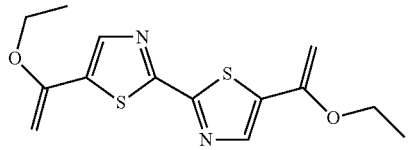 [SMILES: C=C(OCC)c1cnc(-c2ncc(C(=C)OCC)s2)s1]

Tributyl(1-ethoxyvinyl)tin (0.425 mL, 1.26 mmol) and dichlorobis(triphenylphosphine)-palladium(II) (21.5 mg, 0.031 mmol) were added to a stirred solution of 5,5'-dibromo-2,2'-bithiazole (200 mg, 0.613 mmol) in dimethylformamide (4 mL) under nitrogen. The reaction mixture was heated at 100° C. for 2 h. The reaction was cooled, diluted with ether and aqueous potassium fluoride (0.5 g in 5 mL of water). The mixture was vigorously stirred for 1 h at room temperature, both phases were filtered through CELITE® and then separated. The organic layer was dried over sodium sulfate, filtered and concentrated in vacuo. The crude product was purified by column chromatography (0 to 30% ethyl acetate in hexanes) to yield 5,5'-bis(1-ethoxyvinyl)-2,2'-bithiazole (181 mg, 0.587 mmol, 96% yield) as a yellow solid.

LC-MS retention time 3.06 min; m/z 309.0 (MH+). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (500 MHz, CDCl$_3$) δ ppm 7.95 (s, 2H), 4.69 (d, J=3.1 Hz, 2H), 4.32 (d, J=3.1 Hz, 2H), 3.95 (q, J=6.7 Hz, 4H), 1.36-1.48 (m, 6H).

Intermediate 13

1,1'-(2,2'-Bithiazole-5,5'-diyl)bis(2-bromoethanone)

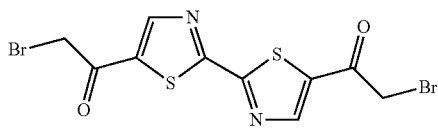 [SMILES: O=C(CBr)c1cnc(-c2ncc(C(=O)CBr)s2)s1]

N-bromosuccinimide (209 mg, 1.174 mmol) was added in one portion to a stirred solution of 5,5'-bis(1-ethoxyvinyl)-2,2'-bithiazole (181 mg, 0.587 mmol) in tetrahydrofuran (3.4 mL) and water (1 mL) at 0° C. The reaction mixture was stirred for 1 h at 0° C., diluted with water (25 mL) and ethyl acetate (25 mL) and the phases were separated. The aqueous layer was extracted with ethyl acetate and the combined organics were washed with sat aq. sodium bicarbonate and brine dried over sodium sulfate, filtered and concentrated to yield crude 1,1'-(2,2'-bithiazole-5,5'-diyl)bis(2-bromoethanone) (241 mg) as a yellow solid. This material was taken into the next step without further purification.

LC-MS retention time 1.84 min; m/z 408.8 (MH+). LC data was recorded on a Shimadzu LC-10AS liquid chromatograph equipped with a PHENOMENEX® Luna C18 3.0×50 mm S10 column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% acetonitrile/95% water/10 mM ammonium acetate and Solvent B was 95% acetonitrile/5% water/10 mM ammonium acetate. MS data was determined using a MICROMASS® Platform for LC in electrospray mode.

Intermediate 14

(2S,2'S)-'2,2-2,2'-(2,2'-Bithiazole-5,5'-diyl)bis(2-oxoethane-2,1-diyl) 1-tert-butyl dipyrrolidine-1,2-dicarboxylate

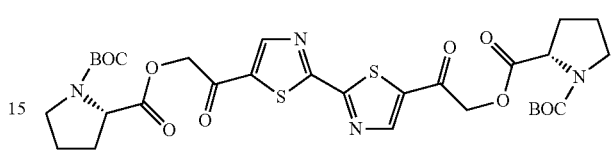

DIEA (0.513 mL, 2.94 mmol) was added to a stirred solution of crude 1,1'-(2,2'-bithiazole-5,5'-diyl)bis(2-bromoethanone) (241 mg, 0.588 mmol), and Boc-L-proline (506 mg, 2.35 mmol) in acetonitrile (10 mL) at room temperature. The reaction mixture was stirred for 5 h at room temperature, concentrated and partitioned between ethyl acetate and saturated aqueous sodium bicarbonate. The organic layer was washed with 1M HCl and brine, dried over sodium sulfate, filtered and concentrated in vacuo to give a crude brown solid that contained (2S,2'S)-'2,2-2,2'-(2,2'-bithiazole-5,5'-diyl)bis(2-oxoethane-2,1-diyl) 1-tert-butyl dipyrrolidine-1,2-dicarboxylate (342 mg). This material was taken into the next step without further purification.

LC-MS retention time 2.68 min; m/z 701.2 (MH+). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode.

Intermediate 15 tert-Butyl (2S)-2-(4-(5'-(2-((2S)-1-(tert-butoxycarbonyl)-2-pyrrolidinyl)-1H-imidazol-5-yl)-2,2'-bi-1,3-thiazol-5-yl)-1H-imidazol-2-yl)-1-pyrrolidinecarboxylate

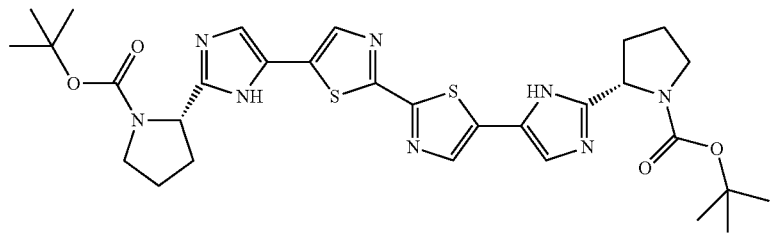 [SMILES: CC(C)(C)OC(=O)N1CCC[C@H]1c1ncc(-c2cnc(-c3ncc(-c4cnc([C@@H]5CCCN5C(=O)OC(C)(C)C)[nH]4)s3)s2)[nH]1]

A stirred solution of crude (2S,2'S)-'2,2-2,2'-(2,2'-bithiazole-5,5'-diyl)bis(2-oxoethane-2,1-diyl) 1-tert-butyl dipyrrolidine-1,2-dicarboxylate (342 mg) and ammonium acetate (1.81 g, 23.5 mmol) in xylenes (10 mL) was heated to 140° C. for 2 h using microwave irradiation. The reaction mixture was concentrated in vacuo and the residue was purified by column chromatography (10 to 80% acetone/hexanes). Fractions containing the desired product were combined concentrated and purified further using preparative HPLC (Waters Sunfire C18 column 30×150 mm 5 u eluted with a gradient of 20 to 100% acetonitrile/water/0.1% TFA). Fractions containing the desired product were filtered through a Strata XC MCX cartridge. The cartridge was washed with methanol and the compound was released from the cartridge by washing the column with a 2M ammonia in methanol solution. The filtrate was evaporated under reduced pressure to yield tert-butyl (2S)-2-(4-(5'-(2-((2S)-1-(tert-butoxycarbonyl)-2-pyrrolidinyl)-1H-imidazol-5-yl)-2,2'-bi-1,3-thiazol-5-yl)-1H-imidazol-2-yl)-1-pyrrolidinecarboxylate (65 mg, 0.10 mmol, 17% yield over three steps) as a yellow solid and a free base.

LC-MS retention time 1.18 min; m/z 639.2 (MH+). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^{1}$H NMR (500 MHz, MeOD-d$_4$) δ ppm 8.04 (s, 2H), 7.47 (br s, 2H), 4.88 (d, J=7.3 Hz, 2H), 3.63-3.77 (m, 2H), 3.51 (dd, J=9.8, 5.8 Hz, 2H), 2.39 (d, J=4.6 Hz, 2H), 1.88-2.08 (m, 6H), 1.47 (br s, 6H), 1.24-1.37 (m, 12H).

Intermediate 16

5,5'-Bis(2-((2S)-2-pyrrolidinyl)-1H-imidazol-4-yl)-2,2'-bi-1,3-thiazole

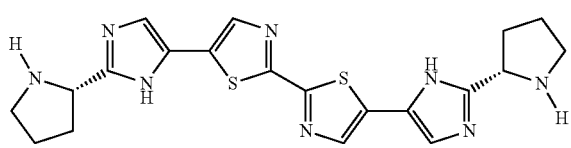 [SMILES: c1nc([C@@H]2CCCN2)[nH]c1-c1cnc(-c2ncc(-c3cnc([C@@H]4CCCN4)[nH]3)s2)s1]

TFA (1.0 mL, 13 mmol) was added to a stirred solution of tert-butyl (2S)-2-(4-(5'-(2-((2S)-1-(tert-butoxycarbonyl)-2-pyrrolidinyl)-1H-imidazol-5-yl)-2,2'-bi-1,3-thiazol-5-yl)-1H-imidazol-2-yl)-1-pyrrolidinecarboxylate (55 mg, 0.086 mmol) in dichloromethane (5 mL) and the reaction mixture was stirred at room temperature for 2 h. The volatiles were removed under vacuum and the crude product was purified by preparative HPLC (Waters Sunfire C18 column 30×150 mm 5 u, eluted with a gradient of 10 to 100% acetonitrile/water/0.1% TFA). Fractions containing the desired product were filtered through a Strata XC MCX cartridge. The cartridge was washed with methanol and the compound was released from the cartridge by washing the column with a 2M ammonia in methanol solution. The filtrate was evaporated under reduced pressure to yield 5,5'-bis(2-((2S)-2-pyrrolidinyl)-1H-imidazol-4-yl)-2,2'-bi-1,3-thiazole (39 mg, 0.085 mmol, 99% yield) as an orange solid.

LC-MS retention time 0.72 min; m/z 439.1 (MH+). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^{1}$H NMR (400 MHz, MeOD-d$_4$) δ ppm 8.03 (s, 2H), 7.58 (s, 2H), 4.90-4.80 (m, 2H), 3.54-3.36 (m, 4H), 2.54-2.42 (m, 2H), 2.35-2.07 (m, 6H).

Example 14

Methyl ((1S)-1-(((2S)-2-(4-(5'-(2-((2S)-1-((2S)-2-((methoxycarbonyl)amino)-3-methylbutanoyl)-2-pyrrolidinyl)-1H-imidazol-4-yl)-2,2'-bi-1,3-thiazol-5-yl)-1H-imidazol-2-yl)-1-pyrrolidinyl)carbonyl)-2-methylpropyl)carbamate

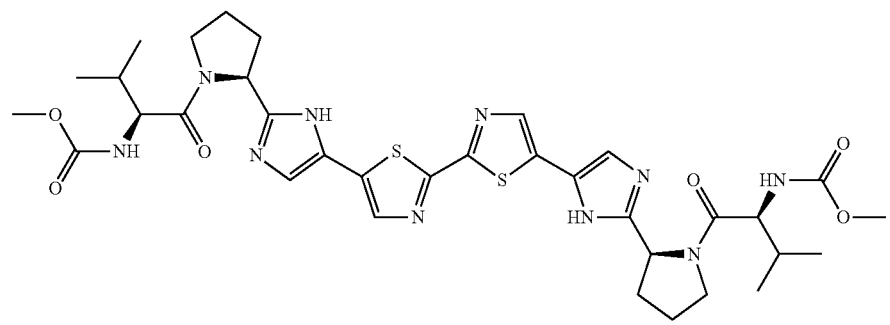

HATU (135 mg, 0.356 mmol) was added to a stirred solution of 5,5'-bis(2-((2S)-2-pyrrolidinyl)-1H-imidazol-4-yl)-2,2'-bi-1,3-thiazole (40 mg, 0.091 mmol), (S)-2-(methoxycarbonylamino)-3-methylbutanoic acid (64 mg, 0.37 mmol) and DIEA (0.16 mL, 0.91 mmol) in dimethylformamide (2 mL) at room temperature. The reaction was stirred for 16 h, diluted with methanol (2 mL) and water (2 mL), stirred for 15 min and concentrated to dryness in vacuo. The crude product was purified by preparative HPLC (Waters Sunfire C18 column 30×150 mm 5 u, eluted with a gradient of 10 to 80% acetonitrile/water/0.1% TFA) to yield a trifluoroacetate salt of methyl ((1S)-1-(((2S)-2-(4-(5'-(2-((2S)-1-((2S)-2-((methoxycarbonyl)amino)-3-methylbutanoyl)-2-pyrrolidinyl)-1H-imidazol-4-yl)-2,2'-bi-1,3-thiazol-5-yl)-1H-imidazol-2-yl)-1-pyrrolidinyl)carbonyl)-2-methylpropyl)carbamate (46 mg, 0.046 mmol, 50% yield) as a yellow solid.

LC-MS retention time 1.04 min; m/z 753.1 (MH$^+$). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (400 MHz, MeOD-d$_4$) δ ppm 8.19 (s, 2H), 7.82 (s, 2H), 5.23-5.17 (m, 2H), 4.23 (d, J=7.3 Hz, 2H), 4.13-4.01 (m, 2H), 3.90-3.80 (m, 2H), 3.66 (s, 6H), 2.57-2.44 (m, 2H), 2.38-1.98 (m, 8H), 0.94 (d, J=6.8 Hz, 6H), 0.91 (d, J=6.8 Hz, 6H).

Example 15

Methyl ((1S)-3-methoxy-1-(((2S)-2-(4-(5'-(2-((2S)-1-(N-(methoxycarbonyl)-O-methyl-L-homoseryl)-2-pyrrolidinyl)-1H-imidazol-4-yl)-2,2'-bi-1,3-thiazol-5-yl)-1H-imidazol-2-yl)-1-pyrrolidinyl)carbonyl)propyl)carbamate

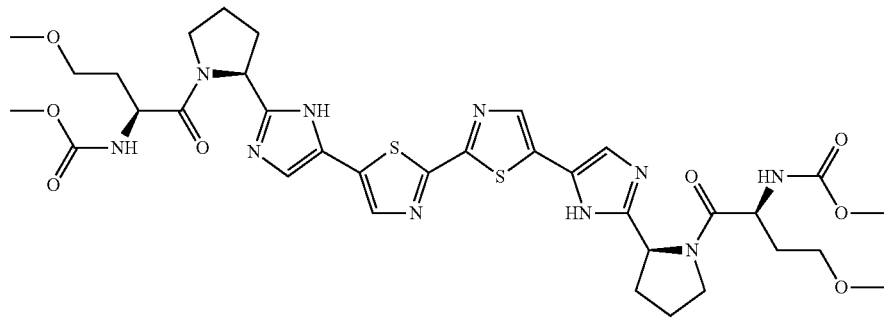

HATU (135 mg, 0.356 mmol) was added to a stirred solution of 5,5'-bis(2-((2S)-2-pyrrolidinyl)-1H-imidazol-4-yl)-2,2'-bi-1,3-thiazole (40 mg, 0.091 mmol), (S)-4-methoxy-2-(methoxycarbonylamino)butanoic acid (69.7 mg, 0.365 mmol) and DIEA (0.16 mL, 0.91 mmol) in dimethylformamide (2 mL) at room temperature. The reaction was stirred for 16 h, diluted with methanol (2 mL) and water (2 mL), stirred for 15 min and concentrated to dryness in vacuo. The crude product was purified by preparative HPLC (Waters Sunfire C18 column 30×150 mm 5 u, eluted with a gradient of 10 to 70% acetonitrile/water/0.1% TFA) to yield a trifluoroacetate salt of methyl ((1S)-3-methoxy-1-(((2S)-2-(4-(5'-(2-((2S)-1-(N-(methoxycarbonyl)-O-methyl-L-homoseryl)-2-pyrrolidinyl)-1H-imidazol-4-yl)-2,2'-bi-1,3-thiazol-5-yl)-1H-imidazol-2-yl)-1-pyrrolidinyl)carbonyl)propyl)-carbamate (66 mg, 0.064 mmol, 71% yield) as an orange solid.

LC-MS retention time 0.91 min; m/z 785.1 (MH$^+$). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (400 MHz, MeOD-d$_4$) δ ppm 8.21 (s, 2H), 7.84 (s, 2H), 5.24 (dd, J=8.4, 5.4 Hz, 2H), 4.58 (dd, J=8.9, 4.6 Hz, 2H), 4.29 (dd, J=8.8, 4.8 Hz, 2H), 4.04-3.81 (m, 2H), 3.73-3.64 (m, 12H), 3.56-3.42 (m, 4H), 2.58-2.43 (m, 2H), 2.30-1.76 (m, 10H).

Example 16

Dimethyl (2,2'-bi-1,3-thiazole-5,5'-diylbis(1H-imidazole-4,2-diyl(2S)-2,1-pyrrolidinediyl((1R)-2-oxo-1-phenyl-2,1-ethanediyl)))biscarbamate

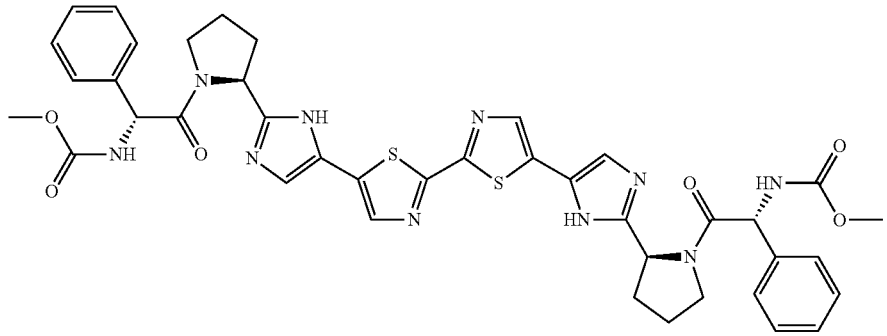

HATU (135 mg, 0.356 mmol) was added to a stirred solution of 5,5'-bis(2-((2S)-2-pyrrolidinyl)-1H-imidazol-4-yl)-2,2'-bi-1,3-thiazole (40 mg, 0.091 mmol), (R)-2-(methoxycarbonylamino)-2-phenylacetic acid (76 mg, 0.37 mmol) and DIEA (0.16 mL, 0.91 mmol) in dimethylformamide (2 mL) at room temperature. The reaction was stirred for 16 h, diluted with methanol (2 mL) and water (2 mL), stirred for 15 min and concentrated to dryness in vacuo. The crude product was purified by preparative HPLC (Waters Sunfire C18 column 30×150 mm 5 u, eluted with a gradient of 10 to 70% acetonitrile/water/0.1% TFA) to yield a trifluoroacetate salt of dimethyl (2,2'-bi-1,3-thiazole-5,5'-diylbis(1H-imidazole-4,2-diyl(2S)-2,1-pyrrolidinediyl((1R)-2-oxo-1-phenyl-2,1-ethanediyl)))biscarbamate (37 mg, 0.036 mmol, 39% yield) as a yellow solid.

LC-MS retention time 1.21 min; m/z 821.1 (MH$^+$). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (400 MHz, MeOD-d$_4$) δ ppm 8.29 (s, 2H), 7.87 (s, 2H), 7.48-7.06 (m, 10H), 5.52-5.49 (m, 2H), 5.27 (dd, J=8.0, 3.8 Hz, 2H), 4.06-3.97 (m, 2H), 3.67-3.63 (m, 2H), 3.64 (s, 6H), 2.43-2.30 (m, 2H), 2.22-1.90 (m, 6H).

Example 17

(1R,1'R)-2,2'-(2,2'-Bi-1,3-thiazole-5,5'-diylbis(1H-imidazole-4,2-diyl(2S)-2,1-pyrrolidinediyl))bis(N,N-dimethyl-2-oxo-1-phenylethanamine)

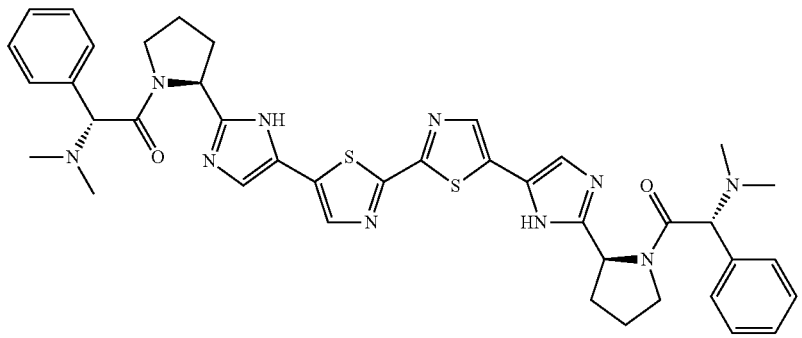 [SMILES: CN(C)[C@@H](C(=O)N1CCC[C@H]1c1ncc(-c2cnc(-c3ncc(-c4cnc([C@@H]5CCCN5C(=O)[C@@H](c5ccccc5)N(C)C)[nH]4)s3)s2)[nH]1)c1ccccc1]

HATU (135 mg, 0.356 mmol) was added to a stirred solution of 5,5'-bis(2-((2S)-2-pyrrolidinyl)-1H-imidazol-4-yl)-2,2'-bi-1,3-thiazole (40 mg, 0.091 mmol), (R)-2-(dimethylamino)-2-phenylacetic acid, hydrochloride (79 mg, 0.365 mmol) and DIEA (0.16 mL, 0.91 mmol) in dimethylformamide (2 mL) at room temperature. The reaction was stirred for 16 h, diluted with methanol (2 mL) and water (2 mL), stirred for 15 min and concentrated to dryness in vacuo. The crude product was purified by preparative HPLC (Waters Sunfire C18 column 30×150 mm 5 u, eluted with a gradient of 10 to 70% acetonitrile/water/0.1% TFA) and then repurified by HPLC (Waters Sunfire C18 column 30×100 mm 5 u, eluted with a gradient of 10 to 80% methanol/water/0.1% TFA) to yield a trifluoroacetate salt of (1R,1'R)-2,2'-(2,2'-bi-1,3-thiazole-5,5'-diylbis(1H-imidazole-4,2-diyl(2S)-2,1-pyrrolidinediyl))bis(N,N-dimethyl-2-oxo-1-phenylethanamine) (20 mg, 0.016 mmol, 18% yield) as an orange solid.

LC-MS retention time 0.89 min; m/z 761.1 (MH$^+$). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (400 MHz, MeOD-d$_4$) δ ppm 8.15-8.12 (m, 2H), 7.68-7.66 (m, 2H), 7.64-7.56 (m, 10H), 5.38-5.33 (m, 2H), 5.20 (dd, J=7.8, 3.8 Hz, 2H), 4.06-3.98 (m, 2H), 3.17-3.07 (m, 2H), 2.80 (br s, 12H), 2.31-2.01 (m, 6H), 1.99-1.84 (m, 2H).

Example 18

Methyl ((1R)-1-(((2S)-2-(4-(5'-(2-((2S)-1-(((2R)-2-((methoxycarbonyl)amino)-3-methylbutanoyl)-2-pyrrolidinyl)-1H-imidazol-4-yl)-2,2'-bi-1,3-thiazol-5-yl)-1H-imidazol-2-yl)-1-pyrrolidinyl)carbonyl)-2-methylpropyl)carbamate umn 30×150 mm 5 u, eluted with a gradient of 10 to 70% acetonitrile/water/0.1% TFA) to yield a trifluoroacetate salt of methyl ((1R)-1-(((2S)-2-(4-(5'-(2-((2S)-1-(((2R)-2-((methoxycarbonyl)amino)-3-methylbutanoyl)-2-pyrrolidinyl)-1H-imidazol-4-yl)-2,2'-bi-1,3-thiazol-5-yl)-1H-imidazol-2-yl)-1-pyrrolidinyl)carbonyl)-2-methylpropyl) carbamate (53 mg, 0.052 mmol, 46% yield) as a yellow solid.

LC-MS retention time 1.11 min; m/z 753.1 (MH$^+$). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (500 MHz, MeOD-d$_4$) δ ppm 8.27 (s, 2H), 7.87 (s, 2H), 5.32-5.35 (m, 2H), 4.24 (d, J=7.3 Hz, 2H), 4.12-4.04 (m, 2H), 3.86-3.86 (m, 2H), 3.65 (s, 6H), 2.57-2.43 (m, 2H), 2.25-2.02 (m, 8H), 1.07-0.95 (m, 12H).

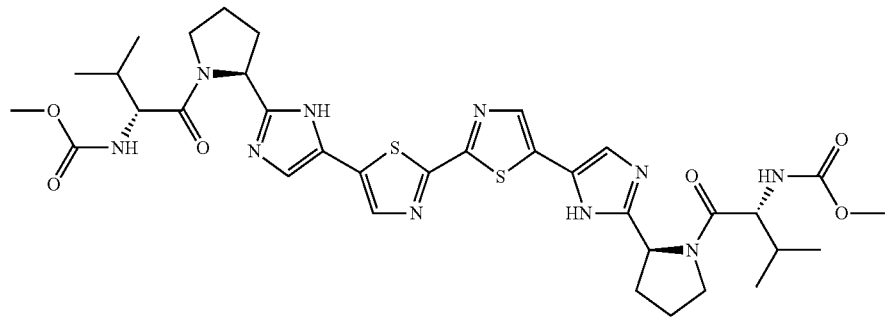

HATU (135 mg, 0.356 mmol) was added to a stirred solution of 5,5'-bis(2-((2S)-2-pyrrolidinyl)-1H-imidazol-4-yl)-2,2'-bi-1,3-thiazole (40 mg, 0.091 mmol), (R)-2-(methoxycarbonylamino)-3-methylbutanoic acid (80 mg, 0.456 mmol) and DIEA (0.16 mL, 0.91 mmol) in dimethylformamide (2 mL) at room temperature. The reaction was stirred for 16 h, diluted with methanol (2 mL) and water (2 mL), stirred for 15 min and concentrated to dryness in vacuo. The crude product was purified by preparative HPLC (Waters Sunfire C18 col-

Example 19

Methyl ((1S,2R)-2-methoxy-1-(((2S)-2-(4-(5'-(2-((2S)-1-(N-(methoxycarbonyl)-O-methyl-L-threonyl)-2-pyrrolidinyl)-1H-imidazol-4-yl)-2,2'-bi-1,3-thiazol-5-yl)-1H-imidazol-2-yl)-1-pyrrolidinyl)carbonyl)propyl)carbamate

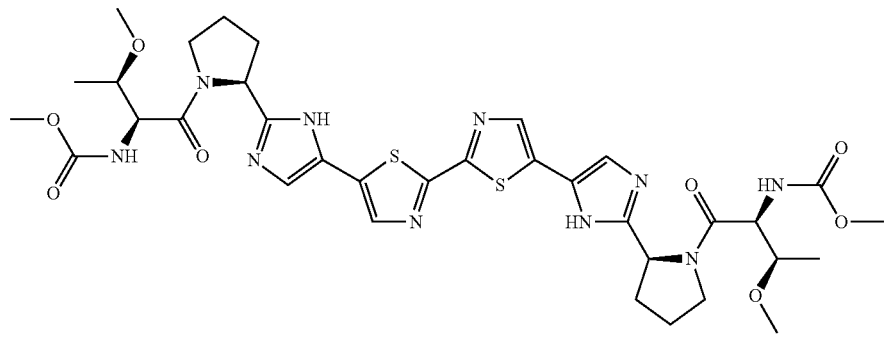

HATU (66 mg, 0.17 mmol) was added to a stirred solution of 5,5'-bis(2-((2S)-2-pyrrolidinyl)-1H-imidazol-4-yl)-2,2'-bi-1,3-thiazole (40 mg, 0.045 mmol), (2S,3R)-3-methoxy-2-(methoxycarbonylamino)butanoic acid (34 mg, 0.18 mmol) and DIEA (0.078 mL, 0.45 mmol) in dimethylformamide (2 mL) at room temperature. The reaction was stirred for 16 h, diluted with methanol (2 mL) and water (2 mL), stirred for 15 min and concentrated to dryness in vacuo. The crude product was purified by preparative HPLC (Waters Sunfire C18 column 30×150 mm 5 u, eluted with a gradient of 10 to 70% acetonitrile/water/0.1% TFA) and then repurified by HPLC (Waters Sunfire C18 column 30×100 mm 5 u, eluted with a gradient of 10 to 70% methanol/water/0.1% TFA) to yield a trifluoroacetate salt of methyl ((1S,2R)-2-methoxy-1-(((2S)-2-(4-(5'-(2-((2S)-1-(N-(methoxycarbonyl)-O-methyl-L-threonyl)-2-pyrrolidinyl)-1H-imidazol-4-yl)-2,2'-bi-1,3-thiazol-5-yl)-1H-imidazol-2-yl)-1-pyrrolidinyl)carbonyl)propyl)carbamate (4.7 mg, 4.5 μmol, 10% yield) as an orange solid.

LC-MS retention time 0.93 min; m/z 785.1 (MH$^+$). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. Partial $^1$H NMR (500 MHz, MeOD-d$_4$) δ ppm 8.30-8.22 (m, 2H), 7.93-7.87 (m, 2H), 5.26-5.20 (m, 2H), 4.47 (d, J=4.3 Hz, 2H), 4.08-4.00 (m, 2H), 3.90-3.81 (m, 2H), 3.73-3.64 (m, 2H), 3.67 (s, 6H), 3.41-3.26 (m, 3H), 2.59-2.47 (m, 2H), 2.36-2.06 (m, 6H), 1.20-1.10 (m, 6H).

Example 20

Methyl ((1S)-2-((2S)-2-(4-(5'-(2-((2S)-1-(N-(methoxycarbonyl)-L-alanyl)-2-pyrrolidinyl)-1H-imidazol-4-yl)-2,2'-bi-1,3-thiazol-5-yl)-1H-imidazol-2-yl)-1-pyrrolidinyl)-1-methyl-2-oxoethyl)carbamate

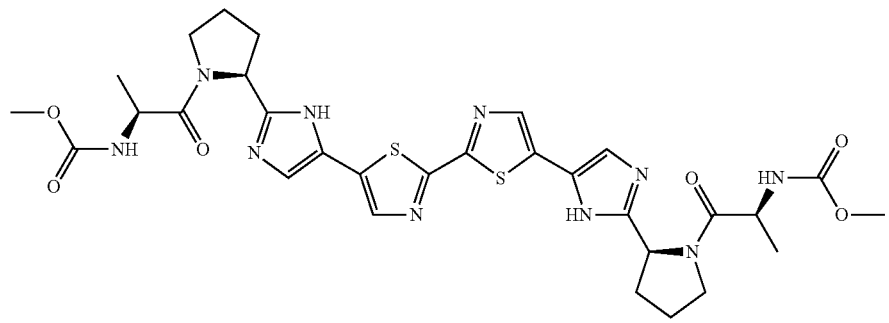

HATU (66 mg, 0.17 mmol) was added to a stirred solution of 5,5'-bis(2-((2S)-2-pyrrolidinyl)-1H-imidazol-4-yl)-2,2'-bi-1,3-thiazole (40 mg, 0.045 mmol), (S)-2-(methoxycarbonylamino)propanoic acid (26 mg, 0.18 mmol) and DIEA (0.078 mL, 0.45 mmol) in dimethylformamide (2 mL) at room temperature. The reaction was stirred for 16 h, diluted with methanol (2 mL) and water (2 mL), stirred for 15 min and concentrated to dryness. The crude product was purified by preparative HPLC (Waters Sunfire C18 column 30×150 mm 5 u, eluted with a gradient of 10 to 80% acetonitrile/water/0.1% TFA) and then repurified by HPLC (Waters Sunfire C18 column 30×100 mm 5 u, eluted with a gradient of 10 to 80% methanol/water/0.1% TFA) to yield a trifluoroacetate salt of methyl ((1S)-2-((2S)-2-(4-(5'-(2-((2S)-1-(N-(methoxycarbonyl)-L-alanyl)-2-pyrrolidinyl)-1H-imidazol-4-yl)-2,2'-bi-1,3-thiazol-5-yl)-1H-imidazol-2-yl)-1-pyrrolidinyl)-1-methyl-2-oxoethyl)carbamate (1.9 mg, 2.0 μmol, 4.6% yield) as an orange solid.

LC-MS retention time 0.83 min; m/z 697.1 (MH$^+$). LC data was recorded on a Shimadzu LC-10AS liquid chromatograph equipped with a Waters Sunfire 5 u C18 4.6×50 mm column using a SPD-10AV UV-Vis detector at a detector wave length of 220 nm. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% acetonitrile/90% water/0.1% TFA and Solvent B was 90% acetonitrile/10% water/0.1% TFA. MS data was determined using a MICROMASS® Platform for LC in electrospray mode. $^1$H NMR (500 MHz, MeOD-d$_4$) δ ppm 8.24 (s, 2H), 7.89 (m, 2H), 5.23 (dd, J=8.1, 6.0 Hz, 2H), 4.48 (q, J=6.9 Hz, 2H), 4.01-3.93 (m, 2H), 3.88-3.81 (m, 2H), 3.65 (s, 6H), 2.58-2.46 (m, 2H), 2.29-2.09 (m, 6H), 1.32 (d, J=7.0 Hz, 6H).

Examples 21 to 28

LCMS Condition

Column = PHENOMENEX ® Luna 4.6 × 50 mm S10
Start % B = 0
Final % B = 100
Gradient time = 2 min
Stop time = 3 min
Flow Rate = 4 mL/min
Wavelength = 220 nm
Solvent A = 0.1% TFA in 10% methanol/90% H$_2$O
Solvent B = 0.1% TFA in 90% methanol/10% H$_2$O Scheme 6

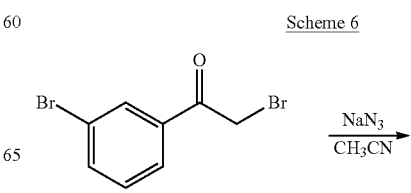

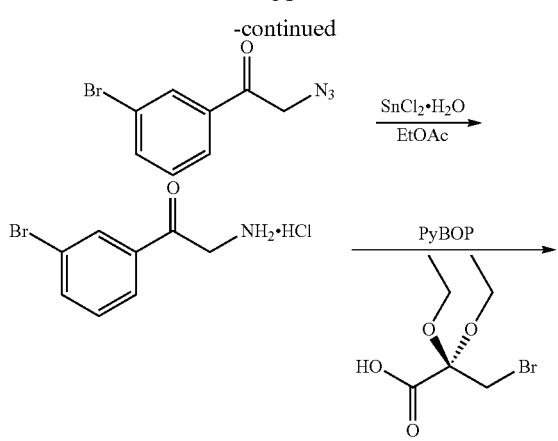

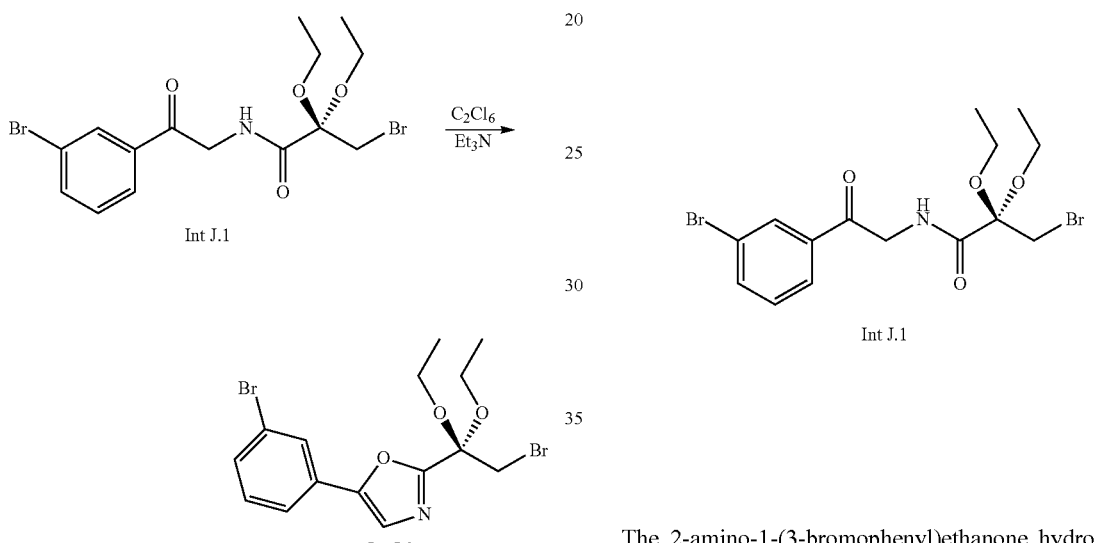

(Synthesis, 1445 (2009))

2-Amino-1-(3-bromophenyl)ethanone hydrochloride

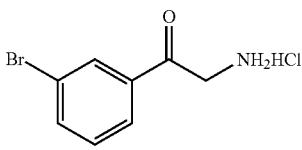

Sodium azide (3.6 g, 55 mmol) was added to a solution of 3-bromophenacetyl bromide (6.2 g, 23 mmol) in acetonitrile (200 mL) and the reaction mixture was stirred 4 h at 65° C. The solvent was removed by rotary evaporation and the residue taken up in EtOAc and washed with half saturated NaHCO$_3$ solution, brine, and dried over Na$_2$SO$_4$. The resultant azide (5.4 g, 23 mmol) was taken up in EtOAc (75 mL) and treated with SnCl$_2$.2H$_2$O (15.2 g, 61 mmol) and the reaction was heated at 60° C. for 3 h. A substantial precipitate formed upon cooling which was filtered and dried under vacuum to 2-amino-1-(3-bromophenyl)ethanone hydrochloride 4.6 g (81%).

3-Bromo-N-[2-(3-bromophenyl)-2-oxoethyl]-2,2-diethoxypropanamide

The 2-amino-1-(3-bromophenyl)ethanone hydrochloride (4.6 g, 19 mmol), HO$_2$CC(OEt)$_2$CH$_2$Br (5.0 g, 21 mmol), and NMM (12.5 mL, 113 mmol) were suspended in anhyd THF (270 mL) under N$_2$ and PyBOP (10.8 g, 21 mmol) was added in one portion. The reaction mixture was stirred for 18 h and concentrated to ¼ vol and the precipitates were removed by filtration (HCl salt of NMM). The mother liquor was taken up in dichloromethane and washed with water. After concentration, the crude residue was subjected to flash chromatography (silica gel) eluting with 60% EtOAc/hexanes to give Intermediate J.1, 5.3 g (65%). $^1$H NMR (500 MHz, DMSO-d$_6$): δ 8.27 (t, J=5.5 Hz, 1H), 8.14 (t, J=1.5 Hz, 1H), 8.00 (dt, J=7.9, 1.2 Hz, 1H), 7.87 (dd, J=8.8, 1.8 Hz, 1H), 7.51 (t, J=7.9 Hz, 1H), 4.65 (d, J=5.8 Hz, 2H), 3.67 (s, 2H) 3.58-3.46 (m, 4H), 1.18 (t, J=7.0 Hz, 6H). LCMS: 2.2 min; LRMS: Calcd. for C$_{15}$H$_{19}$Br$_2$NO$_4$: 435.98. Found: 435.98 (M+H)$^+$.

| Intermediate J.1a Prepared from commercial source of 4-bromophenacylamine HCl | 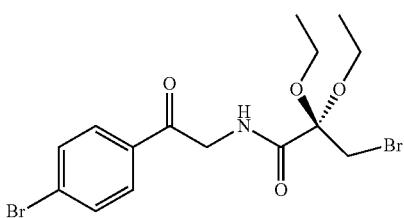 | LRMS: 2.2 min Anal. Calcd. for C$_{15}$H$_{19}$Br$_2$NO$_4$: 438.14; found: 438.11 (M + 2)$^+$. |

2-(2-Bromo-1,1-diethoxyethyl)-5-(3-bromophenyl)oxazole

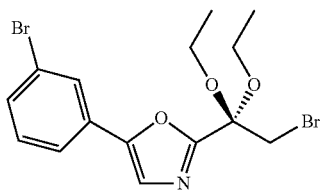

Int. J.2

Hexachloroethane (6.9 g, 29 mmol) was added in one portion to a solution of Intermediate J.1 (6.4 g, 14.6 mmol), Et₃N (15 mL), and Ph₃P (7.6 g, 29 mmol) in anhyd CH₂Cl₂ (170 mL) under N₂. The reaction mixture was stirred 18 h and divided into 2 volumes. Each volume was charged directly to a BIOTAGE® silica gel cartridge (40 M) and eluted with 10% to 30% B over 800 mL (A=hexanes; B=EtOAc). The products from each run were recombined to give J.2, 4.7 g (76%). $^1$H NMR (300 MHz, DMSO-$d_6$): δ 7.96 (t, J=1.8 Hz, 1H), 7.86 (s, 1H), 7.74 (dt, J=8.1, 1.1 Hz, 1H), 7.59 (dd, J=8.1, 1.2 Hz, 1H), 7.45 (t, J=7.7 Hz, 1H), 4.05 (s, 2H), 3.67-3.57 (m, 2H), 3.46-3.36 (m, 2H), 1.15 (t, J=7.0 Hz, 6H). LCMS: 2.4 min; LRMS Anal. Calcd. for $C_{15}H_{17}Br_2NO_3$: 417.97. Found: 417.96 (M+H)⁺.

| Intermediate J.2a (Derived from Intermediate J.1a) | 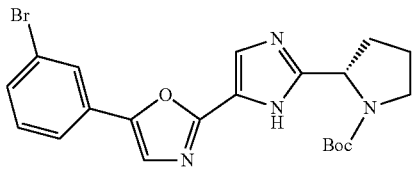 | RT = 2.3 minutes LCMS: Anal. Calcd. for $C_{15}H_{17}Br_2NO_3$: 417.97; found: 418.09 (M + H)⁺. |
|---|---|---|

Scheme 7

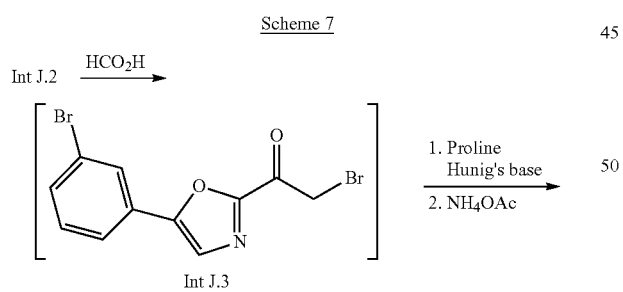

2-Bromo-1-[5-(3-bromophenyl)oxazol-2-yl]ethanone

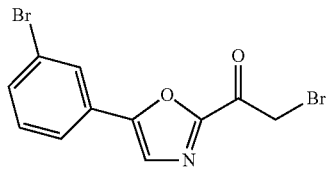

Int J.3

Intermediate J.2 (4.7 g, 11.2 mmol) was taken up in 98% HCO₂H (50 mL) and heated at 80° C. for 1.5 h. Upon being cooled a precipitate formed and was isolated by filtration to give J.3, 3.0 g (78%). LCMS: 3.1 min; LRMS Anal. Calcd. for $C_{11}H_8Br_2NO_2$: 343.89. Found: 344.02 (M+H)⁺.

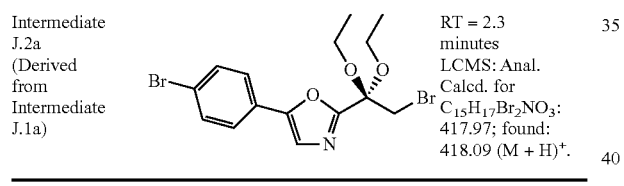

Int J.4

Hunig's base (3.1 mL, 18 mmol) was added dropwise to a solution of the Intermediate J.3 (3.0 g, 8.6 mmol) and N-Boc-L-Proline (2.0 g, 9.6 mmol) in acetonitrile (80 mL) and the reaction mixture stirred 18 h, concentrated, and directly applied (CH₂Cl₂) to a 40 (S) BIOTAGE® silica gel column. Gradient elution was performed from 15 to 45% B (A=Hexanes; B=EtOAc). The intermediate ester 4 g (97%) was taken up in xylenes (60 mL). Excess ammonium acetate (8 g) was added and solution was stirred in a screw capped pressure vessel heated at 140° C. for 3 h. The reaction was diluted with EtOAc (3 vol) and washed with sat'd NaHCO₃ and brine. After concentration, the crude product was charged to a 40 (M) BIOTAGE® silica gel column and eluted under gradient conditions from 60 to 100% B (A=Hexanes; B=EtOAc) to give Intermediate J.4, 1.5 g (39%). $^1$H NMR (300 MHz, DMSO-$d_6$): δ=7.95 (s, 1H), 7.8 (s, 1H), 7.75 (d, J=8.1 Hz, 1H), 7.54 (d, J=8.8 Hz, 1H), 7.43 (t, J=8.1 Hz, 1H), 4.86-4.78 (br.s, 1H), 3.53 (br. s, 1H), 3.36 (br. s, 1H), 2.24 (br. s, 1H) 2.02-1.83 (m, 3H), 1.40/1.17 (s, 9H). LCMS: 1.97 min; LRMS: Calcd. for $C_{21}H_{24}BrN_4O_3$: 459.10. Found: 459.08 (M+H)⁺.

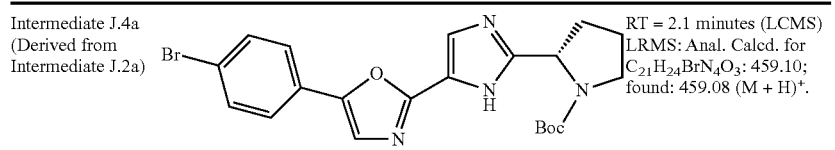

Intermediate J.4a (Derived from Intermediate J.2a)

RT = 2.1 minutes (LCMS)
LRMS: Anal. Calcd. for $C_{21}H_{24}BrN_4O_3$: 459.10; found: 459.08 $(M + H)^+$.

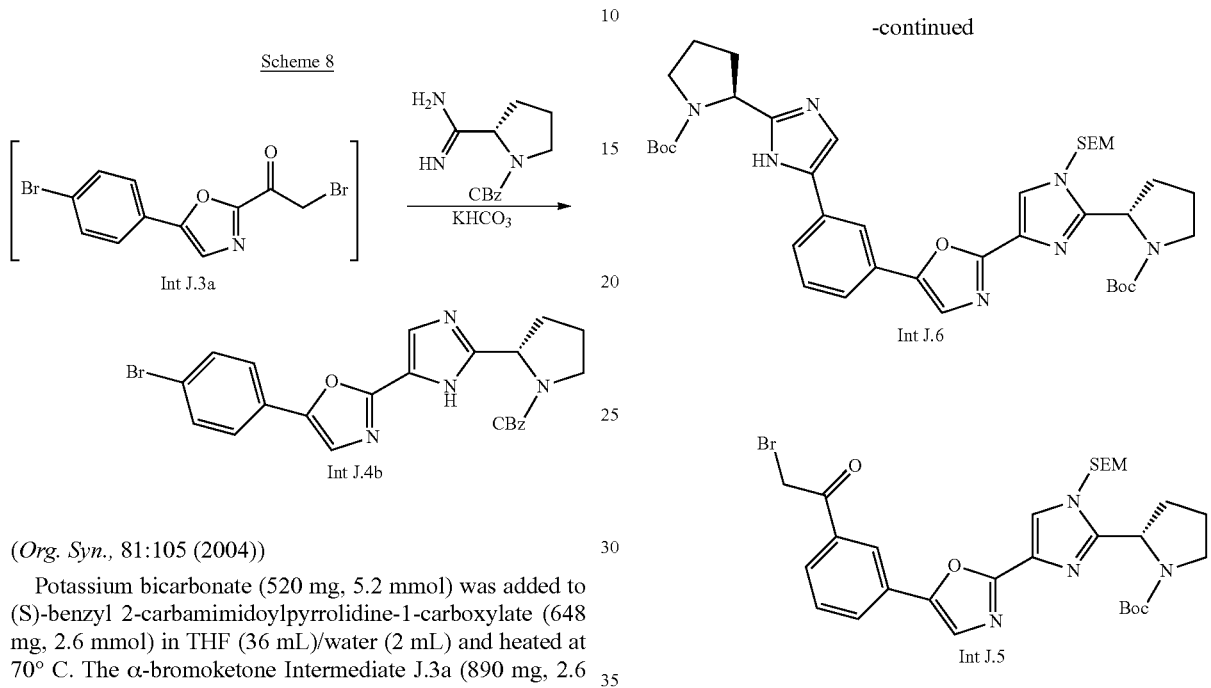

Scheme 8

Int J.3a

Int J.4b

Int J.6

(Org. Syn., 81:105 (2004))

Potassium bicarbonate (520 mg, 5.2 mmol) was added to (S)-benzyl 2-carbamimidoylpyrrolidine-1-carboxylate (648 mg, 2.6 mmol) in THF (36 mL)/water (2 mL) and heated at 70° C. The α-bromoketone Intermediate J.3a (890 mg, 2.6 mmol) [prepare from Intermediate J.2a as described for J.3] was dissolved in THF (15 mL) and added dropwise over 15 min and the reaction mixture was stirred at that temperature over 48 h. The THF was removed by rotary evaporation and the residue partition between water and $CH_2Cl_2$. The organic layer was concentrated and the crude product applied to a 25 (M) BIOTAGE® silica gel column and eluted 60% EtOAc in hexanes to give Intermediate J.4b, 257 mg (20%). RT=2.0 min. LRMS: Anal. Calcd. for $C_{24}H_{22}BrN_4O_3$: 494.09. Found: 493.06 $(M+H)^+$.

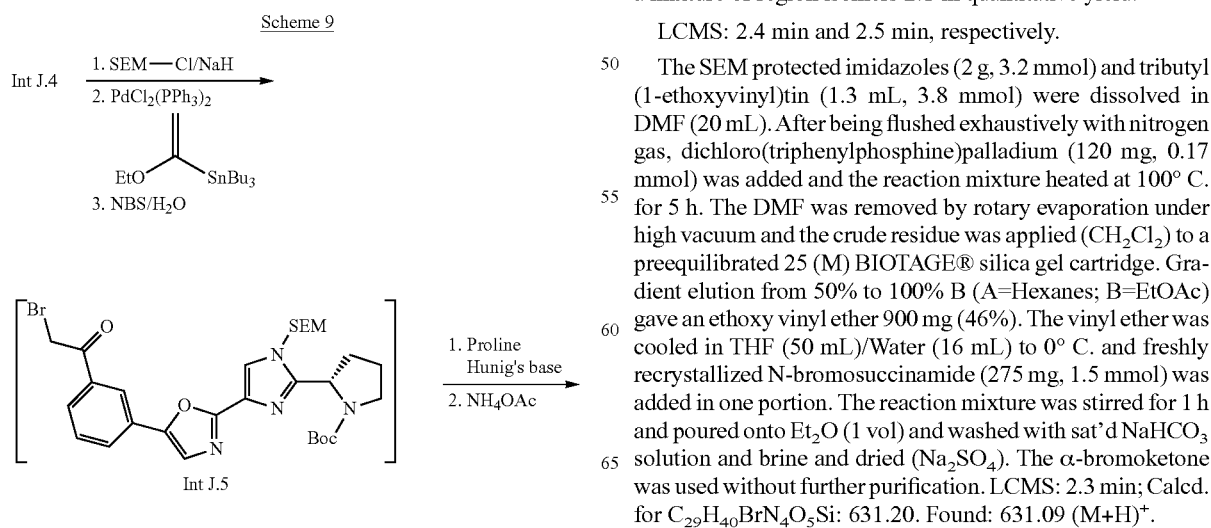

Scheme 9

Int J.5

Unwashed 60% sodium hydride (152 mg, 3.8 mmol) was added in one portion to a stirred solution of Intermediate J.4 (1.5 g, 3.2 mmol) in dry DMF (35 mL) under nitrogen. After 30 min, SEM-Cl (0.6 mL, 3.6 mmol) was added and the reaction mixture was stirred for 18 h. The solvent was removed by rotary evaporation under high vacuum and the crude residue applied ($CH_2Cl_2$) to a 40 (M) BIOTAGE® silica gel cartridge. Gradient elution from 40% to 100% B (A=Hexanes; B=EtOAc) gave the SEM protected product as a mixture of region isomers 2:1 in quantitative yield.

LCMS: 2.4 min and 2.5 min, respectively.

The SEM protected imidazoles (2 g, 3.2 mmol) and tributyl (1-ethoxyvinyl)tin (1.3 mL, 3.8 mmol) were dissolved in DMF (20 mL). After being flushed exhaustively with nitrogen gas, dichloro(triphenylphosphine)palladium (120 mg, 0.17 mmol) was added and the reaction mixture heated at 100° C. for 5 h. The DMF was removed by rotary evaporation under high vacuum and the crude residue was applied ($CH_2Cl_2$) to a preequilibrated 25 (M) BIOTAGE® silica gel cartridge. Gradient elution from 50% to 100% B (A=Hexanes; B=EtOAc) gave an ethoxy vinyl ether 900 mg (46%). The vinyl ether was cooled in THF (50 mL)/Water (16 mL) to 0° C. and freshly recrystallized N-bromosuccinamide (275 mg, 1.5 mmol) was added in one portion. The reaction mixture was stirred for 1 h and poured onto $Et_2O$ (1 vol) and washed with sat'd $NaHCO_3$ solution and brine and dried ($Na_2SO_4$). The α-bromoketone was used without further purification. LCMS: 2.3 min; Calcd. for $C_{29}H_{40}BrN_4O_5Si$: 631.20. Found: 631.09 $(M+H)^+$.

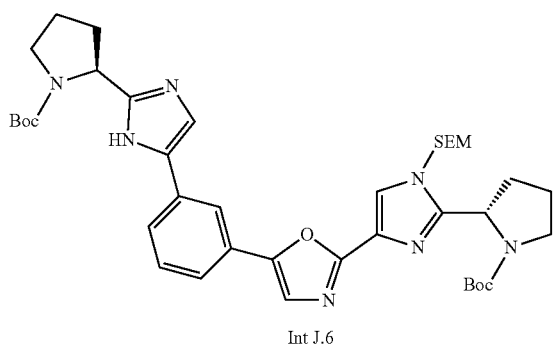 [SMILES: CC(C)(C)OC(=O)N1CCC[C@H]1c1ncc(-c2cccc(-c3cnc(-c4cn(COCC[Si](C)(C)C)c([C@@H]5CCCN5C(=O)OC(C)(C)C)n4)o3)c2)[nH]1]

Int J.6

Hunig's base (0.25 mL, 1.5 mmol) was added dropwise to a solution of the α-bromoketone Intermediate J.5 (750 mg, 1.2 mmol) and N-Boc-L-Proline (256 mg, 1.2 mmol) in acetonitrile (40 mL) and the reaction mixture stirred 18 h, concentrated, and directly applied to a 25 (M) BIOTAGE® silica gel column. Gradient elution was performed from 30 to 100% B (A=Hexanes; B=EtOAc). The ester 700 mg (77%) was taken up in xylenes (20 mL). Excess ammonium acetate (1.1 g) was added and solution was stirred in a screw capped pressure vessel heated at 140° C. for 3 h. The reaction was diluted with EtOAc (3 vol) and washed with sat'd $NaHCO_3$ solution and brine. After concentration, the crude product was charged to a 25 (S) BIOTAGE® silica gel column and eluted under gradient conditions from 50 to 100% B (A=Hexanes; B=EtOAc) to give Intermediate J.6, 450 mg (66%). LCMS: 2.11 min; LRMS: Calcd. for $C_{39}H_{56}N_7O_6Si$: 746.40. Found: 746.34 $(M+H)^+$.

| | | |
|---|---|---|
| Intermediate J.6a (Derived from Intermediate J.5 and N-Boc-L-Alanine) | 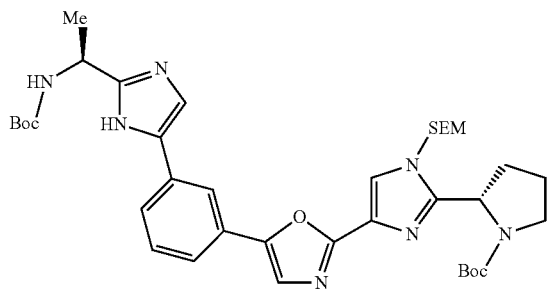 [SMILES: C[C@H](NC(=O)OC(C)(C)C)c1ncc(-c2cccc(-c3cnc(-c4cn(COCC[Si](C)(C)C)c([C@@H]5CCCN5C(=O)OC(C)(C)C)n4)o3)c2)[nH]1] | RT = 2.1 minutes LCMS: Anal. Calcd. for $C_{37}H_{54}N_7O_6Si$: 720.39; found: 720.32 $(M + H)^+$. |
| Intermediate J.6b (Derived from Intermediate J.4a according to the sequence in Scheme 9) | 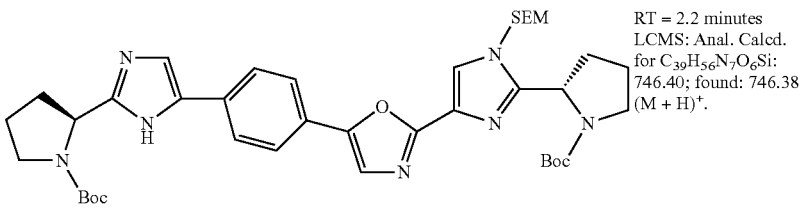 | RT = 2.2 minutes LCMS: Anal. Calcd. for $C_{39}H_{56}N_7O_6Si$: 746.40; found: 746.38 $(M + H)^+$. |
| Intermediate J.6c (Derived from Intermediate J.4b according to the sequence in Scheme 9) | 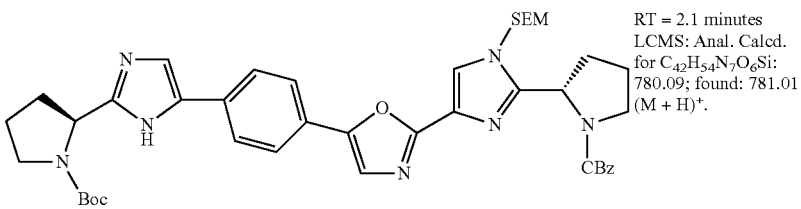 | RT = 2.1 minutes LCMS: Anal. Calcd. for $C_{42}H_{54}N_7O_6Si$: 780.09; found: 781.01 $(M + H)^+$. |

Scheme 10
Methyl ((1R)-2-((2S)-2-(4-(3-(2-(2-((2S))-1-((2R)-2-((methoxycarbonyl)amino)-2-phenylacetyl)-2-pyrrolidinyl)-1H-imidazol-4-yl)-1,3-oxazol-5-yl)phenyl)-1H-imidazol-2-yl)-1-pyrrolidinyl)-2-oxo-1-phenylethyl)carbamate Int J.6 → 1. TFA CH₂Cl₂ 2. HATU Cap-4

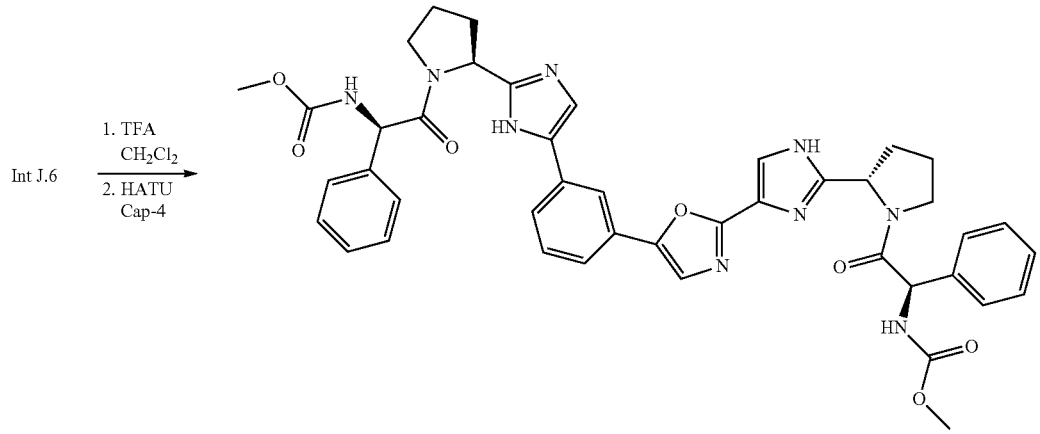

Example 21

Intermediate J.6, (450 mg, 0.6 mmol) was dissolved in CH₂Cl₂ (30 mL) and TFA (11 mL) was added and the reaction was stirred 20 hr. The solvents were removed in vacuo, and the TFA salt (120 mg) was eluted (MeOH) through a UCT (CHQAX15M25) exchange resin to obtain the free base. LCMS: 1.1 min; LRMS Calcd. for $C_{23}H_{26}N_2O$: 416.22. Found: 416.60 (M+H)⁺.

HATU (60 mg, 0.16 mmol) was added to a rapidly stirred solution of the free base (31 mg, 0.075 mmol), N-methoxy-carbonyl-(R)-phenylalanine (33.4 mg, 0.16 mmol), and Hunig's base (0.13 mL, 0.75 mmol) in DMF (1 mL). The reaction mixture was stirred 16 hours before being diluted with CH₃OH (1 vol) and directly subjected to semi prep HPLC (PHENOMENEX® Gemini 30×100 mm S10; 10%-100% B over 8 min; Flow Rate=40 mL/min; Wavelength=220 nm; Solvent A=Ammonium acetate 10 mM in 95:5 H₂O/ACN; Solvent B=Ammonium acetate 10 mM in 10:90 H₂O/ACN) to give Example 21, 8.8 mg (13%) (AcOH salt). ¹H NMR (300 MHz, DMSO-d₆): δ=12.26-11.79 (m, 2H), 8.10 (br. s., 1H), 7.78-7.71 (s, 3H), 7.63-7.55 (m, 3H), 7.46-7.30 (m, 9H), 7.05-6.91 (m, 2H), 5.56-5.06 (series m, 4H), 3.89 (br.s, 1H), 3.55-3.51 (m, 6H), 3.39-3.32 (m, 2H), 3.14 (br. s, 1H) 2.08-1.80 (m, 8H).

LCMS: 1.6 min; HRMS Calcd. for $C_{43}H_{44}N_9O_2$: 798.3364. Found: 798.3378 (M+H)⁺.

Examples 22 to 28

Example 22
(Derived from Intermediate J.6 and Cap-1)

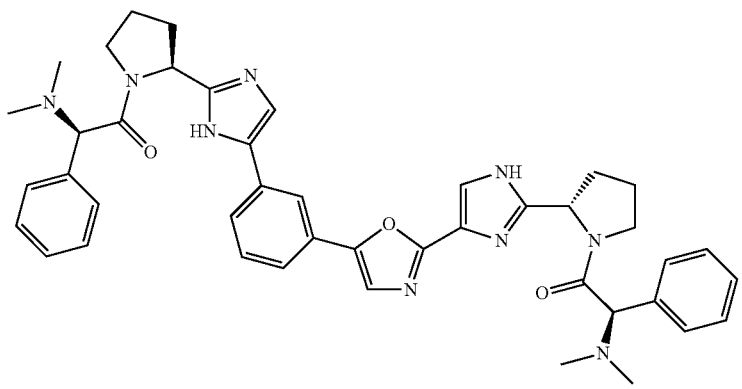 [SMILES: CN(C)[C@@H](C(=O)N1CCC[C@H]1c1nc(-c2ncc(-c3cccc(-c4cnc([C@@H]5CCCN5C(=O)[C@@H](c5ccccc5)N(C)C)[nH]4)c3)o2)c[nH]1)c1ccccc1]

(1R)-2-((2S)-2-(4-(3-(2-(2-((2S)-1-((2R)-2-(Dimethylamino)-2-phenylacetyl)-2-pyrrolidinyl)-1H-imidazol-4-yl)-1,3-oxazol-5-yl)phenyl)-1H-imidazol-2-yl)-1-pyrrolidinyl)-N,N-dimethyl-2-oxo-1-phenylethanamine RT = 1.3 minutes
HRMS: Anal. Calcd. for $C_{43}H_{48}N_9O_3$: 738.3880; found: 738.3864 (M + H)⁺.

| | | |
|---|---|---|
| Example 23 (Derived from Intermediate J.6a and Cap-4) | 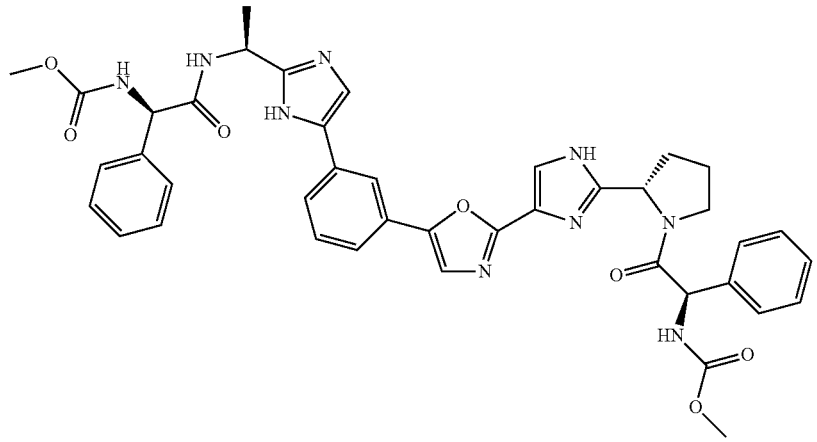 [SMILES: COC(=O)N[C@@H](C(=O)N[C@@H](C)c1ncc(-c2cccc(-c3cnc(-c4c[nH]c([C@@H]5CCCN5C(=O)[C@H](NC(=O)OC)c5ccccc5)n4)o3)c2)[nH]1)c1ccccc1]  Methyl ((1R)-2-((2S)-2-(4-(5-(3-(2-((1S)-1-(((2R)-2-((methoxycarbonyl)amino)-2-phenylacetyl)amino)ethyl)-1H-imidazol-4-yl)phenyl)-1,3-oxazol-2-yl)-1H-imidazol-2-yl)-1-pyrrolidinyl)-2-oxo-1-phenylethyl) carbamate | RT = 1.6 minutes HRMS: Anal. Calcd. for $C_{41}H_{42}N_9O_3$: 772.3207; found: 772.3227 (M + H)⁺. |
| Example 24 (Derived from Intermediate J.6a and Cap-1) | 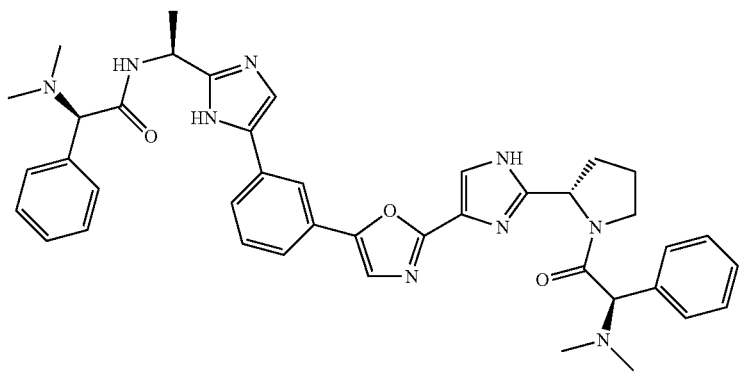 [SMILES: C[C@H](NC(=O)[C@@H](c1ccccc1)N(C)C)c1ncc(-c2cccc(-c3cnc(-c4c[nH]c([C@@H]5CCCN5C(=O)[C@@H](c5ccccc5)N(C)C)n4)o3)c2)[nH]1]  (2R)-2-(Dimethylamino)-N-((1S)-1-(4-(3-(2-(2-((2S)-1-((2R)-2-(dimethylamino)-2-phenylacetyl)-2-pyrrolidinyl)-1H-imidazol-4-yl)-1,3-oxazol-5-yl)phenyl)-1H-imidazol-2-yl)ethyl)-2-phenylacetamide | RT = 1.3 minutes HRMS: Anal. Calcd. for $C_{41}H_{46}N_9O_3$: 712.3738; found: 712.3738 (M + H)⁺. |
| Example 25 (Derived from Intermediate J.6b and Cap-4) | 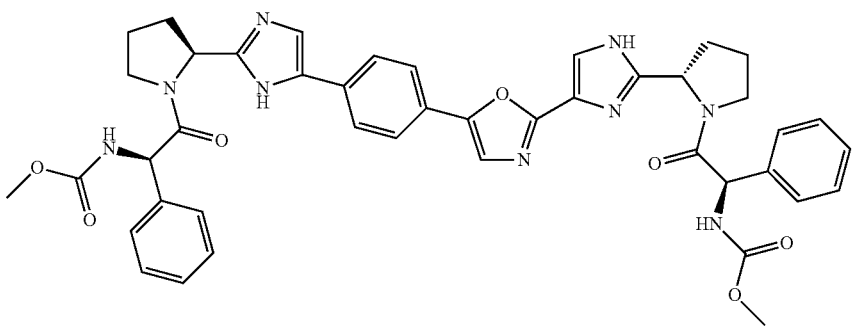 [SMILES: COC(=O)N[C@@H](C(=O)N1CCC[C@H]1c1nc(-c2ncc(-c3ccc(-c4cnc([C@@H]5CCCN5C(=O)[C@H](NC(=O)OC)c5ccccc5)[nH]4)cc3)o2)c[nH]1)c1ccccc1]  Methyl ((1R)-2-((2S)-2-(4-(4-(2-(2-((2S)-1-((2R)-2-((methoxycarbonyl)amino)-2-phenylacetyl)-2-pyrrolidinyl)-1H-imidazol-4-yl)-1,3-oxazol-5-yl)phenyl)-1H-imidazol-2-yl)-1-pyrrolidinyl)-2-oxo-1-phenylethyl)carbamate | RT = 1.7 minutes HRMS: Anal. Calcd. for $C_{43}H_{44}N_9O_7$: 798.3364; found: 798.3387 (M + H)⁺. |

| Example 26 (Derived from Intermediate J.6b and Cap-1) | 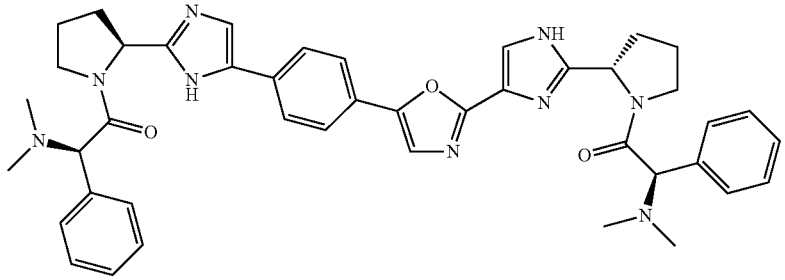 [SMILES: CN(C)[C@@H](C(=O)N1CCC[C@H]1c1nc(-c2ncc(-c3ccc(-c4cnc([C@@H]5CCCN5C(=O)[C@@H](c5ccccc5)N(C)C)[nH]4)cc3)o2)c[nH]1)c1ccccc1] | RT = 1.5 minutes HRMS: Anal. Calcd. for $C_{43}H_{48}N_9O_3$: 738.3880; found: 738.3878 (M + H)+. |

(1R)-2-((2S)-2-(4-(4-(2-(2-((2S)-1-((2R)-2-(Dimethylamino)-2-phenylacetyl)-2-pyrrolidinyl)-1H-imidazol-4-yl)-1,3-oxazol-5-yl)phenyl)-1H-imidazol-2-yl)-1-pyrrolidinyl)-N,N-dimethyl-2-oxo-1-phenylethanamine

| Example 27 (Derived from Intermediate J.6c and Cap-4) | 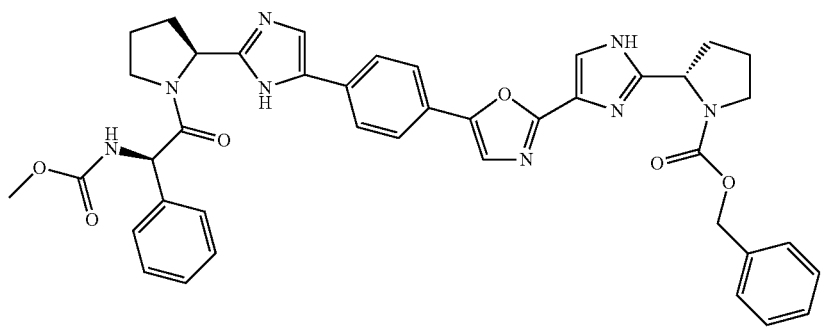 [SMILES: COC(=O)N[C@@H](C(=O)N1CCC[C@H]1c1ncc(-c2ccc(-c3cnc(-c4c[nH]c([C@@H]5CCCN5C(=O)OCc5ccccc5)n4)o3)cc2)[nH]1)c1ccccc1] | RT = 1.8 minutes HRMS: Anal. Calcd. for $C_{41}H_{41}N_8O_6$: 741.3149; found: 741.3140 (M + H)+. |

Benzyl (2S)-2-(4-(5-(4-(2-((2S)-1-((2R)-2-((methoxycarbonyl)amino)-2-phenylacetyl)-2-pyrrolidinyl)-1H-imidazol-4-yl)phenyl)-1,3-oxazol-2-yl)-1H-imidazol-2-yl)-1-pyrrolidinecarboxylate

| Example 28 (Derived from Intermediate J.6c and Cap-1) | 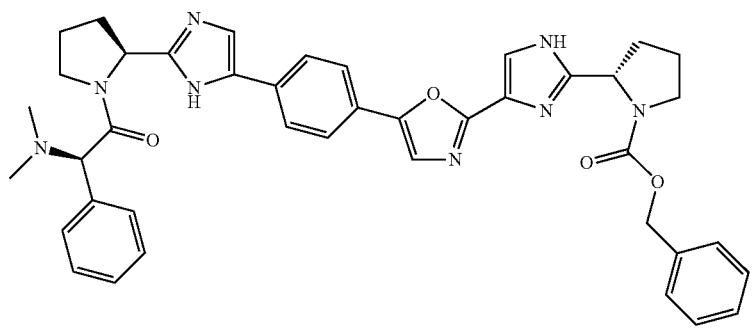 [SMILES: CN(C)[C@@H](C(=O)N1CCC[C@H]1c1ncc(-c2ccc(-c3cnc(-c4c[nH]c([C@@H]5CCCN5C(=O)OCc5ccccc5)n4)o3)cc2)[nH]1)c1ccccc1] | RT = 1.6 minutes HRMS: Anal. Calcd. for $C_{41}H_{43}N_8O_4$: 711.3407; found: 711.3428 (M + H)+. |

Benzyl (2S)-2-(4-(5-(4-(2-((2S)-1-((2R)-2-((N,N-dimethyl)amino)-2-phenylacetyl)-2-pyrrolidinyl)-1H-imidazol-4-yl)phenyl)-1,3-oxazol-2-yl)-1H-imidazol-2-yl)-1-pyrrolidinecarboxylate

Examples 29 to 32

Scheme 11

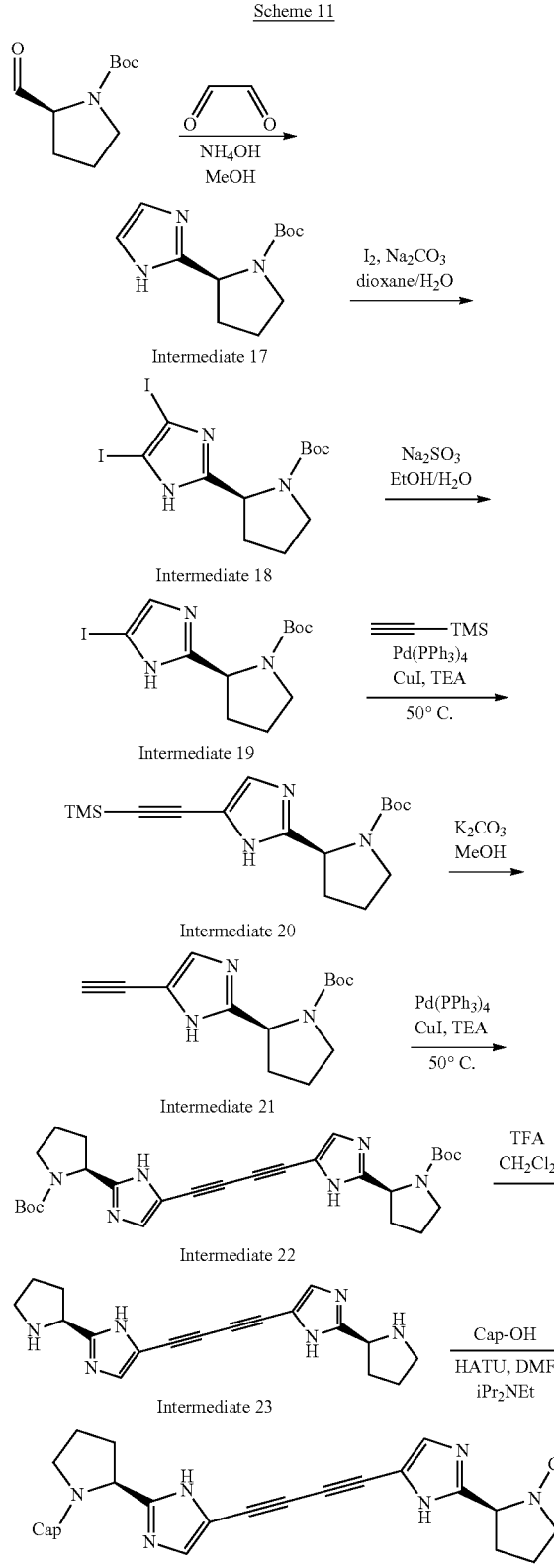

Examples 29-32

Intermediate 17

(S)-tert-Butyl 2-(1H-imidazol-2-yl)pyrrolidine-1-carboxylate

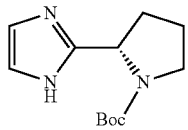 [SMILES: CC(C)(C)OC(=O)N1CCC[C@H]1c1ncc[nH]1]

Glyoxal (2.0 mL of 40% in water) was added dropwise over 11 minutes to a methanol solution of NH$_4$OH (32 mL) and (S)-Boc-prolinal (8.56 g, 43.0 mmol) and the reaction was stirred at ambient temperature for 19 hours. The volatile component was removed in vacuo and the residue was purified by a flash chromatography (silica gel, ethyl acetate) followed by a recrystallization (ethyl acetate, room temperature) to provide (S)-tert-butyl 2-(1H-imidazol-2-yl)pyrrolidine-1-carboxylate as a white fluffy solid (4.43 g, 18.6 mmol, 43% yield). $^1$H NMR (DMSO-d$_6$, 400 MHz) δ ppm 11.68/11.59 (br s, 1H), 6.94 (s, 1H), 6.76 (s, 1H), 4.76 (m, 1H), 3.48 (m, 1H), 3.35-3.29 (m, 1H), 2.23-1.73 (m, 4H), 1.39/1.15 (s, 9H). LCMS. RT=0.87 min; >95% homogeneity index; LC/MS: Anal. Calcd. for [M+H]$^+$ C$_{12}$H$_{20}$N$_3$O$_2$ 238.16. Found 238.22. The compound shown to have a 98.9 ee % when analyzed under the chiral HPLC conditions noted below.
Column: CHIRALPAK® AD, 10 um, 4.6×50 mm
Solvent: 1.7% ethanol/heptane (isocratic)
Flow rate: 1 mL/min
Wavelength: either 220 or 256 nm
Relative retention time: 3.25 min (R), 5.78 minutes (S)

Intermediate 18

(S)-tert-Butyl 2-(4,5-diiodo-1H-imidazol-2-yl)pyrrolidine-1-carboxylate

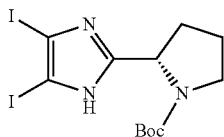 [SMILES: CC(C)(C)OC(=O)N1CCC[C@H]1c1nc(I)c(I)[nH]1]

Iodine (16.17 g, 63.7 mmol) was added to a solution of (S)-tert-butyl 2-(1H-imidazol-2-yl)pyrrolidine-1-carboxylate (6.87 g, 29.0 mmol) and sodium carbonate (9.21 g, 87 mmol) in dioxane (72 mL) and water (72 mL) at ambient temperature. The flask was covered with aluminum foil and stirrer for 16 hours. The reaction mixture was diluted with ethyl acetate and a saturated aqueous solution of sodium thiosulfate. The mixture was stirred for 15 minutes and the phases were separated. The aqueous phase was extracted several times with ethyl acetate. The combined organic phases were dried (Na$_2$SO$_4$), filtered and concentrated in vacuo to afford (S)-tert-butyl 2-(4,5-diiodo-1H-imidazol-2-yl)pyrrolidine-1-carboxylate (12.5 g 88%) as a tan solid.

LC-MS retention time 1.40 min; Calcd. for C$_{12}$H$_{17}$H$_2$N$_3$O$_2$ 488.94. Found m/z 489.96 [M+H]$^+$. LC data was recorded on a Shimadzu LC-10AS liquid chromatograph equipped with a Waters Sunfire 5 u C18 4.6×50 mm column using a SPD-10AV UV-V is detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (500 MHz, MeOD) δ ppm 4.72-4.84 (m, 1H), 3.58-3.70 (m, 1H), 3.43-3.54 (m, 1H), 2.36 (br s, 1H), 1.88-2.08 (m, 3H), 1.47 (br s, 3H), 1.27 (br s, 6H).

Intermediate 19

(S)-tert-Butyl 2-(5-iodo-1H-imidazol-2-yl)pyrrolidine-1-carboxylate

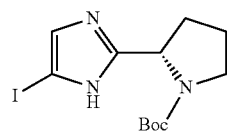 [SMILES: CC(C)(C)OC(=O)N1CCC[C@H]1c1ncc(I)[nH]1]

Sodium sulfite (10.31 g, 82 mmol) was added to a solution of (S)-tert-butyl 2-(4,5-diiodo-1H-imidazol-2-yl)pyrrolidine-1-carboxylate (4.0 g, 8.2 mmol) in ethanol (75 mL) and water (75 mL). The suspension was heated with an oil bath at 100° C. for 4 hours and at 90° C. for 16 h. The reaction was diluted with ethyl acetate and water. The layers were separated and the aqueous layer was extracted several times with ethyl acetate. The combined organic phases were dried (brine, $Na_2SO_4$), filtered and concentrated in vacuo. The residue was purified by a flash chromatography (sample was dry loaded on silica gel and eluted with, 0 to 40% ethyl acetate/$CH_2Cl_2$) to afford (S)-tert-butyl 2-(5-iodo-1H-imidazol-2-yl)pyrrolidine-1-carboxylate (2.17 g, 73.1%) as a white solid.

LC-MS retention time 0.930 min; Calcd. for $C_{12}H_{18}IN_3O_2$ 363.04. Found m/z 364.06 [M+H]$^+$. LC data was recorded on a Shimadzu LC-10AS liquid chromatograph equipped with a Waters Sunfire 5 u C18 4.6×50 mm column using a SPD-10AV UV-V is detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min and an analysis time of 4 min where Solvent A was 10% acetonitrile/90% water/0.1% TFA and Solvent B was 90% acetonitrile/10% water/0.1% TFA. $^1$H NMR (500 MHz, MeOD) δ ppm 7.52-7.64 (m, 1H), 4.95-5.10 (m, 1H), 3.57-3.70 (m, 1H), 3.47-3.57 (m, 1H), 2.37-2.55 (m, 1H), 1.94-2.10 (m, 3H), 1.46 (s, 4H), 1.27 (s, 5H).

Intermediate 20

(S)-tert-Butyl 2-(5-((trimethylsilyl)ethynyl)-1H-imidazol-2-yl)pyrrolidine-1-carboxylate

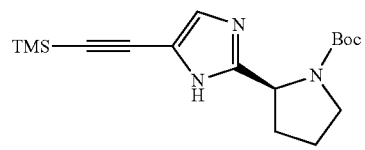 [SMILES: CC(C)(C)OC(=O)N1CCC[C@H]1c1ncc(C#C[Si](C)(C)C)[nH]1]

A solution of (S)-tert-butyl 2-(5-iodo-1H-imidazol-2-yl)pyrrolidine-1-carboxylate (1 g, 2.75 mmol), triethylamine (1.92 mL, 13.8 mmol) and copper(I) iodide (0.105 g, 0.551 mmol) in DMF (30 mL) was degassed under vacuum and backfilled with nitrogen. Ethynyltrimethylsilane (1.35 g, 13.8 mmol) and Pd(Ph$_3$P)$_4$ (0.159 g, 0.138 mmol) were added and then the reaction was sealed and heated at 50° C. for 1d. The reaction was concentrated to remove the volatiles and the residue was purified on a BIOTAGE® (silica gel, eluted with 0 to 40% ethyl acetate/hexanes) to yield (S)-tert-butyl 2-(5-((trimethylsilyl)ethynyl)-1H-imidazol-2-yl)pyrrolidine-1-carboxylate (751 mg, 2.25 mmol, 82% yield) as brownish foam.

LC-MS retention time 1.500 min; m/z 334.14 (MH$^+$). LC data was recorded on a Shimadzu LC-10AS liquid chromatograph equipped with a Sunfire 5 u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% $CH_3CN$/90% $H_2O$/0.1% TFA and Solvent B was 10% $H_2O$/90% $CH_3CN$/0.1% TFA. MS data was determined using a MICROMASS® Platform for LC in electrospray mode. $^1$H NMR (500 MHz, MeOD) δ ppm 7.18 (br s, 1H), 4.78-4.85 (m, 1H), 3.53-3.72 (m, 1H), 3.37-3.52 (m, 1H), 2.18-2.38 (m, 1H), 1.85-2.05 (m, 3H), 1.45 (br s, 3H), 1.14-1.31 (m, 6H), 0.12-0.27 (m, 9H).

Intermediate 21

(S)-tert-Butyl 2-(5-ethynyl-1H-imidazol-2-yl)pyrrolidine-1-carboxylate

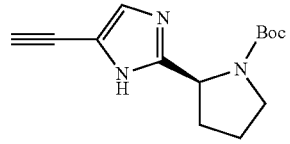 [SMILES: C#Cc1cnc([C@@H]2CCCN2C(=O)OC(C)(C)C)[nH]1]

$K_2CO_3$ (118 mg, 0.855 mmol) was added to a solution of (S)-tert-butyl 2-(5-((trimethylsilyl)ethynyl)-1H-imidazol-2-yl)pyrrolidine-1-carboxylate (950 mg, 2.85 mmol) in MeOH (25 mL) and the reaction mixture was stirred at RT for 1 h and then heated at 25° C. for 3 h. The reaction was concentrated to remove the volatiles and the residue was taken into MeOH and filtered through a Strata XC MCX cartridge. The cartridge was washed with methanol and the compound was release from the cartridge by eluting with a solution of 2M of ammonia/methanol (40 mL) and concentrated to give a (S)-tert-butyl 2-(5-ethynyl-1H-imidazol-2-yl)pyrrolidine-1-carboxylate (530 mg, 1.41 mmol, 49.6% yield).

LC-MS retention time 0.882 min; m/z 206.05 (MH$^+$). LC data was recorded on a Shimadzu LC-10AS liquid chromatograph equipped with a Sunfire 5 u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% $CH_3CN$/90% $H_2O$/0.1% TFA and Solvent B was 10% $H_2O$/90% $CH_3CN$/0.1% TFA. MS data was determined using a MICROMASS® Platform for LC in electrospray mode. $^1$H NMR (500 MHz, MeOD) δ ppm 7.19 (br s, 1H), 4.78-4.85 (m, 1H), 3.55-3.70 (m, 1H) 3.38-3.55 (m, 2H), 3.37 (s, 1H), 2.18-2.38 (m, 1H) 1.85-2.05 (m, 3H) 1.45 (br s, 3H) 1.25 (s, 6H).

Intermediate 22

(2S,2'S)-tert-Butyl 2,2'-(5,5'-(buta-1,3-diyne-1,4-diyl)bis(1H-imidazole-5,2-diyl))dipyrrolidine-1-carboxylate

A solution of (S)-tert-butyl 2-(6-(4-bromophenyl)-1H-benzo[d]imidazol-2-yl)pyrrolidine-1-carboxylate (674 mg, 1.53 mmol, for its preparation, see PCT Publication No. WO 2008/021927)), (S)-tert-butyl 2-(5-ethynyl-1H-imidazol-2-yl)pyrrolidine-1-carboxylate (518 mg, 1.98 mmol), copper(I) iodide (29.0 mg, 0.152 mmol) and triethylamine (0.64 mL, 4.6 mmol) in DMF (15 mL) was degassed under vacuum for 10 min and backfilled with $N_2$. $Pd(Ph_3P)_4$ (176 mg, 0.152 mmol) was then added and the reaction was sealed and heated at 50° C. for 16 h. The reaction mixture was concentrated to remove the volatiles and the residue was dissolved into a minimal amount of MeOH and then partitioned between EtOAc and water. The layers were separated and the organic layer was concentrated and purified on a BIOTAGE® (300 g silica gel, eluted with 20 to 100% EtOAc/DCM) to yield (S)-tert-butyl 2-(5-((4-(2-((S)-1-(tert-butoxycarbonyl)pyrrolidin-2-yl)-1H-benzo[d]imidazol-6-yl)phenyl)ethynyl)-1H-imidazol-2-yl)pyrrolidine-1-carboxylate (305 mg) and a mixture of this product with (2S,2'S)-tert-butyl 2,2'-(5,5'-(buta-1,3-diyne-1,4-diyl)bis(1H-imidazole-5,2-diyl))dipyrrolidine-1-carboxylate. The mixture was further purified by preparative HPLC (acetonitrile/water/0.1% TFA) to provide a TFA salt of (S)-tert-butyl 2-(5-((4-(2-((S)-1-(tert-butoxycarbonyl)pyrrolidin-2-yl)-1H-benzo[d]imidazol-6-yl)phenyl)ethynyl)-1H-imidazol-2-yl)pyrrolidine-1-carboxylate (100 mg) and a TFA salt of (2S,2'S)-tert-butyl 2,2'-(5,5'-(buta-1,3-diyne-1,4-diyl)bis(1H-imidazole-5,2-diyl))dipyrrolidine-1-carboxylate (128 mg) as white solid.

LC-MS retention time 1.178 min; m/z 521.20 (MH$^+$). LC data was recorded on a Shimadzu LC-10AS liquid chromatograph equipped with a Sunfire 5 u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% $CH_3CN$/90% $H_2O$/0.1% TFA and Solvent B was 10% $H_2O$/90% $CH_3CN$/0.1% TFA. MS data was determined using a MICROMASS® Platform for LC in electrospray mode. $^1$H NMR (500 MHz, MeOD) δ ppm 7.77 (br s, 2H), 4.97 (br s, 2H), 3.62 (br s, 2H), 3.51 (br s, 2H), 2.43 (br s, 2H), 2.01 (br s, 6H), 1.46 (br s, 9H), 1.28 (br s, 9H).

Intermediate 23

1,4-Bis(2-((S)-pyrrolidin-2-yl)-1H-imidazol-5-yl)buta-1,3-diyne

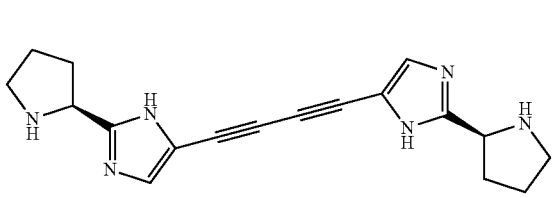 [SMILES: C(C#Cc1cnc([C@@H]2CCCN2)[nH]1)#Cc1cnc([C@@H]2CCCN2)[nH]1]

TFA (2.0 mL, 26 mmol) was added to a solution of (2S,2'S)-tert-butyl 2,2'-(5,5'-(buta-1,3-diyne-1,4-diyl)bis(1H-imidazole-5,2-diyl))dipyrrolidine-1-carboxylate (128 mg) in DCM (10 mL) and the mixture was stirred for 3 h at rt. The reaction was concentrated and purified by preparative HPLC (acetonitrile/water/0.1% TFA) to provide a TFA salt of 1,4-bis(2-((S)-pyrrolidin-2-yl)-1H-imidazol-5-yl)buta-1,3-diyne (94.5 mg) as tan solid.

LC-MS retention time 0.558 min; m/z 321.10 (MH+). LC data was recorded on a Shimadzu LC-10AS liquid chromatograph equipped with a Sunfire 5 u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% $CH_3CN$/90% $H_2O$/0.1% TFA and Solvent B was 10% $H_2O$/90% $CH_3CN$/0.1% TFA. MS data was determined using a MICROMASS® Platform for LC in electrospray mode. $^1$H NMR (500 MHz, MeOD) δ ppm 7.47-7.60 (m, 2H), 4.72-4.87 (m, 2H), 3.36-3.53 (m, 4H), 2.42-2.57 (m, 2H), 2.20-2.35 (m, 4H), 2.06-2.20 (m, 2H).

Example 29

Dimethyl (1R,1'R)-2,2'-((2S,2'S)-2,2'-(5,5'-(buta-1,3-diyne-1,4-diyl)bis(1H-imidazole-5,2-diyl))bis(pyrrolidine-2,1-diyl))bis(2-oxo-1-phenylethane-2,1-diyl) dicarbamate

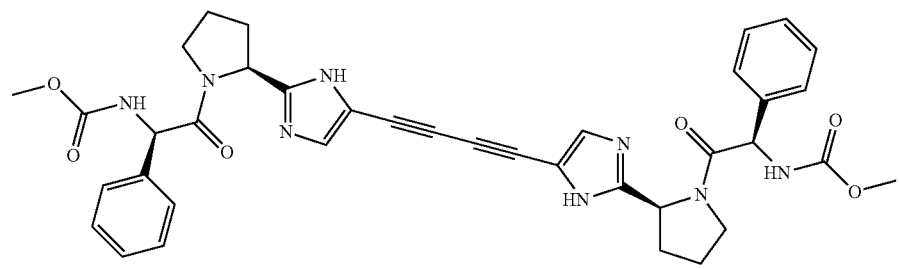

HATU (29.4 mg, 0.077 mmol) was added to a stirring solution of a TFA salt of 1,4-bis(2-((S)-pyrrolidin-2-yl)-1H-imidazol-5-yl)buta-1,3-diyne (20 mg), (R)-2-(methoxycarbonylamino)-2-phenylacetic acid (16.2 mg, 0.077 mmol) and DIEA (0.045 mL, 0.26 mmol) in DMF (2 mL) and the reaction was stirred 5 h at RT. The crude reaction was concentrated to dryness and purified by preparative HPLC (acetonitrile/water/0.1% TFA) to provide a TFA salt dimethyl (1R,1'R)-2,2'-((2S,2'S)-2,2'-(5,5'-(buta-1,3-diyne-1,4-diyl)bis(1H-imidazole-5,2-diyl))bis(pyrrolidine-2,1-diyl))bis(2-oxo-1-phenylethane-2,1-diyl)dicarbamate (16.5 mg) as orange solid.

LC-MS retention time 1.222 min; m/z 703.10 (MH+). LC data was recorded on a Shimadzu LC-10AS liquid chromatograph equipped with an XTERRA® C18 S7 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% $H_2O$/0.1% TFA and Solvent B was 10% $H_2O$/90% MeOH/0.1% TFA. MS data was determined using a MICROMASS® Platform for LC in electrospray mode. $^1$H NMR (500 MHz, MeOD) δ ppm 7.68-7.82 (m, 2H), 7.18-7.48 (m, 10H), 5.48-5.55 (m, 2H), 5.17-5.23 (m, 2H), 3.94-4.02 (m, 2H), 3.64-3.70 (m, 8H), 1.90-2.36 (m, 8H).

Example 30

(2R,2'R)-1,1'-((2S,2'S)-2,2'-(5,5'-(Buta-1,3-diyne-1,4-diyl)bis(1H-imidazole-5,2-diyl))bis(pyrrolidine-2,1-diyl))bis(2-phenyl-2-(piperidin-1-yl)ethanone)

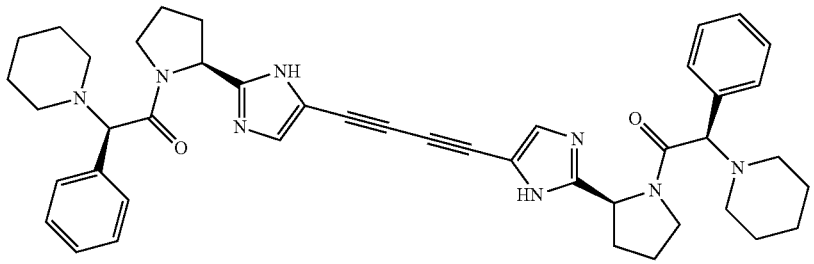 [SMILES: O=C([C@@H](c1ccccc1)N1CCCCC1)N1CCC[C@H]1c1ncc(C#CC#Cc2cnc([C@@H]3CCCN3C(=O)[C@@H](c3ccccc3)N3CCCCC3)[nH]2)[nH]1]

HATU (29.4 mg, 0.077 mmol) was added to a stirring solution of a TFA salt of 1,4-bis(2-((S)-pyrrolidin-2-yl)-1H-imidazol-5-yl)buta-1,3-diyne (20 mg), (R)-2-phenyl-2-(piperidin-1-yl)acetic acid (16.9 mg, 0.077 mmol) and DIEA (0.045 mL, 0.26 mmol) in DMF (2 mL) and the reaction was stirred 5 h at RT. The crude reaction was concentrated to dryness and purified by preparative HPLC (acetonitrile/water/0.1% TFA) and then repurified by preparative HPLC (acetonitrile/water/10 mM ammonium acetate) to yield (2R,2'R)-1,1'-((2S,2'S)-2,2'-(5,5'-(buta-1,3-diyne-1,4-diyl)bis(1H-imidazole-5,2-diyl))bis(pyrrolidine-2,1-diyl))bis(2-phenyl-2-(piperidin-1-yl)ethanone) (1.5 mg) as beige solid.

LC-MS retention time 0.950 min; m/z 723.39 (MH+). LC data was recorded on a Shimadzu LC-10AS liquid chromatograph equipped with a Sunfire 5 u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% $CH_3CN$/90% $H_2O$/0.1% TFA and Solvent B was 10% $H_2O$/90% $CH_3CN$/0.1% TFA. MS data was determined using a MICROMASS® Platform for LC in electrospray mode.

Example 31

Dimethyl (2S,2'S)-1,1'-((2S,2'S)-2,2'-(5,5'-(buta-1,3-diyne-1,4-diyl)bis(1H-imidazole-5,2-diyl))bis(pyrrolidine-2,1-diyl))bis(3-methyl-1-oxobutane-2,1-diyl)dicarbamate

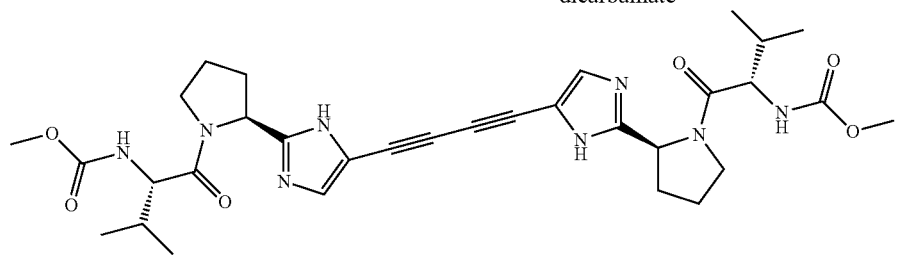

HATU (29.4 mg, 0.077 mmol) was added to a stirring solution of a TFA salt of 1,4-bis(2-((S)-pyrrolidin-2-yl)-1H-imidazol-5-yl)buta-1,3-diyne (20 mg), (S)-2-(methoxycarbonylamino)-3-methylbutanoic acid (13.54 mg, 0.077 mmol) and DIEA (0.045 mL, 0.26 mmol) in DMF (2 mL) and the reaction was stirred 5 h at RT. The crude reaction was concentrated to dryness and purified by preparative HPLC (acetonitrile/water/0.1% TFA) and then repurified by preparative HPLC (acetonitrile/water/10 mM ammonium acetate) to yield a TFA salt of dimethyl (2S,2'S)-1,1'-((2S,2'S)-2,2'-(5,5'-(buta-1,3-diyne-1,4-diyl)bis(1H-imidazole-5,2-diyl))bis(pyrrolidine-2,1-diyl))bis(3-methyl-1-oxobutane-2,1-diyl)dicarbamate (10.3 mg) as yellow solid.

LC-MS retention time 1.060 min; m/z 635.13 (MH+). LC data was recorded on a Shimadzu LC-10AS liquid chromatograph equipped with an XTERRA® C18 S7 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% MeOH/90% $H_2O$/0.1% TFA and Solvent B was 10% $H_2O$/90% MeOH/0.1% TFA. MS data was determined using a MICROMASS® Platform for LC in electrospray mode. $^1$H NMR (500 MHz, MeOD) δ ppm 7.76-7.83 (m, 2H), 5.11-5.17 (m, 2H), 4.22 (d, J=7.0 Hz, 2H), 3.99-4.08 (m, 2H), 3.73-3.88 (m, 2H), 3.72-3.55 (m, 6H), 2.40-2.52 (m, 2H), 2.19-2.31 (m, 2H), 1.96-2.18 (m, 6H), 0.85-1.00 (m, 12H).

Example 32

Dimethyl (2S,2'S)-1,1'-((2S,2'S)-2,2'-(5,5'-(buta-1,3-diyne-1,4-diyl)bis(1H-imidazole-5,2-diyl))bis(pyrrolidine-2,1-diyl))bis(1-oxopropane-2,1-diyl)dicarbamate

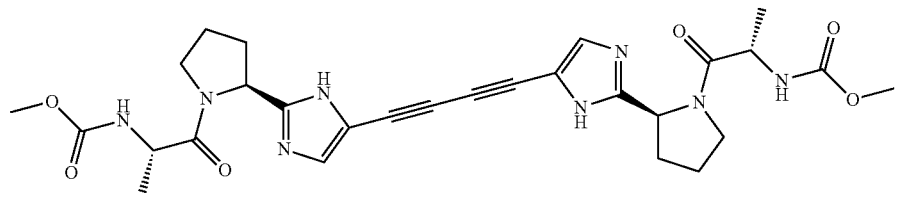

HATU (29.4 mg, 0.077 mmol) was added to a stirring solution of a TFA salt of 1,4-bis(2-((S)-pyrrolidin-2-yl)-1H-imidazol-5-yl)buta-1,3-diyne (20 mg), (S)-2-(methoxycarbonylamino)propanoic acid (11.37 mg, 0.077 mmol) and DIEA (0.045 mL, 0.26 mmol) in DMF (2 mL) and the reaction was stirred 5 h at RT. The crude reaction was concentrated to dryness and purified by preparative HPLC (acetonitrile/water/0.1% TFA) and then repurified by preparative HPLC (acetonitrile/water/10 mM ammonium acetate) to yield a TFA salt of dimethyl (2S,2'S)-1,1'-((2S,2'S)-2,2'-(5,5'-(buta-1,3-diyne-1,4-diyl)bis(1H-imidazole-5,2-diyl))bis(pyrrolidine-2,1-diyl))bis(1-oxopropane-2,1-diyl)dicarbamate (13.1 mg) as yellow solid.

LC-MS retention time 0.727 min; m/z 579.24 (MH+). LC data was recorded on a Shimadzu LC-10AS liquid chromatograph equipped with a Sunfire 5 u C18 4.6×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 10% $CH_3CN$/90% $H_2O$/0.1% TFA and Solvent B was 10% $H_2O$/90% $CH_3CN$/0.1% TFA. MS data was determined using a MICROMASS® Platform for LC in electrospray mode.

Example 33

Scheme 12

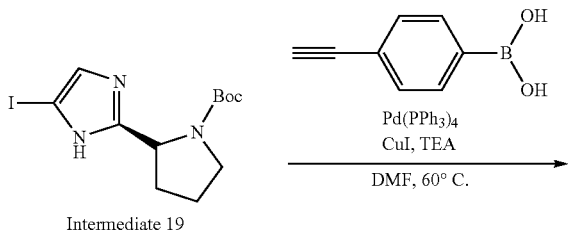

Intermediate 19

-continued

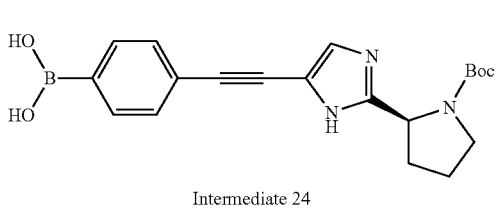

Intermediate 24

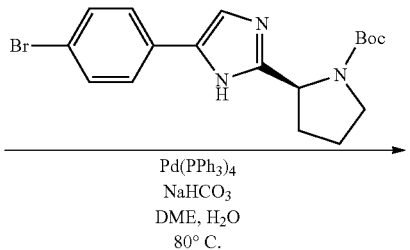

Pd(PPh₃)₄
NaHCO₃
DME, H₂O
80° C.

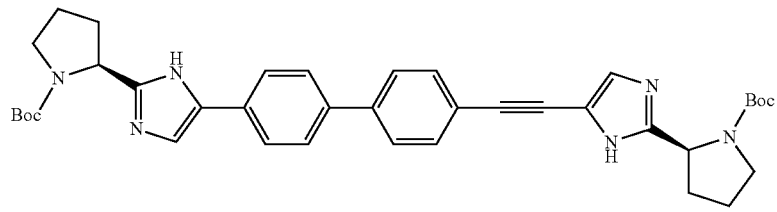

Intermediate 25

TFA
DCE

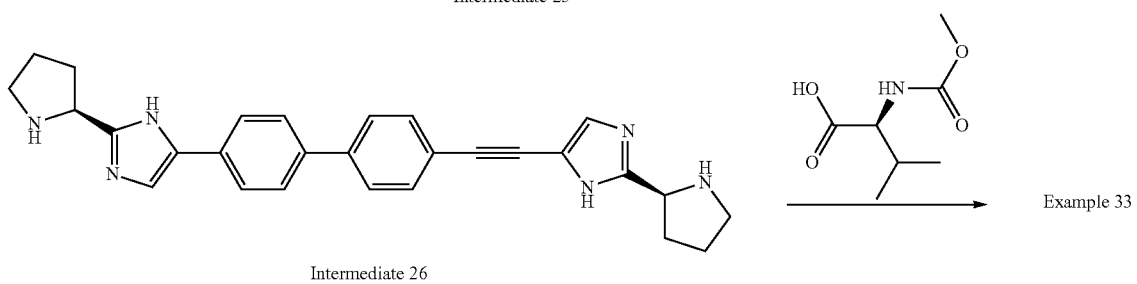

Intermediate 26

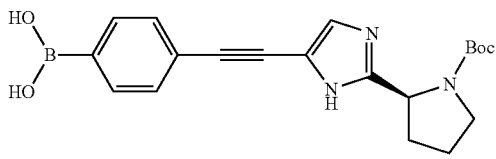 [SMILES: CC(C)(C)OC(=O)N1CCC[C@H]1c1ncc(C#Cc2ccc(B(O)O)cc2)[nH]1]

Example 33

Intermediate 24

(S)-4-((2-(1-(tert-Butoxycarbonyl)pyrrolidin-2-yl)-1H-imidazol-5-yl)ethynyl)phenylboronic acid

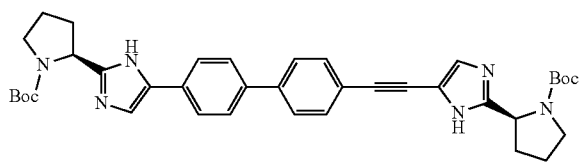 [SMILES: CC(C)(C)OC(=O)N1CCC[C@H]1c1ncc(C#Cc2ccc(-c3ccc(-c4cnc([C@@H]5CCCN5C(=O)OC(C)(C)C)[nH]4)cc3)cc2)[nH]1]

Nitrogen was bubbled through a solution of (S)-tert-butyl 2-(5-iodo-1H-imidazol-2-yl)pyrrolidine-1-carboxylate (150 mg, 0.41 mmol), 4-ethynylphenylboronic acid (90 mg, 0.62 mmol) and copper(I) iodide (15.7 mg, 0.083 mmol) in DMF (5 mL) and triethylamine (0.30 mL, 2.0 mmol) for 15 min. Then Pd(PPh₃)₄ (23.86 mg, 0.021 mmol) was added and the reaction mixture was vacuum flushed with nitrogen (4×,), sealed and heated at 60° C. ON. The crude reaction was concentrated to dryness, dissolved into DMF/MeOH and purified by Prep HPLC (MeOH/water with ammonium acetate buffer) to yield (S)-4-((2-(1-(tert-butoxycarbonyl)pyrrolidin-2-yl)-1H-imidazol-5-yl)ethynyl)phenylboronic acid (113.8 mg, 0.299 mmol) as a light yellow solid.

LC-MS retention time 2.152 min; m/z 380.30 (MH−). LC data was recorded on a Shimadzu LC-10AS liquid chromatograph equipped with a PHENOMENEX® Luna 10 u C18 3.0×50 mm column using a SPD-10AV UV-Vis detector at a detector wave length of 220 nM. The elution conditions employed a flow rate of 5 ml/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H₂O/10 mM ammonium acetate and Solvent B was 5% H₂O/95% MeOH/10 mM ammonium acetate. MS data was determined using a MICROMASS® Platform for LC in electrospray mode. ¹H NMR (400 MHz, MeOD) δ ppm 7.65 (br d, J=6.8 Hz, 4H), 7.44 (d, J=7.8 Hz, 4H), 7.24 (s, 2H), 3.71-3.59 (m, 2H), 3.53-3.42 (m, 2H), 2.40-2.20 (m, 2H), 2.09-1.88 (m, 8H), 1.27 (s, 9H).

Intermediate 25

(S)-tert-Butyl 2-(5-((4'-(2-((S)-1-(tert-butoxycarbonyl)pyrrolidin-2-yl)-1H-imidazol-5-yl)biphenyl-4-yl)ethynyl)-1H-imidazol-2-yl)pyrrolidine-1-carboxylate Nitrogen was bubbled through a solution of (S)-4-((2-(1-(tert-butoxycarbonyl)pyrrolidin-2-yl)-1H-imidazol-5-yl)ethynyl)phenylboronic acid (26.6 mg), (S)-tert-butyl 2-(4-(4-bromophenyl)-1H-imidazol-2-yl)pyrrolidine-1-carboxylate (30.1 mg, 0.077 mmol, for its preparation, see PCT Publication No. WO 2008/021927) and sodium bicarbonate (29.3 mg, 0.349 mmol) in DME (1.5 mL) and water (0.30 mL) for 15 min. Then Pd(PPh₃)₄ (4.0 mg, 3.5 μmol) was added and the reaction was vacuum flushed with nitrogen (4×), sealed and heated at 80° C. for 1 d. The reaction was concentrated with a stream of nitrogen, dissolved into DMF/MeOH and purified by prep. HPLC (MeOH/water 10 mM ammonium acetate) to yield (S)-tert-butyl 2-(5-((4'-(2-((S)-1-(tert-butoxycarbonyl)pyrrolidin-2-yl)-1H-imidazol-4-yl)biphenyl-4-yl)ethynyl)-1H-imidazol-2-yl)pyrrolidine-1-carboxylate (17.8 mg, 0.027 mmol)) as a yellow solid.

LC-MS retention time 2.725 min; m/z 647.62 (MH−). LC data was recorded on a Shimadzu LC-10AS liquid chromatograph equipped with a PHENOMENEX® Luna 10 u C18 3.0×50 mm column using a SPD-10AV UV-Vis detector at a detector wave length of 220 nM. The elution conditions employed a flow rate of 5 ml/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, MeOD) δ ppm 7.78 (d, J=8.5 Hz, 2H), 7.67 (d, J=8.0 Hz, 4H), 7.55 (d, J=8.3 Hz, 2H), 7.37 (s, 1H), 7.26 (s, 1H), 5.03-4.85 (m, 2H), 3.74-3.60 (m, 2H), 3.57-3.43 (m, 2H), 2.46-2.23 (m, 2H), 2.13-1.89 (m, 6H) 1.55-1.19 (m, 18H).

Intermediate 26

2-((S)-Pyrrolidin-2-yl)-5-((4'-(2-((S)-pyrrolidin-2-yl)-1H-imidazol-5-yl)biphenyl-4-yl)ethynyl)-1H-imidazole

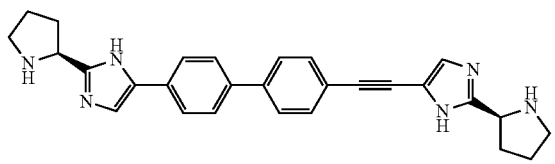 [SMILES: C(#Cc1cnc([C@@H]2CCCN2)[nH]1)c1ccc(-c2ccc(-c3cnc([C@@H]4CCCN4)[nH]3)cc2)cc1]

TFA (0.25 mL, 3.2 mmol) was added to a stirring solution of (S)-tert-butyl 2-(5-((4'-(2-((S)-1-(tert-butoxycarbonyl)pyrrolidin-2-yl)-1H-imidazol-4-yl)biphenyl-4-yl)ethynyl)-1H-imidazol-2-yl)pyrrolidine-1-carboxylate (17.8 mg) in DCE (1 mL) and stirred at rt for 1 h. The crude reaction was concentrated to yield a TFA salt of 2-((S)-pyrrolidin-2-yl)-5-((4'-(2-((S)-pyrrolidin-2-yl)-1H-imidazol-4-yl)biphenyl-4-yl)ethynyl)-1H-imidazole (24 mg).

LC-MS retention time 2.268 min; m/z 449.22 (MH−). LC data was recorded on a Shimadzu LC-10AS liquid chromatograph equipped with a PHENOMENEX® Luna 10 u C18 3.0×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, MeOD) δ ppm 7.89 (d, J=8.5 Hz, 2H), 7.83 (s, 1H), 7.77 (d, J=8.5 Hz, 2H), 7.72 (d, J=8.5 Hz, 2H), 7.60 (d, J=8.5 Hz, 2H), 7.49 (s, 1H), 5.07 (dd, J=7.5, 9.0 Hz, 1H), 4.96-4.83 (m, 1H) (masked by solvent peak), 3.62-3.42 (m, 4H), 2.71-2.11 (m, 8H).

Example 33

Methyl ((1S)-1-(((2S)-2-(4-(4'-((2-((2S)-1-((2S)-2-((methoxycarbonyl)amino)-3-methylbutanoyl)-2-pyrrolidinyl)-1H-imidazol-4-yl)ethynyl)-4-biphenylyl)-1H-imidazol-2-yl)-1-pyrrolidinyl)carbonyl)-2-methylpropyl)carbamate

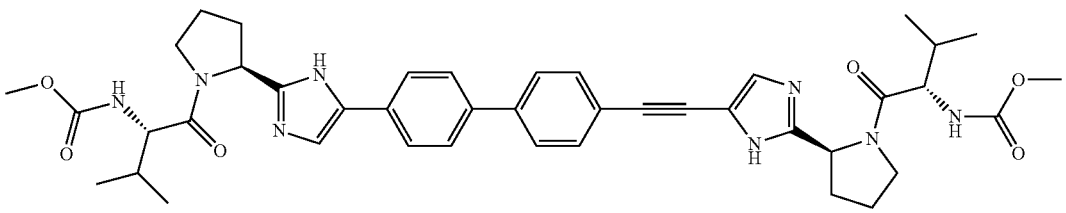

HATU (30.8 mg, 0.081 mmol) was added to a stirring solution of a TFA salt of 2-((S)-pyrrolidin-2-yl)-5-((4'-(2-((S)-pyrrolidin-2-yl)-1H-imidazol-4-yl)biphenyl-4-yl)ethynyl)-1H-imidazole (24 mg) and (S)-2-(methoxycarbonylamino)-3-methylbutanoic acid (14.2 mg, 0.081 mmol) in DMF (0.5 mL) and TEA (0.023 mL, 0.16 mmol) and stirred 1 h. Then the reaction was diluted with MeOH, filtered and purified by prep HPLC (MeOH/water w/10 mM ammonium acetate) to yield methyl ((1S)-1-(((2S)-2-(4-(4'-((2-((2S)-1-((2S)-2-((methoxycarbonyl)amino)-3-methylbutanoyl)-2-pyrrolidinyl)-1H-imidazol-4-yl)ethynyl)-4-biphenylyl)-1H-imidazol-2-yl)-1-pyrrolidinyl)carbonyl)-2-methylpropyl)carbamate (13.3 mg) as a light yellow solid.

LC-MS retention time 2.502 min; m/z 763.56 (MH+). LC data was recorded on a Shimadzu LC-10AS liquid chromatograph equipped with a PHENOMENEX® Luna 10 u C18 3.0×50 mm column using a SPD-10AV UV-Vis detector at a detector wave length of 220 nM. The elution conditions employed a flow rate of 5 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. Complex mixture of rotamers. $^1$H NMR (400 MHz, MeOD) δ ppm 7.84-7.73 (m, 2H), 7.70-7.64 (m, 4H), 7.58-7.52 (m, 2H), 7.40-7.21 (m, 2H), 5.37-5.08 (m, 2H), 4.26-3.79 (m, 6H), 3.70-3.48 (m, 6H), 2.48-1.95 (m, 10H), 1.02-1.87 (m, 12H).

Example 34

Dimethyl (1,3-butadiyne-1,4-diylbis(1H-imidazole-4,2-diyl(1R,3S,5R)-2-azabicyclo[3.1.0]hexane-3,2-diyl((1S)-2-oxo-1-(tetrahydro-2H-pyran-4-yl)-2,1-ethanediyl)))biscarbamate

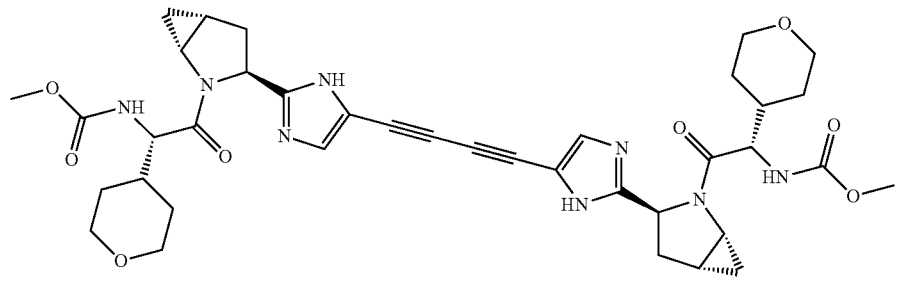

A TFA salt of the title compound (9 mg) was prepared in an analogous manner to Examples 29-32, utilizing 1,4-bis(2-((1R,3S,5R)-2-azabicyclo[3.1.0]hexan-3-yl)-1H-imidazol-5-yl)buta-1,3-diyne and (S)-2-(methoxycarbonylamino)-2-(tetrahydro-2H-pyran-4-yl)acetic acid as starting materials. 1,4-bis(2-((1R,3S,5R)-2-azabicyclo[3.1.0]hexan-3-yl)-1H-imidazol-5-yl)buta-1,3-diyne was prepared in an analogous manner to Intermediate 23, utilizing (1R,3S,5R)-tert-butyl 3-(1H-imidazol-2-yl)-2-azabicyclo[3.1.0]hexane-2-carboxylate as a starting material.

LC-MS retention time 2.407 min; m/z 743.68 (MH+). LC data was recorded on a Shimadzu LC-10AS liquid chromatograph equipped with a PHENOMENEX® Luna 3 u C18 2.0×50 mm column using a SPD-10AV UV-Vis detector at a detector wave length of 220 nM. The elution conditions employed a flow rate of 0.8 mL/min, a gradient of 100% Solvent A/0% Solvent B to 0% Solvent A/100% Solvent B, a gradient time of 4 min, a hold time of 1 min, and an analysis time of 5 min where Solvent A was 10% MeOH/90% $H_2O$/0.1% trifluoroacetic acid and Solvent B was 10% $H_2O$/90% MeOH/0.1% trifluoroacetic acid. MS data was determined using a MICROMASS® Platform for LC in electrospray mode. $^1$H NMR (400 MHz, MeOD) δ ppm 7.71 (s, 1H), 5.04 (dd, J=9.0, 6.0 Hz, 1H), 4.57 (d, J=7.5 Hz, 1H), 3.89-4.00 (m, 4H), 3.67-3.76 (m, 4H), 3.66 (s, 6H), 3.34-3.43 (m, 4H), 2.48-2.56 (m, 2H), 2.36-2.45 (m, 2H), 1.97-2.08 (m, 4H), 1.53-1.62 (m, 2H), 1.35-1.53 (m, 6H), 1.03-1.12 (m, 2H), 0.82 (br. s., 2H).

Scheme 13

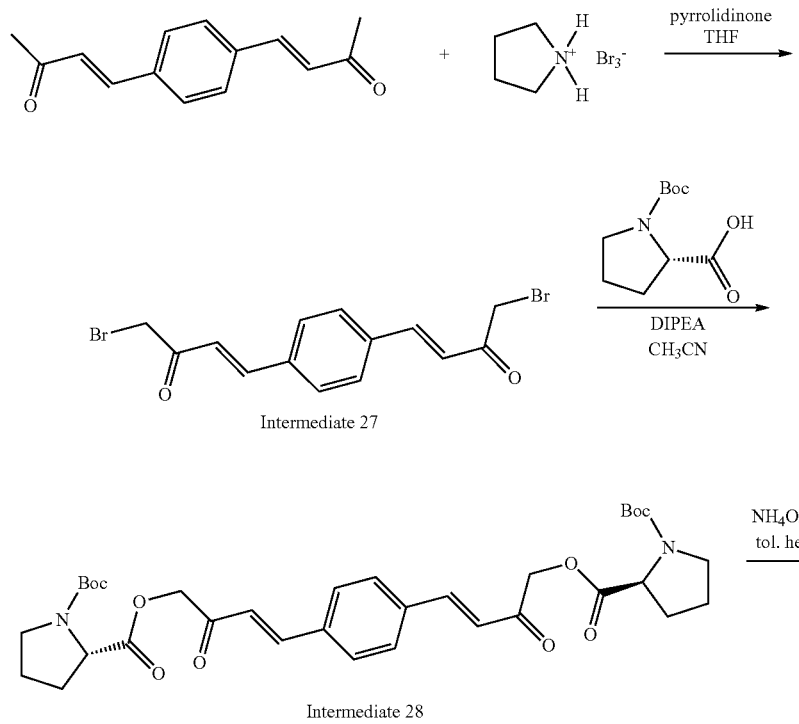

-continued

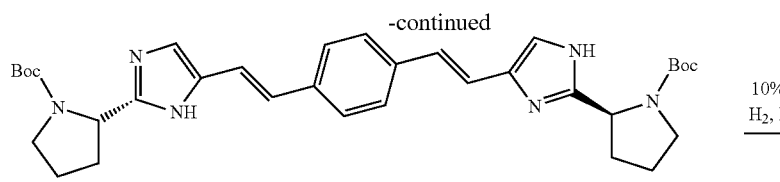

Intermediate 29

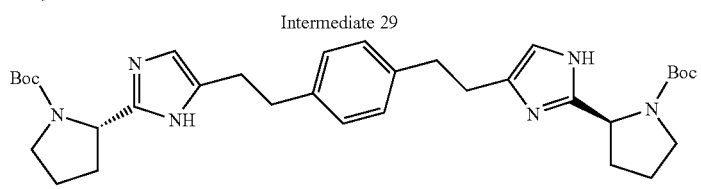

Intermediate 30

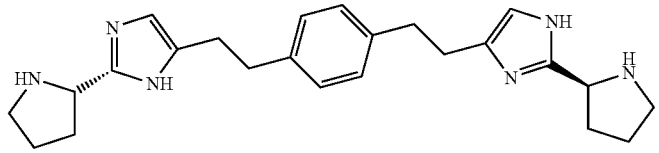

Intermediate 31

Intermediate 27

(3E,3'E)-4,4'-(1,4-phenylene)bis(1-bromobut-3-en-2-one)

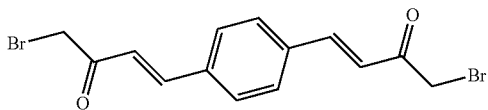 [SMILES: O=C(/C=C/c1ccc(/C=C/C(=O)CBr)cc1)CBr]

Pyrrolidine hydrotribromide (18.55 g, 37.4 mmol) in THF (375 mL) was added via a slow stream to a stirred solution of (3E,3'E)-4,4'-(1,4-phenylene)dibut-3-en-2-one (4.00 g, 18.7 mmol) (prepared according to a procedure in Pharmazie (1986), 41(6), 430-1 from terephthalaldehyde and acetone) and pyrrolidinone (2.84 mL, 37.4 mmole) in THF (185 mL) at rt and under argon. The reaction mixture was stirred in the dark for 2 h, filtered (flushed with THF), and the filtrate was concentrated. The residue was slurried with DCM, filtered and the solids were triturated with DCM to yield (3E,3'E)-4,4'-(1,4-phenylene)bis(1-bromobut-3-en-2-one) (4.63 g) as a yellow solid. The material was used without further purification.

LC-MS retention time 1.912 min; m/z 742.33 (2 MH−). PHENOMENEX® Luna 5 u C18 4.6×30 mm column using a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% acetonitrile/90% $H_2O$/5 nM ammonium acetate and Solvent B was 10% $H_2O$/90% acetonitrile/5 mM ammonium acetate.

Intermediate 28

(2S,2'S)-'2,2-((3E,3'E)-4,4'-(1,4-phenylene)bis(2-oxobut-3-ene-4,1-diyl)) 1-tert-butyl dipyrrolidine-1,2-dicarboxylate

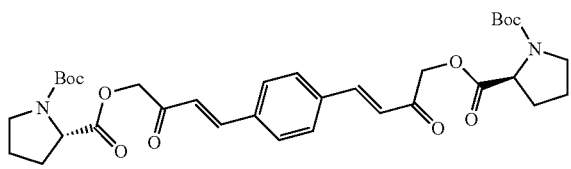 [SMILES: CC(C)(C)OC(=O)N1CCC[C@H]1C(=O)OCC(=O)/C=C/c1ccc(/C=C/C(=O)COC(=O)[C@@H]2CCCN2C(=O)OC(C)(C)C)cc1]

DIEA (1 mL) was added to a stirred solution of (3E,3'E)-4,4'-(1,4-phenylene)bis(1-bromobut-3-en-2-one) (1.2 g, 3.22 mmoles) and (S)-1-(tert-butoxycarbonyl)pyrrolidine-2-carboxylic acid (1.39 g, 6.44 mmoles) in 15 mL acetonitrile and then the reaction mixture was stirred under argon for 16 hrs. The reaction mixture was diluted with ethyl acetate (100 mL) and water (100 mL) and the layers were separated. The aqueous phase was extracted with ethyl acetate (3×50 mL) and the combined organic phases were washed with water (2×100 mL) and brine (100 mL), dried over magnesium sulfate and filtered. The organic solvent was removed under vacuum to yield (2S,2'S)-'2,2-((3E,3'E)-4,4'-(1,4-phenylene)bis(2-oxobut-3-ene-4,1-diyl)) 1-tert-butyl dipyrrolidine-1,2-dicarboxylate (1.52 g) as a foam. The compound was used without further purification.

LC-MS retention time 2.235 min; m/z 639.06 (MH−). PHENOMENEX® Luna 5 u C18 4.6×30 mm column using a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% acetonitrile/90% $H_2O$/0.1% ammonium acetate and Solvent B was 10% $H_2O$/90% acetonitrile/0.1 ammonium acetate.

Intermediate 29

(2S,2'S)-tert-butyl 2,2'-(4,4'-(1E,1'E)-2,2'-(1,4-phenylene)bis(ethene-2,1-diyl)bis(1H-imidazole-4,2-diyl))dipyrrolidine-1-carboxylate

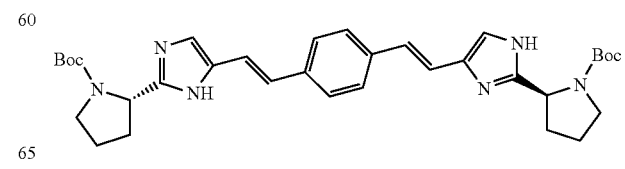

Ammonium acetate (1.8 g) was added to a solution of (2S,2'S)-'2,2-((3E,3'E)-4,4'-(1,4-phenylene)bis(2-oxobut-3-ene-4,1-diyl)) 1-tert-butyl dipyrrolidine-1,2-dicarboxylate ((1.5 g, 2.34 mmoles, 77% pure) in toluene (40 mL). The reaction mixture was heated at reflux and water was removed via a Dean-Stark trap. Once the reaction was complete, the reaction mixture was evaporated under vacuum and the residue was dissolved into ethyl acetate (250 mL) and washed with aqueous sodium carbonate (3×100 mL), water (100 mL) and brine (100 mL). The organic layer was dried over magnesium sulfate, filtered and concentrated. The residue was purified on a BIOTAGE® (0-10% methanol in ethyl acetate) to yield (2S,2'S)-tert-butyl 2,2'-(4,4'-(1E,1'E)-2,2'-(1,4-phenylene)bis(ethene-2,1-diyl)bis(1H-imidazole-4,2-diyl)) dipyrrolidine-1-carboxylate (305 mg).

LC-MS retention time 1.318 min; m/z 601 (MH+). PHENOMENEX® Luna 5 u C18 4.6×30 mm column using a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% acetonitrile/90% $H_2O$/0.05% TFA and Solvent B was 10% $H_2O$/90% acetonitrile/0.05% TFA.

Intermediate 30

(2S,2'S)-tert-butyl 2,2'-(4,4'-(2,2'-(1,4-phenylene)bis(ethane-2,1-diyl))bis(1H-imidazole-4,2-diyl))dipyrrolidine-1-carboxylate

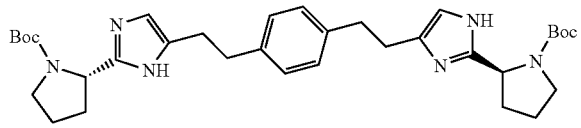 [SMILES: CC(C)(C)OC(=O)N1CCC[C@H]1c1nc(CCc2ccc(CCc3cnc([C@@H]4CCCN4C(=O)OC(C)(C)C)[nH]3)cc2)c[nH]1]

A solution (2S,2'S)-tert-butyl 2,2'-(4,4'-(1E,1'E)-2,2'-(1,4-phenylene)bis(ethene-2,1-diyl)bis(1H-imidazole-4,2-diyl)) dipyrrolidine-1-carboxylate (500 mg) and 10% Pd-on-C (500 mg) in methanol (50 mL) was stirred under a balloon of hydrogen for 3 hrs. The reaction mixture was filtered through CELITE® and the cake washed with methanol (5×5 mL). The filtrate was concentrated under vacuum to yield (2S,2'S)-tert-butyl 2,2'-(4,4'-(2,2'-(1,4-phenylene)bis(ethane-2,1-diyl))bis(1H-imidazole-4,2-diyl))dipyrrolidine-1-carboxylate (419 mg) as a pale yellow solid. The material was used without further purification.

LC-MS retention time 1.280 min; m/z 605 (MH+). PHENOMENEX® Luna 5 u C18 4.6×30 mm column using a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% acetonitrile/90% $H_2O$/0.05% TFA and Solvent B was 10% $H_2O$/90% acetonitrile/0.05% TFA.

Intermediate 31

1-(2-(2-((S)-pyrrolidin-2-yl)-1H-imidazol-4-yl)ethyl)-4-(2-(2-((S)-pyrrolidin-2-yl)-1H-imidazol-5-yl)ethyl)benzene

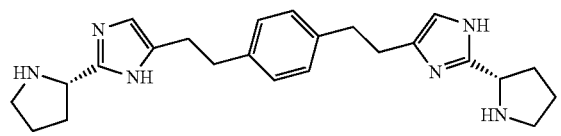 [SMILES: c1cc(CCc2cnc([C@@H]3CCCN3)[nH]2)ccc1CCc1c[nH]c([C@@H]2CCCN2)n1]

TFA (91 mL) was added to a stirred solution of (2S,2'S)-tert-butyl 2,2'-(4,4'-(2,2'-(1,4-phenylene)bis(ethane-2,1-diyl))bis(1H-imidazole-4,2-diyl))dipyrrolidine-1-carboxylate (416 mg, 0.069 mmole) in dichloromethane (10 mL) and the reaction was stirred at rt for 2 h. Additional TFA (0.5 mL) was added and the stirring was continued for another 2 h. The reaction mixture was dried under vacuum to yield a TFA salt of the desired product as an opaque red oil. The crude product was loaded onto an OASIS® MCX ion exchange cartridge (35 cc, 6 g) with dichloromethane/methanol and then the product was eluted in the form of the free base with a solution of 2M $NH_3$ in methanol. The fractions containing the desired product were combined and evaporated under vacuum to yield 1-(2-(2-((S)-pyrrolidin-2-yl)-1H-imidazol-4-yl)ethyl)-4-(2-(2-((S)-pyrrolidin-2-yl)-1H-imidazol-5-yl)ethyl)benzene (325 mg) as a yellow oil.

LC-MS retention time 0.152 min and 0.432 min; m/z 405 and 405 (MH+). PHENOMENEX® Luna 5 u C18 4.6×30 mm column using a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% acetonitrile/90% $H_2O$/0.05% TFA and Solvent B was 10% $H_2O$/90% acetonitrile/0.05% TFA. $^1$H NMR (400 MHz, MeOD) δ ppm 7.09 (s, 4H), 6.62 (s, 2H), 4.20 (t, J=7.0 Hz, 2H), 3.18-2.77 (m, 12H), 2.25-2.10 (m, 2H), 2.02-1.75 (m, 8H).

Intermediate 32

1-((E)-2-(2-((S)-pyrrolidin-2-yl)-1H-imidazol-4-yl)vinyl)-4-((E)-2-(2-((S)-pyrrolidin-2-yl)-1H-imidazol-5-yl)vinyl)benzene

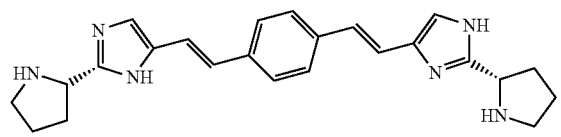

Trifluoroacetic acid (1 mL) was added to a stirred solution of (2S,2'S)-tert-butyl 2,2'-(4,4'-(1E,1'E)-2,2'-(1,4-phenylene) bis(ethene-2,1-diyl)bis(1H-imidazole-4,2-diyl))dipyrrolidine-1-carboxylate (500 mg, 0.83 mmoles) in dichloromethane (10 mL) at room temperature and the reaction mixture was stirred for 2 h. Additional trifluoroacetic acid (0.5 mL) was added and the reaction was stirred for an additional 2 h. The reaction mixture was dried under vacuum to yield a TFA salt of the desired product as an opaque red oil. The crude product was absorbed onto an OASIS® MCS ion exchange cartridge 35 mL (6 g) with dichloromethane/methanol and the product was retrieved in the form of the free base with a solution of 2M $NH_3$ in methanol. The fractions containing the desired product are combined and concentrated to yield 1-((E)-2-(2-((S)-pyrrolidin-2-yl)-1H-imidazol-4-yl)vinyl)-4-((E)-2-(2-((S)-pyrrolidin-2-yl)-1H-imidazol-5-yl)vinyl)benzene (325 mg) as a yellow oil.

LC-MS retention time 0.150 min and 0.855 min; m/z 401 and 401 (MH+). PHENOMENEX® Luna 5 u C18 4.6×30 mm column using a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% acetonitrile/90% $H_2O$/0.05% TFA and Solvent B was 10% $H_2O$/90% acetonitrile/0.05% TFA. $^1$H NMR (400 MHz, MeOD) δ ppm 7.47 (s, 4H), 7.10 (s, 2H), 7.04 (s, 4H), 4.32 (t, J=7.3 Hz, 2H), 3.25-3.12 (m, 2H), 3.10-2.95 (m, 2H), 2.35-2.20 (m, 2H), 1.80-2.10 (m, 6H).

Example 35

(1R)-2-((2S)-2-(4-((E)-2-(4-((E)-2-(2-((2S)-1-((2R)-2-(diethylamino)-2-phenylacetyl)-2-pyrrolidinyl)-1H-imidazol-5-yl)vinyl)phenyl)vinyl)-1H-imidazol-2-yl)-1-pyrrolidinyl)-N,N-diethyl-2-oxo-1-phenylethanamine

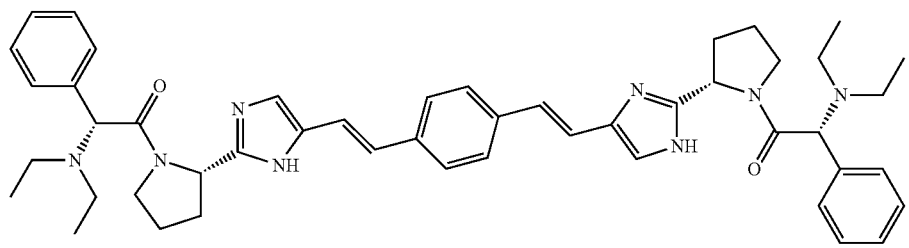 [SMILES: CCN(CC)[C@@H](C(=O)N1CCC[C@H]1c1nc(/C=C/c2ccc(/C=C/c3cnc([C@@H]4CCCN4C(=O)[C@@H](c4ccccc4)N(CC)CC)[nH]3)cc2)c[nH]1)c1ccccc1]

HATU (76 mg, 0.20 mmol) was added to a stirred solution of (R)-2-(diethylamino)-2-phenylacetic acid (49 mg, 0.20 mmol) in DMF (1 mL) and DIPEA (0.14 mL, 0.80 mmole) and the mixture was stirred for 5 minutes. Then a solution of 1-((E)-2-(2-((S)-pyrrolidin-2-yl)-1H-imidazol-4-yl)vinyl)-4-((E)-2-(2-((S)-pyrrolidin-2-yl)-1H-imidazol-5-yl)vinyl) benzene (40 mg, 0.10 mmol) in DMF (1 mL) was added and the resulting solution was stirred under argon for 16 hrs. The reaction mixture was purified directly by HPLC and the resulting TFA salt of the desired product was absorbed onto an SCX ion-exchange cartridge with methanol and liberated with a solution of 2 M $NH_3$ in methanol. The fractions containing the desired product were concentrated to yield (1R)-2-((2S)-2-(4-((E)-2-(4-((E)-2-(2-((2S)-1-((2R)-2-(diethylamino)-2-phenylacetyl)-2-pyrrolidinyl)-1H-imidazol-5-yl) vinyl)phenyl)vinyl)-1H-imidazol-2-yl)-1-pyrrolidinyl)-N,N-diethyl-2-oxo-1-phenylethanamine (35.8 mg) as a pale yellow solid.

LC-MS retention time 1.087 min; m/z 780 (MH+). PHENOMENEX® Luna 5 u C18 4.6×30 mm column using a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% acetonitrile/90% $H_2O$/0.05% TFA and Solvent B was 10% $H_2O$/90% acetonitrile/0.05% TFA.

Example 36 dimethyl (1,4-phenylenebis((E)-2,1-ethenediyl-1H-imidazole-4,2-diyl(2S)-2,1-pyrrolidinediyl((1R)-2-oxo-1-phenyl-2,1-ethanediyl)))biscarbamate

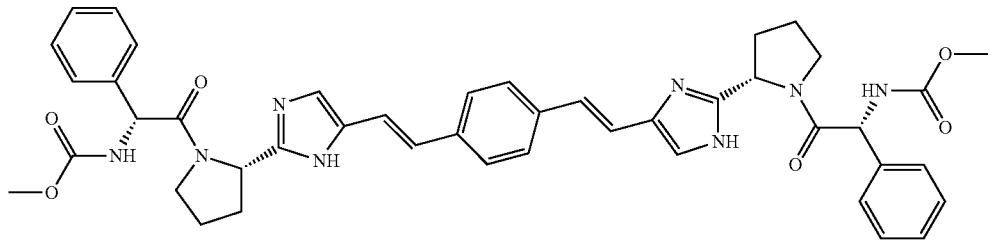

The title compound was prepared in an analogous manner to Example 35 utilizing (R)-2-(methoxycarbonylamino)-2-phenylacetic acid as the carboxylate coupling partner in the amide coupling to yield dimethyl (1,4-phenylenebis((E)-2,1-ethenediyl-1H-imidazole-4,2-diyl(2S)-2,1-pyrrolidinediyl ((1R)-2-oxo-1-phenyl-2,1-ethanediyl)))biscarbamate (26.6 mg) as a pale yellow solid.

LC-MS retention time 1.270 and 1.325 min; m/z 783 and 783 (MH+). PHENOMENEX® Luna 5 u C18 4.6×30 mm column using a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% acetonitrile/90% $H_2O$/0.05% TFA and Solvent B was 10% $H_2O$/90% acetonitrile/0.05% TFA.

Example 37 methyl ((1S)-2-((2S)-2-(4-((E)-2-(4-((E)-2-(2-((2S)-1-(N-(methoxycarbonyl)-L-alanyl)-2-pyrrolidinyl)-1H-imidazol-4-yl)vinyl)phenyl)vinyl)-1H-imidazol-2-yl)-1-pyrrolidinyl)-1-methyl-2-oxoethyl)carbamate

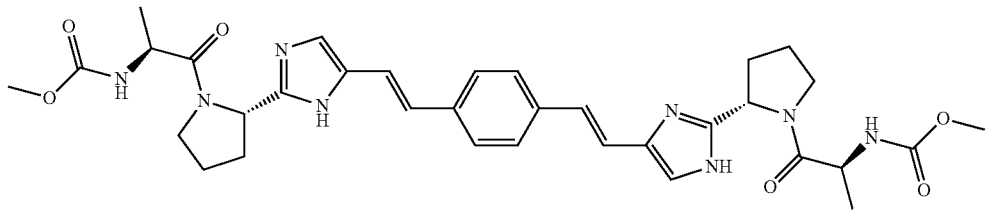

The title compound was prepared in an analogous manner to Example 35 utilizing (S)-2-(methoxycarbonylamino)propanoic acid as the carboxylate coupling partner in the amide coupling to yield methyl ((1S)-2-((2S)-2-(4-((E)-2-(4-((E)-2-(2-((2S)-1-(N-(methoxycarbonyl)-L-alanyl)-2-pyrrolidinyl)-1H-imidazol-4-yl)vinyl)phenyl)vinyl)-1H-imidazol-2-yl)-1-pyrrolidinyl)-1-methyl-2-oxoethyl)carbamate (15.2 mg) as a pale yellow solid.

LC-MS retention time 1.058 min; m/z 659 (MH+). PHENOMENEX® Luna 5 u C18 4.6×30 mm column using a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% acetonitrile/90% $H_2O$/0.05% TFA and Solvent B was 10% $H_2O$/90% acetonitrile/0.05% TFA.

Example 38 methyl ((1S)-1-(((2S)-2-(4-((E)-2-(4-((E)-2-(2-((2S)-1-((2S)-2-((methoxycarbonyl)amino)-3-methylbutanoyl)-2-pyrrolidinyl)-1H-imidazol-4-yl)vinyl)phenyl)vinyl)-1H-imidazol-2-yl)-1-pyrrolidinyl)carbonyl)-2-methylpropyl)carbamate

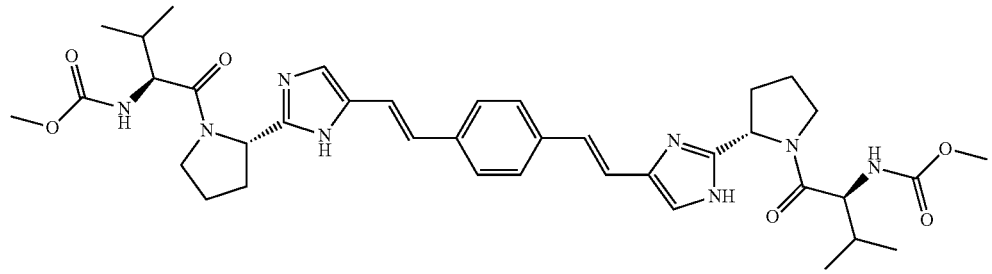

The title compound was prepared in an analogous manner to Example 35 utilizing (S)-2-(methoxycarbonylamino)-3-methylbutanoic acid as the carboxylate coupling partner in the amide coupling to yield methyl ((1S)-1-(((2S)-2-(4-((E)-2-(4-((E)-2-(2-((2S)-1-((2S)-2-((methoxycarbonyl)amino)-3-methylbutanoyl)-2-pyrrolidinyl)-1H-imidazol-4-yl)vinyl)phenyl)vinyl)-1H-imidazol-2-yl)-1-pyrrolidinyl)carbonyl)-2-methylpropyl)carbamate (37.6 mg) as a pale yellow solid.

LC-MS retention time 1.198 min; m/z 715 (MH+). PHENOMENEX® Luna 5 u C18 4.6×30 mm column using a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% acetonitrile/90% H$_2$O/0.05% TFA and Solvent B was 10% H$_2$O/90% acetonitrile/0.05% TFA.

Example 39 methyl ((1S,2R)-2-methoxy-1-(((2S)-2-(4-((E)-2-(4-((E)-2-(2-((2S)-1-(N-(methoxycarbonyl)-O-methyl-L-threonyl)-2-pyrrolidinyl)-1H-imidazol-4-yl)vinyl)phenyl)vinyl)-1H-imidazol-2-yl)-1-pyrrolidinyl)carbonyl)propyl)carbamate

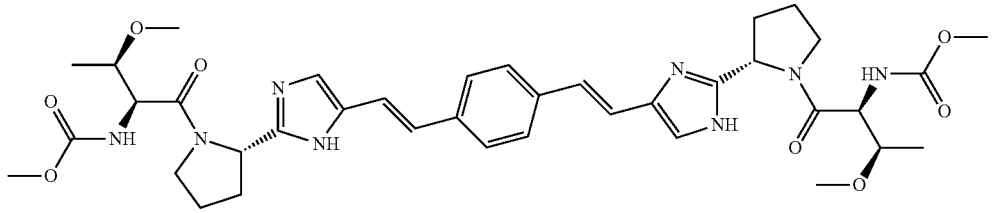

The title compound was prepared in an analogous manner to Example 35 utilizing (2S,3R)-3-methoxy-2-(methoxycarbonylamino)butanoic acid as the carboxylate coupling partner in the amide coupling to yield methyl ((1S,2R)-2-methoxy-1-(((2S)-2-(4-((E)-2-(4-((E)-2-(2-((2S)-1-(N-(methoxycarbonyl)-O-methyl-L-threonyl)-2-pyrrolidinyl)-1H-imidazol-4-yl)vinyl)phenyl)vinyl)-1H-imidazol-2-yl)-1-pyrrolidinyl)carbonyl)propyl)carbamate (21.9 mg) as a pale yellow solid.

LC-MS retention time 1.132 min; m/z 747 (MH+). PHENOMENEX® Luna 5 u C18 4.6×30 mm column using a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% acetonitrile/90% H$_2$O/0.05% TFA and Solvent B was 10% H$_2$O/90% acetonitrile/0.05% TFA.

Example 40

(1R)-2-((2S)-2-(4-(2-(4-(2-(2-((2S)-1-((2R)-2-(diethylamino)-2-phenylacetyl)-2-pyrrolidinyl)-1H-imidazol-5-yl)ethyl)phenyl)ethyl)-1H-imidazol-2-yl)-1-pyrrolidinyl)-N,N-diethyl-2-oxo-1-phenylethanamine

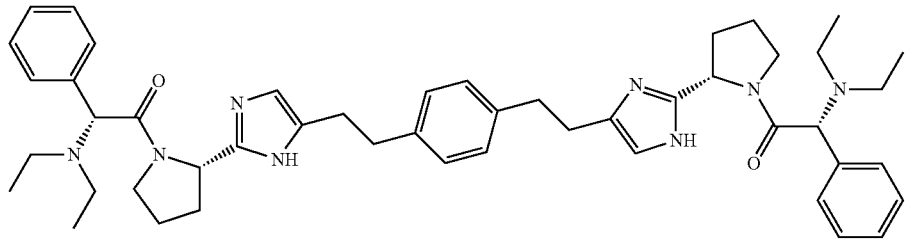 [SMILES: CCN(CC)[C@@H](C(=O)N1CCC[C@H]1c1nc(CCc2ccc(CCc3cnc([C@@H]4CCCN4C(=O)[C@@H](c4ccccc4)N(CC)CC)[nH]3)cc2)c[nH]1)c1ccccc1]

HATU (76 mg, 0.2 mmole) was added to a stirred solution of (R)-2-(diethylamino)-2-phenylacetic acid (49 mg, 0.2 mmole) in DMF (1 mL) and DIEA (0.14 mL) and the mixture was stirred for 5 minutes. The 1-(2-(2-((S)-pyrrolidin-2-yl)-1H-imidazol-4-yl)ethyl)-4-(2-(2-((S)-pyrrolidin-2-yl)-1H-imidazol-5-yl)ethyl)benzene (40 mg) in DMF (1 mL) was added and the reaction mixture was stirred under argon for 16 hrs. The reaction mixture was purified directly by prep HPLC. The solid obtained, the TFA salt, was loaded onto an SCX ion exchange cartridge with methanol, then the product was isolated as the free base by eluting with a solution of 2 M $NH_3$ in methanol to yield (1R)-2-((2S)-2-(4-(2-(4-(2-(2-((2S)-1-((2R)-2-(diethylamino)-2-phenylacetyl)-2-pyrrolidinyl)-1H-imidazol-5-yl)ethyl)phenyl)ethyl)-1H-imidazol-2-yl)-1-pyrrolidinyl)-N,N-diethyl-2-oxo-1-phenylethanamine (40 mg) as a white solid.

LC-MS retention time 1.038 min; m/z 784 (MH+). PHENOMENEX® Luna 5 u C18 4.6×30 mm column using a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% acetonitrile/90% $H_2O$/0.05% TFA and Solvent B was 10% $H_2O$/90% acetonitrile/0.05% TFA.

Example 41 dimethyl (1,4-phenylenebis(2,1-ethanediyl-1H-imidazole-4,2-diyl(2S)-2,1-pyrrolidinediyl((1R)-2-oxo-1-phenyl-2,1-ethanediyl)))biscarbamate

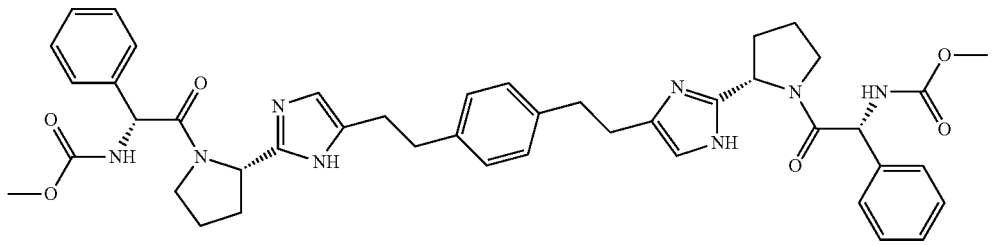

The title compound was prepared in an analogous manner to Example 40 utilizing (R)-2-(methoxycarbonylamino)-2-phenylacetic acid as the carboxylate coupling partner in the amide coupling to yield dimethyl (1,4-phenylenebis(2,1-ethanediyl-1H-imidazole-4,2-diyl(2S)-2,1-pyrrolidinediyl((1R)-2-oxo-1-phenyl-2,1-ethanediyl)))biscarbamate (30.9 mg) as a white solid.

LC-MS retention time 1.247 and 1.298 min; m/z 787 and 787 (MH+). PHENOMENEX® Luna 5 u C18 4.6×30 mm column using a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% acetonitrile/90% $H_2O$/0.05% TFA and Solvent B was 10% $H_2O$/90% acetonitrile/0.05% TFA.

Example 42 methyl ((1S)-2-((2S)-2-(4-(2-(4-(2-(2-((2S)-1-(N-(methoxycarbonyl)-L-alanyl)-2-pyrrolidinyl)-1H-imidazol-4-yl)ethyl)phenyl)ethyl)-1H-imidazol-2-yl)-1-pyrrolidinyl)-1-methyl-2-oxoethyl)carbamate

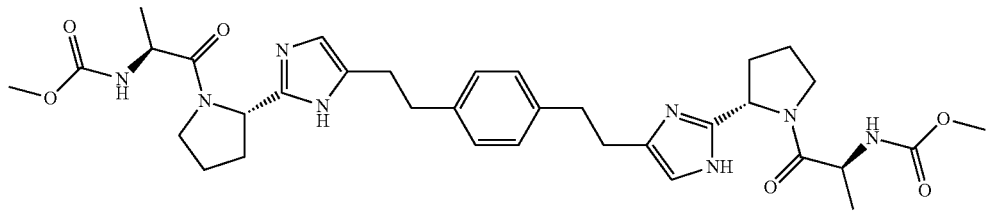

The title compound was prepared in an analogous manner to Example 40 utilizing (S)-2-(methoxycarbonylamino)propanoic acid as the carboxylate coupling partner in the amide coupling to yield methyl ((1S)-2-((2S)-2-(4-(2-(4-(2-(2-((2S)-1-(N-(methoxycarbonyl)-L-alanyl)-2-pyrrolidinyl)-1H-imidazol-4-yl)ethyl)phenyl)ethyl)-1H-imidazol-2-yl)-1-pyrrolidinyl)-1-methyl-2-oxoethyl)carbamate (23.2 mg) as a white solid.

LC-MS retention time 1.017 min; m/z 663 (MH+). PHENOMENEX® Luna 5 u C18 4.6×30 mm column using a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% acetonitrile/90% H$_2$O/0.05% TFA and Solvent B was 10% H$_2$O/90% acetonitrile/0.05% TFA.

Example 43 methyl ((1S)-1-(((2S)-2-(4-(2-(4-(2-(2-((2S)-1-((2S)-2-((methoxycarbonyl)amino)-3-methylbutanoyl)-2-pyrrolidinyl)-1H-imidazol-4-yl)ethyl)phenyl)ethyl)-1H-imidazol-2-yl)-1-pyrrolidinyl)carbonyl)-2-methylpropyl)carbamate

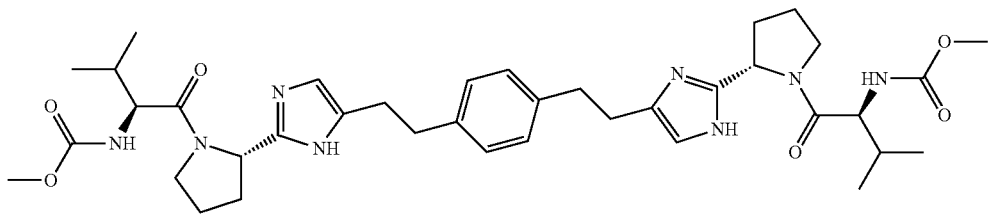

The title compound was prepared in an analogous manner to Example 40 utilizing (S)-2-(methoxycarbonylamino)-3-methylbutanoic acid as the carboxylate coupling partner in the amide coupling to yield methyl ((1S)-1-(2S)-2-(4-(2-(4-(2-(2-((2S)-1-((2S)-2-((methoxycarbonyl)amino)-3-methylbutanoyl)-2-pyrrolidinyl)-1H-imidazol-4-yl)ethyl)phenyl)ethyl)-1H-imidazol-2-yl)-1-pyrrolidinyl)carbonyl)-2-methylpropyl)carbamate (40.0 mg) as a white solid.

LC-MS retention time 1.162 min; m/z 720 (MH+). PHENOMENEX® Luna 5 u C18 4.6×30 mm column using a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% acetonitrile/90% H$_2$O/0.05% TFA and Solvent B was 10% H$_2$O/90% acetonitrile/0.05% TFA.

Example 44 methyl ((1S,2R)-2-methoxy-1-(((2S)-2-(4-(2-(4-(2-(2-((2S)-1-(N-(methoxycarbonyl)-O-methyl-L-threonyl)-2-pyrrolidinyl)-1H-imidazol-4-yl)ethyl)phenyl)ethyl)-1H-imidazol-2-yl)-1-pyrrolidinyl)carbonyl)propyl)carbamate

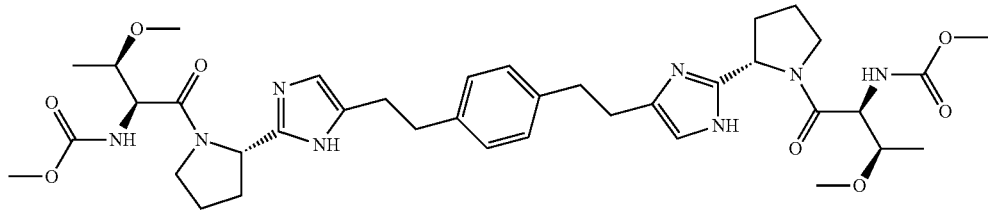

The title compound was prepared in an analogous manner to Example 40 utilizing (2S,3R)-3-methoxy-2-(methoxycarbonylamino)butanoic acid as the carboxylate coupling partner in the amide coupling to yield methyl ((1S,2R)-2-methoxy-1-(((2S)-2-(4-(2-(4-(2-(2-((2S)-1-(N-(methoxycarbonyl)-O-methyl-L-threonyl)-2-pyrrolidinyl)-1H-imidazol-4-yl)ethyl)phenyl)ethyl)-1H-imidazol-2-yl)-1-pyrrolidinyl)carbonyl)propyl)carbamate (34.4 mg) as a white solid.

LC-MS retention time 1.097 min; m/z 751 (MH+). PHENOMENEX® Luna 5 u C18 4.6×30 mm column using a detector wave length of 220 nM. The elution conditions employed a flow rate of 4 mL/min, a gradient of 100% Solvent A/0% Solvent B to 0% Solvent A/100% Solvent B, a gradient time of 2 min, a hold time of 1 min, and an analysis time of 3 min where Solvent A was 10% acetonitrile/90% $H_2O$/0.05% TFA and Solvent B was 10% $H_2O$/90% acetonitrile/0.05% TFA.

Example M1

Intermediate M1a (S)-tert-Butyl 2-(5-(4-ethynylphenyl)-1H-imidazol-2-yl)pyrrolidine-1-carboxylate

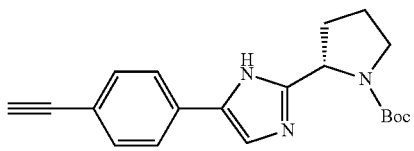 [SMILES: C#Cc1ccc(-c2cnc([C@@H]3CCCN3C(=O)OC(C)(C)C)[nH]2)cc1]

Pd(Ph$_3$P)$_4$ (0.115 g, 0.099 mmol) was added to a mixture of tributyl(ethynyl)stannane (1.539 g, 4.88 mmol), (S)-tert-butyl 2-(4-(4-bromophenyl)-1H-imidazol-2-yl)pyrrolidine-1-carboxylate (0.965 g, 2.46 mmol; for its preparation, see PCT Publication No. WO 2008/021927) and LiCl (0.277 g, 6.53 mmol) in dioxane (20 mL) in a sealed pressure tube. The mixture was purged with nitrogen, sealed and heated at 80° C. for 3 hr. After it was allowed to cool to ambient temperature, the volatile component was removed in vacuo and the residue was partitioned between $CH_3CN$ and hexanes (2:1 ratio in volume). The hexane layer was washed with an equal volume of $CH_3CN$. The combined $CH_3CN$ phase was rotervaped, and the resultant crude material was purified with a BIOTAGE® (100 g silica gel; 40-50% EtOAc/hexanes) to afford Intermediate M1a as a dull orange solid (591 mg). $^1$H NMR (DMSO-d$_6$, δ=2.50 ppm, 400 MHz): 12.21/11.95/11.88 (three 'br s', 1H), 7.74 (d, J=8.3, 1.6H), 7.66-7.47 (m, 1.66H), 7.41 (d, J=8.3, 1.6H), 7.32 (m, 0.14H), 4.84-4.75 (m, 1H), 4.19/4.12 (two 's', 1H), 3.52 (m, 1H), 3.39-3.29 (m, 1H), 2.28-1.77 (m, 4H), 1.39/1.15 (two 's', 9H). LC/MS: Anal. Calcd. for (M+H)$^+$ C$_{20}$H$_{24}$N$_3$O$_2$: 338.18. Found, 338.28.

Intermediate M1b (S)-tert-Butyl 2-(5-(4-((2-((S)-1-(tert-butoxycarbonyl)pyrrolidin-2-yl)-1H-imidazol-5-yl)ethynyl)phenyl)-1H-imidazol-2-yl)pyrrolidine-1-carboxylate

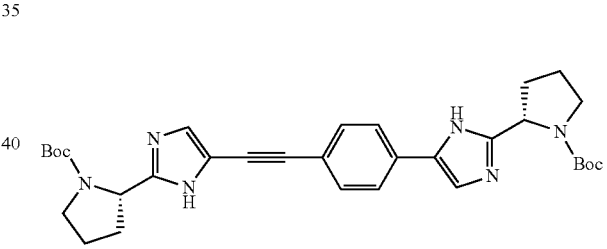

A mixture of CuI (10.8 mg, 0.057 mmol) and Pd(Ph$_3$P)$_4$ (55 mg, 0.048 mmol) was added to a DMF (6 mL) solution of Intermediate M1a (505 mg, 1.50 mmol), (S)-tert-butyl 2-(5-bromo-1H-imidazol-2-yl)pyrrolidine-1-carboxylate (328.5 mg, 1.039 mmol; for its preparation, see PCT Publication No. WO 2008/021927) and Et$_3$N (0.4 mL, 2.87 mmol), purged with nitrogen and heated at 90° C. for 24 h. The reaction mixture was concentrated to remove primarily the excess Et$_3$N, and the residue was diluted with MeOH and submitted to a reverse phase HPLC purification (MeOH/water/TFA; column. PHENOMENEX® Luna, 30×100 mm S10). The fractions containing the coupled product were neutralized with excess NH$_3$/MeOH (2.0 N) and the volatile component was removed in vacuo. The residue was partitioned between $CH_2Cl_2$ and dilute NaHCO$_3$ solution. The aqueous phase was extracted with $CH_2Cl_2$ (2×), and the combined organic phase was dried (MgSO$_4$) and evaporated in vacuo to afford Intermediate M1b as a light yellow semi-solid foam (160.8 mg). $^1$H NMR (DMSO-d$_6$, δ=2.50 ppm, 400 MHz): 12.51-11.88 ('m', 2H), 7.82-7.15 (m, 6H), 4.78 (m, 2H), 3.52 (m, 2H), 3.39-3.30 (m, 2H), 2.27-1.77 (m, 8H), 1.40 (s, 7.45H), 1.18/1.16 (two overlapping 's', 10.55 H). LC/MS: Anal. Calcd. for (M+H)$^+$ C$_{32}$H$_{41}$N$_6$O$_4$: 573.32. Found, 573.27.

111

Intermediate M1c 2-((S)-Pyrrolidin-2-yl)-5-(4-((2-((S)-pyrrolidin-2-yl)-1H-imidazol-5-yl)ethynyl)phenyl)-1H-imidazole

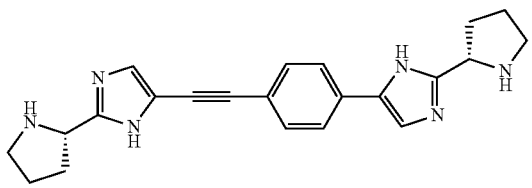 [SMILES: C(#Cc1cnc([C@@H]2CCCN2)[nH]1)c1ccc(-c2cnc([C@@H]3CCCN3)[nH]2)cc1]

25% TFA/CH$_2$Cl$_2$ (1 mL) was added to Intermediate M1b (19.4 mg, 0.0339 mmol) and stirred at ambient condition for 135 min. The volatile component was removed in vacuo and the residue was free-based with MCX (MeOH wash; 2.0 N NH$_3$/MeOH elution) to afford Intermediate M1c as an off-white solid (13.2 mg). $^1$H NMR (DMSO-d$_6$, δ=2.50 ppm, 400 MHz): 7.75 (d, J=8.3, 2H), 7.49 (s, 1H), 7.41 (d, J=8.3, 2H), 7.30 (s, 1H), 4.17 (m, 2H), 2.99-2.80 (m, 4H), 2.08 (m, 2H), 1.92-1.65 (m, 6H). LC/MS: Anal. Calcd. for (M+H)$^+$ C$_{22}$H$_{25}$N$_6$: 373.21. Found, 373.25.

Example M1

Methyl ((1R)-2-((2S)-2-(4-(4-((2-((2S)-1-((2R)-2-((methoxycarbonyl)amino)-2-phenylacetyl)-2-pyrrolidinyl)-1H-imidazol-4-yl)ethynyl)phenyl)-1H-imidazol-2-yl)-1-pyrrolidinyl)-2-oxo-1-phenylethyl)carbamate

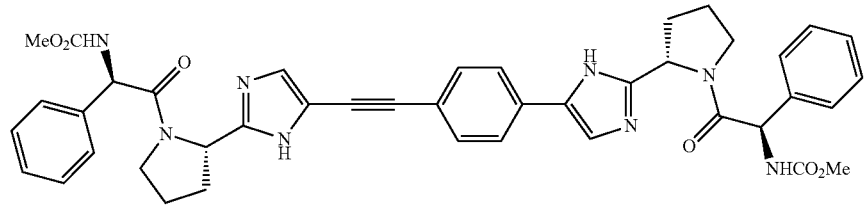

HATU (22.2 mg, 0.058 mmol) was added to a DMF (0.8 mL) solution of Intermediate M1c (11 mg, 0.030 mmol), (R)-2-(methoxycarbonylamino)-2-phenylacetic acid (13.2 mg, 0.063 mmol) and DIEA (0.025 mL, 0.14 mmol), and stirred for 2 hr. It was diluted with MeOH and submitted to a reverse phase HPLC purification (MeOH/water/TFA; column. PHENOMENEX® Luna, 30×50 mm S10) and the fractions were rotervaped to afford the TFA salt of Example M1 as a white foam/solid (14.4 mg). $^1$H NMR (DMSO-d$_6$, δ=2.50 ppm, 400 MHz): 8.13-7.65 (m, 7.5H), 7.42-6.95 (m, 10.5 H), 5.69-5.07 (m, 4H), 3.92-3.85 (m, 2H), 3.53/3.52 (two overlapping 's', 6H), 3.20-3.08 (m, 2H), 2.30-1.78 (m, 8H). LC/MS: Anal. Calcd. for (M+H)$^+$ C$_{42}$H$_{43}$N$_8$O$_6$: 755.33. Found, 755.33. R$_f$=1.26 min under the following LC condition: Column=PHENOMENEX® Luna 3×50 mm S10; Start % B=0; Final % B=100; Gradient time=2 min; Stop time=3 min; Flow Rate=4 mL/min; Wavelength=220 nm; Solvent A=0.1% TFA in 10% methanol/90% H$_2$O; Solvent B=0.1% TFA in 90% methanol/10% H$_2$O.

112

Examples M2 and M3

Intermediate M2a (S)-tert-Butyl 2-(5-(4-(2-(2-((S)-1-(tert-butoxycarbonyl)pyrrolidin-2-yl)-1H-imidazol-5-yl)ethyl)phenyl)-1H-imidazol-2-yl)pyrrolidine-1-carboxylate

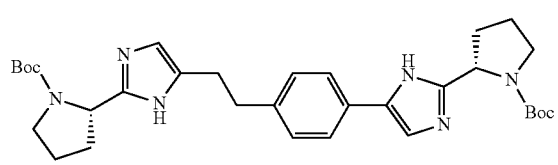 [SMILES: CC(C)(C)OC(=O)N1CCC[C@H]1c1ncc(CCc2ccc(-c3cnc([C@@H]4CCCN4C(=O)OC(C)(C)C)[nH]3)cc2)[nH]1]

A mixture of Intermediate M1b (75 mg, 0.13 mmol) and 10% Pd/C (48 mg) in MeOH (2 mL) was stirred under a balloon of hydrogen for 7.5 hr. The reaction mixture was filtered through a pad of CELITE®, and the filtrate was evaporated in vacuo to afford Intermediate M2a as an off-white foam/solid (70.1 mg). $^1$H NMR (DMSO-d$_6$, δ=2.50 ppm, 400 MHz): 12.03-11.26 (seven 'br s', 2H), 7.63-7.49 (m, 2.04H), 7.38 (app br s, 0.79H), 7.21-7.13 (m, 2.21H), 6.62 (app s, 0.56H), 6.44 (app s, 0.4H), 4.75 (m, 2H), 3.51 (m, 2H), 3.38-3.29 (m, 2H), 2.86-2.66 (m, 4H), 2.26-1.80 (m, 8H), 1.40 (s, 7.4H), 1.15/1.13 (overlapping 's', 10.6 H). LC/MS: Anal. Calcd. for (M+H)$^+$ C$_{32}$H$_{45}$N$_6$O$_4$: 577.35. Found, 577.27.

Intermediate M2b 2-((S)-Pyrrolidin-2-yl)-5-(4-(2-(2-((S)-pyrrolidin-2-yl)-1H-imidazol-5-yl)ethyl)phenyl)-1H-imidazole

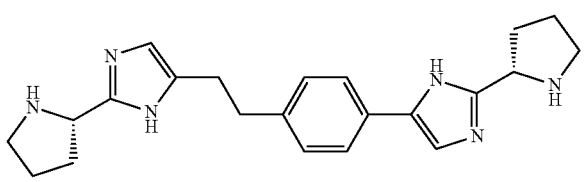 [SMILES: c1cc(-c2cnc([C@@H]3CCCN3)[nH]2)ccc1CCc1cnc([C@@H]2CCCN2)[nH]1]

A mixture of Intermediate M2a (67.5 mg, 0.117 mmol) and 25% TFA/CH$_2$Cl$_2$ (2 mL) was stirred at room temperature for 90 min. The volatile component was removed in vacuo and the residue was free-based with MCX (MeOH wash; 2.0 M NH$_3$/MeOH) to afford Intermediate M2b as yellow foam (44 mg). $^1$H NMR (DMSO-d$_6$, δ=2.50 ppm, 400 MHz): 11.74 (too broad to integrate), 7.61 (d, J=7.8, 2H), 7.32 (br s, 1H), 7.16 (d, J=8.1, 2H), 6.53 (br s, 1H), 4.13 (app t, J=7.1, 1H), 4.04 (app t, J=7.1, 1H), 2.98-2.67 (m, 8H), 2.07-1.64 (m, 8H). LC/MS: Anal. Calcd. for (M+H)+ $C_{22}H_{29}N_6$: 377.25. Found, 377.21.

Example M2

Methyl ((1R)-2-((2S)-2-(4-(4-(2-(2-((2S)-1-((2R)-2-((methoxycarbonyl)amino)-2-phenylacetyl)-2-pyrrolidinyl)-1H-imidazol-4-yl)ethyl)phenyl)-1H-imidazol-2-yl)-1-pyrrolidinyl)-2-oxo-1-phenylethyl) carbamate

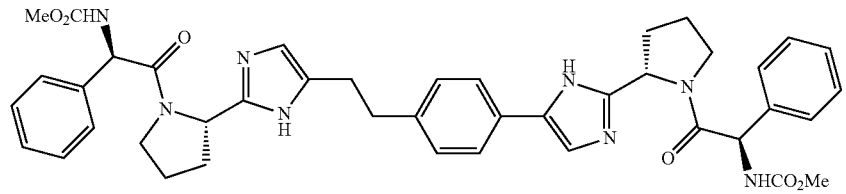

HATU (44.2 mg, 0.116 mmol) was added to a DMF (1.5 mL) solution of Intermediate M2b (20.7 mg, 0.030 mmol), (R)-2-(methoxycarbonylamino)-2-phenylacetic acid (25.3 mg, 0.12 mmol) and DIEA (0.045 mL, 0.26 mmol), and stirred for 40 min. The volatile component was removed in vacuo and the residue was passed through MCX (MeOH wash; 2.0 M $NH_3$/MeOH elution), the fraction was concentrated and purified with a reverse phase HPLC (MeOH/water/TFA; column. PHENOMENEX® Luna, 30×50 mm S10) to afford the TFA salt of Example M2 as a white foam (27 mg). $^1$H NMR (DMSO-$d_6$, δ=2.50 ppm, 400 MHz): 14.11/13.95 (overlapping 'br s', 2H), 8.01-7.02 (m, 18H), 5.75-5.69/5.52-5.48/5.39-5.31/5.18-5.13 (four 'm', 4H), 3.94-3.64 (m, ~2H), 3.54/3.52/3.50 (three overlapping 's', 6H), 3.19-2.83 (m, 6H), 2.43-1.84 (m, 8H). LC/MS: Anal. Calcd. for (M+H)+ $C_{42}H_{42}N_8O_6$: 759.36. Found 759.26. $R_t$=1.24 min under the following LC condition: Column=PHENOMENEX® Luna 3×50 mm S10; Start % B=0; Final % B=100; Gradient time=2 min; Stop time=3 min; Flow Rate=4 mL/min; Wavelength=220 nm; Solvent A=0.1% TFA in 10% methanol/90% $H_2O$; Solvent B=0.1% TFA in 90% methanol/10% $H_2O$.

Example M3

[(1R)-2-((2S)-2-(4-(4-(2-(2-((2S)-1-((2R)-2-(Dimethylamino)-2-phenylacetyl)-2-pyrrolidinyl)-1H-imidazol-4-yl)ethyl)phenyl)-1H-imidazol-2-yl)-1-pyrrolidinyl)-N,N-dimethyl-2-oxo-1-phenylethanamine]

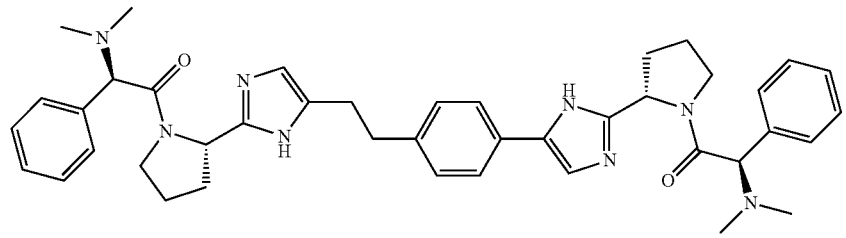 [SMILES: CN(C)[C@@H](C(=O)N1CCC[C@H]1c1ncc(CCc2ccc(-c3cnc([C@@H]4CCCN4C(=O)[C@@H](c4ccccc4)N(C)C)[nH]3)cc2)[nH]1)c1ccccc1]

Example M3 (TFA salt) was prepared from Intermediate M2b and the HCl salt (R)-2-(dimethylamino)-2-phenylacetic acid according to the procedure described for the preparation of Example M2. LC/MS: Anal. Calcd. For (M+H)+ $C_{42}H_{51}N_8O_2$: 699.41. Found 699.33. $R_t$=1.0 min under the following LC condition: Column=PHENOMENEX® Luna 3×50 mm S10; Start % B=0; Final % B=100; Gradient time=2 min; Stop time=3 min; Flow Rate=4 mL/min; Wavelength=220 nm; Solvent A=0.1% TFA in 10% methanol/90% $H_2O$; Solvent B=0.1% TFA in 90% methanol/10% $H_2O$.

Examples M4 to M8

Intermediate M4a (2S,2'S)-tert-Butyl 2,2'-(5,5'-(1,4-phenylenebis(ethyne-2,1-diyl))bis(1H-imidazole-5,2-diyl))dipyrrolidine-1-carboxylate

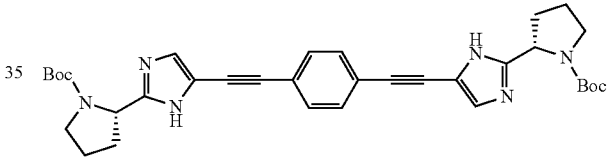

A sealed tube containing a mixture of CuI (4 mg, 0.02 mmol), $PdCl_2(Ph_3P)_2$ (49 mg, 0.04 mmol), 1,4-diethynylbenzene (18 mg, 0.14 mmol), (S)-tert-butyl 2-(5-iodo-1H-imidazol-2-yl)pyrrolidine-1-carboxylate (100 mg, 0.28 mmol), $iPr_2NH$ (0.06 mL, 0.42 mmol) in THF (2 mL) was heated at 85° C. for 3 hr. After it was allowed to cool to ambient temperature, the mixture was diluted with EtOAc (5 mL), and then washed with water (2 mL, 2×) and brine (2 mL), dried ($MgSO_4$) and evaporated in vacuo. The residue was purified with Prep HPLC (MeOH/water/TFA) to afford Intermediate M4a as a light yellow solid (30 mg). $^1$H NMR ($CD_3OD$, δ=3.33 ppm, 400 MHz): 7.74 (s, 2H), 7.63 (s, 4H), 5.04 (m, 2H), 3.75-3.50 (m, 4H), 2.5 (m, 2H), 2.07 (m, 6H), 1.50/1.32 (two 's', 18H). LC/MS: Anal. Calcd. for (M+H)+ $C_{34}H_{41}N_6O_4$: 597.32. Found 597.39.

Intermediate M4b 1,4-Bis((2-((S)-pyrrolidin-2-yl)-1H-imidazol-5-yl)ethynyl)benzene

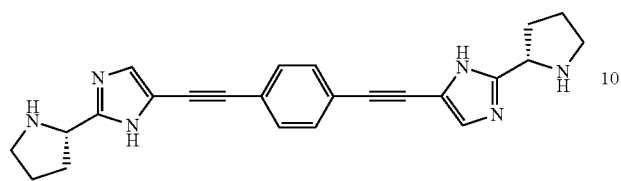

TFA (0.5 mL) was added to a CH₂Cl₂ (5 mL) solution of Intermediate M4a (150 mg, 0.193 mmol) and was stirred at ambient temperature for 2 hr. Then, an additional TFA (2 mL) was added, and stirring was continued for 2 hr. The volatile component was removed in vacuo to obtain an opaque reddish solid. The product was free-based with SPE cartridge (3 g; CH₂Cl₂/MeOH wash; 2.0 M NH₃/MeOH elution) to afford Intermediate M4b as a yellow solid (65 mg). LC/MS: Anal. Calcd. for (M+H)⁺ $C_{24}H_{25}N_6$: 397.21. Found 397.25.

Example M4

Methyl((1S)-1-(((2S)-2-(4-((4-((2-((2S)-1-((2S)-2-((methoxycarbonyl)amino)-3-methylbutanoyl)-2-pyrrolidinyl)-1H-imidazol-4-yl)ethynyl)phenyl)ethynyl)-1H-imidazol-2-yl)-1-pyrrolidinyl)carbonyl)-2-methylpropyl)carbamate

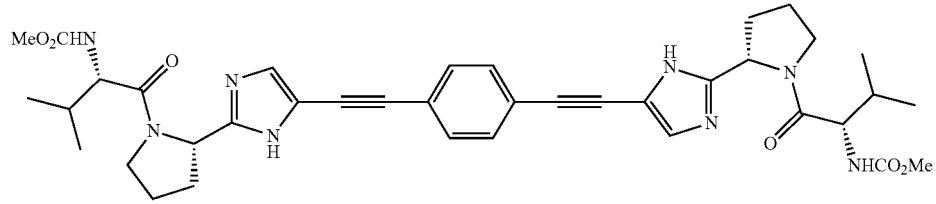

HATU (19 mg, 0.05 mmol) was added to a DMF (1 mL) solution of (S)-2-(methoxycarbonylamino)-3-methylbutanoic acid (9 mg, 0.05 mmol) and DIEA (0.22 mL, 0.125 mmol) and stirred for 5 min. A DMF (1.0 mL) solution of Intermediate M4b (10 mg, 0.025 mmol) was added and the reaction mixture was stirred for 16 hr. The mixture was diluted with water (1 mL) and concentrated in vacuo. The residue was diluted with MeOH (1 mL) and submitted to a reverse phase HPLC purification (MeOH/water/TFA) to afford the TFA salt of Example M4, which was free-based with SCX cartridge (MeOH wash; 2.0 M NH₃/MeOH elution) to afford Example M4 as a white solid (11.9 mg). ¹H NMR (CD₃OD, δ=3.33 ppm, 400 MHz): 7.72 (s, 2H), 7.61 (s, 4H), 5.17 (m, 2H), 4.23 (app d, J=7.6, 2H), 4.08 (m, 1.64H), 3.85 (m, 2.1H), 3.67 (overlap of 's' and 'm', 6.26H), 2.51 (m, 2H), 2.35-2.0 (m, 8H), 1.0-0.9 (m, 12H). LC/MS: Anal. Calcd. for (M+H)⁺ $C_{38}H_{47}N_8O_6$: 711.36. Found 711.43. $R_t$=1.24 min under the following LC condition: Column=Luna 5 μC18 4.6×30 mm; Start % B=0; Final % B=100; Gradient time=2 min; Stop time=3 min; Flow Rate=4 mL/min; Wavelength=220 nm; Solvent A=0.05% TFA in 10% CH₃CN/90% H₂O; Solvent B=0.05% TFA in 90% CH₃CN/10% H₂O.

Examples M5 to M7

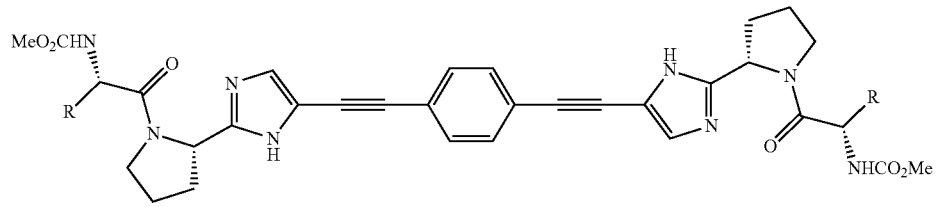

Examples M5 to M7 were prepared in a free base form from Intermediate M4b and appropriate acid coupling partners according to the procedure described for the preparation of Example M4.

| Example | Compound Name | R | $R_t$ (LC-Cond. is the same as Example M4); MS data |
|---|---|---|---|
| M5 | Methyl ((1S,2R)-2-methoxy-1-(((2S)-2-(4-((2-((2S)-1-(N-(methoxycarbonyl)-O-methyl-L-threonyl)-2-pyrrolidinyl)-1H-imidazol-4-yl)ethynyl)phenyl)ethynyl)-1H-imidazol-2-yl)-1-pyrrolidinyl)carbonyl)propyl)carbamate | 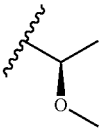 | 1.17 min.; LC/MS: Anal. Calcd. for $(M + H)^+$ $C_{38}H_{47}N_8O_8$: 743.35; found 743.43. |
| M6 | Methyl ((1S)-2-((2S)-2-(4-((4-((2-((2S)-1-(N-(methoxycarbonyl)-L-alanyl)-2-pyrrolidinyl)-1H-imidazol-4-yl)ethynyl)phenyl)ethynyl)-1H-imidazol-2-yl)-1-pyrrolidinyl)-1-methyl-2-oxoethyl)carbamate |  | 1.13 min; LC/MS: Anal. Calcd. for $(M + H)^+$ $C_{34}H_{39}N_8O_6$: 655.3; found 655.0 |
| M7 | Methyl ((1S)-3-methoxy-1-(((2S)-2-(4-((4-((2-((2S)-1-(N-(methoxycarbonyl)-O-methyl-L-homoseryl)-2-pyrrolidinyl)-1H-imidazol-4-yl)ethynyl)phenyl)ethynyl)-1H-imidazol-2-yl)-1-pyrrolidinyl)carbonyl)propyl)carbamate | 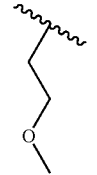 [SMILES: *CCOC] | 1.17 min; LC/MS: Anal. Calcd. for $(M + H)^+$ $C_{38}H_{47}N_8O_8$: 743.35; found 743. |

Synthesis of Common Caps

Compound Analysis Conditions

Purity assessment and low resolution mass analysis were conducted on a Shimadzu LC system coupled with Waters MICROMASS® ZQ MS system. It should be noted that retention times may vary slightly between machines. Additional LC conditions applicable to the current section, unless noted otherwise.

Cond.-MS-W1

| | |
|---|---|
| Column = | XTERRA ® 3.0 × 50 mm S7 |
| Start % B = | 0 |
| Final % B = | 100 |
| Gradient time = | 2 min |
| Stop time = | 3 min |
| Flow Rate = | 5 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |

Cond.-MS-W2

| | |
|---|---|
| Column = | XTERRA ® 3.0 × 50 mm S7 |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |

Cond.-MS-W5

| | |
|---|---|
| Column = | XTERRA ® 3.0 × 50 mm S7 |
| Start % B = | 0 |
| Final % B = | 30 |
| Gradient time = | 2 min |
| Stop time = | 3 min |
| Flow Rate = | 5 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |

Cond.-D1

| | |
|---|---|
| Column = | XTERRA ® C18 3.0 × 50 mm S7 |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |

Cond.-D2

| | |
|---|---|
| Column = | PHENOMENEX ® Luna 4.6 × 50 mm S10 |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |

Cond.-M3

| | |
|---|---|
| Column = | XTERRA ® C18 3.0 × 50 mm S7 |
| Start % B = | 0 |
| Final % B = | 40 |
| Gradient time = | 2 min |
| Stop time = | 3 min |
| Flow Rate = | 5 mL/min |
| Wavelength = | 220 nm |
| Solvent A = | 0.1% TFA in 10% methanol/90% H$_2$O |
| Solvent B = | 0.1% TFA in 90% methanol/10% H$_2$O |

Condition I

| | |
|---|---|
| Column = | PHENOMENEX ® Luna 3.0 × 50 mm S10 |
| Start % B = | 0 |
| Final % B = | 100 |
| Gradient time = | 2 min |
| Stop time = | 3 min |
| Flow Rate = | 4 mL/min |
| Wavelength = | 220 nm |
| Solvent A = | 0.1% TFA in 10% methanol/90% H$_2$O |
| Solvent B = | 0.1% TFA in 90% methanol/10% H$_2$O |

Condition II

| | |
|---|---|
| Column = | PHENOMENEX ® Luna 4.6 × 50 mm S10 |
| Start % B = | 0 |
| Final % B = | 100 |
| Gradient time = | 2 min |
| Stop time = | 3 min |
| Flow Rate = | 5 mL/min |
| Wavelength = | 220 nm |
| Solvent A = | 0.1% TFA in 10% methanol/90% H$_2$O |
| Solvent B = | 0.1% TFA in 90% methanol/10% H$_2$O |

Condition III

| | |
|---|---|
| Column = | XTERRA ® C18 3.0 × 50 mm S7 |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% H$_2$O |
| Solvent B = | 0.1% TFA in 90% methanol/10% H$_2$O |

Cap-1

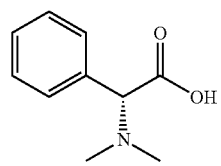

(R)-2-(dimethylamino)-2-phenylacetic acid

A suspension of 10% Pd/C (2.0 g) in methanol (10 mL) was added to a mixture of (R)-2-phenylglycine (10 g, 66.2 mmol), formaldehyde (33 mL of 37% wt. in water), 1N HCl (30 mL) and methanol (30 mL), and exposed to H$_2$ (60 psi) for 3 hours. The reaction mixture was filtered through diatomaceous earth (CELITE®), and the filtrate was concentrated in vacuo. The resulting crude material was recrystallized from isopropanol to provide the HCl salt of Cap-1 as a white needle (4.0 g). Optical rotation: −117.1° [c=9.95 mg/mL in H$_2$O; 2=589 nm]. $^1$H NMR (DMSO-d$_6$, δ=2.5 ppm, 500 MHz): δ 7.43-7.34 (m, 5H), 4.14 (s, 1H), 2.43 (s, 6H); LC (Cond. I): RT=0.25; LC/MS: Anal. Calcd. for [M+H]$^+$ C$_{10}$H$_{14}$NO$_2$ 180.10. Found 180.17; HRMS: Anal. Calcd. for [M+H]$^+$ C$_{10}$H$_{14}$NO$_2$ 180.1025. Found 180.1017.

Cap-2

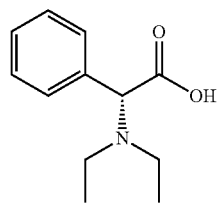

(R)-2-(diethylamino)-2-phenylacetic acid

NaBH$_3$CN (6.22 g, 94 mmol) was added in portions over a few minutes to a cooled (ice/water) mixture of (R)-2-Phenylglycine (6.02 g, 39.8 mmol) and methanol (100 mL), and stirred for 5 minutes. Acetaldehyde (10 mL) was added dropwise over 10 minutes and stirring was continued at the same cooled temperature for 45 minutes and at ambient temperature for ~6.5 hours. The reaction mixture was cooled back with ice-water bath, treated with water (3 mL) and then quenched with a dropwise addition of concentrated HCl over ~45 minutes until the pH of the mixture was ~1.5-2.0. The cooling bath was removed and the stirring was continued while adding concentrated HCl in order to maintain the pH of the mixture around 1.5-2.0. The reaction mixture was stirred overnight, filtered to remove the white suspension, and the filtrate was concentrated in vacuo. The crude material was recrystallized from ethanol to afford the HCl salt of Cap-2 as a shining white solid in two crops (crop-1: 4.16 g; crop-2: 2.19 g). $^1$H NMR (DMSO-d$_6$, δ=2.5 ppm, 400 MHz): 10.44 (1.00, br s, 1H), 7.66 (m, 2H), 7.51 (m, 3H), 5.30 (s, 1H), 3.15 (br m, 2H), 2.98 (br m, 2H), 1.20 (app br s, 6H). Crop-1: [α]$^{25}$ −102.21° (c=0.357, H$_2$O); crop-2: [α]$^{25}$ −99.7° (c=0.357, H$_2$O). LC (Cond. I): RT=0.43 min; LC/MS: Anal. Calcd. for [M+H]$^+$ C$_{12}$H$_{18}$NO$_2$: 208.13. Found 208.26.

Cap-3

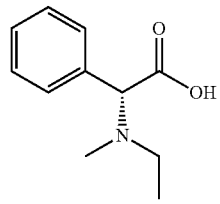

Acetaldehyde (5.0 mL, 89.1 mmol) and a suspension of 10% Pd/C (720 mg) in methanol/H$_2$O (4 mL/1 mL) was sequentially added to a cooled (~15° C.) mixture of (R)-2- phenylglycine (3.096 g, 20.48 mmol), 1N HCl (30 mL) and methanol (40 mL). The cooling bath was removed and the reaction mixture was stirred under a balloon of $H_2$ for 17 hours. An additional acetaldehyde (10 mL, 178.2 mmol) was added and stirring continued under $H_2$ atmosphere for 24 hours [Note: the supply of $H_2$ was replenished as needed throughout the reaction]. The reaction mixture was filtered through diatomaceous earth (CELITE®), and the filtrate was concentrated in vacuo. The resulting crude material was recrystallized from isopropanol to provide the HCl salt of (R)-2-(ethylamino)-2-phenylacetic acid as a shining white solid (2.846 g). $^1$H NMR (DMSO-$d_6$, δ=2.5 ppm, 400 MHz): δ 14.15 (br s, 1H), 9.55 (br s, 2H), 7.55-7.48 (m, 5H), 2.88 (br m, 1H), 2.73 (br m, 1H), 1.20 (app t, J=7.2, 3H). LC (Cond. I): RT=0.39 min; >95% homogeneity index; LC/MS: Anal. Calcd. for [M+H]$^+$ $C_{10}H_{14}NO_2$: 180.10. Found 180.18.

A suspension of 10% Pd/C (536 mg) in methanol/$H_2O$ (3 mL/1 mL) was added to a mixture of (R)-2-(ethylamino)-2-phenylacetic acid/HCl (1.492 g, 6.918 mmol), formaldehyde (20 mL of 37% wt. in water), 1N HCl (20 mL) and methanol (23 mL). The reaction mixture was stirred under a balloon of $H_2$ for ~72 hours, where the $H_2$ supply was replenished as needed. The reaction mixture was filtered through diatomaceous earth (CELITE®) and the filtrate was concentrated in vacuo. The resulting crude material was recrystallized from isopropanol (50 mL) to provide the HCl salt of Cap-3 as a white solid (985 mg). $^1$H NMR (DMSO-$d_6$, δ=2.5 ppm, 400 MHz): δ 10.48 (br s, 1H), 7.59-7.51 (m, 5H), 5.26 (s, 1H), 3.08 (app br s, 2H), 2.65 (br s, 3H), 1.24 (br m, 3H). LC (Cond. I): RT=0.39 min; >95% homogeneity index; LC/MS: Anal. Calcd. for [M+H]$^+$ $C_{11}H_{16}NO_2$: 194.12. Found 194.18; HRMS: Anal. Calcd. for [M+H]$^+$ $C_{11}H_{16}NO_2$: 194.1180. Found 194.1181.

Cap-4

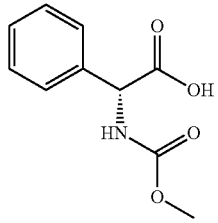

(R)-2-(methoxycarbonylamino)-2-phenylacetic acid $ClCO_2Me$ (3.2 mL, 41.4 mmol) was added dropwise to a cooled (ice/water) THF (410 mL) semi-solution of (R)-tert-butyl 2-amino-2-phenylacetate/HCl (9.877 g, 40.52 mmol) and diisopropylethylamine (14.2 mL, 81.52 mmol) over 6 min, and stirred at similar temperature for 5.5 hours. The volatile component was removed in vacuo, and the residue was partitioned between water (100 mL) and ethyl acetate (200 mL). The organic layer was washed with 1N HCl (25 mL) and saturated $NaHCO_3$ solution (30 mL), dried ($MgSO_4$), filtered, and concentrated in vacuo. The resultant colorless oil was triturated from hexanes, filtered and washed with hexanes (100 mL) to provide (R)-tert-butyl 2-(methoxycarbonylamino)-2-phenylacetate as a white solid (7.7 g). $^1$H NMR (DMSO-$d_6$, δ=2.5 ppm, 400 MHz): 7.98 (d, J=8.0, 1H), 7.37-7.29 (m, 5H), 5.09 (d, J=8, 1H), 3.56 (s, 3H), 1.33 (s, 9H). LC (Cond. I): RT=1.53 min; ~90% homogeneity index; LC/MS: Anal. Calcd. for [M+Na]$^+$ $C_{14}H_{19}NNaO_4$: 288.12. Found 288.15.

TFA (16 mL) was added dropwise to a cooled (ice/water) $CH_2Cl_2$ (160 mL) solution of the above product over 7 minutes, and the cooling bath was removed and the reaction mixture was stirred for 20 hours. Since the deprotection was still not complete, an additional TFA (1.0 mL) was added and stirring continued for an additional 2 hours. The volatile component was removed in vacuo, and the resulting oil residue was treated with diethyl ether (15 mL) and hexanes (12 mL) to provide a precipitate. The precipitate was filtered and washed with diethyl ether/hexanes (~1:3 ratio; 30 mL) and dried in vacuo to provide Cap-4 as a fluffy white solid (5.57 g). Optical rotation: −176.9° [c=3.7 mg/mL in $H_2O$; λ=589 nm]. $^1$H NMR (DMSO-$d_6$, δ=2.5 ppm, 400 MHz): δ 12.84 (br s, 1H), 7.96 (d, J=8.3, 1H), 7.41-7.29 (m, 5H), 5.14 (d, J=8.3, 1H), 3.55 (s, 3H). LC (Cond. I): RT=1.01 min; >95% homogeneity index; LC/MS: Anal. Calcd. for [M+H]$^+$ $C_{10}H_{12}NO_4$ 210.08. Found 210.17; HRMS: Anal. Calcd. for [M+H]$^+$ $C_{10}H_{12}NO_4$ 210.0766. Found 210.0756.

Cap-5

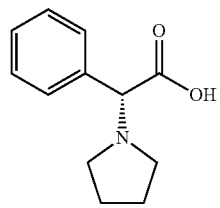 [SMILES: O=C(O)[C@@H](c1ccccc1)N1CCCC1]

A mixture of (R)-2-phenylglycine (1.0 g, 6.62 mmol), 1,4-dibromobutane (1.57 g, 7.27 mmol) and $Na_2CO_3$ (2.10 g, 19.8 mmol) in ethanol (40 mL) was heated at 100° C. for 21 hours. The reaction mixture was cooled to ambient temperature and filtered, and the filtrate was concentrated in vacuo. The residue was dissolved in ethanol and acidified with 1N HCl to pH 3-4, and the volatile component was removed in vacuo. The resulting crude material was purified by a reverse phase HPLC (water/methanol/TFA) to provide the TFA salt of Cap-5 as a semi-viscous white foam (1.0 g). $^1$H NMR (DMSO-$d_6$, δ=2.5, 500 MHz) δ 10.68 (br s, 1H), 7.51 (m, 5H), 5.23 (s, 1H), 3.34 (app br s, 2H), 3.05 (app br s, 2H), 1.95 (app br s, 4H);

RT=0.30 minutes (Cond. I); >98% homogeneity index; LC/MS: Anal. Calcd. for [M+H]$^+$ $C_{12}H_{16}NO_2$: 206.12. Found 206.25.

Cap-6

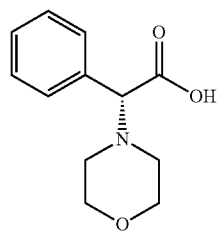 [SMILES: O=C(O)[C@@H](c1ccccc1)N1CCOCC1]

The TFA salt of Cap-6 was synthesized from (R)-2-phenylglycine and 1-bromo-2-(2-bromoethoxy)ethane by using the method of preparation of Cap-5. $^1$H NMR (DMSO-$d_6$, δ=2.5, 500 MHz) δ 12.20 (br s, 1H), 7.50 (m, 5H), 4.92 (s, 1H), 3.78 (app br s, 4H), 3.08 (app br s, 2H), 2.81 (app br s, 2H); RT=0.32 minutes (Cond. I); >98%; LC/MS: Anal. Calcd. for [M+H]$^+$ $C_{12}H_{16}NO_3$: 222.11. Found 222.20; HRMS: Anal. Calcd. for [M+H]$^+$ $C_{12}H_{16}NO_3$: 222.1130. Found 222.1121.

Cap-7

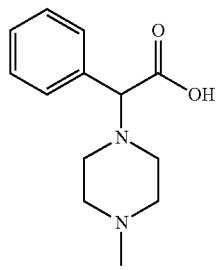

Cap-7a: enantiomer-1
Cap-7b: enantiomer-2

A $CH_2Cl_2$ (200 mL) solution of p-toluenesulfonyl chloride (8.65 g, 45.4 mmol) was added dropwise to a cooled (−5° C.) $CH_2Cl_2$ (200 mL) solution of (S)-benzyl 2-hydroxy-2-phenylacetate (10.0 g, 41.3 mmol), triethylamine (5.75 mL, 41.3 mmol) and 4-dimethylaminopyridine (0.504 g, 4.13 mmol), while maintaining the temperature between −5° C. and 0° C. The reaction was stirred at 0° C. for 9 hours, and then stored in a freezer (−25° C.) for 14 hours. It was allowed to thaw to ambient temperature and washed with water (200 mL), 1N HCl (100 mL) and brine (100 mL), dried (MgSO$_4$), filtered, and concentrated in vacuo to provide benzyl 2-phenyl-2-(tosyloxy)acetate as a viscous oil which solidified upon standing (16.5 g). The chiral integrity of the product was not checked and that product was used for the next step without further purification. $^1$H NMR (DMSO-$d_6$, δ=2.5, 500 MHz) δ 7.78 (d, J=8.6, 2H), 7.43-7.29 (m, 10H), 7.20 (m, 2H), 6.12 (s, 1H), 5.16 (d, J=12.5, 1H), 5.10 (d, J=12.5, 1H), 2.39 (s, 3H). RT=3.00 (Cond. III); >90% homogeneity index; LC/MS: Anal. Calcd. for [M+H]$^+$ $C_{22}H_{20}NaO_5S$: 419.09. Found 419.04.

A THF (75 mL) solution of benzyl 2-phenyl-2-(tosyloxy)acetate (6.0 g, 15.1 mmol), 1-methylpiperazine (3.36 mL, 30.3 mmol) and N,N-diisopropylethylamine (13.2 mL, 75.8 mmol) was heated at 65° C. for 7 hours. The reaction was allowed to cool to ambient temperature and the volatile component was removed in vacuo. The residue was partitioned between ethylacetate and water, and the organic layer was washed with water and brine, dried (MgSO$_4$), filtered, and concentrated in vacuo. The resulting crude material was purified by flash chromatography (silica gel, ethyl acetate) to provide benzyl 2-(4-methylpiperazin-1-yl)-2-phenylacetate as an orangish-brown viscous oil (4.56 g). Chiral HPLC analysis (CHIRALCEL® OD-H) indicated that the sample is a mixture of stereoisomers in a 38.2 to 58.7 ratio. The separation of the stereoisomers were effected as follow: the product was dissolved in 120 mL of ethanol/heptane (1:1) and injected (5 mL/injection) on chiral HPLC column (Chiracel OJ, 5 cm ID×50 cm L, 20 μm) eluting with 85:15 Heptane/ethanol at 75 mL/min, and monitored at 220 nm. Stereoisomer-1 (1.474 g) and stereoisomer-2 (2.2149 g) were retrieved as viscous oil. $^1$H NMR (CDCl$_3$, δ=7.26, 500 MHz) 7.44-7.40 (m, 2H), 7.33-7.24 (m, 6H), 7.21-7.16 (m, 2H), 5.13 (d, J=12.5, 1H), 5.08 (d, J=12.5, 1H), 4.02 (s, 1H), 2.65-2.38 (app br s, 8H), 2.25 (s, 3H). RT=2.10 (Cond. III); >98% homogeneity index; LC/MS: Anal. Calcd. for [M+H]$^+$ $C_{20}H_{25}N_2O_2$: 325.19. Found 325.20.

A methanol (10 mL) solution of either stereoisomer of benzyl 2-(4-methylpiperazin-1-yl)-2-phenylacetate (1.0 g, 3.1 mmol) was added to a suspension of 10% Pd/C (120 mg) in methanol (5.0 mL). The reaction mixture was exposed to a balloon of hydrogen, under a careful monitoring, for <50 minutes. Immediately after the completion of the reaction, the catalyst was filtered through diatomaceous earth (CELITE®) and the filtrate was concentrated in vacuo to provide Cap-7, contaminated with phenylacetic acid as a tan foam (867.6 mg; mass is above the theoretical yield). The product was used for the next step without further purification. $^1$H NMR (DMSO-$d_6$, δ=2.5, 500 MHz) δ 7.44-7.37 (m, 2H), 7.37-7.24 (m, 3H), 3.92 (s, 1H), 2.63-2.48 (app. br s, 2H), 2.48-2.32 (m, 6H), 2.19 (s, 3H); RT=0.31 (Cond. II); >90% homogeneity index; LC/MS: Anal. Calcd. for [M+H]$^+$ $C_{13}H_{19}N_2O_2$: 235.14. Found 235.15; HRMS: Anal. Calcd. for [M+H]$^+$ $C_{13}H_{19}N_2O_2$: 235.1447. Found 235.1440.

The synthesis of Cap-8 and Cap-9 was conducted according to the synthesis of Cap-7 by using appropriate amines for the SN$_2$ displacement step (i.e., 4-hydroxypiperidine for Cap-8 and (S)-3-fluoropyrrolidine for Cap-9) and modified conditions for the separation of the respective stereoisomeric intermediates, as described below.

Cap-8

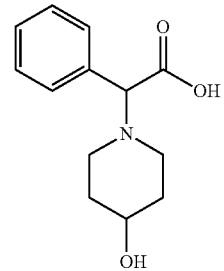

8a: enantiomer-1
8b: enantiomer-2

The stereoisomeric separation of the intermediate benzyl 2-(4-hydroxypiperidin-1-yl)-2-phenyl acetate was effected by employing the following conditions: the compound (500 mg) was dissolved in ethanol/heptane (5 mL/45 mL). The resulting solution was injected (5 mL/injection) on a chiral HPLC column (Chiracel OJ, 2 cm ID×25 cm L, 10 μm) eluting with 80:20 heptane/ethanol at 10 mL/min, monitored at 220 nm, to provide 186.3 mg of stereoisomer-1 and 209.1 mg of stereoisomer-2 as light-yellow viscous oils. These benzyl ester was hydrogenolysed according to the preparation of Cap-7 to provide Cap-8: $^1$H NMR (DMSO-$d_6$, δ=2.5, 500 MHz) 7.40 (d, J=7, 2H), 7.28-7.20 (m, 3H), 3.78 (s 1H), 3.46 (m, 1H), 2.93 (m, 1H), 2.62 (m, 1H), 2.20 (m, 2H), 1.70 (m, 2H), 1.42 (m, 2H). RT=0.28 (Cond. II); >98% homogeneity index; LC/MS: Anal. Calcd. for [M+H]$^+$ $C_{13}H_{18}NO_3$:

236.13. Found 236.07; HRMS: Calcd. for [M+H]$^+$ $C_{13}H_{18}NO_3$: 236.1287. Found 236.1283.

Cap-9

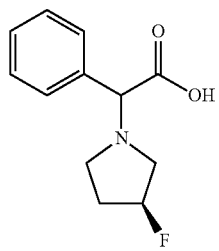

9a: diastereomer-1
9b: diastereomer-2

The diastereomeric separation of the intermediate benzyl 2-((S)-3-fluoropyrrolidin-1-yl)-2-phenylacetate was effected by employing the following conditions: the ester (220 mg) was separated on a chiral HPLC column (Chiracel OJ-H, 0.46 cm ID×25 cm L, 5 μm) eluting with 95% $CO_2$/5% methanol with 0.1% TFA, at 10 bar pressure, 70 mL/min flow rate, and a temperature of 35° C. The HPLC elute for the respective stereoisomers was concentrated, and the residue was dissolved in $CH_2Cl_2$ (20 mL) and washed with an aqueous medium (10 mL water+1 mL saturated $NaHCO_3$ solution). The organic phase was dried ($MgSO_4$), filtered, and concentrated in vacuo to provide 92.5 mg of fraction-1 and 59.6 mg of fraction-2. These benzyl esters were hydrogenolysed according to the preparation of Cap-7 to prepare Caps 9a and 9b. Cap-9a (diastereomer-1; the sample is a TFA salt as a result of purification on a reverse phase HPLC using $H_2O$/methanol/TFA solvent): $^1$H NMR (DMSO-$d_6$, δ=2.5, 400 MHz) 7.55-7.48 (m, 5H), 5.38 (d of m, J=53.7, 1H), 5.09 (br s, 1H), 3.84-2.82 (br m, 4H), 2.31-2.09 (m, 2H). RT=0.42 (Cond. I); >95% homogeneity index; LC/MS: Anal. Calcd. for [M+H]$^+$ $C_{12}H_{15}FNO_2$: 224.11. Found 224.14; Cap-9b (diastereomer-2): $^1$H NMR (DMSO-$d_6$, δ=2.5, 400 MHz) 7.43-7.21 (m, 5H), 5.19 (d of m, J=55.9, 1H), 3.97 (s, 1H), 2.95-2.43 (m, 4H), 2.19-1.78 (m, 2H). RT=0.44 (Cond. I); LC/MS: Anal. Calcd. for [M+H]$^+$ $C_{12}H_{15}FNO_2$: 224.11. Found 224.14.

Cap-10

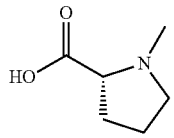

To a solution of D-proline (2.0 g, 17 mmol) and formaldehyde (2.0 mL of 37% wt. in $H_2O$) in methanol (15 mL) was added a suspension of 10% Pd/C (500 mg) in methanol (5 mL). The mixture was stirred under a balloon of hydrogen for 23 hours. The reaction mixture was filtered through diatomaceous earth (CELITE®) and concentrated in vacuo to provide Cap-10 as an off-white solid (2.15 g). $^1$H NMR (DMSO-$d_6$, δ=2.5, 500 MHz) 3.42 (m, 1H), 3.37 (dd, J=9.4, 6.1, 1H), 2.85-2.78 (m, 1H), 2.66 (s, 3H), 2.21-2.13 (m, 1H), 1.93-1.84 (m, 2H), 1.75-1.66 (m, 1H). RT=0.28 (Cond. II); >98% homogeneity index; LC/MS: Anal. Calcd. for [M+H]$^+$ $C_6H_{12}NO_2$: 130.09. Found 129.96.

Cap-11

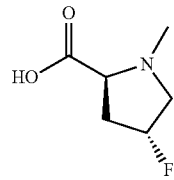

A mixture of (2S,4R)-4-fluoropyrrolidine-2-carboxylic acid (0.50 g, 3.8 mmol), formaldehyde (0.5 mL of 37% wt. in $H_2O$), 12 N HCl (0.25 mL) and 10% Pd/C (50 mg) in methanol (20 mL) was stirred under a balloon of hydrogen for 19 hours. The reaction mixture was filtered through diatomaceous earth (CELITE®) and the filtrate was concentrated in vacuo. The residue was recrystallized from isopropanol to provide the HCl salt of Cap-11 as a white solid (337.7 mg). $^1$H NMR (DMSO-$d_6$, δ=2.5, 500 MHz) 5.39 (d m, J=53.7, 1H), 4.30 (m, 1H), 3.90 (ddd, J=31.5, 13.5, 4.5, 1H), 3.33 (dd, J=25.6, 13.4, 1H), 2.85 (s, 3H), 2.60-2.51 (m, 1H), 2.39-2.26 (m, 1H). RT=0.28 (Cond. II); >98% homogeneity index; LC/MS: Anal. Calcd. for [M+H]$^+$ $C_6H_{11}FNO_2$: 148.08. Found 148.06.

Cap-12 (Same as Cap 52)

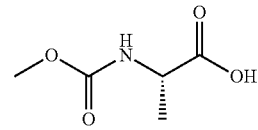

(S)-2-(methoxycarbonylamino)propanoic acid

L-Alanine (2.0 g, 22.5 mmol) was dissolved in 10% aqueous sodium carbonate solution (50 mL), and a THF (50 mL) solution of methyl chloroformate (4.0 mL) was added to it. The reaction mixture was stirred under ambient conditions for 4.5 hours and concentrated in vacuo. The resulting white solid was dissolved in water and acidified with 1N HCl to a pH ~2-3. The resulting solutions was extracted with ethyl acetate (3×100 mL), and the combined organic phase was dried ($Na_2SO_4$), filtered, and concentrated in vacuo to provide a colorless oil (2.58 g). 500 mg of this material was purified by a reverse phase HPLC ($H_2O$/methanol/TFA) to provide 150 mg of Cap-12 as a colorless oil. $^1$H NMR (DMSO-$d_6$, δ=2.5, 500 MHz) 7.44 (d, J=7.3, 0.8H), 7.10 (br s, 0.2H), 3.97 (m, 1H), 3.53 (s, 3H), 1.25 (d, J=7.3, 3H).

Cap-13

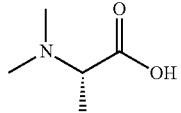

A mixture of L-alanine (2.5 g, 28 mmol), formaldehyde (8.4 g, 37 wt. %), 1N HCl (30 mL) and 10% Pd/C (500 mg) in methanol (30 mL) was stirred under a hydrogen atmosphere (50 psi) for 5 hours. The reaction mixture was filtered through diatomaceous earth (CELITE®) and the filtrate was concentrated in vacuo to provide the HCl salt of Cap-13 as an oil which solidified upon standing under vacuum (4.4 g; the mass is above theoretical yield). The product was used without further purification. $^1$H NMR (DMSO-$d_6$, δ=2.5, 500 MHz) δ 12.1 (br s, 1H), 4.06 (q, J=7.4, 1H), 2.76 (s, 6H), 1.46 (d, J=7.3, 3H).

Cap-14

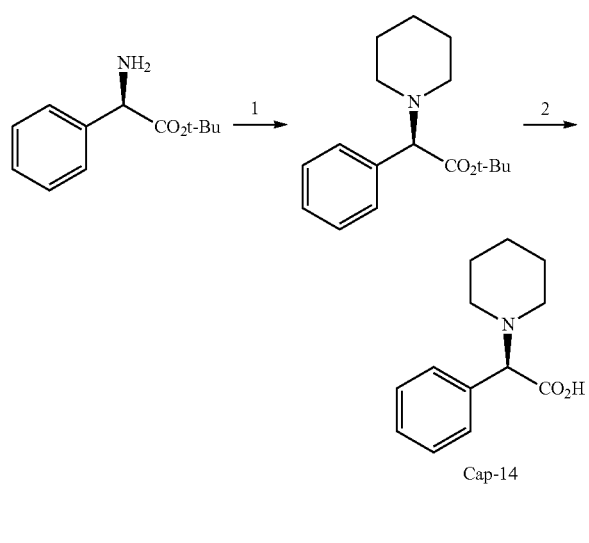

(R)-2-phenyl-2-(piperidin-1-yl)acetic acid

Step 1

A mixture of (R)-(−)-D-phenylglycine tert-butyl ester (3.00 g, 12.3 mmol), NaBH$_3$CN (0.773 g, 12.3 mmol), KOH (0.690 g, 12.3 mmol) and acetic acid (0.352 mL, 6.15 mmol) were stirred in methanol at 0° C. To this mixture was added glutaric dialdehyde (2.23 mL, 12.3 mmol) dropwise over 5 minutes. The reaction mixture was stirred as it was allowed to warm to ambient temperature and stirring was continued at the same temperature for 16 hours. The solvent was subsequently removed and the residue was partitioned with 10% aqueous NaOH and ethyl acetate. The organic phase was separated, dried (MgSO$_4$), filtered and concentrated to dryness to provide a clear oil. This material was purified by reverse-phase preparative HPLC (Primesphere C-18, 30×100 mm; CH$_3$CN—H$_2$O-0.1% TFA) to give the intermediate ester (2.70 g, 56%) as a clear oil. $^1$H NMR (400 MHz, CDCl$_3$) δ 7.53-7.44 (m, 3H), 7.40-7.37 (m, 2H), 3.87 (d, J=10.9 Hz, 1H), 3.59 (d, J=10.9 Hz, 1H), 2.99 (t, J=11.2 Hz, 1H), 2.59 (t, J=11.4 Hz, 1H), 2.07-2.02 (m, 2H), 1.82 (d, J=1.82 Hz, 3H), 1.40 (s, 9H). LC/MS: Anal. Calcd. for C$_{17}$H$_{25}$NO$_2$: 275. Found: 276 (M+H)$^+$.

Step 2

To a stirred solution of the intermediate ester (1.12 g, 2.88 mmol) in dichloromethane (10 mL) was added TFA (3 mL). The reaction mixture was stirred at ambient temperature for 4 hours and then it was concentrated to dryness to give a light yellow oil. The oil was purified using reverse-phase preparative HPLC (Primesphere C-18, 30×100 mm; CH$_3$CN—H$_2$O-0.1% TFA). The appropriate fractions were combined and concentrated to dryness in vacuo. The residue was then dissolved in a minimum amount of methanol and applied to applied to MCX LP extraction cartridges (2×6 g). The cartridges were rinsed with methanol (40 mL) and then the desired compound was eluted using 2M ammonia in methanol (50 mL). Product-containing fractions were combined and concentrated and the residue was taken up in water. Lyophilization of this solution provided the title compound (0.492 g, 78%) as a light yellow solid. $^1$H NMR (DMSO-$d_6$) δ 7.50 (s, 5H), 5.13 (s, 1H), 3.09 (br s, 2H), 2.92-2.89 (m, 2H), 1.74 (m, 4H), 1.48 (br s, 2H). LC/MS: Anal. Calcd. for C$_{13}$H$_{17}$NO$_2$: 219. Found: 220 (M+H)$^+$.

Cap-15

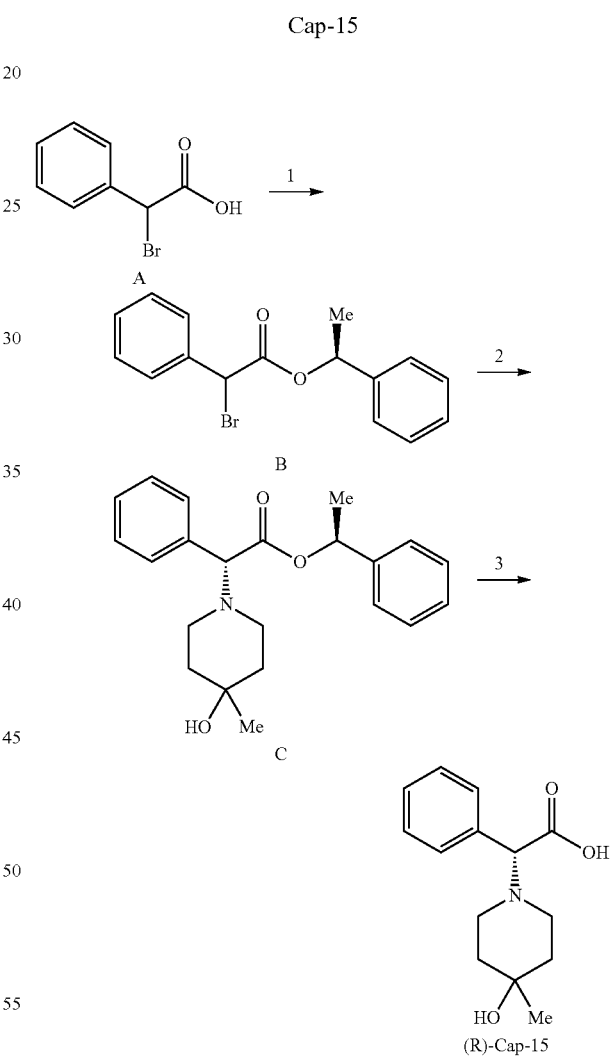

Step 1

(S)-1-Phenylethyl 2-bromo-2-phenylacetate: To a mixture of α-bromophenylacetic acid (10.75 g, 0.050 mol), (S)-(−)-1-phenylethanol (7.94 g, 0.065 mol) and DMAP (0.61 g, 5.0 mmol) in dry dichloromethane (100 mL) was added solid EDCI (12.46 g, 0.065 mol) all at once. The resulting solution was stirred at room temperature under Ar for 18 hours and then it was diluted with ethyl acetate, washed (H₂O×2, brine), dried (Na₂SO₄), filtered, and concentrated to give a pale yellow oil. Flash chromatography (SiO₂/hexane-ethyl acetate, 4:1) of this oil provided the title compound (11.64 g, 73%) as a white solid. $^1$H NMR (400 MHz, CDCl₃) δ 7.53-7.17 (m, 10H), 5.95 (q, J=6.6 Hz, 0.5H), 5.94 (q, J=6.6 Hz, 0.5H), 5.41 (s, 0.5H), 5.39 (s, 0.5H), 1.58 (d, J=6.6 Hz, 1.5H), 1.51 (d, J=6.6 Hz, 1.5H).

Step 2

(S)-1-Phenylethyl (R)-2-(4-hydroxy-4-methylpiperidin-1-yl)-2-phenylacetate: To a solution of (S)-1-phenylethyl 2-bromo-2-phenylacetate (0.464 g, 1.45 mmol) in THF (8 mL) was added triethylamine (0.61 mL, 4.35 mmol), followed by tetrabutylammonium iodide (0.215 g, 0.58 mmol). The reaction mixture was stirred at room temperature for 5 minutes and then a solution of 4-methyl-4-hydroxypiperidine (0.251 g, 2.18 mmol) in THF (2 mL) was added. The mixture was stirred for 1 hour at room temperature and then it was heated at 55-60° C. (oil bath temperature) for 4 hours. The cooled reaction mixture was then diluted with ethyl acetate (30 mL), washed (H₂O×2, brine), dried (MgSO₄), filtered and concentrated. The residue was purified by silica gel chromatography (0-60% ethyl acetate-hexane) to provide first the (S,R)-isomer of the title compound (0.306 g, 60%) as a white solid and then the corresponding (S,S)-isomer (0.120 g, 23%), also as a white solid. (S,R)-isomer: $^1$H NMR (CD₃OD) δ 7.51-7.45 (m, 2H), 7.41-7.25 (m, 8H), 5.85 (q, J=6.6 Hz, 1H), 4.05 (s, 1H), 2.56-2.45 (m, 2H), 2.41-2.29 (m, 2H), 1.71-1.49 (m, 4H), 1.38 (d, J=6.6 Hz, 3H), 1.18 (s, 3H). LCMS: Anal. Calcd. for C₂₂H₂₂NO₃: 353. Found: 354 (M+H)⁺. (S,S)-isomer: $^1$H NMR (CD₃OD) δ 7.41-7.30 (m, 5H), 7.20-7.14 (m, 3H), 7.06-7.00 (m, 2H), 5.85 (q, J=6.6 Hz, 1H), 4.06 (s, 1H), 2.70-2.60 (m, 1H), 2.51 (dt, J=6.6, 3.3 Hz, 1H), 2.44-2.31 (m, 2H), 1.75-1.65 (m, 1H), 1.65-1.54 (m, 3H), 1.50 (d, J=6.8 Hz, 3H), 1.20 (s, 3H). LCMS: Anal. Calcd. for C₂₂H₂₂NO₃: 353. Found: 354 (M+H)⁺.

Step 3

(R)-2-(4-Hydroxy-4-methylpiperidin-1-yl)-2-phenylacetic acid: To a solution of (S)-1-phenylethyl (R)-2-(4-hydroxy-4-methylpiperidin-1-yl)-2-phenylacetate (0.185 g, 0.52 mmol) in dichloromethane (3 mL) was added trifluoroacetic acid (1 mL) and the mixture was stirred at room temperature for 2 hours. The volatiles were subsequently removed in vacuo and the residue was purified by reverse-phase preparative HPLC (Primesphere C-18, 20×100 mm; CH₃CN—H₂O-0.1% TFA) to give the title compound (as TFA salt) as a pale bluish solid (0.128 g, 98%). LCMS: Anal. Calcd. for C₁₄H₁₉NO₃: 249. Found: 250 (M+H)⁺.

Cap-16

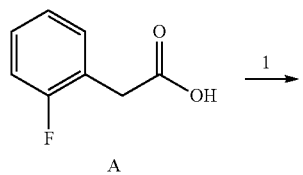

A

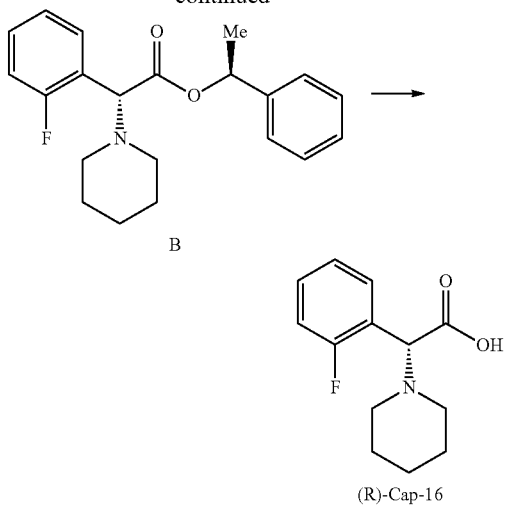

B (R)-Cap-16

Step 1

(S)-1-Phenylethyl 2-(2-fluorophenyl)acetate: A mixture of 2-fluorophenylacetic acid (5.45 g, 35.4 mmol), (S)-1-phenylethanol (5.62 g, 46.0 mmol), EDCI (8.82 g, 46.0 mmol) and DMAP (0.561 g, 4.60 mmol) in CH₂Cl₂ (100 mL) was stirred at room temperature for 12 hours. The solvent was then concentrated and the residue partitioned with H₂O-ethyl acetate. The phases were separated and the aqueous layer back-extracted with ethyl acetate (2×). The combined organic phases were washed (H₂O, brine), dried (Na₂SO₄), filtered, and concentrated in vacuo. The residue was purified by silica gel chromatography (BIOTAGE®/0-20% ethyl acetate-hexane) to provide the title compound as a colorless oil (8.38 g, 92%). $^1$H NMR (400 MHz, CD₃OD) δ 7.32-7.23 (m, 7H), 7.10-7.04 (m, 2), 5.85 (q, J=6.5 Hz, 1H), 3.71 (s, 2H), 1.48 (d, J=6.5 Hz, 3H).

Step 2

(R)—((S)-1-Phenylethyl) 2-(2-fluorophenyl)-2-(piperidin-1-yl)acetate: To a solution of (S)-1-phenylethyl 2-(2-fluorophenyl)acetate (5.00 g, 19.4 mmol) in THF (1200 mL) at 0° C. was added DBU (6.19 g, 40.7 mmol) and the solution was allowed to warm to room temperature while stirring for 30 minutes. The solution was then cooled to −78° C. and a solution of CBr₄ (13.5 g, 40.7 mmol) in THF (100 mL) was added and the mixture was allowed to warm to −10° C. and stirred at this temperature for 2 hours. The reaction mixture was quenched with saturated aq. NH₄Cl and the layers were separated. The aqueous layer was back-extracted with ethyl acetate (2×) and the combined organic phases were washed (H₂O, brine), dried (Na₂SO₄), filtered, and concentrated in vacuo. To the residue was added piperidine (5.73 mL, 58.1 mmol) and the solution was stirred at room temperature for 24 hours. The volatiles were then concentrated in vacuo and the residue was purified by silica gel chromatography (BIOTAGE®/0-30% diethyl ether-hexane) to provide a pure mixture of diastereomers (2:1 ratio by $^1$H NMR) as a yellow oil (2.07 g, 31%), along with unreacted starting material (2.53 g, 51%). Further chromatography of the diastereomeric mixture (BIOTAGE®/0-10% diethyl ether-toluene) provided the title compound as a colorless oil (0.737 g, 11%). $^1$H NMR (400 MHz, CD₃OD) δ 7.52 (ddd, J=9.4, 7.6, 1.8 Hz, 1H), 7.33-7.40 (m, 1), 7.23-7.23 (m, 4H), 7.02-7.23 (m, 4H), 5.86 (q, J=6.6 Hz, 1H), 4.45 (s, 1H), 2.39-2.45 (m, 4H), 1.52-1.58 (m, 4H), 1.40-1.42 (m, 1H), 1.38 (d, J=6.6 Hz, 3H). LCMS: Anal. Calcd. for $C_{21}H_{24}FNO_2$: 341. Found: 342 $(M+H)^+$.

Step 3

(R)-2-(2-fluorophenyl)-2-(piperidin-1-yl)acetic acid: A mixture of (R)—((S)-1-phenylethyl) 2-(2-fluorophenyl)-2-(piperidin-1-yl)acetate (0.737 g, 2.16 mmol) and 20% Pd(OH)$_2$/C (0.070 g) in ethanol (30 mL) was hydrogenated at room temperature and atmospheric pressure (H$_2$ balloon) for 2 hours. The solution was then purged with Ar, filtered through diatomaceous earth (CELITE®), and concentrated in vacuo. This provided the title compound as a colorless solid (0.503 g, 98%). $^1$H NMR (400 MHz, CD$_3$OD) δ 7.65 (ddd, J=9.1, 7.6, 1.5 Hz, 1H), 7.47-7.53 (m, 1H), 7.21-7.30 (m, 2H), 3.07-3.13 (m, 4H), 1.84 (br s, 4H), 1.62 (br s, 2H). LCMS: Anal. Calcd. for $C_{13}H_{16}FNO_2$: 237. Found: 238 $(M+H)^+$.

Cap-17

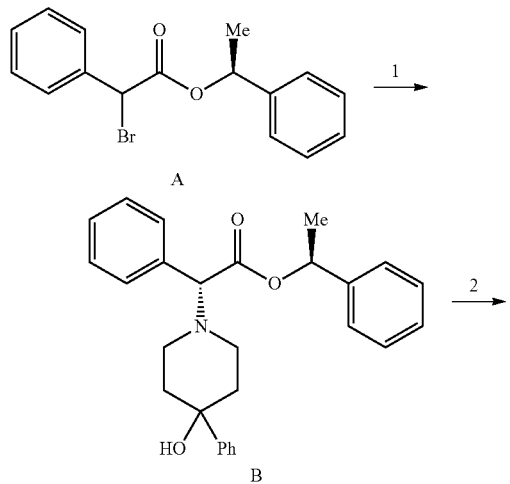

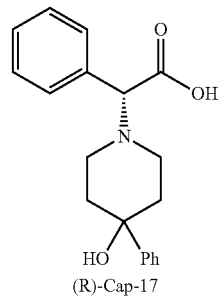

(R)-Cap-17

Step 1

(S)-1-Phenylethyl (R)-2-(4-hydroxy-4-phenylpiperidin-1-yl)-2-phenylacetate: To a solution of (S)-1-phenylethyl 2-bromo-2-phenylacetate (1.50 g, 4.70 mmol) in THF (25 mL) was added triethylamine (1.31 mL, 9.42 mmol), followed by tetrabutylammonium iodide (0.347 g, 0.94 mmol). The reaction mixture was stirred at room temperature for 5 minutes and then a solution of 4-phenyl-4-hydroxypiperidine (1.00 g, 5.64 mmol) in THF (5 mL) was added. The mixture was stirred for 16 hours and then it was diluted with ethyl acetate (100 mL), washed (H$_2$O×2, brine), dried (MgSO$_4$), filtered and concentrated. The residue was purified on a silica gel column (0-60% ethyl acetate-hexane) to provide an approximately 2:1 mixture of diastereomers, as judged by $^1$H NMR. Separation of these isomers was performed using supercritical fluid chromatography (CHIRALCEL® OJ-H, 30×250 mm; 20% ethanol in CO$_2$ at 35° C.), to give first the (R)-isomer of the title compound (0.534 g, 27%) as a yellow oil and then the corresponding (S)-isomer (0.271 g, 14%), also as a yellow oil. (S,R)-isomer: $^1$H NMR (400 MHz, CD$_3$OD) δ 7.55-7.47 (m, 4H), 7.44-7.25 (m, 10H), 7.25-7.17 (m, 1H), 5.88 (q, J=6.6 Hz, 1H), 4.12 (s, 1H), 2.82-2.72 (m, 1H), 2.64 (dt, J=11.1, 2.5 Hz, 1H), 2.58-2.52 (m, 1H), 2.40 (dt, J=11.1, 2.5 Hz, 1H), 2.20 (dt, J=12.1, 4.6 Hz, 1H), 2.10 (dt, J=12.1, 4.6 Hz, 1H), 1.72-1.57 (m, 2H), 1.53 (d, J=6.5 Hz, 3H). LCMS: Anal. Calcd. for $C_{27}H_{29}NO_3$: 415. Found: 416 $(M+H)^+$; (S,S)-isomer: $H^1$NMR (400 MHz, CD$_3$OD) δ 7.55-7.48 (m, 2H), 7.45-7.39 (m, 2H), 7.38-7.30 (m, 5H), 7.25-7.13 (m, 4H), 7.08-7.00 (m, 2H), 5.88 (q, J=6.6 Hz, 1H), 4.12 (s, 1H), 2.95-2.85 (m, 1H), 2.68 (dt, J=11.1, 2.5 Hz, 1H), 2.57-2.52 (m, 1H), 2.42 (dt, J=11.1, 2.5 Hz, 1H), 2.25 (dt, J=12.1, 4.6 Hz, 1H), 2.12 (dt, J=12.1, 4.6 Hz, 1H), 1.73 (dd, J=13.6, 3.0 Hz, 1H), 1.64 (dd, J=13.6, 3.0 Hz, 1H), 1.40 (d, J=6.6 Hz, 3H). LCMS: Anal. Calcd. for $C_{27}H_{29}NO_3$: 415. Found: 416 $(M+H)^+$.

The following esters were prepared in similar fashion:

Intermediate-17a

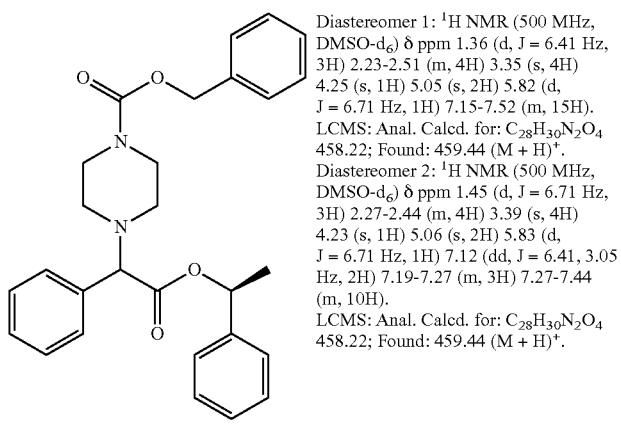

Diastereomer 1: $^1$H NMR (500 MHz, DMSO-d$_6$) δ ppm 1.36 (d, J = 6.41 Hz, 3H) 2.23-2.51 (m, 4H) 3.35 (s, 4H) 4.25 (s, 1H) 5.05 (s, 2H) 5.82 (d, J = 6.71 Hz, 1H) 7.15-7.52 (m, 15H). LCMS: Anal. Calcd. for: $C_{28}H_{30}N_2O_4$ 458.22; Found: 459.44 $(M + H)^+$.
Diastereomer 2: $^1$H NMR (500 MHz, DMSO-d$_6$) δ ppm 1.45 (d, J = 6.71 Hz, 3H) 2.27-2.44 (m, 4H) 3.39 (s, 4H) 4.23 (s, 1H) 5.06 (s, 2H) 5.83 (d, J = 6.71 Hz, 1H) 7.12 (dd, J = 6.41, 3.05 Hz, 2H) 7.19-7.27 (m, 3H) 7.27-7.44 (m, 10H).
LCMS: Anal. Calcd. for: $C_{28}H_{30}N_2O_4$ 458.22; Found: 459.44 $(M + H)^+$.

-continued

| | | |
|---|---|---|
| Intermediate-17b | 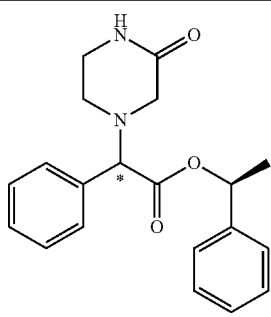 | Diastereomer 1: RT = 11.76 minutes (Cond'n II); LCMS: Anal. Calcd. for: $C_{20}H_{22}N_2O_3$ 338.16 Found: 339.39 $(M + H)^+$; Diastereomer 2: RT = 10.05 minutes (Cond'n II); LCMS: Anal. Calcd. for: $C_{20}H_{22}N_2O_3$ 338.16; Found: 339.39 $(M + H)^+$. |
| Intermediate-17c | 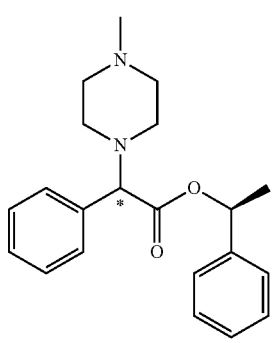 [SMILES: C[C@H](OC(=O)C(c1ccccc1)N1CCN(C)CC1)c1ccccc1] | Diastereomer 1: $T_R$ = 4.55 minutes (Cond'n I); LCMS: Anal. Calcd. for: $C_{21}H_{26}N_2O_2$ 338.20 Found: 339.45 $(M + H)^+$; Diastereomer 2: $T_R$ = 6.00 minutes (Cond'n I); LCMS: Anal. Calcd. for: $C_{21}H_{26}N_2O_2$ 338.20 Found: 339.45 $(M + H)^+$. |
| Intermediate-17d | 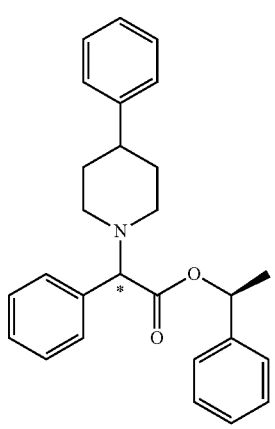 [SMILES: C[C@H](OC(=O)C(c1ccccc1)N1CCC(c2ccccc2)CC1)c1ccccc1] | Diastereomer 1: RT = 7.19 minutes (Cond'n I); LCMS: Anal. Calcd. for: $C_{27}H_{29}NO_2$ 399.22 Found: 400.48 $(M + H)^+$; Diastereomer 2: RT = 9.76 minutes (Cond'n I); LCMS: Anal. Calcd. for: $C_{27}H_{29}NO_2$ 399.22 Found: 400.48 $(M + H)^+$. |

Chiral SFC Conditions for Determining Retention Time
  Condition I
Column: CHIRALPAK® AD-H Column, 4.62×50 mm, 5 μm
Solvents: 90% $CO_2$-10% methanol with 0.1% DEA
Temp: 35° C.
Pressure: 150 bar
Flow rate: 2.0 mL/min.
UV monitored at 220 nm
Injection: 1.0 mg/3 mL methanol
  Condition II
Column: CHIRALCEL® OD-H Column, 4.62×50 mm, 5 μm
Solvents: 90% CO2-10% methanol with 0.1% DEA
Temp: 35° C.
Pressure: 150 bar
Flow rate: 2.0 mL/min.
UV monitored at 220 nm
Injection: 1.0 mg/mL methanol Cap-17, Step 2; (R)-2-(4-Hydroxy-4-phenylpiperidin-1-yl)-2-phenylacetic acid: To a solution of (S)-1-phenylethyl (R)-2-(4-hydroxy-4-phenylpiperidin-1-yl)-2-phenylacetate (0.350 g, 0.84 mmol) in dichloromethane (5 mL) was added trifluoroacetic acid (1 mL) and the mixture was stirred at room temperature for 2 hours. The volatiles were subsequently removed in vacuo and the residue was purified by reverse-phase preparative HPLC (Primesphere C-18, 20×100 mm; $CH_3CN$—$H_2O$-0.1% TFA) to give the title compound (as TFA salt) as a white solid (0.230 g, 88%). LCMS: Anal. Calcd. for $C_{19}H_{21}NO_3$: 311.15. Found: 312 $(M+H)^+$.

The following carboxylic acids were prepared in optically pure form in a similar fashion:

Cap-17a 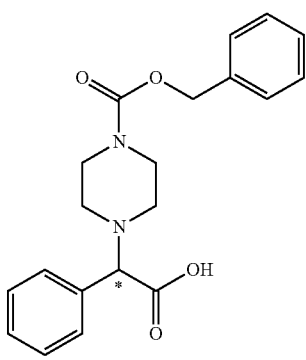 [SMILES: O=C(O)C(c1ccccc1)N1CCN(C(=O)OCc2ccccc2)CC1] RT = 2.21 (Cond'n II); ¹H NMR (500 MHz, DMSO-d$_6$) δ ppm 2.20-2.35 (m, 2H) 2.34-2.47 (m, 2H) 3.37 (s, 4H) 3.71 (s, 1H) 5.06 (s, 2H) 7.06-7.53 (m, 10H). LCMS: Anal. Calcd. for: $C_{20}H_{22}N_2O_4$ 354.16; Found: 355.38 $(M + H)^+$.

Cap-17b 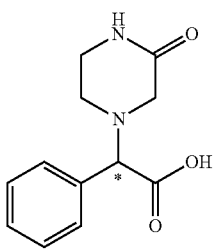 [SMILES: O=C1CN(C(C(=O)O)c2ccccc2)CCN1] RT = 0.27 (Cond'n III); LCMS: Anal. Calcd. for: $C_{12}H_{14}N_2O_3$ 234.10; Found: 235.22 $(M + H)^+$.

Cap-17c 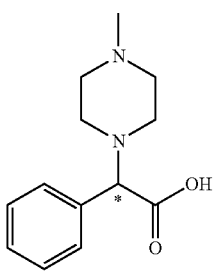 [SMILES: CN1CCN(C(C(=O)O)c2ccccc2)CC1] RT = 0.48 (Cond'n II); LCMS: Anal. Calcd. for: $C_{13}H_{18}N_2O_2$ 234.14; Found: 235.31 $(M + H)^+$.

Cap-17d 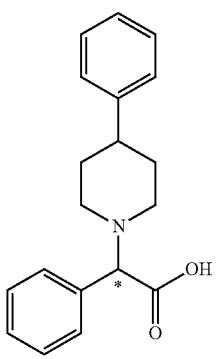 [SMILES: O=C(O)C(c1ccccc1)N1CCC(c2ccccc2)CC1] RT = 2.21 (Cond'n I); LCMS: Anal. Calcd. for: $C_{19}H_{21}NO_2$ 295.16; Found: 296.33 $(M + H)^+$.

LCMS Conditions for Determining Retention Time

Condition I

Column: PHENOMENEX ® Luna 4.6 × 50 mm S10
Start % B = 0
Final % B = 100
Gradient Time = 4 min
Flow Rate = 4 mL/min
Wavelength = 220

Solvent A = 10% methanol - 90% H$_2$O - 0.1% TFA
Solvent B = 90% methanol - 10% H$_2$O - 0.1% TFA Condition II Column: Waters-Sunfire 4.6 × 50 mm S5
Start % B = 0
Final % B = 100

-continued

Gradient Time = 2 min
Flow Rate = 4 mL/min
Wavelength = 220
Solvent A = 10% methanol - 90% H₂O - 0.1% TFA
Solvent B = 90% methanol - 10% H₂O - 0.1% TFA Condition III Column: PHENOMENEX ® 10μ 3.0 × 50 mm
Start % B = 0
Final % B = 100
Gradient Time = 2 min
Flow Rate = 4 mL/min
Wavelength = 220
Solvent A = 10% methanol - 90% H₂O - 0.1% TFA
Solvent B = 90% methanol - 10% H₂O - 0.1% TFA Cap-18

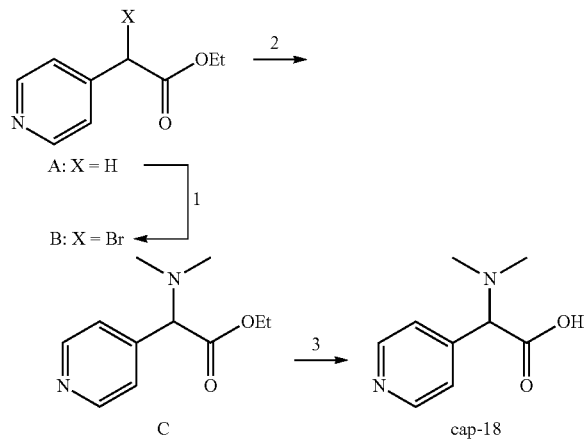

Step 1

(R,S)-Ethyl 2-(4-pyridyl)-2-bromoacetate: To a solution of ethyl 4-pyridylacetate (1.00 g, 6.05 mmol) in dry THF (150 mL) at 0° C. under argon was added DBU (0.99 mL, 6.66 mmol). The reaction mixture was allowed to warm to room temperature over 30 minutes and then it was cooled to −78° C. To this mixture was added CBr₄ (2.21 g, 6.66 mmol) and stirring was continued at −78° C. for 2 hours. The reaction mixture was then quenched with sat. aq. NH₄Cl and the phases were separated. The organic phase was washed (brine), dried (Na₂SO₄), filtered, and concentrated in vacuo. The resulting yellow oil was immediately purified by flash chromatography (SiO₂/hexane-ethyl acetate, 1:1) to provide the title compound (1.40 g, 95%) as a somewhat unstable yellow oil. $^1$H NMR (400 MHz, CDCl₃) δ 8.62 (dd, J=4.6, 1.8 Hz, 2H), 7.45 (dd, J=4.6, 1.8 Hz, 2H), 5.24 (s, 1H), 4.21-4.29 (m, 2H), 1.28 (t, J=7.1 Hz, 3H). LCMS: Anal. Calcd. for C₉H₁₀BrNO₂: 242, 244. Found: 243, 245 (M+H)⁺.

Step 2

(R,S)-Ethyl 2-(4-pyridyl)-2-(N,N-dimethylamino)acetate: To a solution of (R,S)-ethyl 2-(4-pyridyl)-2-bromoacetate (1.40 g, 8.48 mmol) in DMF (10 mL) at room temperature was added dimethylamine (2M in THF, 8.5 mL, 17.0 mmol). After completion of the reaction (as judged by thin layer chromatography) the volatiles were removed in vacuo and the residue was purified by flash chromatography (BIOTAGE®, 40+M SiO₂ column; 50%-100% ethyl acetate-hexane) to provide the title compound (0.539 g, 31%) as a light yellow oil. $^1$H NMR (400 MHz, CDCl₃) δ 8.58 (d, J=6.0 Hz, 2H), 7.36 (d, J=6.0 Hz, 2H), 4.17 (m, 2H), 3.92 (s, 1H), 2.27 (s, 6H), 1.22 (t, J=7.0 Hz). LCMS: Anal. Calcd. for C₁₁H₁₆N₂O₂: 208. Found: 209 (M+H)⁺.

Step 3

(R,S)-2-(4-Pyridyl)-2-(N,N-dimethylamino)acetic acid: To a solution of (R,S)-ethyl 2-(4-pyridyl)-2-(N,N-dimethylamino)acetate (0.200 g, 0.960 mmol) in a mixture of THF-methanol-H₂O (1:1:1, 6 mL) was added powdered LiOH (0.120 g, 4.99 mmol) at room temperature. The solution was stirred for 3 hours and then it was acidified to pH 6 using 1N HCl. The aqueous phase was washed with ethyl acetate and then it was lyophilized to give the dihydrochloride of the title compound as a yellow solid (containing LiCl). The product was used as such in subsequent steps. $^1$H NMR (400 MHz, DMSO-d₆) δ 8.49 (d, J=5.7 Hz, 2H), 7.34 (d, J=5.7 Hz, 2H), 3.56 (s, 1H), 2.21 (s, 6H).

The following examples were prepared in similar fashion using the method described above;

| | | |
|---|---|---|
| Cap-19 | 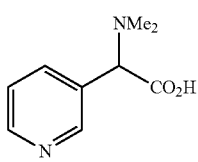 [SMILES: CN(C)C(C(=O)O)c1cccnc1] | LCMS: Anal. Calcd. for C₉H₁₂N₂O₂: 180; found: 181 (M + H)⁺. |
| Cap-20 | 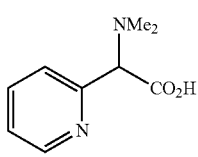 [SMILES: CN(C)C(C(=O)O)c1ccccn1] | LCMS: no ionization. $^1$H NMR (400 MHz, CD₃OD) δ 8.55 (d, J = 4.3 Hz, 1H), 7.84 (app t, J = 5.3 Hz, 1H), 7.61 (d, J = 7.8 Hz, 1H), 7.37 (app t, J = 5.3 Hz, 1H), 4.35 (s, 1H), 2.60 (s, 6H). |

| | | |
|---|---|---|
| Cap-21 | 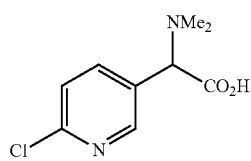 [SMILES: CN(C)C(C(=O)O)c1ccc(Cl)nc1] | LCMS: Anal. Calcd. for $C_9H_{11}ClN_2O_2$: 214, 216; found: 215, 217 $(M + H)^+$. |
| Cap-22 | 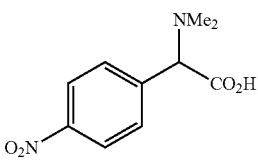 [SMILES: CN(C)C(C(=O)O)c1ccc([N+](=O)[O-])cc1] | LCMS: Anal. Calcd. for $C_{10}H_{12}N_2O_4$: 224; found: 225 $(M + H)^+$. |
| Cap-23 | 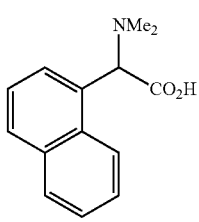 [SMILES: CN(C)C(C(=O)O)c1cccc2ccccc12] | LCMS: Anal. Calcd. for $C_{14}H_{15}NO_2$: 229; found: 230 $(M + H)^+$. |
| Cap-24 | 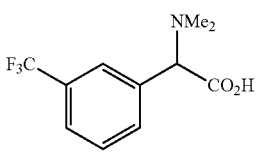 | LCMS: Anal. Calcd. for $C_{11}H_{12}F_3NO_2$: 247; found: 248 $(M + H)^+$. |
| Cap-25 | 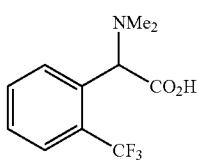 [SMILES: CN(C)C(C(=O)O)c1ccccc1C(F)(F)F] | LCMS: Anal. Calcd. for $C_{11}H_{12}F_3NO_2$: 247; found: 248 $(M + H)^+$. |
| Cap-26 | 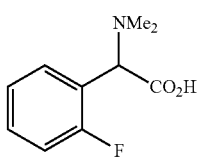 [SMILES: CN(C)C(C(=O)O)c1ccccc1F] | LCMS: Anal. Calcd. for $C_{10}H_{12}FNO_2$: 197; found: 198 $(M + H)^+$. |
| Cap-27 | 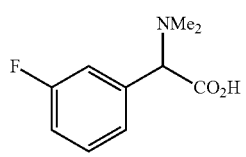 | LCMS: Anal. Calcd. for $C_{10}H_{12}FNO_2$: 247; found: 248 $(M + H)^+$. |
| Cap-28 | 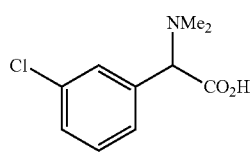 [SMILES: CN(C)C(C(=O)O)c1cccc(Cl)c1] | LCMS: Anal. Calcd. for $C_{10}H_{12}ClNO_2$: 213; found: 214 $(M + H)^+$. |
| Cap-29 | 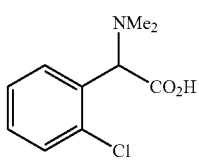 [SMILES: CN(C)C(C(=O)O)c1ccccc1Cl] | LCMS: Anal. Calcd. for $C_{10}H_{12}ClNO_2$: 213; found: 214 $(M + H)^+$. |

-continued
| | | |
|---|---|---|
| Cap-30 | 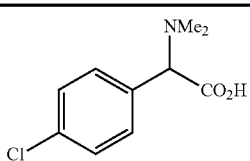 | LCMS: Anal. Calcd. for $C_{10}H_{12}ClNO_2$: 213; found: 214 $(M + H)^+$. |
| Cap-31 | 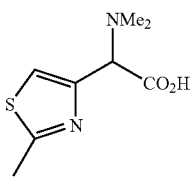 | LCMS: Anal. Calcd. for $C_8H_{12}N_2O_2S$: 200; found: 201 $(M + H)^+$. |
| Cap-32 | 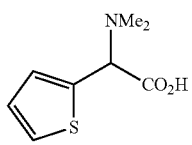 [SMILES: CN(C)C(C(=O)O)c1cccs1] | LCMS: Anal. Calcd. for $C_8H_{11}NO_2S$: 185; found: 186 $(M + H)^+$. |
| Cap-33 | 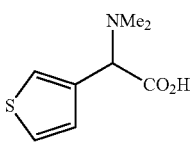 [SMILES: CN(C)C(C(=O)O)c1ccsc1] | LCMS: Anal. Calcd. for $C_8H_{11}NO_2S$: 185; found: 186 $(M + H)^+$. |
| Cap-34 | 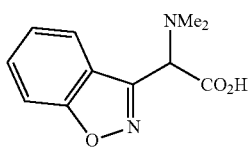 [SMILES: CN(C)C(C(=O)O)c1noc2ccccc12] | LCMS: Anal. Calcd. for $C_{11}H_{12}N_2O_3$: 220; found: 221 $(M + H)^+$. |
| Cap-35 | 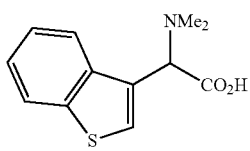 [SMILES: CN(C)C(C(=O)O)c1csc2ccccc12] | LCMS: Anal. Calcd. for $C_{12}H_{13}NO_2S$: 235; found: 236 $(M + H)^+$. |
| Cap-36 | 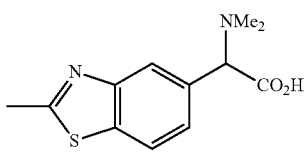 [SMILES: Cc1nc2cc(C(C(=O)O)N(C)C)ccc2s1] | LCMS: Anal. Calcd. for $C_{12}H_{14}N_2O_2S$: 250; found: 251 $(M + H)^+$. |
Cap-37
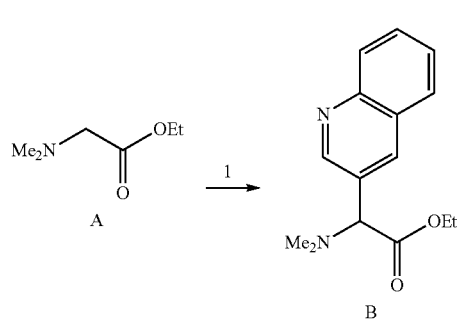
-continued
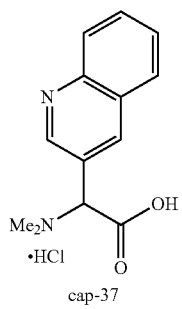
cap-37

Step 1

(R,S)-Ethyl 2-(quinolin-3-yl)-2-(N,N-dimethylamino)acetate: A mixture of ethyl N,N-dimethylaminoacetate (0.462 g, 3.54 mmol), $K_3PO_4$ (1.90 g, 8.95 mmol), Pd(t-$Bu_3$P)$_2$ (0.090 g, 0.176 mmol), 3-bromoquinoline and toluene (10 mL) was degassed with a stream of Ar bubbles for 15 minutes. The reaction mixture was then heated at 100° C. for 12 hours, after which it was cooled to room temperature and poured into $H_2O$. The mixture was extracted with ethyl acetate (2×) and the combined organic phases were washed ($H_2O$, brine), dried ($Na_2SO_4$), filtered, and concentrated in vacuo. The residue was purified first by reverse-phase preparative HPLC (Primesphere C-18, 30×100 mm; $CH_3CN$—$H_2O$-5 mM $NH_4OAc$) and then by flash chromatography ($SiO_2$/hexane-ethyl acetate, 1:1) to provide the title compound (0.128 g, 17%) as an orange oil. $^1H$ NMR (400 MHz, $CDCl_3$) δ 8.90 (d, J=2.0 Hz, 1H), 8.32 (d, J=2.0 Hz, 1H), 8.03-8.01 (m, 2H), 7.77 (ddd, J=8.3, 6.8, 1.5 Hz, 1H), 7.62 (ddd, J=8.3, 6.8, 1.5 Hz, 1H), 4.35 (s, 1H), 4.13 (m, 2H), 2.22 (s, 6H), 1.15 (t, J=7.0 Hz, 3H). LCMS: Anal. Calcd. for $C_{15}H_{18}N_2O_2$: 258. Found: 259 (M+H)$^+$.

Step 2

(R,S) 2-(Quinolin-3-yl)-2-(N,N-dimethylamino)acetic acid: A mixture of (R,S)-ethyl 2-(quinolin-3-yl)-2-(N,N-dimethylamino)acetate (0.122 g, 0.472 mmol) and 6M HCl (3 mL) was heated at 100° C. for 12 hours. The solvent was removed in vacuo to provide the dihydrochloride of the title compound (0.169 g, >100%) as a light yellow foam. The unpurified material was used in subsequent steps without further purification. LCMS: Anal. Calcd. for $C_{13}H_{14}N_2O_2$: 230. Found: 231 (M+H)$^+$.

Cap-38

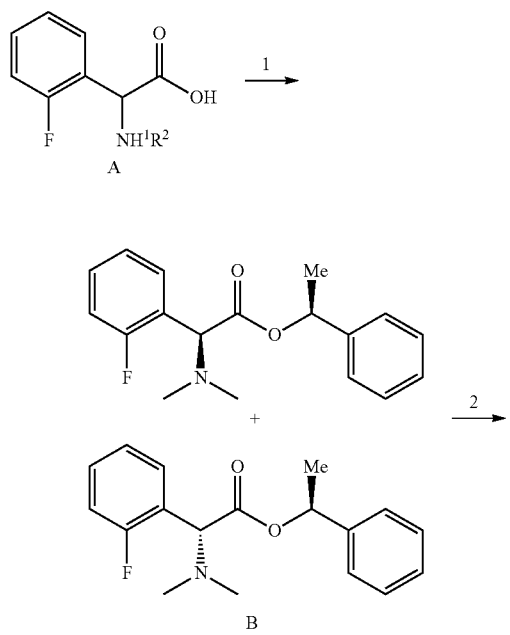

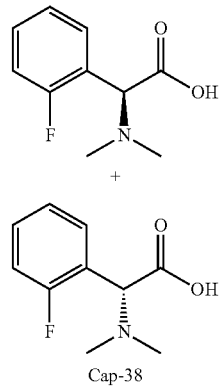

Cap-38

Step 1

(R)—((S)-1-phenylethyl) 2-(dimethylamino)-2-(2-fluorophenyl)acetate and (S)—((S)-1-phenylethyl) 2-(dimethylamino)-2-(2-fluorophenyl)acetate: To a mixture of (RS)-2-(dimethylamino)-2-(2-fluorophenyl)acetic acid (2.60 g, 13.19 mmol), DMAP (0.209 g, 1.71 mmol) and (S)-1-phenylethanol (2.09 g, 17.15 mmol) in $CH_2Cl_2$ (40 mL) was added EDCI (3.29 g, 17.15 mmol) and the mixture was allowed to stir at room temperature for 12 hours. The solvent was then removed in vacuo and the residue partitioned with ethyl acetate-$H_2O$. The layers were separated, the aqueous layer was back-extracted with ethyl acetate (2×) and the combined organic phases were washed ($H_2O$, brine), dried ($Na_2SO_4$), filtered, and concentrated in vacuo. The residue was purified by silica gel chromatography (BIOTAGE®/0-50% diethyl ether-hexane). The resulting pure diastereomeric mixture was then separated by reverse-phase preparative HPLC (Primesphere C-18, 30×100 mm; $CH_3CN$—$H_2O$-0.1% TFA) to give first (S)-1-phenethyl (R)-2-(dimethylamino)-2-(2-fluorophenyl)acetate (0.501 g, 13%) and then (S)-1-phenethyl (S)-2-(dimethylamino)-2-(2-fluorophenyl)acetate (0.727 g, 18%), both as their TFA salts. (S,R)-isomer: $^1H$ NMR (400 MHz, $CD_3OD$) δ 7.65-7.70 (m, 1H), 7.55-7.60 (ddd, J=9.4, 8.1, 1.5 Hz, 1H), 7.36-7.41 (m, 2H), 7.28-7.34 (m, 5H), 6.04 (q, J=6.5 Hz, 1H), 5.60 (s, 1H), 2.84 (s, 6H), 1.43 (d, J=6.5 Hz, 3H). LCMS: Anal. Calcd. for $C_{18}H_{20}FNO_2$: 301. Found: 302 (M+H)$^+$; (S,S)-isomer: $^1H$ NMR (400 MHz, $CD_3OD$) δ 7.58-7.63 (m, 1H), 7.18-7.31 (m, 6H), 7.00 (dd, J=8.5, 1.5 Hz, 2H), 6.02 (q, J=6.5 Hz, 1H), 5.60 (s, 1H), 2.88 (s, 6H), 1.54 (d, J=6.5 Hz, 3H). LCMS: Anal. Calcd. for $C_{18}H_{20}FNO_2$: 301. Found: 302 (M+H)$^+$.

Step 2

(R)-2-(dimethylamino)-2-(2-fluorophenyl)acetic acid: A mixture of (R)—((S)-1-phenylethyl) 2-(dimethylamino)-2-(2-fluorophenyl)acetate TFA salt (1.25 g, 3.01 mmol) and 20% Pd(OH)$_2$/C (0.125 g) in ethanol (30 mL) was hydrogenated at room temperature and atmospheric pressure ($H_2$ balloon) for 4 hours. The solution was then purged with Ar, filtered through diatomaceous earth (CELITE®), and concentrated in vacuo. This gave the title compound as a colorless solid (0.503 g, 98%). $^1H$ NMR (400 MHz, $CD_3OD$) δ 7.53-7.63 (m, 2H), 7.33-7.38 (m, 2H), 5.36 (s, 1H), 2.86 (s, 6H). LCMS: Anal. Calcd. for $C_{10}H_{12}FNO_2$: 197. Found: 198 (M+H)$^+$.

The S-isomer could be obtained from (S)—((S)-1-phenyl-ethyl) 2-(dimethylamino)-2-(2-fluorophenyl)acetate TFA salt in similar fashion.

Cap-39

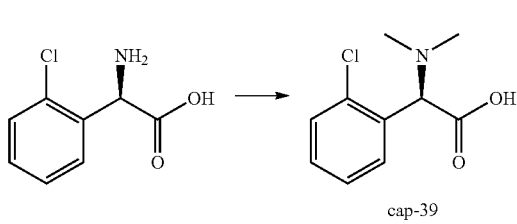

cap-39

A mixture of (R)-(2-chlorophenyl)glycine (0.300 g, 1.62 mmol), formaldehyde (35% aqueous solution, 0.80 mL, 3.23 mmol) and 20% Pd(OH)$_2$/C (0.050 g) was hydrogenated at room temperature and atmospheric pressure (H$_2$ balloon) for 4 hours. The solution was then purged with Ar, filtered through diatomaceous earth (CELITE®) and concentrated in vacuo. The residue was purified by reverse-phase preparative HPLC (Primesphere C-18, 30×100 mm; CH$_3$CN—H$_2$O-0.1% TFA) to give the TFA salt of the title compound (R)-2-(dimethylamino)-2-(2-chlorophenyl)acetic acid as a colorless oil (0.290 g, 55%). $^1$H NMR (400 MHz, CD$_3$OD) δ 7.59-7.65 (m, 2H), 7.45-7.53 (m, 2H), 5.40 (s, 1H), 2.87 (s, 6H). LCMS: Anal. Calcd. for C$_{10}$H$_{12}$ClNO$_2$: 213. Found: 214 (M+H)$^+$.

Cap-40

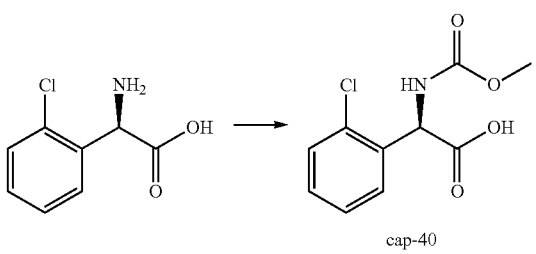 [SMILES: N[C@@H](C(=O)O)c1ccccc1Cl ; COC(=O)N[C@@H](C(=O)O)c1ccccc1Cl]

cap-40

To an ice-cold solution of (R)-(2-chlorophenyl)glycine (1.00 g, 5.38 mmol) and NaOH (0.862 g, 21.6 mmol) in H$_2$O (5.5 mL) was added methyl chloroformate (1.00 mL, 13.5 mmol) dropwise. The mixture was allowed to stir at 0° C. for 1 hour and then it was acidified by the addition of conc. HCl (2.5 mL). The mixture was extracted with ethyl acetate (2×) and the combined organic phase was washed (H$_2$O, brine), dried (Na$_2$SO$_4$), filtered, and concentrated in vacuo to give the title compound (R)-2-(methoxycarbonylamino)-2-(2-chlorophenyl)acetic acid as a yellow-orange foam (1.31 g, 96%). $^1$H NMR (400 MHz, CD$_3$OD) δ 7.39-7.43 (m, 2H), 7.29-7.31 (m, 2H), 5.69 (s, 1H), 3.65 (s, 3H). LCMS: Anal. Calcd. for C$_{10}$H$_{10}$ClNO$_4$: 243. Found: 244 (M+H)$^+$.

Cap-41

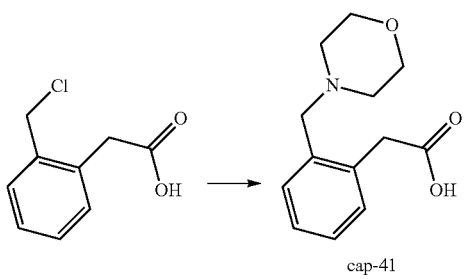 [SMILES: O=C(O)Cc1ccccc1CCl ; O=C(O)Cc1ccccc1CN1CCOCC1]

cap-41

To a suspension of 2-(2-(chloromethyl)phenyl)acetic acid (2.00 g, 10.8 mmol) in THF (20 mL) was added morpholine (1.89 g, 21.7 mmol) and the solution was stirred at room temperature for 3 hours. The reaction mixture was then diluted with ethyl acetate and extracted with H$_2$O (2×). The aqueous phase was lyophilized and the residue was purified by silica gel chromatography (BIOTAGE®/0-10% methanol-CH$_2$Cl$_2$) to give the title compound 2-(2-(Morpholinomethyl)phenyl)acetic acid as a colorless solid (2.22 g, 87%). $^1$H NMR (400 MHz, CD$_3$OD) δ 7.37-7.44 (m, 3H), 7.29-7.33 (m, 1H), 4.24 (s, 2H), 3.83 (br s, 4H), 3.68 (s, 2H), 3.14 (br s, 4H). LCMS: Anal. Calcd. for C$_{13}$H$_{17}$NO$_3$: 235. Found: 236 (M+H)$^+$.

The following examples were similarly prepared using the method described for Cap-41:

| Cap-42 | 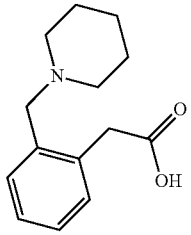 [SMILES: O=C(O)Cc1ccccc1CN1CCCCC1] | LCMS: Anal. Calcd. for C$_{14}$H$_{19}$NO$_2$: 233; found: 234 (M + H)$^+$. |
|---|---|---|
| Cap-43 | 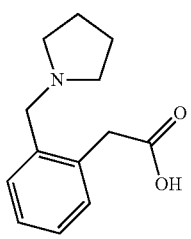 [SMILES: O=C(O)Cc1ccccc1CN1CCCC1] | LCMS: Anal. Calcd. for C$_{13}$H$_{17}$NO$_2$: 219; found: 220 (M + H)$^+$. |
| Cap-44 | 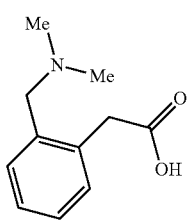 [SMILES: CN(C)Cc1ccccc1CC(=O)O] | LCMS: Anal. Calcd. for C$_{11}$H$_{15}$NO$_2$: 193; found: 194 (M + H)$^+$. |

-continued

Cap-45 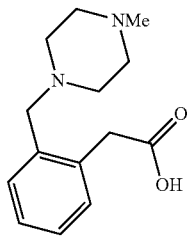 [SMILES: CN1CCN(Cc2ccccc2CC(=O)O)CC1] LCMS: Anal. Calcd. for C$_{14}$H$_{20}$N$_2$O$_2$: 248; found: 249 (M + H)$^+$.

Cap-45a

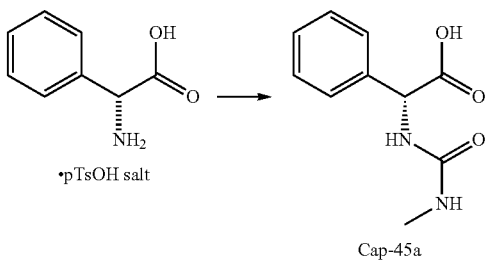

Cap-45a

HMDS (1.85 mL, 8.77 mmol) was added to a suspension of (R)-2-amino-2-phenylacetic acid p-toluenesulfonate (2.83 g, 8.77 mmol) in CH$_2$Cl$_2$ (10 mL) and the mixture was stirred at room temperature for 30 minutes. Methyl isocyanate (0.5 g, 8.77 mmol) was added in one portion stirring continued for 30 minutes. The reaction was quenched by addition of H$_2$O (5 mL) and the resulting precipitate was filtered, washed with H$_2$O and n-hexanes, and dried under vacuum. (R)-2-(3-methylureido)-2-phenylacetic acid (1.5 g; 82%) was recovered as a white solid and it was used without further purification. $^1$H NMR (500 MHz, DMSO-d$_6$) δ ppm 2.54 (d, J=4.88 Hz, 3H) 5.17 (d, J=7.93 Hz, 1H) 5.95 (q, J=4.48 Hz, 1H) 6.66 (d, J=7.93 Hz, 1H) 7.26-7.38 (m, 5H) 12.67 (s, 1H). LCMS: Anal. Calcd. for C$_{10}$H$_{12}$N$_2$O$_3$ 208.08. Found 209.121 (M+H)$^+$; HPLC PHENOMENEX® C-18 3.0×46 mm, 0 to 100% B over 2 minutes, 1 minute hold time, A=90% water, 10% methanol, 0.1% TFA, B=10% water, 90% methanol, 0.1% TFA, RT=1.38 min, 90% homogeneity index.

Cap-46

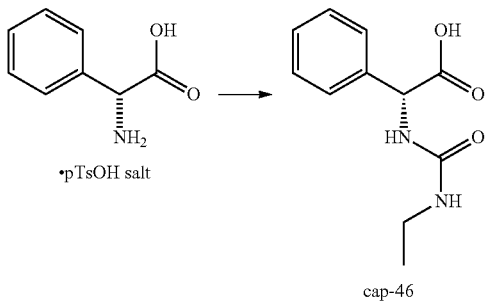 [SMILES: N[C@@H](C(=O)O)c1ccccc1 ; CCNC(=O)N[C@@H](C(=O)O)c1ccccc1]

cap-46

The desired product was prepared according to the method described for Cap-45a. $^1$H NMR (500 MHz, DMSO-d$_6$) δ ppm 0.96 (t, J=7.17 Hz, 3H) 2.94-3.05 (m, 2H) 5.17 (d, J=7.93 Hz, 1H) 6.05 (t, J=5.19 Hz, 1H) 6.60 (d, J=7.63 Hz, 1H) 7.26-7.38 (m, 5H) 12.68 (s, 1H). LCMS: Anal. Calcd. for C$_{11}$H$_{14}$N$_2$O$_3$ 222.10. Found 223.15 (M+H)$^+$. HPLC XTERRA® C-18 3.0×506 mm, 0 to 100% B over 2 minutes, 1 minute hold time, A=90% water, 10% methanol, 0.2% H$_3$PO$_4$, B=10% water, 90% methanol, 0.2% H$_3$PO$_4$, RT=0.87 min, 90% homogeneity index.

Cap-47

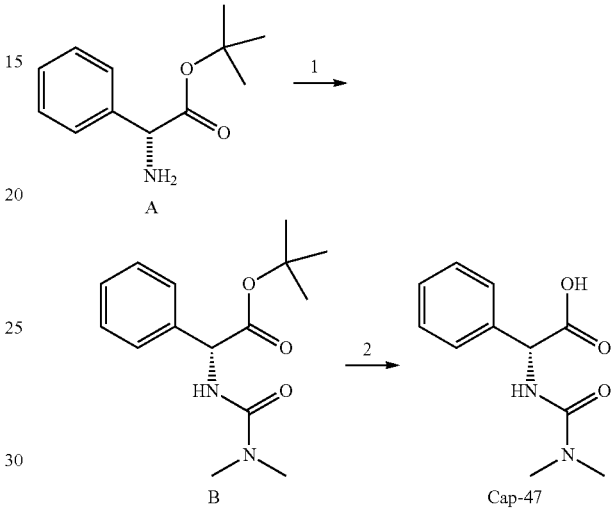

Step 1

(R)-tert-butyl 2-(3,3-dimethylureido)-2-phenylacetate: To a stirred solution of (R)-tert-butyl-2-amino-2-phenylacetate (1.0 g, 4.10 mmol) and Hunig's base (1.79 mL, 10.25 mmol) in DMF (40 mL) was added dimethylcarbamoyl chloride (0.38 mL, 4.18 mmol) dropwise over 10 minutes. After stirring at room temperature for 3 hours, the reaction was concentrated under reduced pressure and the resulting residue was dissolved in ethyl acetate. The organic layer was washed with H$_2$O, 1N aq. HCl and brine, dried (MgSO$_4$), filtered and concentrated under reduced pressure. (R)-tert-butyl 2-(3,3-dimethylureido)-2-phenylacetate was obtained as a white solid (0.86 g; 75%) and used without further purification. $^1$H NMR (500 MHz, DMSO-d$_6$) δ ppm 1.33 (s, 9H) 2.82 (s, 6H) 5.17 (d, J=7.63 Hz, 1H) 6.55 (d, J=7.32 Hz, 1H) 7.24-7.41 (m, 5H). LCMS: Anal. Calcd. for C$_{15}$H$_{22}$N$_2$O$_3$ 278.16. Found 279.23 (M+H)$^+$; HPLC PHENOMENEX® Luna C-18 4.6× 50 mm, 0 to 100% B over 4 minutes, 1 minute hold time, A=90% water, 10% methanol, 0.1% TFA, B=10% water, 90% methanol, 0.1% TFA, RT=2.26 min, 97% homogeneity index.

Step 2

(R)-2-(3,3-dimethylureido)-2-phenylacetic acid: To a stirred solution of ((R)-tert-butyl 2-(3,3-dimethylureido)-2-phenylacetate (0.86 g, 3.10 mmol) in CH$_2$Cl$_2$ (250 mL) was added TFA (15 mL) dropwise and the resulting solution was stirred at rt for 3 hours. The desired compound was then precipitated out of solution with a mixture of EtOAC:Hexanes (5:20), filtered off and dried under reduced pressure. (R)-2-(3,3-dimethylureido)-2-phenylacetic acid was isolated as a white solid (0.59 g, 86%) and used without further purification. $^1$H NMR (500 MHz, DMSO-d$_6$) δ ppm 2.82 (s, 6H) 5.22 (d, J=7.32 Hz, 1H) 6.58 (d, J=7.32 Hz, 1H) 7.28 (t, J=7.17 Hz, 1H) 7.33 (t, J=7.32 Hz, 2H) 7.38-7.43 (m, 2H) 12.65 (s, 1H). LCMS: Anal. Calcd. for $C_{11}H_{14}N_2O_3$: 222.24. Found: 223.21 (M+H)$^+$. HPLC XTERRA® C-18 3.0×50 mm, 0 to 100% B over 2 minutes, 1 minute hold time, A=90% water, 10% methanol, 0.2% $H_3PO_4$, B=10% water, 90% methanol, 0.2% $H_3PO_4$, RT=0.75 min, 93% homogeneity index.

Cap-48

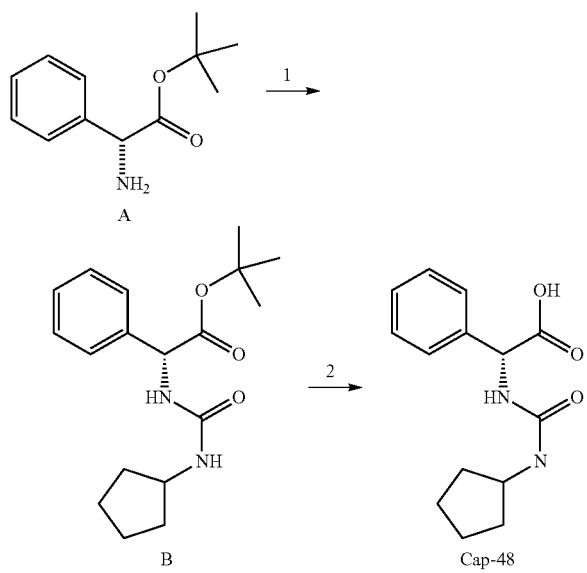

Step 1

(R)-tert-butyl 2-(3-cyclopentylureido)-2-phenylacetate: To a stirred solution of (R)-2-amino-2-phenylacetic acid hydrochloride (1.0 g, 4.10 mmol) and Hunig's base (1.0 mL, 6.15 mmol) in DMF (15 mL) was added cyclopentyl isocyanate (0.46 mL, 4.10 mmol) dropwise and over 10 minutes. After stirring at room temperature for 3 hours, the reaction was concentrated under reduced pressure and the resulting residue was taken up in ethyl acetate. The organic layer was washed with H$_2$O and brine, dried (MgSO$_4$), filtered, and concentrated under reduced pressure. (R)-tert-butyl 2-(3-cyclopentylureido)-2-phenylacetate was obtained as an opaque oil (1.32 g; 100%) and used without further purification. $^1$H NMR (500 MHz, CD$_3$Cl-D) δ ppm 1.50-1.57 (m, 2H) 1.58-1.66 (m, 2H) 1.87-1.97 (m, 2H) 3.89-3.98 (m, 1H) 5.37 (s, 1H) 7.26-7.38 (m, 5H). LCMS: Anal. Calcd. for $C_{18}H_{26}N_2O_3$ 318.19. Found 319.21 (M+H)$^+$; HPLC XTERRA® C-18 3.0× 50 mm, 0 to 100% B over 4 minutes, 1 minute hold time, A=90% water, 10% methanol, 0.1% TFA, B=10% water, 90% methanol, 0.1% TFA, RT=2.82 min, 96% homogeneity index.

Step 2

(R)-2-(3-cyclopentylureido)-2-phenylacetic acid: To a stirred solution of (R)-tert-butyl 2-(3-cyclopentylureido)-2-phenylacetate (1.31 g, 4.10 mmol) in CH$_2$Cl$_2$ (25 mL) was added TFA (4 mL) and trietheylsilane (1.64 mL; 10.3 mmol) dropwise, and the resulting solution was stirred at room temperature for 6 hours. The volatile components were removed under reduced pressure and the crude product was recrystallized in ethyl acetate/pentanes to yield (R)-2-(3-cyclopentylureido)-2-phenylacetic acid as a white solid (0.69 g, 64%). $^1$H NMR (500 MHz, DMSO-d$_6$) δ ppm 1.17-1.35 (m, 2H) 1.42-1.52 (m, 2H) 1.53-1.64 (m, 2H) 1.67-1.80 (m, 2H) 3.75-3.89 (m, 1H) 5.17 (d, J=7.93 Hz, 1H) 6.12 (d, J=7.32 Hz, 1H) 6.48 (d, J=7.93 Hz, 1H) 7.24-7.40 (m, 5H) 12.73 (s, 1H). LCMS: Anal. Calcd. for $C_{14}H_{18}N_2O_3$: 262.31. Found: 263.15 (M+H)$^+$. HPLC XTERRA® C-18 3.0×50 mm, 0 to 100% B over 2 minutes, 1 minute hold time, A=90% water, 10% methanol, 0.2% $H_3PO_4$, B=10% water, 90% methanol, 0.2% $H_3PO_4$, RT=1.24 min, 100% homogeneity index.

Cap-49

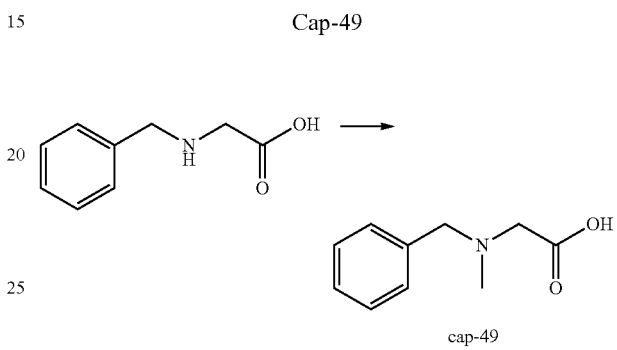

cap-49

To a stirred solution of 2-(benzylamino)acetic acid (2.0 g, 12.1 mmol) in formic acid (91 mL) was added formaldehyde (6.94 mL, 93.2 mmol). After five hours at 70° C., the reaction mixture was concentrated under reduced pressure to 20 mL and a white solid precipitated. Following filtration, the mother liquors were collected and further concentrated under reduced pressure providing the crude product. Purification by reverse-phase preparative HPLC (XTERRA® 30×100 mm, detection at 220 nm, flow rate 35 mL/min, 0 to 35% B over 8 min; A=90% water, 10% methanol, 0.1% TFA, B=10% water, 90% methanol, 0.1% TFA) provided the title compound 2-(benzyl(methyl)-amino)acetic acid as its TFA salt (723 mg, 33%) as a colorless wax. $^1$H NMR (300 MHz, DMSO-d$_6$) δ ppm 2.75 (s, 3H) 4.04 (s, 2H) 4.34 (s, 2H) 7.29-7.68 (m, 5H). LCMS: Anal. Calcd. for: $C_{10}H_{13}NO_2$ 179.09. Found: 180.20 (M+H)$^+$.

Cap-50

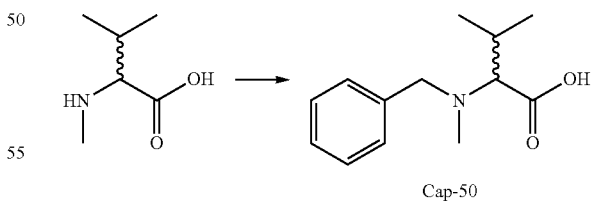

Cap-50

To a stirred solution of 3-methyl-2-(methylamino)butanoic acid (0.50 g, 3.81 mmol) in water (30 mL) was added K$_2$CO$_3$ (2.63 g, 19.1 mmol) and benzyl chloride (1.32 g, 11.4 mmol). The reaction mixture was stirred at ambient temperature for 18 hours. The reaction mixture was extracted with ethyl acetate (30 mL×2) and the aqueous layer was concentrated under reduced pressure providing the crude product which was purified by reverse-phase preparative HPLC (XTERRA® 30×100 mm, detection at 220 nm, flow rate 40 mL/min, 20 to 80% B over 6 min; A=90% water, 10% methanol, 0.1% TFA, B=10% water, 90% methanol, 0.1% TFA) to provide 2-(benzyl(methyl)amino)-3-methylbutanoic acid, TFA salt (126 mg, 19%) as a colorless wax. $^1$H NMR (500 MHz, DMSO-$d_6$) δ ppm 0.98 (d, 3H) 1.07 (d, 3H) 2.33-2.48 (m, 1H) 2.54-2.78 (m, 3H) 3.69 (s, 1H) 4.24 (s, 2H) 7.29-7.65 (m, 5H). LCMS: Anal. Calcd. for: $C_{13}H_{19}NO_2$ 221.14. Found: 222.28 (M+H)$^+$.

Cap-51

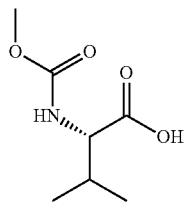

(S)-2-(methoxycarbonylamino)-3-methylbutanoic acid $Na_2CO_3$ (1.83 g, 17.2 mmol) was added to NaOH (33 mL of 1M/$H_2O$, 33 mmol) solution of L-valine (3.9 g, 33.29 mmol) and the resulting solution was cooled with ice-water bath. Methyl chloroformate (2.8 mL, 36.1 mmol) was added dropwise over 15 min, the cooling bath was removed and the reaction mixture was stirred at ambient temperature for 3.25 hr. The reaction mixture was washed with ether (50 mL, 3×), and the aqueous phase was cooled with ice-water bath and acidified with concentrated HCl to a pH region of 1-2, and extracted with $CH_2Cl_2$ (50 mL, 3×). The organic phase was dried (MgSO$_4$) and evaporated in vacuo to afford Cap-51 as a white solid (6 g). $^1$H NMR for the dominant rotamer (DMSO-$d_6$, δ=2.5 ppm, 500 MHz): 12.54 (s, 1H), 7.33 (d, J=8.6, 1H), 3.84 (dd, J=8.4, 6.0, 1H), 3.54 (s, 3H), 2.03 (m, 1H), 0.87 (m, 6H). HRMS: Anal. Calcd. for [M+H]$^+$ $C_7H_{14}NO_4$: 176.0923. Found 176.0922.

Cap-51 (Alternate Route)

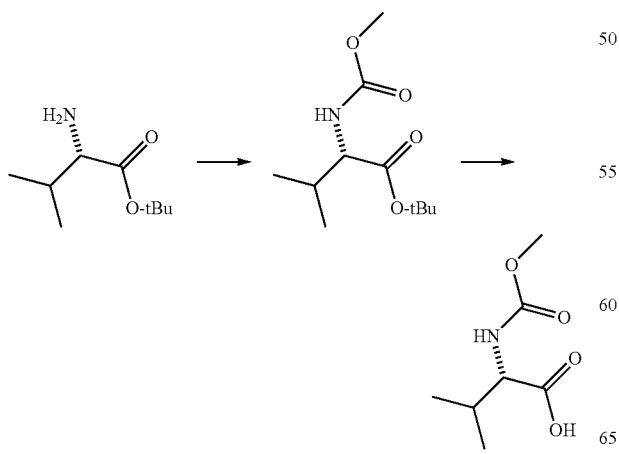

(S)-2-(methoxycarbonylamino)-3-methylbutanoic acid

DIEA (137.5 mL, 0.766 mol) was added to a suspension of (S)-tert-butyl 2-amino-3-methylbutanoate hydrochloride (75.0 g, 0.357 mol) in THF (900 mL), and the mixture was cooled to 0° C. (ice/water bath). Methyl chloroformate (29.0 mL, 0.375 mol) was added dropwise over 45 min, the cooling bath was removed and the heterogeneous mixture was stirred at ambient temperature for 3 h. The solvent was removed under diminished pressure and the residue partitioned between EtOAc and water (1 L each). The organic layer was washed with $H_2O$ (1 L) and brine (1 L), dried (MgSO$_4$), filtered and concentrated under diminished pressure. The crude material was passed through a plug of silica gel (1 kg), eluting with hexanes (4 L) and 15:85 EtOAc/hexanes (4 L) to afford (S)-tert-butyl 2-(methoxycarbonylamino)-3-methylbutanoate as a clear oil (82.0 g, 99% yield). $^1$H-NMR (500 MHz, DMSO-$d_6$, δ=2.5 ppm) 7.34 (d, J=8.6, 1H), 3.77 (dd, J=8.6, 6.1, 1H), 3.53 (s, 3H), 1.94-2.05 (m, 1H), 1.39 (s, 9H), 0.83-0.92 (m, 6H). $^{13}$C-NMR (126 MHz, DMSO-$d_6$, δ=39.2 ppm) 170.92, 156.84, 80.38, 60.00, 51.34, 29.76, 27.62, 18.92, 17.95. LC/MS: [M+Na]$^+$ 254.17.

Trifluoroacetic acid (343 mL, 4.62 mol) and Et$_3$SiH (142 mL, 0.887 mol) were added sequentially to a solution of (S)-tert-butyl 2-(methoxycarbonylamino)-3-methylbutanoate (82.0 g, 0.355 mol) in $CH_2Cl_2$ (675 mL), and the mixture was stirred at ambient temperature for 4 h. The volatile component was removed under diminished pressure and the resultant oil triturated with petroleum ether (600 mL) to afford a white solid, which was filtered and washed with hexanes (500 mL) and petroleum ether (500 mL). Recrystallization from EtOAc/petroleum ether afforded Cap-51 as white flaky crystals (54.8 g, 88% yield). MP=108.5-109.5° C. $^1$H NMR (500 MHz, DMSO-$d_6$, δ=2.5 ppm) 12.52 (s, 1H), 7.31 (d, J=8.6, 1H), 3.83 (dd, J=8.6, 6.1, 1H), 3.53 (s, 3H), 1.94-2.07 (m, 1H), 0.86 (dd, J=8.9, 7.0, 6H). $^{13}$C NMR (126 MHz, DMSO-$d_6$, δ=39.2 ppm) 173.30, 156.94, 59.48, 51.37, 29.52, 19.15, 17.98. LC/MS: [M+H]$^+$=176.11. Anal. Calcd. for $C_7H_{13}NO_4$: C, 47.99; H, 7.48; N, 7.99. Found: C, 48.17; H, 7.55; N, 7.99. Optical Rotation: [α]$_D$=-4.16 (12.02 mg/mL; MeOH). Optical purity: >99.5% ee. Note: the optical purity assessment was made on the methyl ester derivative of Cap-51, which was prepared under a standard TMSCHN$_2$ (benzene/MeOH) esterification protocol. HPLC analytical conditions: column, CHIRALPAK® AD-H (4.6×250 mm, 5 μm); solvent, 95% heptane/5% IPA (isocratic); flow rate, 1 mL/min; temperature, 35° C.; UV monitored at 205 nm.

[Note: Cap-51 could also be purchased from Flamm.]

Cap-52 (Same as Cap 12)

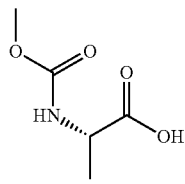

(S)-2-(methoxycarbonylamino)propanoic acid

Cap-52 was synthesized from L-alanine according to the procedure described for the synthesis of Cap-51. For characterization purposes, a portion of the crude material was purified by a reverse phase HPLC (H₂O/methanol/TFA) to afford Cap-52 as a colorless viscous oil. ¹H NMR (DMSO-d₆, δ=2.5 ppm, 500 MHz): 12.49 (br s, 1H), 7.43 (d, J=7.3, 0.88H), 7.09 (app br s, 0.12H), 3.97 (m, 1H), 3.53 (s, 3H), 1.25 (d, J=7.3, 3H).

Cap-53 to -64 were prepared from appropriate starting materials according to the procedure described for the synthesis of Cap-51, with noted modifications if any.

| Cap | Structure | Data |
|---|---|---|
| Cap-53a: (R) Cap-53b: (S) ((S)-2-(methoxy-carbonyl-amino)butanoic acid) | 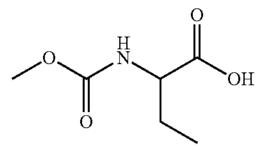 | ¹H NMR (DMSO-d₆, δ = 2.5 ppm, 500 MHz): δ 12.51 (br s, 1H), 7.4 (d, J = 7.9, 0.9H), 7.06 (app s, 0.1H), 3.86-3.82 (m, 1H), 3.53 (s, 3H), 1.75-1.67 (m, 1H), 1.62-1.54 (m, 1H), 0.88 (d, J = 7.3, 3H). RT = 0.77 minutes (Cond. 2); LC/MS: Anal. Calcd. for [M + Na]⁺ C₆H₁₁NNaO₄: 184.06; found 184.07. HRMS Calcd. for [M + Na]⁺ C₆H₁₁NNaO₄: 184.0586; found 184.0592. |
| Cap-54a: (R) Cap-54b: (S) ((S)-2-cyclopropyl-2-(methoxy-carbonyl-amino)acetic acid) | 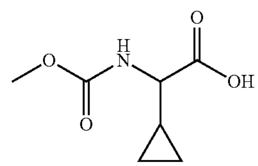 | ¹H NMR (DMSO-d₆, δ = 2.5 ppm, 500 MHz): δ 12.48 (s, 1H), 7.58 (d, J = 7.6, 0.9H), 7.25 (app s, 0.1H), 3.52 (s, 3H), 3.36-3.33 (m, 1H), 1.10-1.01 (m, 1H), 0.54-0.49 (m, 1H), 0.46-0.40 (m, 1H), 0.39-0.35 (m, 1H), 0.31-0.21 (m, 1H). HRMS Calcd. for [M + H]⁺ C₇H₁₂NO₄: 174.0766; found 174.0771 |
| Cap-55 | 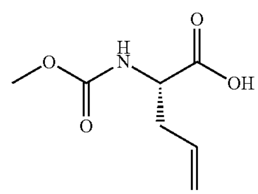 | ¹H NMR (DMSO-d₆, δ = 2.5 ppm, 500 MHz): δ 12.62 (s, 1H), 7.42 (d, J = 8.2, 0.9H), 7.07 (app s, 0.1H), 5.80-5.72 (m, 1H), 5.10 (d, J = 17.1, 1H), 5.04 (d, J = 10.4, 1H), 4.01-3.96 (m, 1H), 3.53 (s, 3H), 2.47-2.42 (m, 1H), 2.35-2.29 (m, 1H). |
| Cap-56 (S)-3-methoxy-2-(methoxy-carbonyl-amino)propanoic acid | 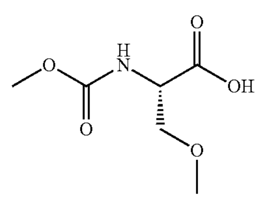 | ¹H NMR (DMSO-d₆, δ = 2.5 ppm, 500 MHz): δ 12.75 (s, 1H), 7.38 (d, J = 8.3, 0.9H), 6.96 (app s, 0.1H), 4.20-4.16 (m, 1H), 3.60-3.55 (m, 2H), 3.54 (s, 3H), 3.24 (s, 3H). |
| Cap-57 | 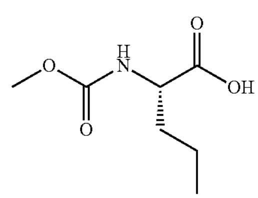 | ¹H NMR (DMSO-d₆, δ = 2.5 ppm, 500 MHz): δ 12.50 (s, 1H), 8.02 (d, J = 7.7, 0.08H), 7.40 (d, J = 7.9, 0.76H), 7.19 (d, J = 8.2, 0.07H), 7.07 (d, J = 6.7, 0.09H), 4.21-4.12 (m, 0.08H), 4.06-3.97 (m, 0.07H), 3.96-3.80 (m, 0.85H), 3.53 (s, 3H), 1.69-1.51 (m, 2H), 1.39-1.26 (m, 2H), 0.85 (t, J = 7.4, 3H). LC (Cond. 2): RT = 1.39 LC/MS: Anal. Calcd. for [M + H]⁺ C₇H₁₄NO₄: 176.09; found 176.06. |
| Cap-58 | 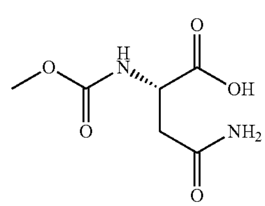 | ¹H NMR (DMSO-d₆, δ = 2.5 ppm, 500 MHz): δ 12.63 (br s, 1H), 7.35 (s, 1H), 7.31 (d, J = 8.2, 1H), 6.92 (s, 1H), 4.33-4.29 (m, 1H), 3.54 (s, 3H), 2.54 (dd, J = 15.5, 5.4, 1H), 2.43 (dd, J = 15.6, 8.0, 1H). RT = 0.16 min (Cond. 2); LC/MS: Anal. Calcd. for [M + H]⁺ C₆H₁₁N₂O₅: 191.07; found 191.14. |
| Cap-59a: (R) Cap-59b: (S) | 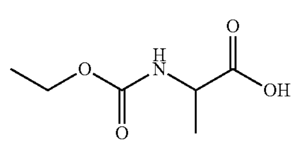 | ¹H NMR (DMSO-d₆, δ = 2.5 ppm, 400 MHz): δ 12.49 (br s, 1H), 7.40 (d, J = 7.3, 0.89H), 7.04 (br s, 0.11H), 4.00-3.95 (m, 3H), 1.24 (d, J = 7.3, 3H), 1.15 (t, J = 7.2, 3H). HRMS: Anal. Calcd. for [M + H]⁺ C₆H₁₂NO₄: 162.0766; found 162.0771. |

-continued

| Cap | Structure | Data |
|---|---|---|
| Cap-60 | 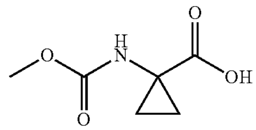 | The crude material was purified with a reverse phase HPLC (H₂O/MeOH/TFA) to afford a colorless viscous oil that crystallized to a white solid upon exposure to high vacuum. ¹H NMR (DMSO-d₆, δ = 2.5 ppm, 400 MHz): δ 12.38 (br s, 1H), 7.74 (s, 0.82H), 7.48 (s, 0.18H), 3.54/3.51 (two s, 3H), 1.30 (m, 2H), 0.98 (m, 2H). HRMS: Anal. Calcd. for [M + H]⁺ C₆H₁₀NO₄: 160.0610; found 160.0604. |
| Cap-61 | 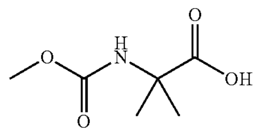 | ¹H NMR (DMSO-d₆, δ = 2.5 ppm, 400 MHz): δ 12.27 (br s, 1H), 7.40 (br s, 1H), 3.50 (s, 3H), 1.32 (s, 6H). HRMS: Anal. Calcd. for [M + H]⁺ C₆H₁₂NO₄: 162.0766; found 162.0765. |
| Cap-62 | 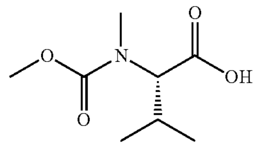 | ¹H NMR (DMSO-d₆, δ = 2.5 ppm, 400 MHz): δ 12.74 (br s, 1H), 4.21 (d, J = 10.3, 0.6H), 4.05 (d, J = 10.0, 0.4H), 3.62/3.60 (two singlets, 3H), 3.0 (s, 3H), 2.14-2.05 (m, 1H), 0.95 (d, J = 6.3, 3H), 0.81 (d, J = 6.6, 3H). LC/MS: Anal. Calcd. for [M − H]⁻ C₈H₁₄NO₄: 188.09; found 188.05. |
| Cap-63 | 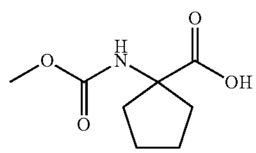 | [Note: the reaction was allowed to run for longer than what was noted for the general procedure.] ¹H NMR (DMSO-d₆, δ = 2.5 ppm, 400 MHz): 12.21 (br s, 1H), 7.42 (br s, 1H), 3.50 (s, 3H), 2.02-1.85 (m, 4H), 1.66-1.58 (m, 4H). LC/MS: Anal. Calcd. for [M + H]⁺ C₈H₁₄NO₄: 188.09; found 188.19. |
| Cap-64 | 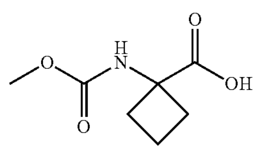 | [Note: the reaction was allowed to run for longer than what was noted for the general procedure.] ¹H NMR (DMSO-d₆, δ = 2.5 ppm, 400 MHz): 12.35 (br s, 1H), 7.77 (s, 0.82H), 7.56/7.52 (overlapping br s, 0.18H), 3.50 (s, 3H), 2.47-2.40 (m, 2H), 2.14-2.07 (m, 2H), 1.93-1.82 (m, 2H). |

Cap-65

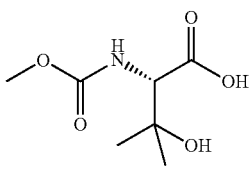

Methyl chloroformate (0.65 mL, 8.39 mmol) was added dropwise over 5 min to a cooled (ice-water) mixture of Na₂CO₃ (0.449 g, 4.23 mmol), NaOH (8.2 mL of 1M/H₂O, 8.2 mmol) and (S)-2-amino-3-hydroxy-3-methylbutanoic acid (1.04 g, 7.81 mmol). The reaction mixture was stirred for 45 min, and then the cooling bath was removed and stirring was continued for an additional 3.75 hr. The reaction mixture was washed with CH₂Cl₂, and the aqueous phase was cooled with ice-water bath and acidified with concentrated HCl to a pH region of 1-2. The volatile component was removed in vacuo and the residue was taken up in a 2:1 mixture of MeOH/CH₂Cl₂ (15 mL) and filtered, and the filtrate was rotervaped to afford Cap-65 as a white semi-viscous foam (1.236 g). ¹H NMR (DMSO-d₆, δ=2.5 ppm, 400 MHz): δ 6.94 (d, J=8.5, 0.9H), 6.53 (br s, 0.1H), 3.89 (d, J=8.8, 1H), 2.94 (s, 3H), 1.15 (s, 3H), 1.13 (s, 3H).

Cap-66 and -67 were prepared from appropriate commercially available starting materials by employing the procedure described for the synthesis of Cap-65.

Cap-66

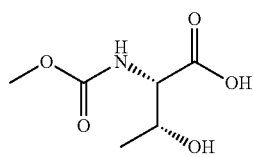

¹H NMR (DMSO-d₆, δ=2.5 ppm, 400 MHz): δ 12.58 (br s, 1H), 7.07 (d, J=8.3, 0.13H), 6.81 (d, J=8.8, 0.67H), 4.10-4.02 (m, 1.15H), 3.91 (dd, J=9.1, 3.5, 0.85H), 3.56 (s, 3H), 1.09 (d, J=6.2, 3H). [Note: only the dominant signals of NH were noted].

Cap-67

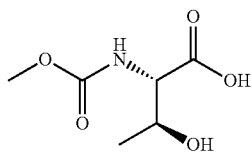

¹H NMR (DMSO-d₆, δ=2.5 ppm, 400 MHz): 12.51 (br s, 1H), 7.25 (d, J=8.4, 0.75H), 7.12 (br d, J=0.4, 0.05H), 6.86 (br s, 0.08H), 3.95-3.85 (m, 2H), 3.54 (s, 3H), 1.08 (d, J=6.3, 3H). [Note: only the dominant signals of NH were noted].

Cap-68

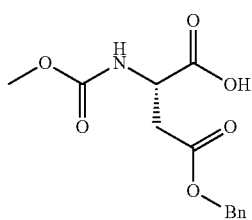 [SMILES: COC(=O)N[C@@H](CC(=O)OCc1ccccc1)C(=O)O]

Methyl chloroformate (0.38 ml, 4.9 mmol) was added drop-wise to a mixture of 1N NaOH (aq) (9.0 ml, 9.0 mmol), 1M NaHCO₃ (aq) (9.0 ml, 9.0 mol), L-aspartic acid 13-benzyl ester (1.0 g, 4.5 mmol) and Dioxane (9 ml). The reaction mixture was stirred at ambient conditions for 3 hr, and then washed with Ethyl acetate (50 ml, 3×). The aqueous layer was acidified with 12N HCl to a pH ~1-2, and extracted with ethyl acetate (3×50 ml). The combined organic layers were washed with brine, dried (Na₂SO₄), filtered, and concentrated in vacuo to afford Cap-68 as a light yellow oil (1.37 g; mass is above theoretical yield, and the product was used without further purification). ¹H NMR (DMSO-d₆, δ=2.5 ppm, 500 MHz): δ 12.88 (br s, 1H), 7.55 (d, J=8.5, 1H), 7.40-7.32 (m, 5H), 5.13 (d, J=12.8, 1H), 5.10 (d, J=12.9, 1H), 4.42-4.38 (m, 1H), 3.55 (s, 3H), 2.87 (dd, J=16.2, 5.5, 1H), 2.71 (dd, J=16.2, 8.3, 1H). LC (Cond. 2): RT=1.90 min; LC/MS: Anal. Calcd. For [M+H]⁺ C₁₃H₁₆NO₆: 282.10. Found 282.12.

Cap-69a and -69b

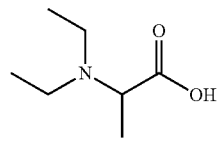

Cap-69a: (R)-enantiomer
Cap-69b: (S)-enantiomer

NaCNBH₃ (2.416 g, 36.5 mmol) was added in batches to a chilled (~15° C.) water (17 mL)/MeOH (10 mL) solution of alanine (1.338 g, 15.0 mmol). A few minutes later acetaldehyde (4.0 mL, 71.3 mmol) was added drop-wise over 4 min, the cooling bath was removed, and the reaction mixture was stirred at ambient condition for 6 hr. An additional acetaldehyde (4.0 mL) was added and the reaction was stirred for 2 hr. Concentrated HCl was added slowly to the reaction mixture until the pH reached ~1.5, and the resulting mixture was heated for 1 hr at 40° C. Most of the volatile component was removed in vacuo and the residue was purified with a DOWEX® 50WX8-100 ion-exchange resin (column was washed with water, and the compound was eluted with dilute NH₄OH, prepared by mixing 18 ml of NH₄OH and 282 ml of water) to afford Cap-69 (2.0 g) as an off-white soft hygroscopic solid. ¹H NMR (DMSO-d₆, δ=2.5 ppm, 400 MHz): δ 3.44 (q, J=7.1, 1H), 2.99-2.90 (m, 2H), 2.89-2.80 (m, 2H), 1.23 (d, J=7.1, 3H), 1.13 (t, J=7.3, 6H).

Cap-70 to -74x were prepared according to the procedure described for the synthesis of Cap-69 by employing appropriate starting materials.

| | | |
|---|---|---|
| Cap-70a: (R) Cap-70b: (S) | 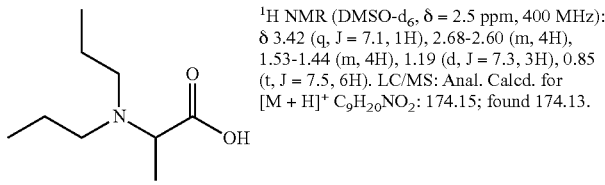 | ¹H NMR (DMSO-d₆, δ = 2.5 ppm, 400 MHz): δ 3.42 (q, J = 7.1, 1H), 2.68-2.60 (m, 4H), 1.53-1.44 (m, 4H), 1.19 (d, J = 7.3, 3H), 0.85 (t, J = 7.5, 6H). LC/MS: Anal. Calcd. for [M + H]⁺ C₉H₂₀NO₂: 174.15; found 174.13. |
| Cap-71a: (R) Cap-71b: (S) | 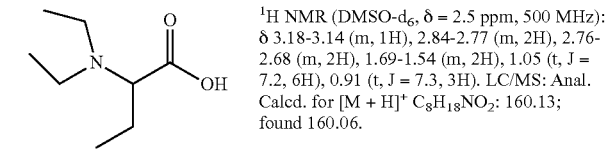 | ¹H NMR (DMSO-d₆, δ = 2.5 ppm, 500 MHz): δ 3.18-3.14 (m, 1H), 2.84-2.77 (m, 2H), 2.76-2.68 (m, 2H), 1.69-1.54 (m, 2H), 1.05 (t, J = 7.2, 6H), 0.91 (t, J = 7.3, 3H). LC/MS: Anal. Calcd. for [M + H]⁺ C₈H₁₈NO₂: 160.13; found 160.06. |
| Cap-72 | 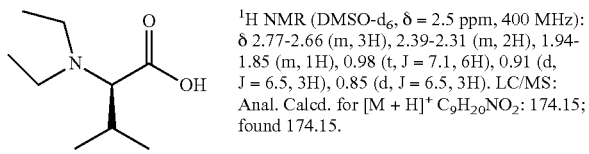 | ¹H NMR (DMSO-d₆, δ = 2.5 ppm, 400 MHz): δ 2.77-2.66 (m, 3H), 2.39-2.31 (m, 2H), 1.94-1.85 (m, 1H), 0.98 (t, J = 7.1, 6H), 0.91 (d, J = 6.5, 3H), 0.85 (d, J = 6.5, 3H). LC/MS: Anal. Calcd. for [M + H]⁺ C₉H₂₀NO₂: 174.15; found 174.15. |

-continued

| | | |
|---|---|---|
| Cap-73 | 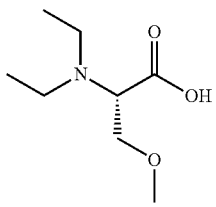 | $^1$H NMR (DMSO-d$_6$, δ = 2.5 ppm, 500 MHz): δ 9.5 (br s, 1H), 3.77 (dd, J = 10.8, 4.1, 1H), 3.69-3.61 (m, 2H), 3.26 (s, 3H), 2.99-2.88 (m, 4H), 1.13 (t, J = 7.2, 6H). |
| Cap-74 | 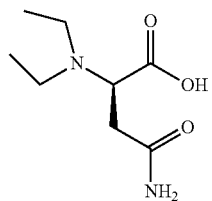 | $^1$H NMR (DMSO-d$_6$, δ = 2.5 ppm, 500 MHz): δ 7.54 (s, 1H), 6.89 (s, 1H), 3.81 (t, J = 6.6, k, 1H), 2.82-2.71 (m, 4H), 2.63 (dd, J = 15.6, 7.0, 1H), 2.36 (dd, J = 15.4, 6.3, 1H), 1.09 (t, J = 7.2, 6H). RT = 0.125 minutes (Cond. 2); LC/MS: Anal. Calcd. for [M + H]$^+$ C$_8$H$_{17}$N$_2$O$_3$: 189.12; found 189.13. |
| Cap-74x | 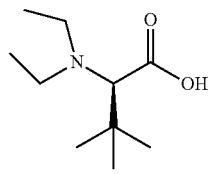 | LC/MS: Anal. Calcd. for [M + H]$^+$ C$_{10}$H$_{22}$NO$_2$: 188.17; found 188.21 |

Cap-75

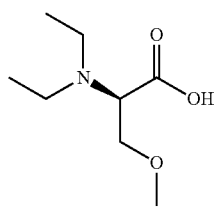

Cap-75, Step a

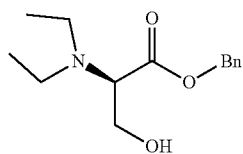 [SMILES: CCN(CC)[C@H](CO)C(=O)OCc1ccccc1]

NaBH$_3$CN (1.6 g, 25.5 mmol) was added to a cooled (ice/water bath) water (25 ml)/methanol (15 ml) solution of H-D-Ser-OBzl HCl (2.0 g, 8.6 mmol). Acetaldehyde (1.5 ml, 12.5 mmol) was added drop-wise over 5 min, the cooling bath was removed, and the reaction mixture was stirred at ambient condition for 2 hr. The reaction was carefully quenched with 12N HCl and concentrated in vacuo. The residue was dissolved in water and purified with a reverse phase HPLC (MeOH/H$_2$O/TFA) to afford the TFA salt of (R)-benzyl 2-(diethylamino)-3-hydroxypropanoate as a colorless viscous oil (1.9 g). $^1$H NMR (DMSO-d$_6$, δ=2.5 ppm, 500 MHz): δ 9.73 (br s, 1H), 7.52-7.36 (m, 5H), 5.32 (d, J=12.2, 1H), 5.27 (d, J=12.5, 1H), 4.54-4.32 (m, 1H), 4.05-3.97 (m, 2H), 3.43-3.21 (m, 4H), 1.23 (t, J=7.2, 6H). LC/MS (Cond. 2): RT=1.38 min; LC/MS: Anal. Calcd. for [M+H]$^+$ C$_{14}$H$_{22}$NO$_3$: 252.16. Found 252.19.

Cap-75

NaH (0.0727 g, 1.82 mmol, 60%) was added to a cooled (ice-water) THF (3.0 mL) solution of the TFA salt (R)-benzyl 2-(diethylamino)-3-hydroxypropanoate (0.3019 g, 0.8264 mmol) prepared above, and the mixture was stirred for 15 min. Methyl iodide (56 μL, 0.90 mmol) was added and stirring was continued for 18 hr while allowing the bath to thaw to ambient condition. The reaction was quenched with water and loaded onto a MeOH pre-conditioned MCX (6 g) cartridge, and washed with methanol followed by compound elution with 2N NH$_3$/Methanol. Removal of the volatile component in vacuo afforded Cap-75, contaminated with (R)-2-(diethylamino)-3-hydroxypropanoic acid, as a yellow semisolid (100 mg). The product was used as is without further purification.

Cap-76

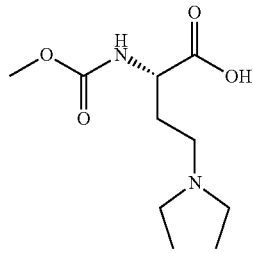 [SMILES: CCN(CC)CC[C@H](NC(=O)OC)C(=O)O]

NaCNBH$_3$ (1.60 g, 24.2 mmol) was added in batches to a chilled (~15° C.) water/MeOH (12 mL each) solution of (S)-4-amino-2-(tert-butoxycarbonylamino) butanoic acid (2.17 g, 9.94 mmol). A few minutes later acetaldehyde (2.7 mL, 48.1 mmol) was added drop-wise over 2 min, the cooling bath was removed, and the reaction mixture was stirred at ambient condition for 3.5 hr. An additional acetaldehyde (2.7 mL, 48.1 mmol) was added and the reaction was stirred for 20.5 hr. Most of the MeOH component was removed in vacuo, and the remaining mixture was treated with concentrated HCl until its pH reached ~1.0 and then heated for 2 hr at 40° C. The volatile component was removed in vacuo, and the residue was treated with 4 M HCl/dioxane (20 mL) and stirred at ambient condition for 7.5 hr. The volatile component was removed in vacuo and the residue was purified with DOWEX® 50WX8-100 ion-exchange resin (column was washed with water and the compound was eluted with dilute NH$_4$OH, prepared from 18 ml of NH$_4$OH and 282 ml of water) to afford intermediate (S)-2-amino-4-(diethylamino) butanoic acid as an off-white solid (1.73 g).

Methyl chloroformate (0.36 mL, 4.65 mmol) was added drop-wise over 11 min to a cooled (ice-water) mixture of Na$_2$CO$_3$ (0.243 g, 2.29 mmol), NaOH (4.6 mL of 1M/H$_2$O, 4.6 mmol) and the above product (802.4 mg). The reaction mixture was stirred for 55 min, and then the cooling bath was removed and stirring was continued for an additional 5.25 hr. The reaction mixture was diluted with equal volume of water and washed with CH$_2$Cl$_2$ (30 mL, 2×), and the aqueous phase was cooled with ice-water bath and acidified with concentrated HCl to a pH region of 2. The volatile component was then removed in vacuo and the crude material was free-based with MCX resin (6.0 g; column was washed with water, and sample was eluted with 2.0 M NH$_3$/MeOH) to afford impure Cap-76 as an off-white solid (704 mg). $^1$H NMR (MeOH-d$_4$, δ=3.29 ppm, 400 MHz): δ 3.99 (dd, J=7.5, 4.7, 1H), 3.62 (s, 3H), 3.25-3.06 (m, 6H), 2.18-2.09 (m, 1H), 2.04-1.96 (m, 1H), 1.28 (t, J=7.3, 6H). LC/MS: Anal. Calcd. for [M+H]$^+$ C$_{10}$H$_{21}$N$_2$O$_4$: 233.15. Found 233.24.

Cap-77a and -77b

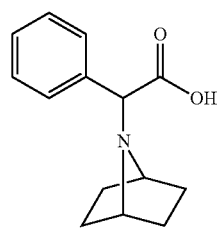

Cap-77a: enantiomer-1
Cap-77b: enantiomer-2

The synthesis of Cap-77 was conducted according to the procedure described for Cap-7 by using 7-azabicyclo[2.2.1] heptane for the SN$_2$ displacement step, and by effecting the stereoisomeric separation of the intermediate benzyl 2-(7-azabicyclo[2.2.1]heptan-7-yl)-2-phenylacetate using the following condition: the intermediate (303.7 mg) was dissolved in ethanol, and the resulting solution was injected on a chiral HPLC column (Chiracel AD-H column, 30×250 mm, 5 um) eluting with 90% CO$_2$-10% EtOH at 70 mL/min, and a temperature of 35° C. to provide 124.5 mg of stereoisomer-1 and 133.8 mg of stereoisomer-2. These benzyl esters were hydrogenolysed according to the preparation of Cap-7 to provide Cap-77: $^1$H NMR (DMSO-d$_6$, δ=2.5 ppm, 400 MHz): δ 7.55 (m, 2H), 7.38-7.30 (m, 3H), 4.16 (s, 1H), 3.54 (app br s, 2H), 2.08-1.88 (m, 4H), 1.57-1.46 (m, 4H). LC (Cond. 1): RT=0.67 min; LC/MS: Anal. Calcd. for [M+H]$^+$ C$_{14}$H$_{18}$NO$_2$: 232.13. Found 232.18. HRMS: Anal. Calcd. for [M+H]$^+$ C$_{14}$H$_{18}$NO$_2$: 232.1338. Found 232.1340.

Cap-78

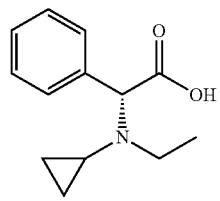 [SMILES: CCN(C1CC1)[C@@H](C(=O)O)c1ccccc1]

NaCNBH$_3$ (0.5828 g, 9.27 mmol) was added to a mixture of the HCl salt of (R)-2-(ethylamino)-2-phenylacetic acid (an intermediate in the synthesis of Cap-3; 0.9923 mg, 4.60 mmol) and (1-ethoxycyclopropoxy)trimethylsilane (1.640 g, 9.40 mmol) in MeOH (10 mL), and the semi-heterogeneous mixture was heated at 50° C. with an oil bath for 20 hr. More (1-ethoxycyclopropoxy)trimethylsilane (150 mg, 0.86 mmol) and NaCNBH$_3$ (52 mg, 0.827 mmol) were added and the reaction mixture was heated for an additional 3.5 hr. It was then allowed to cool to ambient temperature and acidified to a ~pH region of 2 with concentrated HCl, and the mixture was filtered and the filtrate was rotervaped. The resulting crude material was taken up in i-PrOH (6 mL) and heated to effect dissolution, and the non-dissolved part was filtered off and the filtrate concentrated in vacuo. About ⅓ of the resultant crude material was purified with a reverse phase HPLC (H$_2$O/MeOH/TFA) to afford the TFA salt of Cap-78 as a colorless viscous oil (353 mg). $^1$H NMR (DMSO-d$_6$, δ=2.5 ppm, 400 MHz; after D$_2$O exchange): δ 7.56-7.49 (m, 5H), 5.35 (S, 1H), 3.35 (m, 1H), 3.06 (app br s, 1H), 2.66 (m, 1H), 1.26 (t, J=7.3, 3H), 0.92 (m, 1H), 0.83-0.44 (m, 3H).

LC (Cond. 1): RT=0.64 min; LC/MS: Anal. Calcd. for [M+H]$^+$ C$_{13}$H$_{18}$NO$_2$: 220.13. Found 220.21. HRMS: Anal. Calcd. for [M+H]$^+$ C$_{13}$H$_{18}$NO$_2$: 220.1338. Found 220.1343.

Cap-79

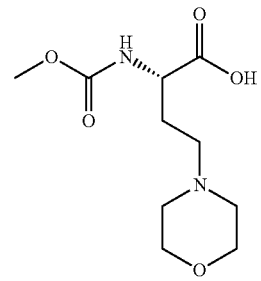 [SMILES: COC(=O)N[C@@H](CCN1CCOCC1)C(=O)O]

Ozone was bubbled through a cooled (−78° C.) CH$_2$Cl$_2$ (5.0 mL) solution Cap-55 (369 mg, 2.13 mmol) for about 50 min until the reaction mixture attained a tint of blue color. Me$_2$S (10 pipet drops) was added, and the reaction mixture was stirred for 35 min. The −78° C. bath was replaced with a −10° C. bath and stirring continued for an additional 30 min, and then the volatile component was removed in vacuo to afford a colorless viscous oil.

NaBH₃CN (149 mg, 2.25 mmol) was added to a MeOH (5.0 mL) solution of the above crude material and morpholine (500 μL, 5.72 mmol) and the mixture was stirred at ambient condition for 4 hr. It was cooled to ice-water temperature and treated with concentrated HCl to bring its pH to ~2.0, and then stirred for 2.5 hr. The volatile component was removed in vacuo, and the residue was purified with a combination of MCX resin (MeOH wash; 2.0 N NH₃/MeOH elution) and a reverse phase HPLC (H₂O/MeOH/TFA) to afford Cap-79 containing unknown amount of morpholine.

In order to consume the morpholine contaminant, the above material was dissolved in CH₂Cl₂ (1.5 mL) and treated with Et₃N (0.27 mL, 1.94 mmol) followed by acetic anhydride (0.10 mL, 1.06 mmol) and stirred at ambient condition for 18 hr. THF (1.0 mL) and H₂O (0.5 mL) were added and stirring continued for 1.5 hr. The volatile component was removed in vacuo, and the resultant residue was passed through MCX resin (MeOH wash; 2.0 N NH₃/MeOH elution) to afford impure Cap-79 as a brown viscous oil, which was used for the next step without further purification.

Cap-80a and -80b

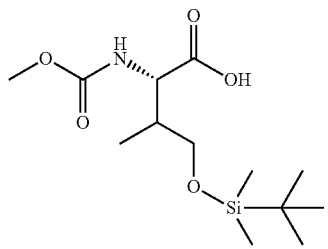

Cap-80a: S/S-diastereomer
Cap-80b: S/R-diastereomer

SOCl₂ (6.60 mL, 90.5 mmol) was added drop-wise over 15 min to a cooled (ice-water) mixture of (S)-3-amino-4-(benzyloxy)-4-oxobutanoic acid (10.04 g, 44.98 mmol) and MeOH (300 mL), the cooling bath was removed and the reaction mixture was stirred at ambient condition for 29 hr. Most of the volatile component was removed in vacuo and the residue was carefully partitioned between EtOAc (150 mL) and saturated NaHCO₃ solution. The aqueous phase was extracted with EtOAc (150 mL, 2×), and the combined organic phase was dried (MgSO₄), filtered, and concentrated in vacuo to afford (S)-1-benzyl 4-methyl 2-aminosuccinate as a colorless oil (9.706 g). ¹H NMR (DMSO-d₆, δ=2.5 ppm, 400 MHz): δ 7.40-7.32 (m, 5H), 5.11 (s, 2H), 3.72 (app t, J=6.6, 1H), 3.55 (s, 3H), 2.68 (dd, J=15.9, 6.3, 1H), 2.58 (dd, J=15.9, 6.8, 1H), 1.96 (s, 2H). LC (Cond. 1): RT=0.90 min; LC/MS: Anal. Calcd. for [M+H]⁺ C₁₂H₁₆NO₄: 238.11. Found 238.22.

Pb(NO₃)₂ (6.06 g, 18.3 mmol) was added over 1 min to a CH₂Cl₂ (80 mL) solution of (S)-1-benzyl 4-methyl 2-aminosuccinate (4.50 g, 19.0 mmol), 9-bromo-9-phenyl-9H-fluorene (6.44 g, 20.0 mmol) and Et₃N (3.0 mL, 21.5 mmol), and the heterogeneous mixture was stirred at ambient condition for 48 hr. The mixture was filtered and the filtrate was treated with MgSO₄ and filtered again, and the final filtrate was concentrated. The resulting crude material was submitted to a BIOTAGE® purification (350 g silica gel, CH₂Cl₂ elution) to afford (S)-1-benzyl 4-methyl 2-(9-phenyl-9H-fluoren-9-ylamino)succinate as highly viscous colorless oil (7.93 g). ¹H NMR (DMSO-d₆, δ=2.5 ppm, 400 MHz): δ 7.82 (m, 2H), 7.39-7.13 (m, 16H), 4.71 (d, J=12.4, 1H), 4.51 (d, J=12.6, 1H), 3.78 (d, J=9.1, NH), 3.50 (s, 3H), 2.99 (m, 1H), 2.50-2.41 (m, 2H, partially overlapped with solvent). LC (Cond. 1): RT=2.16 min; LC/MS: Anal. Calcd. for [M+H]⁺ C₃₁H₂₈NO₄: 478.20. Found 478.19. LiHMDS (9.2 mL of 1.0 M/THF, 9.2 mmol) was added drop-wise over 10 min to a cooled (−78° C.) THF (50 mL) solution of (S)-1-benzyl 4-methyl 2-(9-phenyl-9H-fluoren-9-ylamino)succinate (3.907 g, 8.18 mmol) and stirred for ~1 hr. MeI (0.57 mL, 9.2 mmol) was added drop-wise over 8 min to the mixture, and stirring was continued for 16.5 hr while allowing the cooling bath to thaw to room temperature. After quenching with saturated NH₄Cl solution (5 mL), most of the organic component was removed in vacuo and the residue was partitioned between CH₂Cl₂ (100 mL) and water (40 mL). The organic layer was dried (MgSO₄), filtered, and concentrated in vacuo, and the resulting crude material was purified with a BIOTAGE® (350 g silica gel; 25% EtOAc/hexanes) to afford 3.65 g of a 2S/3S and 2S/3R diastereomeric mixtures of 1-benzyl 4-methyl 3-methyl-2-(9-phenyl-9H-fluoren-9-ylamino)succinate in ~1.0:0.65 ratio (¹H NMR). The stereochemistry of the dominant isomer was not determined at this juncture, and the mixture was submitted to the next step without separation. Partial ¹H NMR data (DMSO-d₆, δ=2.5 ppm, 400 MHz): major diastereomer, δ 4.39 (d, J=12.3, 1H of CH₂), 3.33 (s, 3H, overlapped with H₂O signal), 3.50 (d, J=10.9, NH), 1.13 (d, J=7.1, 3H); minor diastereomer, δ 4.27 (d, J=12.3, 1H of CH₂), 3.76 (d, J=10.9, NH), 3.64 (s, 3H), 0.77 (d, J=7.0, 3H). LC (Cond. 1): RT=2.19 min; LC/MS: Anal. Calcd. for [M+H]⁺ C₃₂H₃₀NO₄: 492.22. Found 492.15.

Diisobutylaluminum hydride (20.57 ml of 1.0 M in hexanes, 20.57 mmol) was added drop-wise over 10 min to a cooled (−78° C.) THF (120 mL) solution of (2S)-1-benzyl 4-methyl 3-methyl-2-(9-phenyl-9H-fluoren-9-ylamino)succinate (3.37 g, 6.86 mmol) prepared above, and stirred at −78° C. for 20 hr. The reaction mixture was removed from the cooling bath and rapidly poured into ~1M H₃PO₄/H₂O (250 mL) with stirring, and the mixture was extracted with ether (100 mL, 2×). The combined organic phase was washed with brine, dried (MgSO₄), filtered and concentrated in vacuo. A silica gel mesh of the crude material was prepared and submitted to chromatography (25% EtOAc/hexanes; gravity elution) to afford 1.1 g of (2S,3S)-benzyl 4-hydroxy-3-methyl-2-(9-phenyl-9H-fluoren-9-ylamino)butanoate, contaminated with benzyl alcohol, as a colorless viscous oil and (2S,3R)-benzyl 4-hydroxy-3-methyl-2-(9-phenyl-9H-fluoren-9-ylamino)butanoate containing the (2S,3R) stereoisomer as an impurity. The later sample was resubmitted to the same column chromatography purification conditions to afford 750 mg of purified material as a white foam. [Note: the (2S,3S) isomer elutes before the (2S,3R) isomer under the above condition]. (2S,3S) isomer: ¹H NMR (DMSO-d₆, δ=2.5 ppm, 400 MHz): 7.81 (m, 2H), 7.39-7.08 (m, 16H), 4.67 (d, J=12.3, 1H), 4.43 (d, J=12.4, 1H), 4.21 (app t, J=5.2, OH), 3.22 (d, J=10.1, NH), 3.17 (m, 1H), 3.08 (m, 1H), ~2.5 (m, 1H, overlapped with the solvent signal), 1.58 (m, 1H), 0.88 (d, J=6.8, 3H). LC (Cond. 1): RT=2.00 min; LC/MS: Anal. Calcd. for [M+H]⁺ C₃₁H₃₀NO₃: 464.45. Found 464.22. (2S,3R) isomer: ¹H NMR (DMSO-d₆, δ=2.5 ppm, 400 MHz): 7.81 (d, J=7.5, 2H), 7.39-7.10 (m, 16H), 4.63 (d, J=12.1, 1H), 4.50 (app t, J=4.9, 1H), 4.32 (d, J=12.1, 1H), 3.59-3.53 (m, 2H), 3.23 (m, 1H), 2.44 (dd, J=9.0, 8.3, 1H), 1.70 (m, 1H), 0.57 (d, J=6.8, 3H). LC (Cond. 1): RT=1.92 min; LC/MS: Anal. Calcd. for [M+H]⁺ C₃₁H₃₀NO₃: 464.45. Found 464.52.

The relative stereochemical assignments of the DIBAL-reduction products were made based on NOE studies conducted on lactone derivatives prepared from each isomer by employing the following protocol: LiHMDS (50 μL of 1.0 M/THF, 0.05 mmol) was added to a cooled (ice-water) THF (2.0 mL) solution of (2S,3S)-benzyl 4-hydroxy-3-methyl-2-(9-phenyl-9H-fluoren-9-ylamino)butanoate (62.7 mg, 0.135 mmol), and the reaction mixture was stirred at similar temperature for ~2 hr. The volatile component was removed in vacuo and the residue was partitioned between $CH_2Cl_2$ (30 mL), water (20 mL) and saturated aqueous $NH_4Cl$ solution (1 mL). The organic layer was dried ($MgSO_4$), filtered, and concentrated in vacuo, and the resulting crude material was submitted to a BIOTAGE® purification (40 g silica gel; 10-15% EtOAc/hexanes) to afford (3S,4S)-4-methyl-3-(9-phenyl-9H-fluoren-9-ylamino)dihydrofuran-2(3H)-one as a colorless film of solid (28.1 mg). (2S,3R)-benzyl 4-hydroxy-3-methyl-2-(9-phenyl-9H-fluoren-9-ylamino)butanoate was elaborated similarly to (3S,4R)-4-methyl-3-(9-phenyl-9H-fluoren-9-ylamino)dihydrofuran-2(3H)-one. (3S,4S)-lactone isomer: $^1$H NMR (DMSO-$d_6$, δ=2.5 ppm, 400 MHz), 7.83 (d, J=7.5, 2H), 7.46-7.17 (m, 11H), 4.14 (app t, J=8.3, 1H), 3.60 (d, J=5.8, NH), 3.45 (app t, J=9.2, 1H), ~2.47 (m, 1H, partially overlapped with solvent signal), 2.16 (m, 1H), 0.27 (d, J=6.6, 3H). LC (Cond. 1): RT=1.98 min; LC/MS: Anal. Calcd. for $[M+Na]^+$ $C_{24}H_{21}NNaO_2$: 378.15. Found 378.42. (3S,4R)-lactone isomer: $^1$H NMR (DMSO-$d_6$, δ=2.5 ppm, 400 MHz), 7.89 (d, J=7.6, 1H), 7.85 (d, J=7.3, 1H), 7.46-7.20 (m, 11H), 3.95 (dd, J=9.1, 4.8, 1H), 3.76 (d, J=8.8, 1H), 2.96 (d, J=3.0, NH), 2.92 (dd, J=6.8, 3, NCH), 1.55 (m, 1H), 0.97 (d, J=7.0, 3H). LC (Cond. 1): RT=2.03 min; LC/MS: Anal. Calcd. for $[M+Na]^+$ $C_{24}H_{21}NNaO_2$: 378.15. Found 378.49. TBDMS-Cl (48 mg, 0.312 mmol) followed by imidazole (28.8 mg, 0.423 mmol) were added to a $CH_2Cl_2$ (3 ml) solution of (2S,3S)-benzyl 4-hydroxy-3-methyl-2-(9-phenyl-9H-fluoren-9-ylamino)butanoate (119.5 mg, 0.258 mmol), and the mixture was stirred at ambient condition for 14.25 hr. The reaction mixture was then diluted with $CH_2Cl_2$ (30 mL) and washed with water (15 mL), and the organic layer was dried ($MgSO_4$), filtered, and concentrated in vacuo. The resultant crude material was purified with a BIOTAGE® (40 g silica gel; 5% EtOAc/hexanes) to afford (2S,3S)-benzyl 4-(tert-butyldimethylsilyloxy)-3-methyl-2-(9-phenyl-9H-fluoren-9-ylamino)butanoate, contaminated with TBDMS based impurities, as a colorless viscous oil (124.4 mg). (2S,3R)-benzyl 4-hydroxy-3-methyl-2-(9-phenyl-9H-fluoren-9-ylamino)butanoate was elaborated similarly to (2S,3R)-benzyl 4-(tert-butyldimethylsilyloxy)-3-methyl-2-(9-phenyl-9H-fluoren-9-ylamino)butanoate. (2S,3S)-silyl ether isomer: $^1$H NMR (DMSO-$d_6$, δ=2.5 ppm, 400 MHz), 7.82 (d, J=4.1, 1H), 7.80 (d, J=4.0, 1H), 7.38-7.07 (m, 16H), 4.70 (d, J=12.4, 1H), 4.42 (d, J=12.3, 1H), 3.28-3.19 (m, 3H), 2.56 (dd, J=10.1, 5.5, 1H), 1.61 (m, 1H), 0.90 (d, J=6.8, 3H), 0.70 (s, 9H), −0.13 (s, 3H), −0.16 (s, 3H). LC (Cond. 1, where the run time was extended to 4 min): RT=3.26 min; LC/MS: Anal. Calcd. for $[M+H]^+$ $C_{37}H_{44}NO_3Si$: 578.31. Found 578.40. (2S,3R)-silyl ether isomer: $^1$H NMR (DMSO-$d_6$, δ=2.5 ppm, 400 MHz), 7.82 (d, J=3.0, 1H), 7.80 (d, J=3.1, 1H), 7.39-7.10 (m, 16H), 4.66 (d, J=12.4, 1H), 4.39 (d, J=12.4, 1H), 3.61 (dd, J=9.9, 5.6, 1H), 3.45 (d, J=9.5, 1H), 3.41 (dd, J=10, 6.2, 1H), 2.55 (dd, J=9.5, 7.3, 1H), 1.74 (m, 1H), 0.77 (s, 9H), 0.61 (d, J=7.1, 3H), −0.06 (s, 3H), −0.08 (s, 3H).

A balloon of hydrogen was attached to a mixture of (2S,3S)-benzyl 4-(tert-butyldimethylsilyloxy)-3-methyl-2-(9-phenyl-9H-fluoren-9-ylamino)butanoate (836 mg, 1.447 mmol) and 10% Pd/C (213 mg) in EtOAc (16 mL) and the mixture was stirred at room temperature for ~21 hr, where the balloon was recharged with $H_2$ as necessary. The reaction mixture was diluted with $CH_2Cl_2$ and filtered through a pad of diatomaceous earth (CELITE®-545), and the pad was washed with EtOAc (200 mL), EtOAc/MeOH (1:1 mixture, 200 mL) and MeOH (750 mL). The combined organic phase was concentrated, and a silica gel mesh was prepared from the resulting crude material and submitted to a flash chromatography (8:2:1 mixture of EtOAc/1-PrOH/$H_2O$) to afford (2S,3S)-2-amino-4-(tert-butyldimethylsilyloxy)-3-methylbutanoic acid as a white fluffy solid (325 mg). (2S,3R)-benzyl 4-(tert-butyldimethylsilyloxy)-3-methyl-2-(9-phenyl-9H-fluoren-9-ylamino)butanoate was similarly elaborated to (2S,3R)-2-amino-4-(tert-butyldimethylsilyloxy)-3-methylbutanoic acid. (2S,3S)-amino acid isomer: $^1$H NMR (Methanol-$d_4$, δ=3.29 ppm, 400 MHz), 3.76 (dd, J=10.5, 5.2, 1H), 3.73 (d, J=3.0, 1H), 3.67 (dd, J=10.5, 7.0, 1H), 2.37 (m, 1H), 0.97 (d, J=7.0, 3H), 0.92 (s, 9H), 0.10 (s, 6H). LC/MS: Anal. Calcd. for $[M+H]^+$ $C_{11}H_{26}NO_3Si$: 248.17. Found 248.44. (2S,3R)-amino acid isomer: $^1$H NMR (Methanol-$d_4$, δ=3.29 ppm, 400 MHz), 3.76-3.75 (m, 2H), 3.60 (d, J=4.1, 1H), 2.16 (m, 1H), 1.06 (d, J=7.3, 3H), 0.91 (s, 9H), 0.09 (s, 6H). Anal. Calcd. for $[M+H]^+$ $C_{11}H_{26}NO_3Si$: 248.17. Found 248.44. Water (1 mL) and NaOH (0.18 mL of 1.0 M/$H_2O$, 0.18 mmol) were added to a mixture of (2S,3S)-2-amino-4-(tert-butyldimethylsilyloxy)-3-methylbutanoic acid (41.9 mg, 0.169 mmol) and $Na_2CO_3$ (11.9 mg, 0.112 mmol), and sonicated for about 1 min to effect dissolution of reactants. The mixture was then cooled with an ice-water bath, methyl chloroformate (0.02 mL, 0.259 mmol) was added over 30 s, and vigorous stirring was continued at similar temperature for 40 min and then at ambient temperature for 2.7 hr. The reaction mixture was diluted with water (5 mL), cooled with ice-water bath and treated drop-wise with 1.0 N HCl aqueous solution (~0.23 mL). The mixture was further diluted with water (10 mL) and extracted with $CH_2Cl_2$ (15 mL, 2×). The combined organic phase was dried ($MgSO_4$), filtered, and concentrated in vacuo to afford Cap-80a as an off-white solid. (2S,3R)-2-amino-4-(tert-butyldimethylsilyloxy)-3-methylbutanoic acid was similarly elaborated to Cap-80b. Cap-80a: $^1$H NMR (DMSO-$d_6$, δ=2.5 ppm, 400 MHz), 12.57 (br s, 1H), 7.64 (d, J=8.3, 0.3H), 7.19 (d, J=8.8, 0.7H), 4.44 (dd, J=8.1, 4.6, 0.3H), 4.23 (dd, J=8.7, 4.4, 0.7H), 3.56/3.53 (two singlets, 3H), 3.48-3.40 (m, 2H), 2.22-2.10 (m, 1H), 0.85 (s, 9H), ~0.84 (d, 0.9H, overlapped with t-Bu signal), 0.79 (d, J=7, 2.1H), 0.02/0.01/0.00 (three overlapping singlets, 6H). LC/MS: Anal. Calcd. for $[M+Na]^+$ $C_{13}H_{27}NNaO_5Si$: 328.16. Found 328.46. Cap-80b: $^1$H NMR ($CDCl_3$, δ=7.24 ppm, 400 MHz), 6.00 (br d, J=6.8, 1H), 4.36 (dd, J=7.1, 3.1, 1H), 3.87 (dd, J=10.5, 3.0, 1H), 3.67 (s, 3H), 3.58 (dd, J=10.6, 4.8, 1H), 2.35 (m, 1H), 1.03 (d, J=7.1, 3H), 0.90 (s, 9H), 0.08 (s, 6H). LC/MS: Anal. Calcd. for $[M+Na]^+$ $C_{13}H_{27}NNaO_5Si$: 328.16. Found 328.53. The crude products were utilized without further purification.

Cap-81

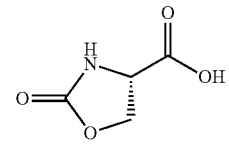

Prepared according to the protocol described by Falb et al. *Synthetic Communications* 1993, 23, 2839.

Cap-82 to Cap-85

Cap-82 to Cap-85 were synthesized from appropriate starting materials according to the procedure described for Cap-51 or Cap-13. The samples exhibited similar spectral profiles as that of their stereoisomers (i.e., Cap-4, Cap-13, Cap-51 and Cap-52, respectively).

Cap-82

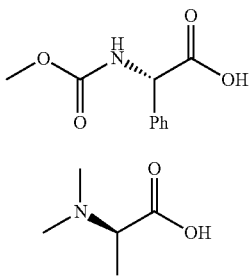

Cap-83

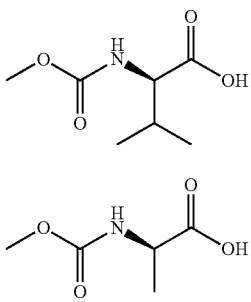

Cap-84

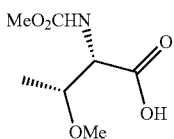

Cap-85

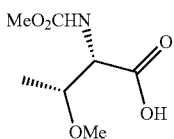

Cap-86

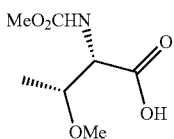

(2S,3R)-3-methoxy-2-(methoxycarbonylamino)butanoic acid

To a mixture of O-methyl-L-threonine (3.0 g, 22.55 mmol), NaOH (0.902 g, 22.55 mmol) in H₂O (15 mL) was added ClCO₂Me (1.74 mL, 22.55 mmol) dropwise at 0° C. The mixture was allowed to stir for 12 h and acidified to pH 1 using 1N HCl. The aqueous phase was extracted with EtOAc and (2×250 mL) and 10% MeOH in CH₂Cl₂ (250 mL) and the combined organic phases were concentrated under in vacuo to afford a colorless oil (4.18 g, 97%) which was of sufficient purity for use in subsequent steps. ¹H NMR (400 MHz, CDCl₃) δ 4.19 (s, 1H), 3.92-3.97 (m, 1H), 3.66 (s, 3H), 1.17 (d, J=7.7 Hz, 3H). LCMS: Anal. Calcd. for C₇H₁₃NO₅: 191. Found: 190 (M−H)⁻.

Cap-87

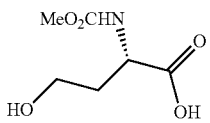

To a mixture of L-homoserine (2.0 g, 9.79 mmol), Na₂CO₃ (2.08 g, 19.59 mmol) in H₂O (15 mL) was added ClCO₂Me (0.76 mL, 9.79 mmol) dropwise at 0° C. The mixture was allowed to stir for 48 h and acidified to pH 1 using 1N HCl. The aqueous phase was extracted with EtOAc and (2×250 mL) and the combined organic phases were concentrated in vacuo to afford a colorless solid (0.719 g, 28%) which was of sufficient purity for use in subsequent steps. ¹H NMR (400 MHz, CDCl₃) δ 4.23 (dd, J=4.5, 9.1 Hz, 1H), 3.66 (s, 3H), 3.43-3.49 (m, 2H), 2.08-2.14 (m, 1H), 1.82-1.89 (m, 1H). LCMS: Anal. Calcd. for C₇H₁₃NO₅: 191. Found: 192 (M+H)⁺.

Cap-88

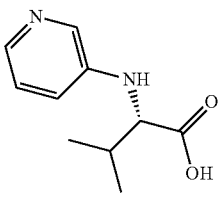

A mixture of L-valine (1.0 g, 8.54 mmol), 3-bromopyridine (1.8 mL, 18.7 mmol), K₂CO₃ (2.45 g, 17.7 mmol) and CuI (169 mg, 0.887 mmol) in DMSO (10 mL) was heated at 100° C. for 12 h. The reaction mixture was cooled to rt, poured into H₂O (ca. 150 mL) and washed with EtOAc (×2). The organic layers were extracted with a small amount of H₂O and the combined aq phases were acidified to ca. pH 2 with 6N HCl. The volume was reduced to about one-third and 20 g of cation exchange resin (Strata) was added. The slurry was allowed to stand for 20 min and loaded onto a pad of cation exchange resin (Strata) (ca. 25 g). The pad was washed with H₂O (200 mL), MeOH (200 mL), and then NH₃ (3M in MeOH, 2×200 mL). The appropriate fractions was concentrated in vacuo and the residue (ca. 1.1 g) was dissolved in H₂O, frozen and lyophyllized. The title compound was obtained as a foam (1.02 g, 62%). ¹H NMR (400 MHz, DMSO-d₆) δ 8.00 (s, br, 1H), 7.68-7.71 (m, 1H), 7.01 (s, br, 1H), 6.88 (d, J=7.5 Hz, 1H), 5.75 (s, br, 1H), 3.54 (s, 1H), 2.04-2.06 (m, 1H), 0.95 (d, J=6.0 Hz, 3H), 0.91 (d, J=6.6 Hz, 3H). LCMS: Anal. Calcd. for C₁₀H₁₄N₂O₂: 194. Found: 195 (M+H)⁺.

Cap-89

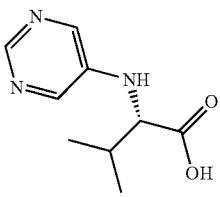

A mixture of L-valine (1.0 g, 8.54 mmol), 5-bromopyrimidine (4.03 g, 17.0 mmol), K₂CO₃ (2.40 g, 17.4 mmol) and CuI (179 mg, 0.94 mmol) in DMSO (10 mL) was heated at 100°

C. for 12 h. The reaction mixture was cooled to RT, poured into H₂O (ca. 150 mL) and washed with EtOAc (×2). The organic layers were extracted with a small amount of H₂O and the combined aq phases were acidified to ca. pH 2 with 6N HCl. The volume was reduced to about one-third and 20 g of cation exchange resin (Strata) was added. The slurry was allowed to stand for 20 min and loaded onto a pad of cation exchange resin (Strata) (ca. 25 g). The pad was washed with H₂O (200 mL), MeOH (200 mL), and then NH₃ (3M in MeOH, 2×200 mL). The appropriate fractions was concentrated in vacuo and the residue (ca. 1.1 g) was dissolved in H₂O, frozen and lyophyllized. The title compound was obtained as a foam (1.02 g, 62%). ¹H NMR (400 MHz, CD₃OD) showed the mixture to contain valine and the purity could not be estimated. The material was used as is in subsequent reactions. LCMS: Anal. Calcd. for $C_9H_{13}N_3O_2$: 195. Found: 196 (M+H)⁺.

Cap-90

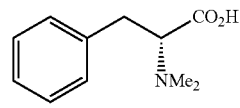 [SMILES: CN(C)[C@H](Cc1ccccc1)C(=O)O]

Cap-90 was prepared according to the method described for the preparation of Cap-1. The crude material was used as is in subsequent steps. LCMS: Anal. Calcd. for $C_{11}H_{15}NO_2$: 193. Found: 192 (M−H)⁻.

The following caps were prepared according to the method used for preparation of Cap-51 unless noted otherwise:

| Cap | Structure | LCMS |
|---|---|---|
| Cap-91 | 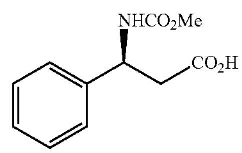 | LCMS: Anal. Calcd. for $C_{11}H_{13}NO_4$: 223; found: 222 (M − H)⁻. |
| Cap-92 | 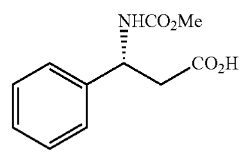 | LCMS: Anal. Calcd. for $C_{11}H_{13}NO_4$: 223; found: 222 (M − H)⁻. |
| Cap-93 | 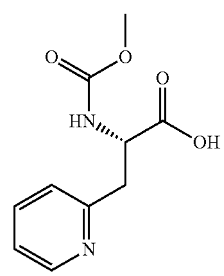 [SMILES: COC(=O)N[C@@H](Cc1ccccn1)C(=O)O] | LCMS: Anal. Calcd. for $C_{10}H_{12}N_2O_4$: 224; found: 225 (M + H)⁺. |
| Cap-94 | 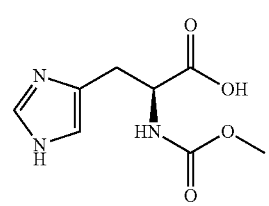 | LCMS: Anal. Calcd. for $C_8H_{11}N_3O_4$: 213; found: 214 (M + H)⁺. |
| Cap-95 | 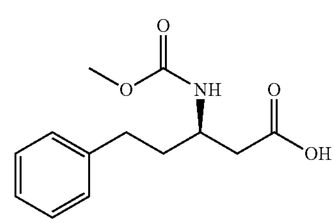 [SMILES: COC(=O)N[C@H](CCc1ccccc1)CC(=O)O] | LCMS: Anal. Calcd. for $C_{13}H_{17}NO_4$: 251; found: 250 (M − H)⁻. |

-continued

| Cap | Structure | LCMS |
| --- | --- | --- |
| Cap-96 | 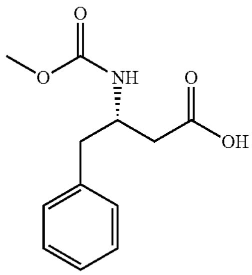 [SMILES: COC(=O)N[C@H](CC(=O)O)Cc1ccccc1] | LCMS: Anal. Calcd. for C$_{12}$H$_{15}$NO$_4$: 237; found: 236 (M − H)$^-$. |
| Cap-97 | 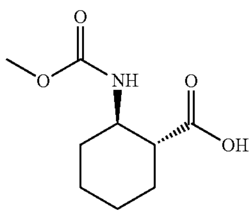 | LCMS: Anal. Calcd. for C$_9$H$_{15}$NO$_4$: 201; found: 200 (M − H)$^-$. |
| Cap-98 | 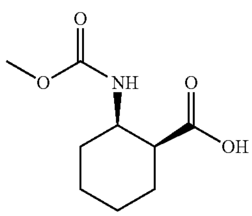 | LCMS: Anal. Calcd. for C$_9$H$_{15}$NO$_4$: 201; found: 202 (M + H)$^+$. |
| Cap-99 | 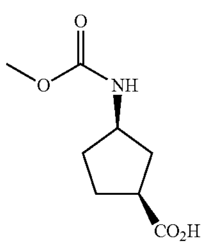 | $^1$H NMR (400 MHz, CD$_3$OD) δ 3.88-3.94 (m, 1H), 3.60, 3.61 (s, 3H), 2.80 (m, 1H), 2.20 (m 1H), 1.82-1.94 (m, 3H), 1.45-1.71 (m, 2H). |
| Cap-99a | 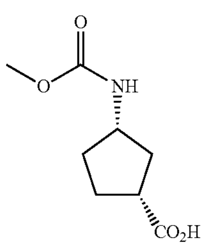 | $^1$H NMR (400 MHz, CD$_3$OD) δ 3.88-3.94 (m, 1H), 3.60, 3.61 (s, 3H), 2.80 (m, 1H), 2.20 (m 1H), 1.82-1.94 (m, 3H), 1.45-1.71 (m, 2H). |
| Cap-100 | 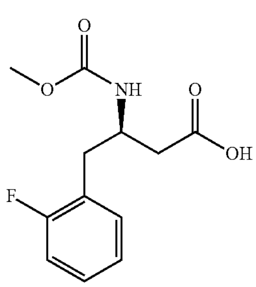 [SMILES: COC(=O)N[C@@H](CC(=O)O)Cc1ccccc1F] | LCMS: Anal. Calcd. for C$_{12}$H$_{14}$NO$_4$F: 255; found: 256 (M + H)$^+$. |

-continued

| Cap | Structure | LCMS |
|---|---|---|
| Cap-101 | (structure: methyl carbamate of L-phenylalanine) | LCMS: Anal. Calcd. for $C_{11}H_{13}NO_4$: 223; found: 222 (M − H)⁻. |
| Cap-102 | (structure: methyl carbamate of D-phenylalanine) | LCMS: Anal. Calcd. for $C_{11}H_{13}NO_4$: 223; found: 222 (M − H)⁻ |
| Cap-103 | (structure: methyl carbamate of 3-(pyridin-2-yl)alanine) | LCMS: Anal. Calcd. for $C_{10}H_{12}N_2O_4$: 224; found: 225 (M + H)⁺. |
| Cap-104 | (structure: trans-4-(methoxycarbonylamino)cyclohexanecarboxylic acid) | $^1$H NMR (400 MHz, CD$_3$OD) δ 3.60 (s, 3H), 3.50-3.53 (m, 1H), 2.66-2.69 and 2.44-2.49 (m, 1H), 1.91-2.01 (m, 2H), 1.62-1.74 (m, 4H), 1.51-1.62 (m, 2H). |
| Cap-105 | (structure: cis-4-(methoxycarbonylamino)cyclohexanecarboxylic acid) | $^1$H NMR (400 MHz, CD$_3$OD) δ 3.60 (s, 3H), 3.33-3.35 (m, 1H, partially obscured by solvent), 2.37-2.41 and 2.16-2.23 (m, 1H), 1.94-2.01 (m, 4H), 1.43-1.53 (m, 2H), 1.17-1.29 (m, 2H). |
| Cap-106 | (structure: 4-(diethylamino)cyclohexanecarboxylic acid)<br>Prepared from cis-4-aminocyclohexane carboxylic acid and acetaldehyde by employing a similar procedure described for the synthesis of Cap-2. The crude HCl salt was passed through MCX (MeOH/H$_2$O/CH$_2$Cl$_2$ wash; 2N NH$_3$/MeOH elution) to afford an oil, which was dissolved in CH$_3$CN/H$_2$O and lyophilized to afford a tan solid. | $^1$H NMR (400 MHz, CD$_3$OD) δ 3.16 (q, J = 7.3 Hz, 4H), 2.38-2.41 (m, 1H), 2.28-2.31 (m, 2H), 1.79-1.89 (m, 2H), 1.74 (app, ddd J = 3.5, 12.5, 15.9 Hz, 2H), 1.46 (app dt J = 4.0, 12.9 Hz, 2H), 1.26 (t, J = 7.3 Hz, 6H) |

-continued
| Cap | Structure | LCMS |
|---|---|---|
| Cap-107 | 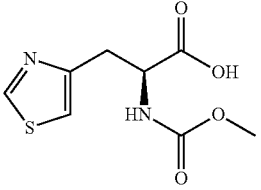 | LCMS: Anal. Calcd. for $C_8H_{10}N_2O_4S$: 230; found: 231 $(M + H)^+$. |
| Cap-108 | 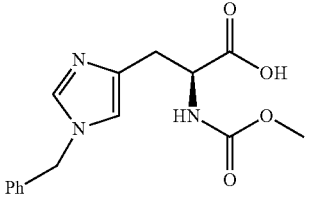 [SMILES: COC(=O)N[C@@H](Cc1cn(Cc2ccccc2)cn1)C(=O)O] | LCMS: Anal. Calcd. for $C_{15}H_{17}N_3O_4$: 303; found: 304 $(M + H)^+$. |
| Cap-109 | 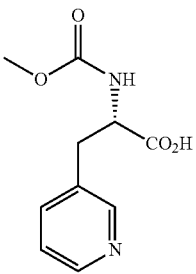 [SMILES: COC(=O)N[C@@H](Cc1cccnc1)C(=O)O] | LCMS: Anal. Calcd. for $C_{10}H_{12}N_2O_4$: 224; found: 225 $(M + H)^+$. |
| Cap-110 | 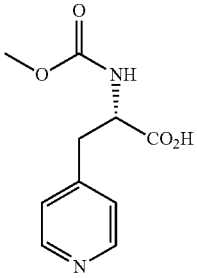 [SMILES: COC(=O)N[C@@H](Cc1ccncc1)C(=O)O] | LCMS: Anal. Calcd. for $C_{10}H_{12}N_2O_4$: 224; found: 225 $(M + H)^+$. |
| Cap-111 | 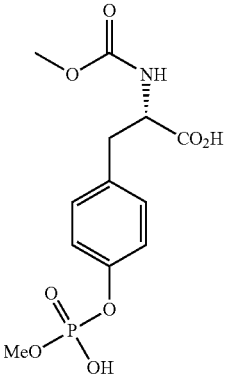 [SMILES: COC(=O)N[C@@H](Cc1ccc(OP(=O)(O)OC)cc1)C(=O)O] | LCMS: Anal. Calcd. for $C_{12}H_{16}NO_8P$: 333; found: 334 $(M + H)^+$. |

| Cap | Structure | LCMS |
|---|---|---|
| Cap-112 | (structure: methyl carbamate of tryptophan) | LCMS: Anal. Calcd. for $C_{13}H_{14}N_2O_4$: 262; found: 263 $(M + H)^+$. |
| Cap-113 | (structure: methyl carbamate of O-benzyl tyrosine) | LCMS: Anal. Calcd. for $C_{18}H_{19}NO_5$: 329; found: 330 $(M + H)^+$. |
| Cap-114 | (structure: azetidine with $CO_2Me$ on N and $CO_2H$) | $^1$H NMR (400 MHz, CDCl$_3$) δ 4.82-4.84 (m, 1H), 4.00-4.05 (m, 2H), 3.77 (s, 3H), 2.56 (s, br, 2H) |
| Cap-115 | (structure with $CO_2H$, NHCO$_2$Me, methyl) | $^1$H NMR (400 MHz, CDCl$_3$) δ 5.13 (s, br, 1H), 4.13 (s, br, 1H), 3.69 (s, 3H), 2.61 (d, J = 5.0 Hz, 2H), 1.28 (d, J = 9.1 Hz, 3H). |
| Cap-116 | (structure with $CO_2H$, NHCO$_2$Me, isopropyl) | $^1$H NMR (400 MHz, CDCl$_3$) δ 5.10 (d, J = 8.6 Hz, 1H), 3.74-3.83 (m, 1H), 3.69 (s, 3H), 2.54-2.61 (m, 2H), 1.88 (sept, J = 7.0 Hz, 1H), 0.95 (d, J = 7.0 Hz, 6H). |

Cap-117 to Cap-123

For the preparation of Cap-117 to Cap-123 the Boc amino acids were obtained from commercially sources and were deprotected by treatment with 25% TFA in CH$_2$Cl$_2$. After complete reaction as judged by LCMS the solvents were removed in vacuo and the corresponding TFA salt of the amino acid was carbamoylated with methyl chloroformate according to the procedure described for Cap-51.

| Cap | Structure | LCMS |
|---|---|---|
| Cap-117 | (structure: methyl carbamate of β-homophenylalanine) | LCMS: Anal. Calcd. for $C_{12}H_{15}NO_4$: 237; found: 238 $(M + H)^+$. |

-continued

| Cap | Structure | LCMS |
|---|---|---|
| Cap-118 | 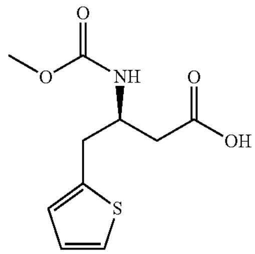 [SMILES: COC(=O)N[C@@H](CC(=O)O)Cc1cccs1] | LCMS: Anal. Calcd. for $C_{10}H_{13}NO_4S$: 243; found: 244 (M + H)+. |
| Cap-119 | 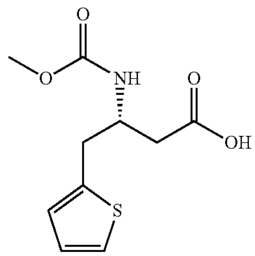 [SMILES: COC(=O)N[C@H](CC(=O)O)Cc1cccs1] | LCMS: Anal. Calcd. for $C_{10}H_{13}NO_4S$: 243; found: 244 (M + H)+. |
| Cap-120 | 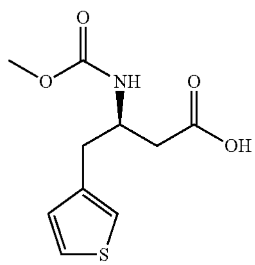 [SMILES: COC(=O)N[C@@H](CC(=O)O)Cc1ccsc1] | LCMS: Anal. Calcd. for $C_{10}H_{13}NO_4S$: 243; found: 244 (M + H)+. |
| Cap-121 | 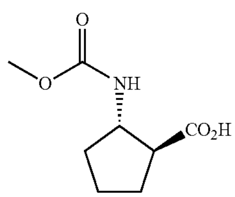 | 1H NMR (400 MHz, CDCl3) δ 4.06-4.16 (m, 1H), 3.63 (s, 3H), 3.43 (s, 1H), 2.82 and 2.66 (s, br, 1H), 1.86-2.10 (m, 3H), 1.64-1.76 (m, 2H), 1.44-1.53 (m, 1H). |
| Cap-122 | 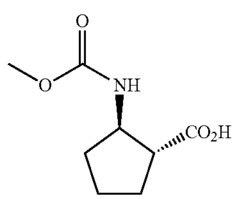 | 1H NMR profile is similar to that of its stereoisomer, Cap-121. |
| Cap-123 | 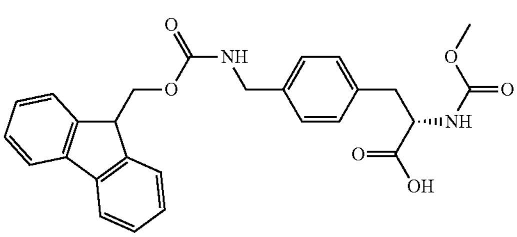 [SMILES: COC(=O)N[C@@H](Cc1ccc(CNC(=O)OCC2c3ccccc3-c3ccccc32)cc1)C(=O)O] | LCMS: Anal. Calcd. for $C_{27}H_{26}N_2O_6$: 474; found: 475 (M + H)+. |

Cap-124

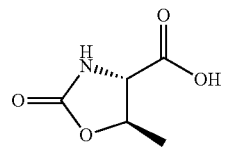

The hydrochloride salt of L-threonine tert-butyl ester was carbamoylated according to the procedure for Cap-51. The crude reaction mixture was acidified with 1N HCl to pH ~1 and the mixture was extracted with EtOAc (2×50 mL). The combined organic phases were concentrated in vacuo to give a colorless oil which solidified on standing. The aqueous layer was concentrated in vacuo and the resulting mixture of product and inorganic salts was triturated with EtOAc-CH$_2$Cl$_2$-MeOH (1:1:0.1) and then the organic phase concentrated in vacuo to give a colorless oil which was shown by LCMS to be the desired product. Both crops were combined to give 0.52 g of a solid. $^1$H NMR (400 MHz, CD$_3$OD) δ 4.60 (m, 1H), 4.04 (d, J=5.0 Hz, 1H), 1.49 (d, J=6.3 Hz, 3H). LCMS: Anal. Calcd. for C$_5$H$_7$NO$_4$: 145. Found: 146 (M+H)$^+$.

Cap-125

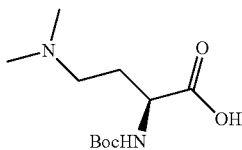 [SMILES: CN(C)CC[C@H](NC(=O)OC(C)(C)C)C(=O)O]

To a suspension of Pd(OH)$_2$, (20%, 100 mg), aqueous formaldehyde (37% wt, 4 ml), acetic acid, (0.5 mL) in methanol (15 mL) was added (S)-4-amino-2-(tert-butoxycarbonylamino)butanoic acid (1 g, 4.48 mmol). The reaction was purged several times with hydrogen and was stirred overnight with an hydrogen balloon room temperature. The reaction mixture was filtered through a pad of diatomaceous earth (CELITE®), and the volatile component was removed in vacuo. The resulting crude material was used as is for the next step. LC/MS: Anal. Calcd. for C$_{11}$H$_{22}$N$_2$O$_4$: 246. Found: 247 (M+H)$^+$.

Cap-126

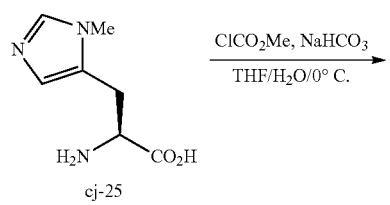

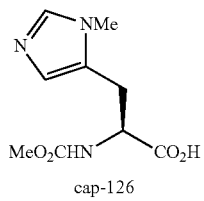

This procedure is a modification of that used to prepare Cap-51. To a suspension of 3-methyl-L-histidine (0.80 g, 4.70 mmol) in THF (10 mL) and H$_2$O (10 mL) at 0° C. was added NaHCO$_3$ (0.88 g, 10.5 mmol). The resulting mixture was treated with ClCO$_2$Me (0.40 mL, 5.20 mmol) and the mixture allowed to stir at 0° C. After stirring for ca. 2 h LCMS showed no starting material remaining. The reaction was acidified to pH 2 with 6 N HCl.

The solvents were removed in vacuo and the residue was suspended in 20 mL of 20% MeOH in CH$_2$Cl$_2$. The mixture was filtered and concentrated to give a light yellow foam (1.21 g.). LCMS and $^1$H NMR showed the material to be a 9:1 mixture of the methyl ester and the desired product. This material was taken up in THF (10 mL) and H$_2$O (10 mL), cooled to 0° C. and LiOH (249.1 mg, 10.4 mmol) was added. After stirring ca. 1 h LCMS showed no ester remaining. Therefore the mixture was acidified with 6N HCl and the solvents removed in vacuo. LCMS and $^1$H NMR confirm the absence of the ester. The title compound was obtained as its HCl salt contaminated with inorganic salts (1.91 g, >100%). The compound was used as is in subsequent steps without further purification. $^1$H NMR (400 MHz, CD$_3$OD) δ 8.84, (s, 1H), 7.35 (s, 1H), 4.52 (dd, J=5.0, 9.1 Hz, 1H), 3.89 (s, 3H), 3.62 (s, 3H), 3.35 (dd, J=4.5, 15.6 Hz, 1H, partially obscured by solvent), 3.12 (dd, J=9.0, 15.6 Hz, 1H).LCMS: Anal. Calcd. for C$_9$H$_{13}$N$_3$O$_4$: 227.09. Found: 228.09 (M+H)$^+$.

Cap-127

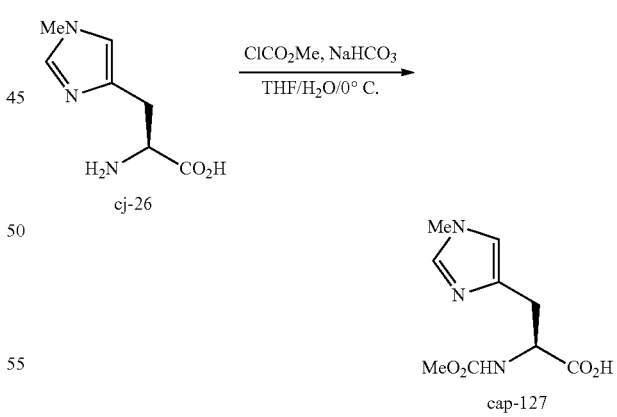

Cap-127 was prepared according to the method for Cap-126 above starting from (S)-2-amino-3-(1-methyl-1H-imidazol-4-yl)propanoic acid (1.11 g, 6.56 mmol), NaHCO$_3$ (1.21 g, 14.4 mmol) and ClCO$_2$Me (0.56 mL, 7.28 mmol). The title compound was obtained as its HCl salt (1.79 g, >100%) contaminated with inorganic salts. LCMS and $^1$H NMR showed the presence of ca. 5% of the methyl ester. The crude mixture was used as is without further purification. $^1$H NMR (400 MHz, CD$_3$OD) δ 8.90 (s, 1H), 7.35 (s, 1H), 4.48 (dd, J=5.0, 8.6 Hz, 1H), 3.89 (s, 3H), 3.62 (s, 3H), 3.35 (m, 1H), 3.08 (m, 1H); LCMS: Anal. Calcd. for $C_9H_{13}N_3O_4$: 227.09. Found: 228 (M+H)+.

Preparation of Cap-128

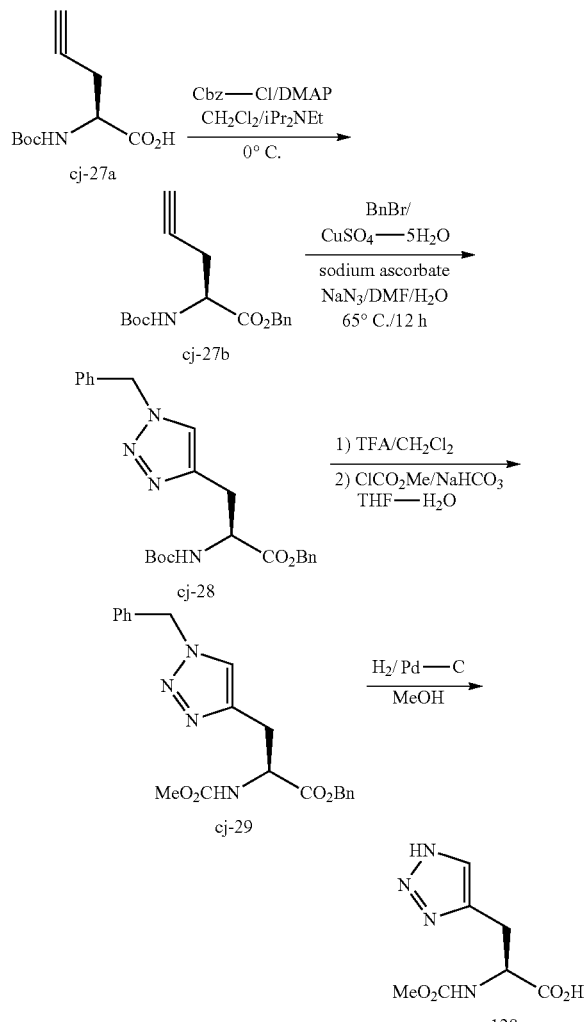

Step 1. Preparation of (S)-benzyl 2-(tert-butoxycarbonylamino)pent-4-ynoate (cj-27b)

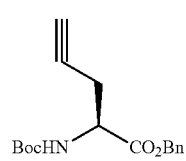

To a solution of cj-27a (1.01 g, 4.74 mmol), DMAP (58 mg, 0.475 mmol) and iPr$_2$NEt (1.7 mL, 9.8 mmol) in CH$_2$Cl$_2$ (100 mL) at 0° C. was added Cbz-Cl (0.68 mL, 4.83 mmol). The solution was allowed to stir for 4 h at 0° C., washed (1N KHSO$_4$, brine), dried (Na$_2$SO$_4$), filtered, and concentrated in vacuo. The residue was purified by flash column chromatography (TLC 6:1 hex:EtOAc) to give the title compound (1.30 g, 91%) as a colorless oil. $^1$H NMR (400 MHz, CDCl$_3$) δ 7.35 (s, 5H), 5.35 (d, br, J=8.1 Hz, 1H), 5.23 (d, J=12.2 Hz, 1H), 5.17 (d, J=12.2 Hz, 1H), 4.48-4.53 (m, 1H), 2.68-2.81 (m, 2H), 2.00 (t, J=2.5 Hz, 1H), 1.44 (s, 9H). LCMS: Anal. Calcd. for $C_{17}H_{21}NO_4$: 303. Found: 304 (M+H)+.

Step 2. Preparation of (S)-benzyl 3-(1-benzyl-1H-1,2,3-triazol-4-yl)-2-(tert-butoxycarbonylamino)propanoate (cj-28)

To a mixture of (S)-benzyl 2-(tert-butoxycarbonylamino)pent-4-ynoate (0.50 g, 1.65 mmol), sodium ascorbate (0.036 g, 0.18 mmol), CuSO$_4$·5H$_2$O (0.022 g, 0.09 mmol) and NaN$_3$ (0.13 g, 2.1 mmol) in DMF-H$_2$O (5 mL, 4:1) at rt was added BnBr (0.24 mL, 2.02 mmol) and the mixture was warmed to 65° C. After 5 h LCMS indicated low conversion. A further portion of NaN$_3$ (100 mg) was added and heating was continued for 12 h. The reaction was poured into EtOAc and H$_2$O and shaken. The layers were separated and the aqueous layer extracted 3× with EtOAc and the combined organic phases washed (H$_2$O×3, brine), dried (Na$_2$SO$_4$), filtered, and concentrated. The residue was purified by flash (BIOTAGE®, 40+M 0-5% MeOH in CH$_2$Cl$_2$; TLC 3% MeOH in CH$_2$Cl$_2$) to afford a light yellow oil which solidified on standing (748.3 mg, 104%). The NMR was consistent with the desired product but suggests the presence of DMF. The material was used as is without further purification. $^1$H NMR (400 MHz, DMSO-d$_6$) δ 7.84 (s, 1H), 7.27-7.32 (m, 10H), 5.54 (s, 2H), 5.07 (s, 2H), 4.25 (m, 1H), 3.16 (dd, J=1.0, 5.3 Hz, 1H), 3.06 (dd, J=5.3, 14.7 Hz), 2.96 (dd, J=9.1, 14.7 Hz, 1H), 1.31 (s, 9H). LCMS: Anal. Calcd. for $C_{24}H_{28}N_4O_4$: 436. Found: 437 (M+H)+.

Step 3. Preparation of (S)-benzyl 3-(1-benzyl-1H-1,2,3-triazol-4-yl)-2-(methoxycarbonylamino)propanoate (cj-29)

A solution of (S)-benzyl 3-(1-benzyl-1H-1,2,3-triazol-4-yl)-2-(tert-butoxycarbonylamino)propanoate (0.52 g, 1.15 mmol) in CH$_2$Cl$_2$ was added TFA (4 mL). The mixture was allowed to stir at room temperature for 2 h. The mixture was concentrated in vacuo to give a colorless oil which solidified on standing. This material was dissolved in THF-H$_2$O and cooled to 0° C. Solid NaHCO$_3$ (0.25 g, 3.00 mmol) was added followed by ClCO$_2$Me (0.25 mL, 3.25 mmol). After stirring for 1.5 h the mixture was acidified to pH ~2 with 6N HCl and then poured into H$_2$O-EtOAc. The layers were separated and the aq phase extracted 2× with EtOAc. The combined org layers were washed (H$_2$O, brine), dried (Na$_2$SO$_4$), filtered, and concentrated in vacuo to give a colorless oil (505.8 mg, 111%, NMR suggested the presence of an unidentified impurity) which solidified while standing on the pump. The material was used as is without further purification. $^1$H NMR (400 MHz, DMSO-d$_6$) δ 7.87 (s, 1H), 7.70 (d, J=8.1 Hz, 1H), 7.27-7.32 (m, 10H), 5.54 (s, 2H), 5.10 (d, J=12.7 Hz, 1H), 5.06 (d, J=12.7 Hz, 1H), 4.32-4.37 (m, 1H), 3.49 (s, 3H), 3.09 (dd, J=5.6, 14.7 Hz, 1H), 2.98 (dd, J=9.6, 14.7 Hz, 1H). LCMS: Anal. Calcd. for C$_{21}$H$_{22}$N$_4$O$_4$: 394. Found: 395 (M+H)$^+$.

Step 4. Preparation of (S)-2-(methoxycarbonylamino)-3-(1H-1,2,3-triazol-4-yl)propanoic acid (Cap-128)

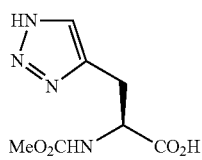

Cap-128

(S)-benzyl 3-(1-benzyl-1H-1,2,3-triazol-4-yl)-2-(methoxycarbonylamino)propanoate (502 mg, 1.11 mmol) was hydrogenated in the presence of Pd—C (82 mg) in MeOH (5 mL) at atmospheric pressure for 12 h. The mixture was filtered through diatomaceous earth (CELITE®) and concentrated in vacuo. (S)-2-(methoxycarbonylamino)-3-(1H-1,2,3-triazol-4-yl)propanoic acid was obtained as a colorless gum (266 mg, 111%) which was contaminated with ca. 10% of the methyl ester. The material was used as is without further purification. $^1$H NMR (400 MHz, DMSO-d$_6$) δ 12.78 (s, br, 1H), 7.59 (s, 1H), 7.50 (d, J=8.0 Hz, 1H), 4.19-4.24 (m, 1H), 3.49 (s, 3H), 3.12 (dd, J=4.8 Hz, 14.9 Hz, 1H), 2.96 (dd, J=9.9, 15.0 Hz, 1H). LCMS: Anal. Calcd. for C$_7$H$_{10}$N$_4$O$_4$: 214. Found: 215 (M+H)$^+$.

Preparation of Cap-129

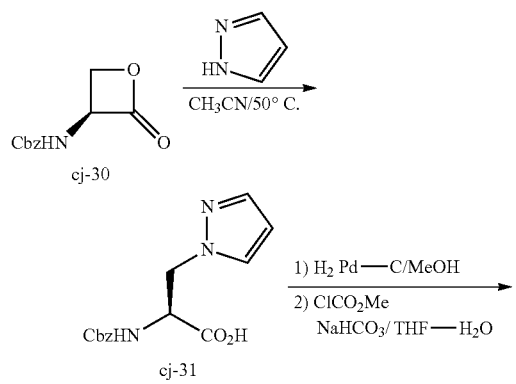

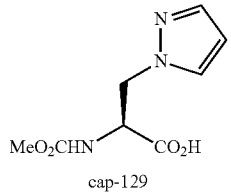

cap-129

Step 1. Preparation of (S)-2-(benzyloxycarbonylamino)-3-(1H-pyrazol-1-yl)propanoic acid (cj-31)

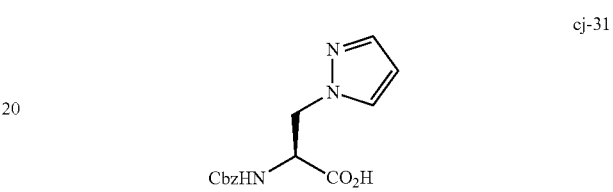

A suspension of (S)-benzyl 2-oxooxetan-3-ylcarbamate (0.67 g, 3.03 mmol), and pyrazole (0.22 g, 3.29 mmol) in CH$_3$CN (12 mL) was heated at 50° C. for 24 h. The mixture was cooled to rt overnight and the solid filtered to afford (S)-2-(benzyloxycarbonylamino)-3-(1H-pyrazol-1-yl)propanoic acid (330.1 mg). The filtrate was concentrated in vacuo and then triturated with a small amount of CH$_3$CN (ca. 4 mL) to afford a second crop (43.5 mg). Total yield 370.4 mg (44%). m.p. 165.5-168° C. lit m.p. 168.5-169.5 [Vederas et al. J. Am. Chem. Soc. 1985, 107, 7105]. $^1$H NMR (400 MHz, CD$_3$OD) δ 7.51 (d, J=2.0, 1H), 7.48 (s, J=1.5 Hz, 1H), 7.24-7.34 (m, 5H), 6.23 m, 1H), 5.05 (d, 12.7H, 1H), 5.03 (d, J=12.7 Hz, 1H), 4.59-4.66 (m, 2H), 4.42-4.49 (m, 1H). LCMS: Anal. Calcd. for C$_{14}$H$_{15}$N$_3$O$_4$: 289. Found: 290 (M+H)$^+$.

Step 2. Preparation of (S)-2-(methoxycarbonylamino)-3-(1H-pyrazol-1-yl)propanoic acid (Cap-129)

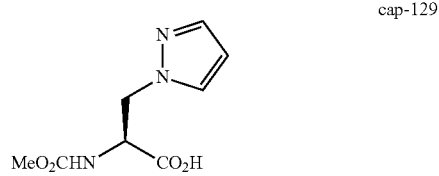

(S)-2-(benzyloxycarbonylamino)-3-(1H-pyrazol-1-yl) propanoic acid (0.20 g, 0.70 mmol) was hydrogenated in the presence of Pd—C (45 mg) in MeOH (5 mL) at atmospheric pressure for 2 h. The product appeared to be insoluble in MeOH, therefore the reaction mixture was diluted with 5 mL H$_2$O and a few drops of 6N HCl. The homogeneous solution was filtered through diatomaceous earth (CELITE®), and the MeOH removed in vacuo. The remaining solution was frozen and lyophyllized to give a yellow foam (188.9 mg). This material was suspended in THF-H$_2$O (1:1, 10 mL) and then cooled to 0° C. To the cold mixture was added NaHCO$_3$ (146.0 mg, 1.74 mmol) carefully (evolution of CO$_2$). After gas evolution had ceased (ca. 15 min) ClCO₂Me (0.06 mL, 0.78 mmol) was added dropwise. The mixture was allowed to stir for 2 h and was acidified to pH ~2 with 6N HCl and poured into EtOAc. The layers were separated and the aqueous phase extracted with EtOAC (×5). The combined organic layers were washed (brine), dried (Na₂SO₄), filtered, and concentrated to give the title compound as a colorless solid (117.8 mg, 79%). ¹H NMR (400 MHz, DMSO-d₆) δ 13.04 (s, 1H), 7.63 (d, J=2.6 Hz, 1H), 7.48 (d, J=8.1 Hz, 1H), 7.44 (d, J=1.5 Hz, 1H), 6.19 (app t, J=2.0 Hz, 1H), 4.47 (dd, J=3.0, 12.9 Hz, 1H), 4.29-4.41 (m, 2H), 3.48 (s, 3H). LCMS: Anal. Calcd. for C₈H₁₁N₃O₄: 213. Found: 214 (M+H)⁺.

Cap-130

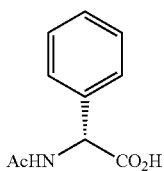 [SMILES: CC(=O)N[C@@H](C(=O)O)c1ccccc1]

Cap-130 was prepared by acylation of commercially available (R)-phenylglycine analgous to the procedure given in: Calmes, M.; Daunis, J.; Jacquier, R.; Verducci, J. *Tetrahedron*, 1987, 43(10), 2285.

Cap-131

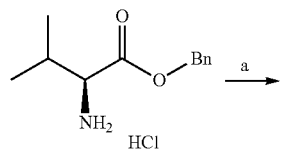

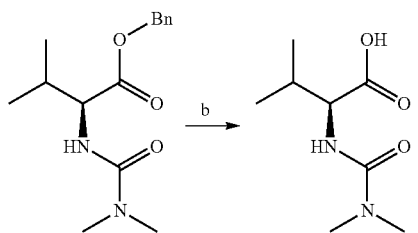

Step a

Dimethylcarbamoyl chloride (0.92 mL, 10 mmol) was added slowly to a solution of (S)-benzyl 2-amino-3-methylbutanoate hydrochloride (2.44 g; 10 mmol) and Hunig's base (3.67 mL, 21 mmol) in THF (50 mL). The resulting white suspension was stirred at room temperature overnight (16 hours) and concentrated under reduced pressure. The residue was partitioned between ethyl acetate and water. The organic layer was washed with brine, dried (MgSO₄), filtered, and concentrated under reduced pressure. The resulting yellow oil was purified by flash chromatography, eluting with ethyl acetate:hexanes (1:1). Collected fractions were concentrated under vacuum providing 2.35 g (85%) of clear oil. ¹H NMR (300 MHz, DMSO-d₆) δ ppm 0.84 (d, J=6.95 Hz, 3H), 0.89 (d, J=6.59 Hz, 3H), 1.98-2.15 (m, 1H), 2.80 (s, 6H), 5.01-5.09 (m, J=12.44 Hz, 1H), 5.13 (d, J=12.44 Hz, 1H), 6.22 (d, J=8.05 Hz, 1H), 7.26-7.42 (m, 5H). LC (Cond. 1): RT=1.76 min; MS: Anal. Calcd. for [M+H]⁺ C₁₆H₂₂N₂O₃: 279.17. Found 279.03.

Step b

To a MeOH (50 mL) solution of the intermediate prepared above (2.35 g; 8.45 mmol) was added Pd/C (10%; 200 mg) and the resulting black suspension was flushed with N₂ (3×) and placed under 1 atm of H₂. The mixture was stirred at room temperature overnight and filtered though a microfiber filter to remove the catalyst. The resulting clear solution was then concentrated under reduced pressure to obtain 1.43 g (89%) of Cap-131 as a white foam, which was used without further purification. ¹H NMR (500 MHz, DMSO-d₆) δ ppm 0.87 (d, J=4.27 Hz, 3H), 0.88 (d, J=3.97 Hz, 3H), 1.93-2.11 (m, 1H), 2.80 (s, 6H), 3.90 (dd, J=8.39, 6.87 Hz, 1H), 5.93 (d, J=8.54 Hz, 1H), 12.36 (s, 1H). LC (Cond. 1): RT=0.33 min; MS: Anal. Calcd. for [M+H]⁺ C₈H₁₇N₂O₃: 189.12. Found 189.04.

Cap-132

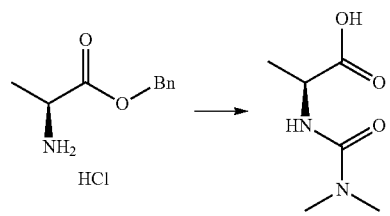

Cap-132 was prepared from (S)-benzyl 2-aminopropanoate hydrochloride according to the method described for Cap-131. ¹H NMR (500 MHz, DMSO-d₆) δ ppm 1.27 (d, J=7.32 Hz, 3H), 2.80 (s, 6H), 4.06 (qt, 1H), 6.36 (d, J=7.32 Hz, 1H), 12.27 (s, 1H). LC (Cond. 1): RT=0.15 min; MS: Anal. Calcd. for [M+H]⁺ C₆H₁₃N₂O₃: 161.09. Found 161.00.

Cap-133

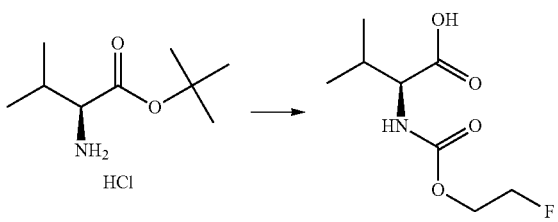

Cap-133 was prepared from (S)-tert-butyl 2-amino-3-methylbutanoate hydrochloride and 2-fluoroethyl chloroformate according to the method described for Cap-47. ¹H NMR (500 MHz, DMSO-d₆) δ ppm 0.87 (t, J=6.71 Hz, 6H), 1.97-2.10 (m, 1H), 3.83 (dd, J=8.39, 5.95 Hz, 1H), 4.14-4.18 (m, 1H), 4.20-4.25 (m, 1H), 4.50-4.54 (m, 1H), 4.59-4.65 (m, 1H), 7.51 (d, J=8.54 Hz, 1H), 12.54 (s, 1H).

Cap-134

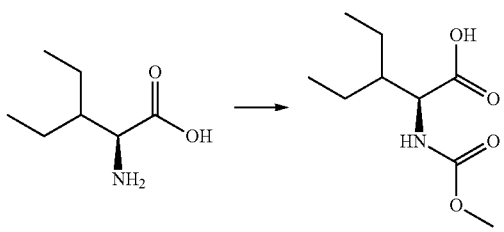

Cap-134 was prepared from (S)-diethyl alanine and methyl chloroformate according to the method described for Cap-51. $^1$H NMR (500 MHz, DMSO-$d_6$) δ ppm 0.72-0.89 (m, 6H), 1.15-1.38 (m, 4H), 1.54-1.66 (m, 1H), 3.46-3.63 (m, 3H), 4.09 (dd, J=8.85, 5.19 Hz, 1H), 7.24 (d, J=8.85 Hz, 1H), 12.55 (s, 1H). LC (Cond. 2): RT=0.66 min; LC/MS: Anal. Calcd. for [M+H]$^+$ $C_9H_{18}NO_4$: 204.12. Found 204.02.

Cap-135

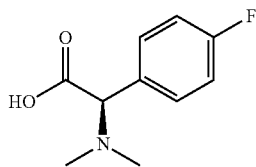

A solution of D-2-amino-(4-fluorophenyl)acetic acid (338 mg, 2.00 mmol), 1N HCl in diethylether (2.0 mL, 2.0 mmol) and formalin (37%, 1 mL) in methanol (5 mL) was subjected to balloon hydrogenation over 10% palladium on carbon (60 mg) for 16 h at 25° C. The mixture was then filtered through CELITE® to afford the HCl salt of Cap-135 as a white foam (316 mg, 80%). $^1$H NMR (300 MHz, MeOH-$d_4$) δ 7.59 (dd, J=8.80, 5.10 Hz, 2H), 7.29 (t, J=8.6 Hz, 2H), 5.17 (s, 1H), 3.05 (v br s, 3H), 2.63 (v br s, 3H); R$_f$=0.19 min (Cond.-MS-W5); 95% homogeneity index; LRMS: Anal. Calcd. for [M+H]$^+$ $C_{10}H_{13}FNO_2$: 198.09. Found: 198.10.

Cap-136

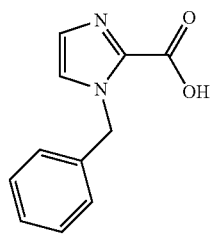 [SMILES: O=C(O)c1nccn1Cc1ccccc1]

To a cooled (−50° C.) suspension of 1-benzyl-1H-imidazole (1.58 g, 10.0 mmol) in anhydrous diethyl ether (50 mL) under nitrogen was added n-butyl lithium (2.5 M in hexanes, 4.0 mL, 10.0 mmol) dropwise. After being stirred for 20 min at −50° C., dry carbon dioxide (passed through Drierite) was bubbled into the reaction mixture for 10 min before it was allowed to warm up to 25° C. The heavy precipitate which formed on addition of carbon dioxide to the reaction mixture was filtered to yield a hygroscopic, white solid which was taken up in water (7 mL), acidified to pH=3, cooled, and induced to crystallize with scratching. Filtration of this precipitate gave a white solid which was suspended in methanol, treated with 1N HCl/diethyl ether (4 mL) and concentrated in vacuo. Lyophilization of the residue from water (5 mL) afforded the HCl salt of Cap-136 as a white solid (817 mg, 40%). $^1$H NMR (300 MHz, DMSO-$d_6$) δ 7.94 (d, J=1.5 Hz, 1H), 7.71 (d, J=1.5 Hz, 1H), 7.50-7.31 (m, 5H), 5.77 (s, 2H); R$_f$=0.51 min (Cond.-MS-W5); 95% homogenity index; LRMS: Anal. Calc. for [M+H]$^+$ $C_{11}H_{12}N_2O_2$: 203.08. Found: 203.11.

Cap-137

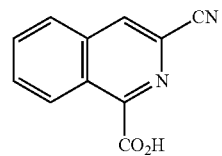

Cap-137, Step a

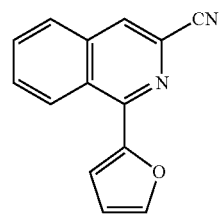 [SMILES: N#Cc1cc2ccccc2c(-c2ccco2)n1]

A suspension of 1-chloro-3-cyanoisoquinoline (188 mg, 1.00 mmol; prepared according to the procedure in WO 2003/099274) (188 mg, 1.00 mmol), cesium fluoride (303.8 mg, 2.00 mmol), bis(tri-tert-butylphosphine)palladium dichloride (10 mg, 0.02 mmol) and 2-(tributylstannyl)furan (378 μL, 1.20 mmol) in anhydrous dioxane (10 mL) under nitrogen was heated at 80° C. for 16 h before it was cooled to 25° C. and treated with saturated, aqueous potassium fluoride solution with vigorous stirring for 1 h. The mixture was partitioned between ethyl acetate and water and the organic phase was separated, washed with brine, dried over $Na_2SO_4$, filtered and concentrated. Purification of the residue on silica gel (elution with 0% to 30% ethyl acetate/hexanes) afforded Cap-137, step a as a white solid which was used as is (230 mg, 105%). R$_f$=1.95 min (Cond.-MS-W2); 90% homogeneity index; LRMS: Anal. Calc. for [M+H]$^+$ $C_{14}H_8N_2O$: 221.07. Found: 221.12.

Cap-137

To a suspension of Cap-137, step a, (110 mg, 0.50 mmol) and sodium periodate (438 mg, 2.05 mmol) in carbon tetrachloride (1 mL), acetonitrile (1 mL) and water (1.5 mL) was added ruthenium trichloride hydrate (2 mg, 0.011 mmol). The mixture was stirred at 25° C. for 2 h and then partitioned between dichloromethane and water. The aqueous layer was separated, extracted twice more with dichloromethane and the combined dichloromethane extracts were dried over $Na_2SO_4$, filtered and concentrated. Trituration of the residue with hexanes afforded Cap-137 (55 mg, 55%) as a grayish-colored solid. $R_t$=1.10 min (Cond.-MS-W2); 90% homogeneity index; LCMS: Anal. Calc. for $[M+H]^+$ $C_{11}H_8N_2O_2$: 200.08. Found: 200.08.

Caps 138 to 158

Synthetic Strategy. Method A.

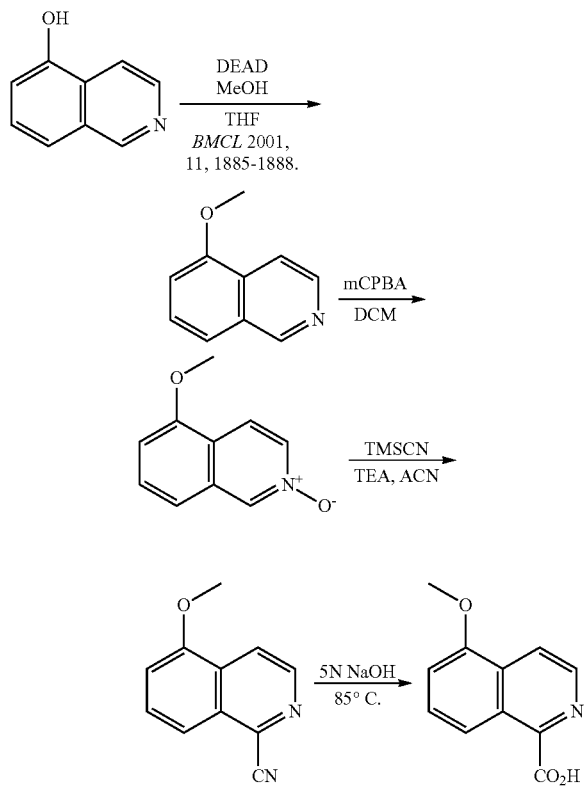

Cap-138

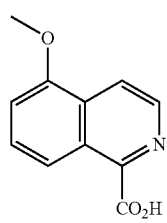

Cap-138, Step a

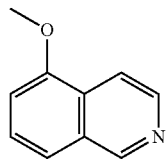

To a stirred suspension of 5-hydroxisoquinoline (prepared according to the procedure in WO 2003/099274) (2.0 g, 13.8 mmol) and triphenylphosphine (4.3 g, 16.5 mmol) in dry tetrahydrofuran (20 mL) was added dry methanol (0.8 mL) and diethyl azodicarboxylate (3.0 mL, 16.5 mmol) portionwise. The mixture was stirred at room temperature for 20 h before it was diluted with ethyl acetate and washed with brine, dried over $Na_2SO_4$, filtered and concentrated. The residue was preabsorbed onto silica gel and purified (elution with 40% ethyl acetate/hexanes) to afford Cap-138, step a as a light yellow solid (1.00 g, 45%). $^1$H NMR (CDCl$_3$, 500 MHz) δ 9.19 (s, 1H), 8.51 (d, J=6.0 Hz, 1H), 7.99 (d, J=6.0 Hz, 1H), 7.52-7.50 (m, 2H), 7.00-6.99 (m, 1H), 4.01 (s, 3H); $R_t$=0.66 min (Cond. D2); 95% homogeneity index;
LCMS: Anal. Calc. for $[M+H]^+$ $C_{10}H_{10}NO$: 160.08. Found 160.10.

Cap-138, Step b

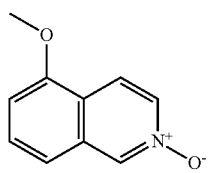

To a stirred solution of Cap-138, step a (2.34 g, 14.7 mmol) in anhydrous dichloromethane (50 mL) at room temperature was added meta-chloroperbenzoic acid (77%, 3.42 g, 19.8 mmol) in one portion. After being stirred for 20 h, powdered potassium carbonate (2.0 g) was added and the mixture was stirred for 1 h at room temperature before it was filtered and concentrated to afford Cap-138, step b as a pale, yellow solid which was sufficiently pure to carry forward (2.15 g, 83.3%). $^1$H NMR (CDCl$_3$, 400 MHz) δ 8.73 (d, J=1.5 Hz, 1H), 8.11 (dd, J=7.3, 1.7 Hz, 1H), 8.04 (d, J=7.1 Hz, 1H), 7.52 (t, J=8.1 Hz, 1H), 7.28 (d, J=8.3 Hz, 1H), 6.91 (d, J=7.8 Hz, 1H), 4.00 (s, 3H); $R_t$=0.92 min, (Cond.-D1); 90% homogenity index; LCMS: Anal. Calc. for $[M+H]^+$ $C_{10}H_{10}NO_2$: 176.07. Found: 176.0.

Cap-138, Step c

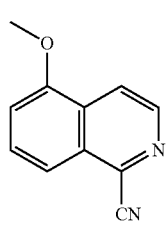

To a stirred solution of Cap-138, step b (0.70 g, 4.00 mmol) and triethylamine (1.1 mL, 8.00 mmol) in dry acetonitrile (20 mL) at room temperature under nitrogen was added trimethylsilylcyanide (1.60 mL, 12.00 mmol). The mixture was heated at 75° C. for 20 h before it was cooled to room temperature, diluted with ethyl acetate and washed with saturated sodium bicarbonate solution and brine prior to drying over Na$_2$SO$_4$ and solvent concentration. The residue was flash chromatographed on silica gel (elution with 5% ethyl acetate/hexanes) to 25% ethyl acetate/hexanes to afford Cap-138, step c (498.7 mg) as a white, crystalline solid along with 223 mg of additional Cap-138, step c recovered from the filtrate. $^1$H NMR (CDCl$_3$, 500 MHz) δ 8.63 (d, J=5.5 Hz, 1H), 8.26 (d, J=5.5 Hz, 1H), 7.88 (d, J=8.5 Hz, 1H), 7.69 (t, J=8.0 Hz, 1H), 7.08 (d, J=7.5 Hz, 1H), 4.04 (s, 3H); R$_t$=1.75 min, (Cond.-D1); 90% homogeneity index; LCMS: Anal. Calc. for [M+H]$^+$ C$_{11}$H$_9$N$_2$O: 185.07. Found: 185.10.

Cap-138

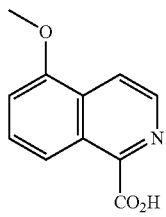

Cap-138, step c (0.45 g, 2.44 mmol) was treated with 5N sodium hydroxide solution (10 mL) and the resulting suspension was heated at 85° C. for 4 h, cooled to 25° C., diluted with dichloromethane and acidified with 1N hydrochloric acid. The organic phase was separated, washed with brine, dried over Na$_2$SO$_4$, concentrated to ¼ volume and filtered to afford Cap-138 as a yellow solid (0.44 g, 88.9%). $^1$H NMR (DMSO-d$_6$, 400 MHz) δ 13.6 (br s, 1H), 8.56 (d, J=6.0 Hz, 1H), 8.16 (d, J=6.0 Hz, 1H), 8.06 (d, J=8.8 Hz, 1H), 7.71-7.67 (m, 1H), 7.30 (d, J=8.0 Hz, 1H), 4.02 (s, 3H); R$_t$=0.70 min (Cond.-D1); 95% homogenity index; LCMS: Anal. Calc. for [M+H]$^+$ C$_{11}$H$_{10}$NO$_3$: 204.07. Found: 204.05.

Synthetic Strategy. Method B (Derived from *Tetrahedron Letters*, 2001, 42, 6707).

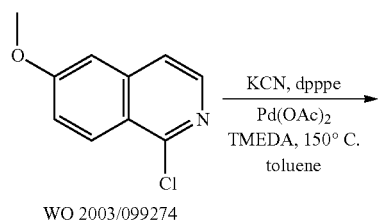

WO 2003/099274

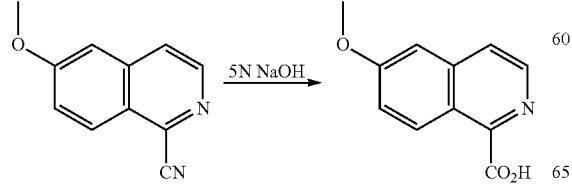

Cap-139

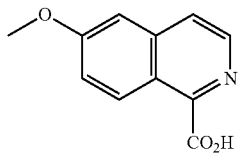

Cap-139, Step a

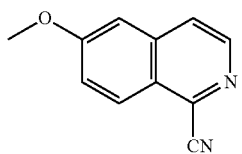

To a thick-walled, screw-top vial containing an argon-degassed suspension of 1-chloro-6-methoxyisoquinoline (1.2 g, 6.2 mmol; prepared according to the procedure in WO 2003/099274), potassium cyanide (0.40 g, 6.2 mmol), 1,5-bis(diphenylphosphino)pentane (0.27 g, 0.62 mmol) and palladium (II) acetate (70 mg, 0.31 mmol) in anhydrous toluene (6 mL) was added N,N,N',N'-tetramethylethylenediamine (0.29 mL, 2.48 mmol). The vial was sealed, heated at 150° C. for 22 h and then allowed to cool to 25° C. The reaction mixture was diluted with ethyl acetate, washed with water and brine, dried over Na$_2$SO$_4$, filtered and concentrated. The residue was purified on silica gel eluting with 5% ethyl acetate/hexanes to 25% ethyl acetate/hexanes to afford Cap-139, step a as a white solid (669.7 mg). $^1$H NMR (CDCl$_3$, 500 MHz) δ 8.54 (d, J=6.0 Hz, 1H), 8.22 (d, J=9.0 Hz, 1H), 7.76 (d, J=5.5 Hz, 1H), 7.41-7.39 (m, 1H), 7.13 (d, J=2.0 Hz, 1H), 3.98 (s, 3H); R$_t$=1.66 min (Cond.-D1); 90% homogenity index; LCMS: Anal. Calc. for [M+H]$^+$ C$_{11}$H$_9$N$_2$O: 185.07. Found: 185.20.

Cap-139

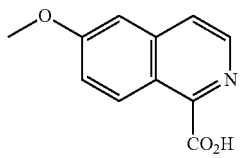

Cap-139 was prepared from the basic hydrolysis of Cap-139, step a with 5N NaOH according to the procedure described for Cap-138. $^1$H NMR (400 MHz, DMSO-d$_6$) δ 13.63 (v br s, 1H), 8.60 (d, J=9.3 Hz, 1H), 8.45 (d, J=5.6 Hz, 1H), 7.95 (d, J=5.9 Hz, 1H), 7.49 (d, J=2.2 Hz, 1H), 7.44 (dd, J=9.3, 2.5 Hz, 1H), 3.95 (s, 3H); R$_t$=0.64 min (Cond.-D1);

90% homogenity index; LCMS: Anal. Calc. for [M+H]$^+$ C$_{11}$H$_{10}$NO$_3$: 204.07. Found: 204.05.

Cap-140

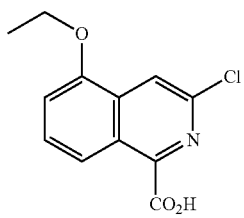 [SMILES: CCOc1cccc2c(C(=O)O)nc(Cl)cc12]

Cap-140, Step a

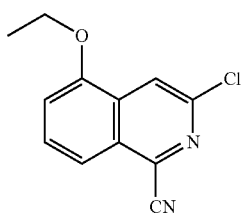 [SMILES: CCOc1cccc2c(C#N)nc(Cl)cc12]

To a vigorously-stirred mixture of 1,3-dichloro-5-ethoxy-isoquinoline (482 mg, 2.00 mmol; prepared according to the procedure in WO 2005/051410), palladium (II) acetate (9 mg, 0.04 mmol), sodium carbonate (223 mg, 2.10 mmol) and 1,5-bis(diphenylphosphino)pentane (35 mg, 0.08 mmol) in dry dimethylacetamide (2 mL) at 25° C. under nitrogen was added N,N,N',N'-tetramethylethylenediamine (60 mL, 0.40 mmol). After 10 min, the mixture was heated to 150° C., and then a stock solution of acetone cyanohydrin (prepared from 457 µL of acetone cyanohydrin in 4.34 mL DMA) was added in 1 mL portions over 18 h using a syringe pump. The mixture was then partitioned between ethyl acetate and water and the organic layer was separated, washed with brine, dried over Na$_2$SO$_4$, filtered and concentrated. The residue was purified on silica gel eluting with 10% ethyl acetate/hexanes to 40% ethyl acetate/hexanes to afford Cap-140, step a as a yellow solid (160 mg, 34%). R$_t$=2.46 min (Cond.-MS-W2); 90% homogenity index; LCMS: Anal. Calc. for [M+H]$^+$ C$_{12}$H$_9$ClN$_2$O: 233.05. Found: 233.08.

Cap-140

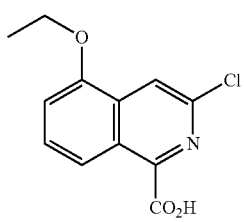

Cap-140 was prepared by the acid hydrolysis of Cap-140, step a with 12N HCl as described in the procedure for the preparation of Cap-141, described below. R$_t$=2.24 min (Cond.-MS-W2); 90% homogenity index; LCMS: Anal. Calc. for [M+H]$^+$ C$_{12}$H$_{11}$ClNO$_3$: 252.04. Found: 252.02.

Cap-141

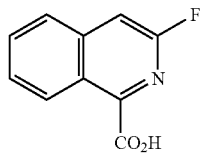 [SMILES: O=C(O)c1nc(F)cc2ccccc12]

Cap-114, Step a

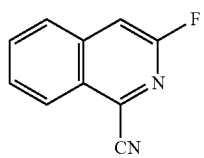 [SMILES: N#Cc1nc(F)cc2ccccc12]

Cap-141, step a was prepared from 1-bromo-3-fluoroisoquinoline (prepared from 3-amino-1-bromoisoquinoline using the procedure outlined in *J. Med. Chem.* 1970, 13, 613) as described in the procedure for the preparation of Cap-140, step a (vide supra). $^1$H NMR (500 MHz, CDCl$_3$) δ 8.35 (d, J=8.5 Hz, 1H), 7.93 (d, J=8.5 Hz, 1H), 7.83 (t, J=7.63 Hz, 1H), 7.77-7.73 (m, 1H), 7.55 (s, 1H); R$_t$=1.60 min (Cond.-D1); 90% homogenity index; LCMS: Anal. Calc. for [M+H]$^+$ C$_{10}$H$_6$FN$_2$: 173.05. Found: 172.99.

Cap-141

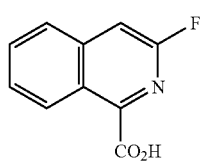 [SMILES: O=C(O)c1nc(F)cc2ccccc12]

Cap-141, step a (83 mg, 0.48 mmol) was treated with 12N HCl (3 mL) and the resulting slurry was heated at 80° C. for 16 h before it was cooled to room temperature and diluted with water (3 mL). The mixture was stirred for 10 min and then filtered to afford Cap-141 as an off-white solid (44.1 mg, 47.8%). The filtrate was diluted with dichloromethane and washed with brine, dried over Na$_2$SO$_4$, and concentrated to afford additional Cap-141 which was sufficiently pure to be carried forward directly (29.30 mg, 31.8%). $^1$H NMR (DMSO-d$_6$, 500 MHz) δ 14.0 (br s, 1H), 8.59-8.57 (m, 1H), 8.10 (d, J=8.5 Hz, 1H), 7.88-7.85 (m, 2H), 7.74-7.71 (m, 1H);

$R_t$=1.33 min (Cond.-D1); 90% homogenity index; LCMS: Anal. Calc. for [M+H]$^+$ C$_{10}$H$_7$FNO$_2$: 192.05. Found: 191.97.

Cap-142

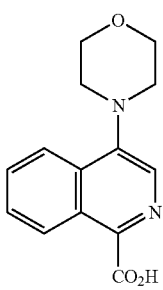 [SMILES: O=C(O)c1ncc(N2CCOCC2)c2ccccc12]

Cap-142, Step a

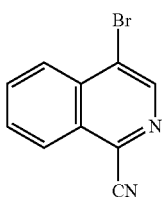

Cap-142, step a was prepared from 4-bromoisoquinoline N-oxide as described in the two-step procedure for the preparation of Cap-138, steps b and c. $R_t$=1.45 min (Cond.-MS-W1); 90% homogenity index; LCMS: Anal. Calc. for [M+H]$^+$ C$_{10}$H$_6$BrN$_2$: 232.97. Found: 233.00.

Cap-142, Step b

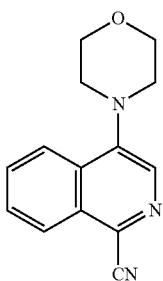

To an argon-degassed suspension of Cap-142, step a (116 mg, 0.50 mmol), potassium phosphate tribasic (170 mg, 0.80 mmol), palladium (II) acetate (3.4 mg, 0.015 mmol) and 2-(dicyclohexylphosphino)biphenyl (11 mg, 0.03 mmol) in anhydrous toluene (1 mL) was added morpholine (61 µL, 0.70 mmol). The mixture was heated at 100° C. for 16 h, cooled to 25° C. and filtered through diatomaceous earth (CELITE®). Purification of the residue on silica gel, eluting with 10% to 70% ethyl acetate/hexanes afforded Cap-142, step b (38 mg, 32%) as a yellow solid, which was carried forward directly.

$R_t$=1.26 min (Cond.-MS-W1); 90% homogenity index; LCMS: Anal. Calc. for [M+H]$^+$ C$_{14}$H$_{14}$N$_3$O: 240.11. Found: 240.13.

Cap-142

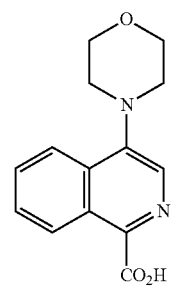

Cap-142 was prepared from Cap-142, step b with 5N sodium hydroxide as described in the procedure for Cap-138. $R_t$=0.72 min (Cond.-MS-W1); 90% homogenity index; LCMS: Anal. Calc. for [M+H]$^+$ C$_{14}$H$_{15}$N$_2$O$_3$: 259.11. Found: 259.08.

Cap-143

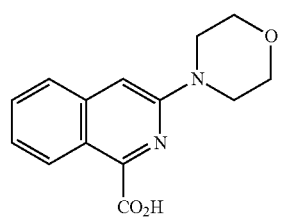

Cap-143, Step a

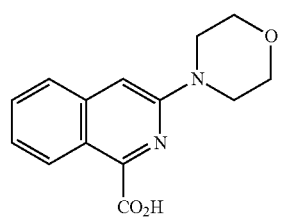

To a stirred solution of 3-amino-1-bromoisoquinoline (444 mg, 2.00 mmol) in anhydrous dimethylformamide (10 mL) was added sodium hydride (60%, unwashed, 96 mg, 2.4 mmol) in one portion. The mixture was stirred at 25° C. for 5 min before 2-bromoethyl ether (90%, 250 µL, 2.00 mmol) was added. The mixture was stirred further at 25° C. for 5 h and at 75° C. for 72 h before it was cooled to 25° C., quenched with saturated ammonium chloride solution and diluted with ethyl acetate. The organic layer was separated, washed with water and brine, dried over Na$_2$SO$_4$, filtered and concentrated. Purification of the residue on silica gel eluting with 0% to 70% ethyl acetate/hexanes afforded Cap-143, step a as a yellow solid (180 mg, 31%). $R_t$=1.75 min (Cond.-MS-W1);

90% homogenity index; LCMS: Anal. Calc. for [M+H]+ $C_{13}H_{14}BrN_2O$: 293.03. Found: 293.04.

Cap-143

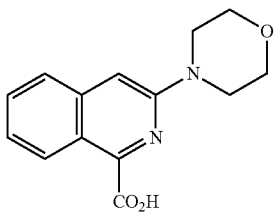 [SMILES: O=C(O)c1nc(N2CCOCC2)cc2ccccc12]

To a cold (−60° C.) solution of Cap-143, step a (154 mg, 0.527 mmol) in anhydrous tetrahydrofuran (5 mL) was added a solution of n-butyllithium in hexanes (2.5 M, 0.25 mL, 0.633 mmol). After 10 min, dry carbon dioxide was bubbled into the reaction mixture for 10 min before it was quenched with 1N HCl and allowed to warm to 25° C. The mixture was then extracted with dichloromethane (3×30 mL) and the combined organic extracts were concentrated in vacuo. Purification of the residue by a reverse phase HPLC (MeOH/water/TFA) afforded Cap-143 (16 mg, 12%). $R_t$=1.10 min (Cond.-MS-W1); 90% homogenity index; LCMS: Anal. Calc. for [M+H]+ $C_{14}H_{15}N_2O_3$: 259.11. Found: 259.08.

Cap-144

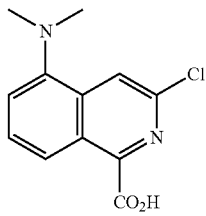 [SMILES: CN(C)c1cccc2c(C(=O)O)nc(Cl)cc12]

Cap-144, Step a

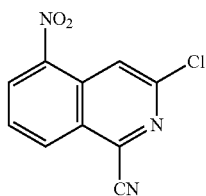 [SMILES: N#Cc1nc(Cl)cc2c([N+](=O)[O-])cccc12]

1,3-Dichloroisoquinoline (2.75 g, 13.89 mmol) was added in small portions to a cold (0° C.) solution of fuming nitric acid (10 mL) and concentrated sulfuric acid (10 mL). The mixture was stirred at 0° C. for 0.5 h before it was gradually warmed to 25° C. where it stirred for 16 h. The mixture was then poured into a beaker containing chopped ice and water and the resulting suspension was stirred for 1 h at 0° C. before it was filtered to afford Cap-144, step a (2.73 g, 81%) as a yellow solid which was used directly. $R_t$=2.01 min. (Cond.-D1); 95% homogenity index; LCMS: Anal. Calc. for [M+H]+ $C_9H_5Cl_2N_2O_2$: 242.97. Found: 242.92.

Cap-144, Step b

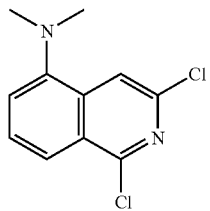

Cap-144, step a (0.30 g, 1.23 mmol) was taken up in methanol (60 mL) and treated with platinum oxide (30 mg), and the suspension was subjected to Parr hydrogenation at 7 psi $H_2$ for 1.5 h. Then formalin (5 mL) and additional platinum oxide (30 mg) were added, and the suspension was resubjected to Parr hydrogenation at 45 psi $H_2$ for 13 h. It was then suction-filtered through diatomaceous earth (CELITE®) and concentrated down to ¼ volume. Suction-filtration of the ensuing precipitate afforded the title compound as a yellow solid which was flash chromatographed on silica gel eluting with 5% ethyl acetate in hexanes to 25% ethyl acetate in hexanes to afford Cap-144, step b (231 mg, 78%) as a pale yellow solid. $R_t$=2.36 min (Cond.-D1); 95% homogenity index; $^1$H NMR (400 MHz, CDCl$_3$) δ 8.02 (s, 1H), 7.95 (d, J=8.6 Hz, 1H), 7.57-7.53 (m, 1H), 7.30 (d, J=7.3 Hz, 1H), 2.88 (s, 6H); LCMS: Anal. Calc. for [M+H]+ $C_{11}H_{11}Cl_2N_2$: 241.03. Found: 241.02. HRMS: Anal. Calc. for [M+H]+ $C_{11}H_{11}Cl_2N_2$: 241.0299. Found: 241.0296.

Cap-144, Step c

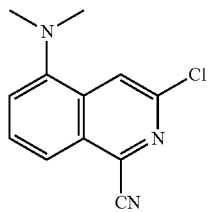 [SMILES: CN(C)c1cccc2c(C#N)nc(Cl)cc12]

Cap-144, step c was prepared from Cap-144, step b according to the procedure described for the preparation of Cap-139, step a. $R_t$=2.19 min (Cond.-D1); 95% homogenity index; LCMS: Anal. Calc. for [M+H]+ $C_{12}H_{11}ClN_3$: 232.06. Found: 232.03. HRMS: Anal. Calc. for [M+H]+ $C_{12}H_{11}ClN_3$: 232.0642. Found: 232.0631.

Cap-144

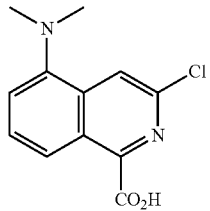

Cap-144 was prepared according to the procedure described for Cap-141. $R_t$=2.36 min (Cond.-D1); 90%; LCMS: Anal. Calc. for [M+H]+ $C_{12}H_{12}ClN_2O_2$: 238.01. Found: 238.09.

Caps-145 to -162

Caps-145 to 162 were prepared from the appropriate 1-chloroisoquinolines according to the procedure described for the preparation of Cap-138 (Method A) or Cap-139 (Method B) unless noted otherwise as outlined below.

| Cap # | Cap | Method | Hydrolysis | $R_t$ (LC-Cond.); % homogeneity index; MS data |
|---|---|---|---|---|
| Cap-145 | 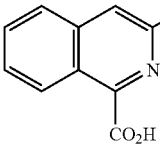<br>Prepared from commercially available 1,3-dichloroisoquinoline | B | 12N HCl | 1.14 min (Cond.-MS-W1); 90%; LCMS: Anal. Calc. for $[M + H]^+$ $C_{10}H_7ClNO_2$: 208.02; found: 208.00. |
| Cap-146 | 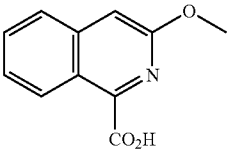<br>Prepared from commercially available 3-hydroxyisoquinoline | A | 5N NaOH | 1.40 min (Cond.-D1); 95%; LCMS: Anal. Calc. for $[M + H]^+$ $C_{11}H_{10}NO_3$: 204.07; found: 204.06. |
| Cap-147 | 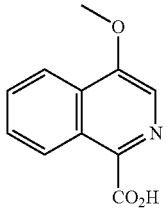<br>Prepared from commercially available 1-chloro-4-hydroxyisoquinoline | B | 5N NaOH | 0.87 min (Cond.-D1); 95%; LCMS: Anal. Calc. for $[M + H]^+$ $C_{11}H_{10}NO_3$: 204.07; found: 204.05. |
| Cap-148 | 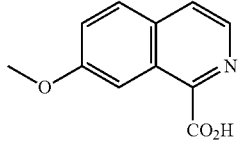<br>Prepared from commercially available 7-hydroxyisoquinoline | A | 5N NaOH | 0.70 min (Cond.-D1); 95%; LCMS: Anal. Calc. for $[M + H]^+$ $C_{11}H_{10}NO_3$: 204.07; found: 204.05. |
| Cap-149 | 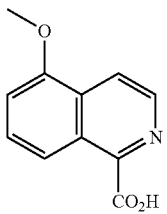<br>Prepared from commercially available 5-hydroxyisoquinoline | A | 5N NaOH | 0.70 min (Cond.-D1); 95%; LCMS: Anal. Calc. for $[M + H]^+$ $C_{11}H_{10}NO_3$: 204.07; found: 204.05. |

| Cap # | Cap | Method | Hydrolysis | $R_t$ (LC-Cond.); % homogeneity index; MS data |
|---|---|---|---|---|
| Cap-150 | 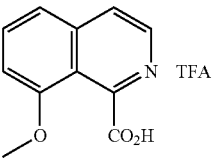<br>Prepared from 8-methoxy-1-chloroisoquinoline, which can be synthesized following the procedure in WO 2003/099274 | A | 12N HCl | 0.26 min (Cond.-D1); 95%; LCMS: Anal. Calc. for [M + H]$^+$ $C_{11}H_{10}NO_3$: 204.07; found: 204.04. |
| Cap-151 3-chloro-5-methoxy-isoquino-line-1-carboxylic acid | 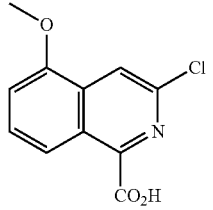 [SMILES: COc1cccc2c(C(=O)O)nc(Cl)cc12]<br>Prepared from 5-methoxy-1,3-dichloroisoquinoline, which can be synthesized following the procedure in WO 2005/051410. | B | 12N HCl | 1.78 min (Cond.-D1); 90%; LCMS: Anal. Calc. for [M + H]$^+$ $C_{11}H_9ClNO_3$: 238.03; found: 238.09. |
| Cap-152 | 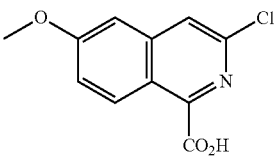 [SMILES: COc1ccc2c(C(=O)O)nc(Cl)cc2c1]<br>Prepared from commercially available 6-methoxy-1,3-dichloroisoquinoline | B | 12N HCl | 1.65 min (Cond.-D1); 95%; LCMS: Anal. Calc. for [M + H]$^+$ $C_{11}H_9ClNO_3$: 238.00; found: 238.09. |
| Cap-153 | 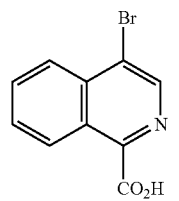 [SMILES: O=C(O)c1ncc(Br)c2ccccc12]<br>Prepared from 4-bromoisoquinoline, which can be synthesized following the procedure in WO 2003/062241 | A | 6N HCl | 1.18 min (Cond.-MS-W1); 95%; LCMS: Anal. Calc. for [M + H]$^+$ $C_{10}H_7BrNO_2$: 251.97; found: 251.95. |

| Cap # | Cap | Method | Hydrolysis | $R_t$ (LC-Cond.); % homogeneity index; MS data |
|---|---|---|---|---|
| Cap-154 | 7-fluoroisoquinoline-1-carboxylic acid<br><br>Prepared from 7-fluoro-1-chloroisoquinoline, which can be synthesized following the procedure in WO 2003/099274 | B | 5N NaOH | 0.28 min (Cond.-MS-W1); 90%; LCMS: Anal. Calc. for [M + H]$^+$ $C_{10}H_7FNO_2$: 192.05; found: 192.03. |
| Cap-155 | 7-chloroisoquinoline-1-carboxylic acid<br><br>Prepared from 1,7-dichloroisoquinoline, which can be synthesized following the procedure in WO 2003/099274 | B | 5N NaOH | 0.59 min (Cond.-MS-W1); 90%; LCMS: Anal. Calc. for [M + H]$^+$ $C_{10}H_7ClNO_2$: 208.02; found: 208.00. |
| Cap-156 | 6-chloroisoquinoline-1-carboxylic acid<br><br>Prepared from 1,6-dichloroisoquinoline, which can be synthesized following the procedure in WO 2003/099274 | B | 5N NaOH | 0.60 min (Cond.-MS-W1); 90%; LCMS: Anal. Calc. for [M + H]$^+$ $C_{10}H_7ClNO_2$: 208.02; found: 208.03. |
| Cap-157 | 4-chloroisoquinoline-1-carboxylic acid<br><br>Prepared from 1,4-dichloroisoquinoline, which can be synthesized following the procedure in WO 2003/062241 | B | 12N HCl | 1.49 min (Cond.-D1); 95%; LCMS: Anal. Calc. for [M + H]$^+$ $C_{10}H_{17}ClNO$: 208.02; found: 208.00. |

| Cap # | Cap | Method | Hydrolysis | $R_t$ (LC-Cond.); % homogeneity index; MS data |
|---|---|---|---|---|
| Cap-158 | 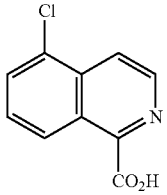 [SMILES: O=C(O)c1nccc2c(Cl)cccc12]<br>Prepared from 1,5-dichloroisoquinoline, which can be synthesized following the procedure in WO 2003/099274 | B | 5N NaOH | 0.69 min (Cond.-MS-W1); 90%; LCMS: Anal. Calc. for $[M+H]^+$ $C_{10}H_7ClNO_2$: 208.02; found: 208.01. |
| Cap-159 | 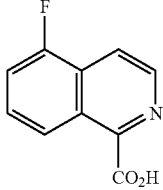<br>Prepared from 5-fluoro-1-chloroisoquinoline, which can be synthesized following the procedure in WO 2003/099274 | B | 5N NaOH | 0.41 min (Cond.-MS-W1); 90%; LCMS: Anal. Calc. for $[M+H]^+$ $C_{10}H_7FNO_2$: 192.05; found: 192.03. |
| Cap-160 | 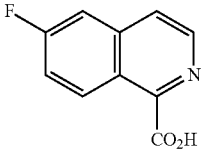<br>Prepared from 6-fluoro-1-chloroisoquinoline, which can be synthesized following the procedure in WO 2003/099274 | B | 5N NaOH | 0.30 min (Cond.-MS-W1); 90%; LCMS: Anal. Calc. for $[M+H]^+$ $C_{10}H_7FNO_2$: 192.05; found: 192.03. |
| Cap-161 | 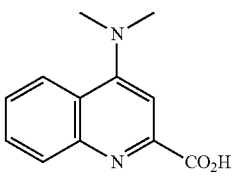 [SMILES: CN(C)c1cc(C(=O)O)nc2ccccc12]<br>Prepared from 4-bromoquinoline-2-carboxylic acid and dimethylamine (DMSO, 100° C.) | — | — | 0.70 min (Cond. D1); 95%; LCMS: Anal. Calc. for $[M+H]^+$ $C_{12}H_{13}N_2O_2$: 217.10; found: 217.06. |

| Cap # | Cap | Method | Hydrolysis | $R_f$ (LC-Cond.); % homogeneity index; MS data |
|---|---|---|---|---|
| Cap-162 | ![structure] Prepared from m-anisidine following the procedure described in J. Hetero. Chem. 1993, 17 and Heterocycles, 2003, 60, 953. | — | — | 0.65 min (Cond.-M3); 95%; LCMS: Anal. Calc. for $[M + H]^+$ $C_{11}H_{10}NO_3$: 204.07; found: 203.94. |

Cap-163

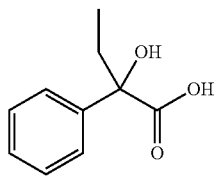

To a solution of 2-ketobutyric acid (1.0 g, 9.8 mmol) in diethylether (25 ml) was added phenylmagnesium bromide (22 ml, 1M in THF) dropwise. The reaction was stirred at ~25° C. under nitrogen for 17.5 h. The reaction was acidified with 1N HCl and the product was extracted with ethyl acetate (3×100 ml). The combined organic layer was washed with water followed by brine and dried over $MgSO_4$. After concentration in vacuo, a white solid was obtained. The solid was recrystallized from hexanes/ethyl acetate to afford Cap-163 as white needles (883.5 mg). $^1H$ NMR (DMSO-$d_6$, δ=2.5 ppm, 500 MHz): 12.71 (br s, 1H), 7.54-7.52 (m, 2H), 7.34-7.31 (m, 2H), 7.26-7.23 (m, 1H), 5.52-5.39 (br s, 1H), 2.11 (m, 1H), 1.88 (m, 1H), 0.79 (app t, J=7.4 Hz, 3H).

Cap-164

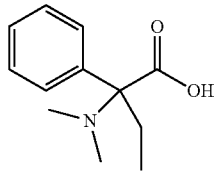

A mixture of 2-amino-2-phenylbutyric acid (1.5 g, 8.4 mmol), formaldehyde (14 mL, 37% in water), 1N HCl (10 mL) and 10% Pd/C (0.5 mg) in MeOH (40 mL) was exposed to $H_2$ at 50 psi in a Parr bottle for 42 h. The reaction was filtered over CELITE® and concentrated in vacuo, the residue was taken up in MeOH (36 mL) and the product was purified with a reverse phase HPLC (MeOH/$H_2O$/TFA) to afford the TFA salt of Cap-164 as a white solid (1.7 g). $^1H$ NMR (DMSO-$d_6$, δ=2.5 ppm, 500 MHz) 7.54-7.47 (m, 5H), 2.63 (m, 1H), 2.55 (s, 6H), 2.31 (m, 1H), 0.95 (app t, J=7.3 Hz, 3H).

Cap-165

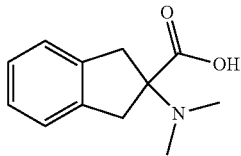

To a mixture of 2-amino-2-indanecarboxylic acid (258.6 mg, 1.46 mmol) and formic acid (0.6 ml, 15.9 mmol) in 1,2-dichloroethane (7 ml) was added formaldehyde (0.6 ml, 37% in water). The mixture was stirred at ~25° C. for 15 min then heated at 70° C. for 8 h. The volatile component was removed in vacuo, and the residue was dissolved in DMF (14 mL) and purified by a reverse phase HPLC (MeOH/$H_2O$/TFA) to afford the TFA salt of Cap-165 as a viscous oil (120.2 mg). $^1H$ NMR (DMSO-$d_6$, δ=2.5 ppm, 500 MHz): 7.29-7.21 (m, 4H), 3.61 (d, J=17.4 Hz, 2H), 3.50 (d, J=17.4 Hz, 2H), 2.75 (s, 6H). LC/MS: Anal. Calcd. for $[M+H]^+$ $C_{12}H_{16}NO_2$: 206.12. Found: 206.07.

Cap-166a and -166b

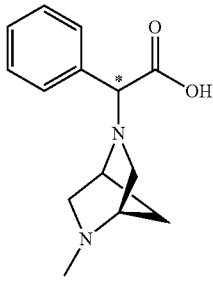

Cap-166a: Diastereomer-1
Cap-166b: Diastereomer-2

Caps-166a and -166b were prepared from (1S,4S)-(+)-2-methyl-2,5-diazabicyclo[2.2.1]heptane (2HBr) according to the method described for the synthesis of Cap-7a and Cap-7b, with the exception that the benzyl ester intermediate was separated using a semi-prep CHIRALCEL® OJ column, 20×250 mm, 10 μm eluting with 85:15 heptane/ethanol mixture at 10 mL/min elution rate for 25 min. Cap-166b: $^1$H NMR (DMSO-d$_6$, δ=2.5 ppm, 500 MHz): 7.45 (d, J=7.3 Hz, 2H), 7.27-7.19 (m, 3H), 4.09 (s, 1H), 3.34 (app br s, 1H), 3.16 (app br s, 1H), 2.83 (d, J=10.1 Hz, 1H), 2.71 (m, 2H), 2.46 (m, 1H), 2.27 (s, 3H), 1.77 (d, J=9.8 Hz, 1H), 1.63 (d, J=9.8 Hz, 1H). LC/MS: Anal. Calcd. for [M+H]$^+$ C$_{14}$H$_{19}$N$_2$O$_2$: 247.14. Found: 247.11.

Cap-167

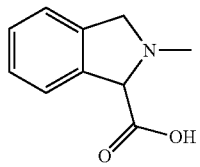

A solution of racemic Boc-1,3-dihydro-2H-isoindole carboxylic acid (1.0 g, 3.8 mmol) in 20% TFA/CH$_2$Cl$_2$ was stirred at ~25° C. for 4 h. All the volatile component was removed in vacuo. A mixture of the resultant crude material, formaldehyde (15 mL, 37% in water), 1N HCl (10 mL) and 10% Pd/C (10 mg) in MeOH was exposed to H$_2$ (40 PSI) in a Parr bottle for 23 h. The reaction mixture was filtered over CELITE® and concentrated in vacuo to afford Cap-167 as a yellow foam (873.5 mg). $^1$H NMR (DMSO-d$_6$, δ=2.5 ppm, 500 MHz) 7.59-7.38 (m, 4H), 5.59 (s, 1H), 4.84 (d, J=14 Hz, 1H), 4.50 (d, J=14.1 Hz, 1H), 3.07 (s, 3H). LC/MS: Anal. Calcd. for [M+H]$^+$ C$_{10}$H$_{12}$NO$_2$: 178.09. Found: 178.65.

Cap-168

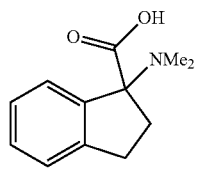 [SMILES: CN(C)C1(C(=O)O)CCc2ccccc21]

Racemic Cap-168 was prepared from racemic Boc-aminoindane-1-carboxylic acid according to the procedure described for the preparation of Cap-167. The crude material was employed as such.

Cap-169

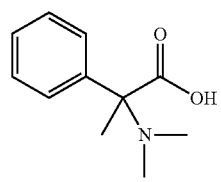

A mixture of 2-amino-2-phenylpropanoic acid hydrochloride (5.0 g, 2.5 mmol), formaldehyde (15 ml, 37% in water), 1N HCl (15 ml), and 10% Pd/C (1.32 g) in MeOH (60 mL) was placed in a Parr bottle and shaken under hydrogen (55 PSI) for 4 days. The reaction mixture was filtered over diatomaceous earth (CELITE®) and concentrated in vacuo. The residue was taken up in MeOH and purified by reverse phase prep-HPLC (MeOH/water/TFA) to afford the TFA salt of Cap-169 as a viscous semi-solid (2.1 g). $^1$H NMR (CDCl$_3$, δ=7.26 ppm, 500 MHz): 7.58-7.52 (m, 2H), 7.39-7.33 (m, 3H), 2.86 (br s, 3H), 2.47 (br s, 3H), 1.93 (s, 3H). LC/MS: Anal. Calcd. for [M+H]$^+$ C$_{11}$H$_{16}$NO$_2$: 194.12. Found: 194.12.

Cap-170

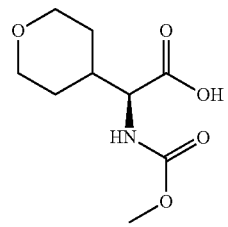

(S)-2-(methoxycarbonylamino)-2-(tetrahydro-2H-pyran-4-yl)acetic acid

To (S)-2-amino-2-(tetrahydro-2H-pyran-4-yl)acetic acid (505 mg; 3.18 mmol; obtained from Astatech) in water (15 ml) was added sodium carbonate (673 mg; 6.35 mmol), and the resultant mixture was cooled to 0° C. and then methyl chloroformate (0.26 ml; 3.33 mmol) was added dropwise over 5 minutes. The reaction was allowed to stir for 18 hours while allowing the bath to thaw to ambient temperature. The reaction mixture was then partitioned between 1N HCl and ethyl acetate. The organic layer was removed and the aqueous layer was further extracted with 2 additional portions of ethyl acetate. The combined organic layers were washed with brine, dried over magnesium sulfate, filtered and concentrated in vacuo to afford Cap-170 a colorless residue. $^1$H NMR (500 MHz, DMSO-d$_6$) δ ppm 12.65 (1H, br s), 7.44 (1H, d, J=8.24 Hz), 3.77-3.95 (3H, m), 3.54 (3H, s), 3.11-3.26 (2H, m), 1.82-1.95 (1H, m), 1.41-1.55 (2H, m), 1.21-1.39 (2H, m); LC/MS: Anal. Calcd. for [M+H]$^+$ C$_9$H$_{16}$NO$_5$: 218.1. Found 218.1.

Cap-171

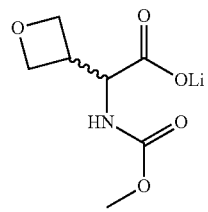

A solution of methyl 2-(benzyloxycarbonylamino)-2-(oxetan-3-ylidene)acetate (200 mg, 0.721 mmol; Il Farmaco (2001), 56, 609-613) in ethyl acetate (7 ml) and CH$_2$Cl$_2$ (4.00 ml) was degassed by bubbling nitrogen for 10 min. Dimethyl dicarbonate (0.116 ml, 1.082 mmol) and Pd/C (20 mg, 0.019 mmol) were then added, the reaction mixture was fitted with a hydrogen balloon and allowed to stir at ambient temperature overnight at which time TLC (95:5 CH$_2$Cl$_2$/MeOH: visualized with stain made from 1 g Ce(NH$_4$)$_2$SO$_4$, 6 g ammonium molybdate, 6 ml sulfuric acid, and 100 ml water) indicated complete conversion. The reaction was filtered through CELITE® and concentrated. The residue was purified via BIOTAGE® (load with dichloromethane on 25 samplet; elute on 25S column with dichloromethane for 3CV then 0 to 5% MeOH/dichloromethane over 250 ml then hold at 5% MeOH/dichloromethane for 250 ml; 9 ml fractions). Collected fractions containing desired material and concentrated to 120 mg (81%) of methyl 2-(methoxycarbonylamino)-2-(oxetan-3-yl) acetate as a colorless oil. $^1$H NMR (500 MHz, chloroform-d) δ ppm 3.29-3.40 (m, J=6.71 Hz, 1H) 3.70 (s, 3H) 3.74 (s, 3H) 4.55 (t, J=6.41 Hz, 1H) 4.58-4.68 (m, 2H) 4.67-4.78 (m, 2H) 5.31 (br s, 1H). LC/MS: Anal. Calcd. for [M+H]$^+$ C$_8$H$_{14}$NO$_5$: 204.2. Found 204.0.

To methyl 2-(methoxycarbonylamino)-2-(oxetan-3-yl)acetate (50 mg, 0.246 mmol) in THF (2 mL) and water (0.5 mL) was added lithium hydroxide monohydrate (10.33 mg, 0.246 mmol). The resultant solution was allowed to stir overnight at ambient temperature. TLC (1:1 EA/Hex; Hanessian stain [1 g Ce(NH$_4$)$_2$SO$_4$, 6 g ammonium molybdate, 6 ml sulfuric acid, and 100 ml water]) indicated ~10% starting material remaining. Added an additional 3 mg LiOH and allowed to stir overnight at which time TLC showed no starting material remaining. Concentrated in vacuo and placed on high vac overnight providing 55 mg lithium 2-(methoxycarbonylamino)-2-(oxetan-3-yl)acetate as a colorless solid. $^1$H NMR (500 MHz, MeOD) δ ppm 3.39-3.47 (m, 1H) 3.67 (s, 3H) 4.28 (d, J=7.93 Hz, 1H) 4.64 (t, J=6.26 Hz, 1H) 4.68 (t, J=7.02 Hz, 1H) 4.73 (d, J=7.63 Hz, 2H).

Cap-172

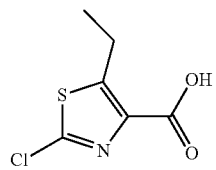

Cap-172, Step a

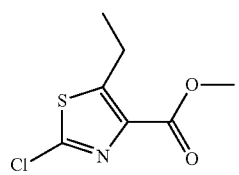

The following diazotization step was adapted from Barton, A. et al., *J. C. S. Perkin Trans 1* 1982, 159-164: A solution of NaNO$_2$ (166 mg, 2.4 mmol) in water (0.6 mL) was added slowly to a stirred, cold (0° C.) solution of methyl 2-amino-5-ethyl-1,3-thiazole-4-carboxylate (186 mg, 1.0 mmol), CuSO$_4$.5H$_2$O (330 mg, 1.32 mmol), NaCl (260 mg, 4.45 mmol) and H$_2$SO$_4$ (5.5 mL) in water (7.5 mL). The mixture was stirred at 0° C. for 45 min and allowed to warm up to room temperature where it stirred further for 1 h before CuCl (118 mg) was added. This mixture was stirred further at room temperature for 16 h before it was diluted with brine and extracted with ether twice. The organic layers were combined, dried over MgSO$_4$ and concentrated to give methyl 2-chloro-5-ethylthiazole-4-carboxylate (i.e., Cap-172, step a) (175 mg, 85%) as an orange oil (80% pure) which was used directly in the next reaction. R$_f$=1.99 min (Cond.-MD1); LC/MS: Anal. Calcd. for [M+H]$^+$ C$_7$H$_9$ClNO$_2$S: 206.01. Found: 206.05.

Cap-172

To a solution of methyl 2-chloro-5-ethylthiazole-4-carboxylate (175 mg) in THF/H$_2$O/MeOH (20 mL/3 mL/12 mL) was added LiOH (305 mg, 12.76 mmol). The mixture was stirred at room temperature overnight before it was concentrated down and neutralized with 1N HCl in ether (25 mL). The residue was extracted twice with ethyl acetate and the organic layers were combined, dried over MgSO$_4$ and evaporated to yield Cap-172 (60 mg, 74%) as a red solid which was used without further purification. $^1$H NMR (300 MHz, DMSO-d$_6$) δ ppm 13.03-13.42 (1H, m), 3.16 (2H, q, J=7.4 Hz), 1.23 (3H, t, J=7.5 Hz). R$_f$=1.78 min (Cond.-MD1);

LC/MS: Anal. Calcd. for [M+H]$^+$ C$_6$H$_7$ClNO$_2$S: 191.99. Found: 191.99.

Cap-173

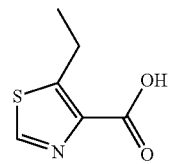

Cap-173, Step a

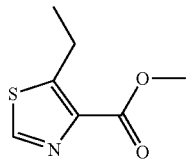

The following diazotization step was adapted from Barton, A. et al., *J. C. S. Perkin Trans I* 1982, 159-164: A solution of NaNO$_2$ (150 mg, 2.17 mmol) in water (1.0 mL) was added dropwise to a stirred, cold (0° C.) solution of methyl 2-amino-5-ethyl-1,3-thiazole-4-carboxylate (186 mg, 1.0 mmol) in 50% H$_3$PO$_2$ (3.2 mL). The mixture was stirred at 0° C. for 1 h and allowed to warm up to room temperature where it stirred further for 2 h. After recooling to 0° C., the mixture was treated slowly with a solution of NaOH (85 mg) in water (10 mL). The mixture was then diluted with saturated NaHCO$_3$ solution and extracted twice with ether. The organic layers were combined, dried over MgSO$_4$ and concentrated to give methyl 5-ethylthiazole-4-carboxylate (i.e., Cap-173, step a) (134 mg, 78%) as an orange oil (85% pure) which was used directly in the next reaction. $R_f$=1.58 min (Cond.-MD1); LC/MS: Anal. Calcd. for $[M+H]^+$ $C_7H_{10}NO_2S$: 172.05. Found: 172.05.

Cap-173

To a solution of methyl 5-ethylthiazole-4-carboxylate (134 mg) in THF/H$_2$O/MeOH (18 mL/2.7 mL/11 mL) was added LiOH (281 mg, 11.74 mmol). The mixture was stirred at room temperature overnight before it was concentrated down and neutralized with 1N HCl in ether (25 mL). The residue was extracted twice with ethyl acetate and the organic layers were combined, dried over MgSO$_4$ and evaporated to yield Cap-173 (90 mg, 73%) as an orange solid which was used without further purification. $^1$H NMR (300 MHz, DMSO-d$_6$) δ ppm 12.74-13.04 (1H, m), 3.20 (2H, q, J=7.3 Hz), 1.25 (3H, t, J=7.5 Hz). $R_f$=1.27 min (Cond.-MD1); LC/MS: Anal. Calcd. for $[M+H]^+$ $C_6H_8NO_2S$: 158.03. Found: 158.04.

Cap-174

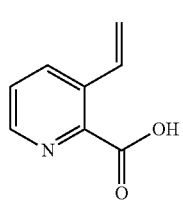

Cap-174, Step a

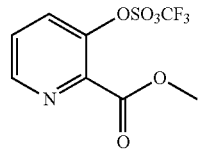

Triflic anhydride (5.0 g, 18.0 mmol) was added dropwise to a cold (0° C.) solution of methyl 3-hydroxypicolinate (2.5 g, 16.3 mmol) and TEA (2.5 mL, 18.0 mmol) in CH$_2$Cl$_2$ (80 mL). The mixture was stirred at 0° C. for 1 h before it was allowed to warm up to room temperature where it stirred for an additional 1 h. The mixture was then quenched with saturated NaHCO$_3$ solution (40 mL) and the organic layer was separated, washed with brine, dried over MgSO$_4$ and concentrated to give methyl 3-(trifluoromethylsulfonyloxy)picolinate (i.e., Cap-174, step a) (3.38 g, 73%) as a dark brown oil (>95% pure) which was used directly without further purification. $^1$H NMR (300 MHz, CDCl$_3$) δ ppm 8.72-8.79 (1H, m), 7.71 (1H, d, J=1.5 Hz), 7.58-7.65 (1H, m), 4.04 (3H, s). $R_f$=1.93 min (Cond.-MD1); LC/MS: Anal. Calcd. for $[M+H]^+$ $C_8H_2F_3NO_5S$: 286.00. Found: 286.08.

Cap-174

To a solution of methyl 3-(trifluoromethylsulfonyloxy)picolinate (570 mg, 2.0 mmol) in DMF (20 mL) was added LiCl (254 mg, 6.0 mmol), tributyl(vinyl)stannane (761 mg, 2.4 mmol) and bis(triphenylphosphine)palladium dichloride (42 mg, 0.06 mmol). The mixture was heated at 100° C. overnight before a saturated solution of KF (20 mL) was added to the reaction mixture at room temperature. This mixture was stirred for 4 h before it was filtered through diatomaceous earth (CELITE®) and the pad was washed with ethyl acetate. The aqueous phase of the filtrate was then separated and concentrated down in vacuo. The residue was treated with 4N HCl in dioxanes (5 mL) and the resulting mixture was extracted with methanol, filtered and evaporated to afford Cap-174 (260 mg) as a green solid which was slightly contaminated with inorganic salts but was used without further purification. $^1$H NMR (300 MHz, DMSO-d$_6$) δ ppm 8.21 (1H, d, J=3.7 Hz), 7.81-7.90 (1H, m), 7.09 (1H, dd, J=7.7, 4.8 Hz), 6.98 (1H, dd, J=17.9, 11.3 Hz), 5.74 (1H, dd, J=17.9, 1.5 Hz), 5.20 (1H, d, J=11.0 Hz). $R_f$=0.39 min (Cond.-MD1); LC/MS: Anal. Calcd. for $[M+H]^+$ $C_8H_8NO_2$: 150.06. Found: 150.07.

Cap-175

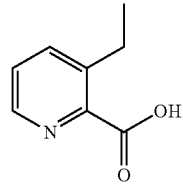

Cap-175, Step a

To a solution of methyl 3-(trifluoromethylsulfonyloxy)picolinate (i.e., Cap-174, step a) (570 mg, 2.0 mmol), an intermediate in the preparation of Cap-174, in DMF (20 mL) was added LiCl (254 mg, 6.0 mmol), tributyl(vinyl)stannane (761 mg, 2.4 mmol) and bis(triphenylphosphine)palladium dichloride (42 mg, 0.06 mmol). The mixture was heated at 100° C. for 4 h before the solvent was removed in vacuo. The residue was taken up in acetonitrile (50 mL) and hexanes (50 mL) and the resulting mixture was washed twice with hexanes. The acetonitrile layer was then separated, filtered through CELITE®, and evaporated. Purification of the residue by flash chromatography on a Horizon instrument (gradient elution with 25% ethyl acetate in hexanes to 65% ethyl acetate in hexanes) afforded methyl 3-vinylpicolinate (i.e., Cap-175, step a) (130 mg, 40%) as a yellow oil. $^1$H NMR (300 MHz, CDCl$_3$) δ ppm 8.60 (1H, dd, J=4.6, 1.7 Hz), 7.94 (1H, d, J=7.7 Hz), 7.33-7.51 (2H, m), 5.72 (1H, d, J=17.2 Hz), 5.47 (1H, d, J=11.0 Hz), 3.99 (3H, s). $R_f$=1.29 min (Cond.-MD1); LC/MS: Anal. Calcd. for $[M+H]^+$ $C_9H_{10}NO_2$: 164.07. Found: 164.06.

Cap-175, Step b

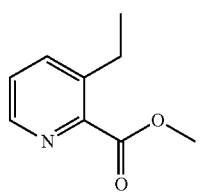

Palladium on carbon (10%, 25 mg) was added to a solution of methyl 3-vinylpicolinate (120 mg, 0.74 mmol) in ethanol (10 mL). The suspension was stirred at room temperature under an atmosphere of hydrogen for 1 h before it was filtered through CELITE® and the pad of CELITE® was washed with methanol. The filtrate was concentrated down to dryness to yield methyl 3-ethylpicolinate (i.e., Cap-175, step b) which was taken directly into the next reaction. $R_f$=1.15 min (Cond.-MD1); LC/MS: Anal. Calcd. for $[M+H]^+ C_9H_{12}NO_2$: 166.09. Found: 166.09.

Cap-175

To a solution of methyl 3-ethylpicolinate in THF/H$_2$O/MeOH (5 mL/0.75 mL/3 mL) was added LiOH (35 mg, 1.47 mmol). The mixture was stirred at room temperature for 2 d before additional LiOH (80 mg) was added. After an additional 24 h at room temperature, the mixture was filtered and the solvent was removed in vacuo. The residue was then treated with 4N HCl in dioxanes (5 mL) and the resulting suspension was concentrated down to dryness to yield Cap-175 as a yellow solid which was used without further purification. $^1$H NMR (300 MHz, DMSO-d$_6$) δ ppm 8.47 (1H, dd, J=4.8, 1.5 Hz), 7.82-7.89 (1H, m), 7.53 (1H, dd, J=7.7, 4.8 Hz), 2.82 (2H, q, J=7.3 Hz), 1.17 (3H, t, J=7.5 Hz). $R_f$=0.36 min (Cond.-MD1); LC/MS: Anal. Calcd. for $[M+H]^+ C_8H_{10}NO_2$: 152.07. Found: 152.10.

Cap-176

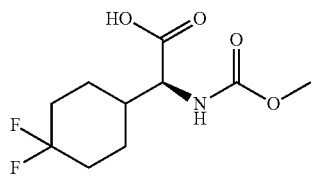 [SMILES: COC(=O)N[C@H](C(=O)O)C1CCC(F)(F)CC1]

(S)-2-(4,4-difluorocyclohexyl)-2-(methoxycarbonylamino)acetic acid

Cap-176, Step a

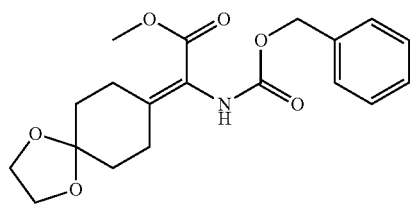 [SMILES: COC(=O)C(NC(=O)OCc1ccccc1)=C1CCC2(CC1)OCCO2]

A solution of 1,4-dioxaspiro[4.5]decan-8-one (15 g, 96 mmol) in EtOAc (150 mL) was added to a solution of methyl 2-(benzyloxycarbonylamino)-2-(dimethoxyphosphoryl)acetate (21.21 g, 64.0 mmol) in 1,1,3,3-tetramethylguanidine (10.45 mL, 83 mmol) and EtOAc (150 mL). The resulting solution was the stirred at ambient temperature for 72 h and then it was diluted with EtOAc (25 mL). The organic layer was washed with 1N HCl (75 mL), H$_2$O (100 mL) and brine (100 mL), dried (MgSO$_4$), filtered and concentrated. The residue was purified via BIOTAGE® (5% to 25% EtOAc/Hexanes; 300 g column). The combined fractions containing the product were then concentrated under vacuum and the residue was re-crystallized from hexanes/EtOAc to give white crystals that corresponded to methyl 2-(benzyloxycarbonylamino)-2-(1,4-dioxaspiro[4.5]decan-8-ylidene)acetate (6.2 g) $^1$H NMR (400 MHz, CDCl$_3$-d) δ ppm 7.30-7.44 (5H, m), 6.02 (1H, br. s.), 5.15 (2H, s), 3.97 (4H, s), 3.76 (3H, br. s.), 2.84-2.92 (2H, m), 2.47 (2H, t, J=6.40 Hz), 1.74-1.83 (4H, m). LC (Cond. OL1): $R_f$=2.89 min. LC/MS: Anal. Calcd. For $[M+Na]^+ C_{19}H_{23}NNaO_6$: 745.21. Found: 745.47.

Cap-176, Step b

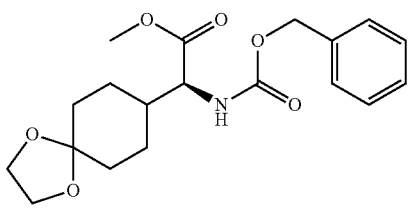 [SMILES: COC(=O)[C@@H](NC(=O)OCc1ccccc1)C1CCC2(CC1)OCCO2]

Ester Cap-176, step b was prepared from alkene Cap-176, step a according to the method of Burk, M. J.; Gross, M. F. and Martinez J. P. (*J. Am. Chem. Soc.*, 1995, 117, 9375-9376 and references therein): A 500 mL high-pressure bottle was charged with alkene Cap-176, step a (3.5 g, 9.68 mmol) in degassed MeOH (200 mL) under a blanket of N$_2$. The solution was then charged with (−)-1,2-Bis((2S,5S)-2,5-dimethylphospholano)ethane(cyclooctadiene)rhodium (I) tetrafluoroborate (0.108 g, 0.194 mmol) and the resulting mixture was flushed with N$_2$ (3×) and charged with H$_2$ (3×). The solution was shaken vigorously under 70 psi of H$_2$ at ambient temperature for 72 h. The solvent was removed under reduced pressure and the remaining residue was taken up in EtOAc. The brownish solution was then filtered through a plug of Silica Gel and eluted with EtOAc. The solvent was concentrated under vacuum to afford a clear oil corresponding to ester Cap-176, step b (3.4 g). $^1$H NMR (500 MHz, CDCl$_3$-d) δ ppm 7.28-7.43 (5H, m), 5.32 (1H, d, J=9.16 Hz), 5.06-5.16 (2H, m), 4.37 (1H, dd, J=9.00, 5.04 Hz), 3.92 (4H, t, J=3.05 Hz), 3.75 (3H, s), 1.64-1.92 (4H, m), 1.37-1.60 (5H, m). LC (Cond. OL1): $R_f$=1.95 min. LC/MS: Anal. Calcd. For $[M+H]^+ C_{19}H_{26}NO_6$: 364.18. Found: 364.27.

Cap-176, Step c

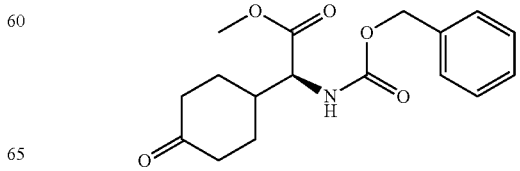

Ester Cap-176, step b (4.78 g, 13.15 mmol) was dissolved in THF (15 mL) followed by sequential addition of water (10 mL), glacial acetic acid (26.4 mL, 460 mmol) and dichloroacetic acid (5.44 mL, 65.8 mmol). The resulting mixture was stirred for 72 h at ambient temperature, and the reaction was quenched by slow addition of solid $Na_2CO_3$ with vigorous stirring until the release of gas was no longer visible. Crude product was extracted into 10% ethyl acetate-dichloromethane and the organic layers were combined, dried ($MgSO_4$) filtered and concentrated. The resulting residue was purified via BIOTAGE® (0 to 30% EtOAc/Hex; 25 g column) to afford ketone Cap-176, step c (3.86 g) as a clear oil. $^1$H NMR (400 MHz, $CDCl_3$-d) δ ppm 7.28-7.41 (5H, m), 5.55 (1H, d, J=8.28 Hz), 5.09 (2H, s), 4.46 (1H, dd, J=8.16, 5.14 Hz), 3.74 (3H, s), 2.18-2.46 (5H, m), 1.96-2.06 (1H, m), 1.90 (1H, ddd, J=12.99, 5.96, 2.89 Hz), 1.44-1.68 (2H, m, J=12.36, 12.36, 12.36, 12.36, 4.77 Hz). LC (Cond. OL1): $R_t$=1.66 min. LC/MS: Anal. Calcd. For [M+Na]$^+$ $C_{17}H_{21}NNaO_5$: 342.13. Found: 342.10.

Cap-176, Step d

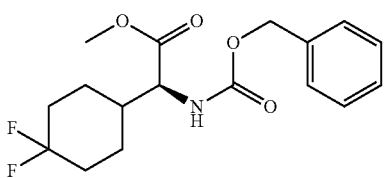 [SMILES: COC(=O)[C@@H](NC(=O)OCc1ccccc1)C1CCC(F)(F)CC1]

DEOXO-FLUOR® (3.13 mL, 16.97 mmol) was added to a solution of ketone Cap-176, step c (2.71 g, 8.49 mmol) in $CH_2Cl_2$ (50 mL) followed by addition of a catalytic amount of EtOH (0.149 mL, 2.55 mmol). The resulting yellowish solution was stirred at rt overnight. The reaction was quenched by addition of sat. aq. $NaHCO_3$ (25 mL) and the mixture was extracted with EtOAc (3×75 mL)). The combined organic layers were dried ($MgSO_4$), filtered and dried to give a yellowish oil. The residue was purified via BIOTAGE® chromatography (2% to 15% EtOAc/Hex; 90 g column) and a white solid corresponding to the difluoro amino acid difluoride Cap-176, step d (1.5 g) was recovered. $^1$H NMR (400 MHz, $CDCl_3$-d) δ ppm 7.29-7.46 (5H, m), 5.34 (1H, d, J=8.28 Hz), 5.12 (2H, s), 4.41 (1H, dd, J=8.66, 4.89 Hz), 3.77 (3H, s), 2.06-2.20 (2H, m), 1.83-1.98 (1H, m), 1.60-1.81 (4H, m), 1.38-1.55 (2H, m). $^{19}$F NMR (376 MHz, $CDCl_3$-d) δ ppm −92.15 (1F, d, J=237.55 Hz), −102.44 (1F, d, J=235.82 Hz). LC (Cond. OL1): $R_t$=1.66 min. LC/MS: Anal. Calcd. For [2M+Na]$^+$ $C_{34}H_{42}F_4N_2NaO_8$: 705.28. Found: 705.18.

Cap-176, Step e

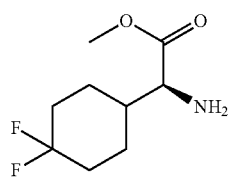

Difluoride Cap-176, step d (4 g, 11.72 mmol) was dissolved in MeOH (120 mL) and charged with Pd/C (1.247 g, 1.172 mmol). The suspension was flushed with $N_2$ (3×) and the reaction mixture was placed under 1 atm of $H_2$ (balloon). The mixture was stirred at ambient temperature for 48 h. The suspension was then filtered though a plug of CELITE® and concentrated under vacuum to give an oil that corresponded to amino acid Cap-176, step e (2.04 g) and that was used without further purification. $^1$H NMR (400 MHz, DMSO-$d_6$) δ ppm 3.62 (3H, s), 3.20 (1H, d, J=5.77 Hz), 1.91-2.09 (2H, m), 1.50-1.88 (7H, m), 1.20-1.45 (2H, m). $^{19}$F NMR (376 MHz, DMSO-$d_6$) δ ppm −89.39 (1F, d, J=232.35 Hz), −100.07 (1F, d, J=232.35 Hz). $^{13}$C NMR (101 MHz, DMSO-$d_6$) δ ppm 175.51 (1C, s), 124.10 (1C, t, J=241.21, 238.90 Hz), 57.74 (1C, s), 51.39 (1C, s), 39.23 (1C, br. s.), 32.02-33.83 (2C, m), 25.36 (1C, d, J=10.02 Hz), 23.74 (1C, d, J=9.25 Hz). LC (Cond. OL2): $R_t$=0.95 min.

LC/MS: Anal. Calcd. For [2M+H]$^+$ $C_{18}H_{31}F_4N_2O_2$: 415.22. Found: 415.40.

Cap-176, Step f

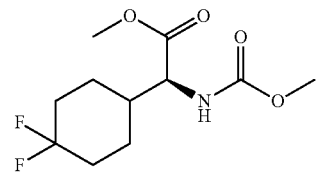 [SMILES: COC(=O)N[C@H](C(=O)OC)C1CCC(F)(F)CC1]

Methyl chloroformate (1.495 mL, 19.30 mmol) was added to a solution of amino acid Cap-176, step e (2 g, 9.65 mmol) and DIEA (6.74 mL, 38.6 mmol) in $CH_2Cl_2$ (100 mL). The resulting solution was stirred at rt for 3 h and volatiles were removed under reduced pressure. The residue was purified via BIOTAGE® (0% to 20% EtOAc/Hex; 90 g column). A clear oil that solidified upon standing under vacuum and corresponding to carbamate Cap-176, step f (2.22 g) was recovered. $^1$H NMR (500 MHz, $CDCl_3$-d) δ ppm 5.27 (1H, d, J=8.55 Hz), 4.39 (1H, dd, J=8.85, 4.88 Hz), 3.77 (3H, s), 3.70 (3H, s), 2.07-2.20 (2H, m), 1.84-1.96 (1H, m), 1.64-1.82 (4H, m), 1.39-1.51 (2H, m). $^{19}$F NMR (471 MHz, $CDCl_3$-d) δ ppm −92.55 (1F, d, J=237.13 Hz), −102.93 (1F, d, J=237.12 Hz). $^{13}$C NMR (126 MHz, $CDCl_3$-d) δ ppm 171.97 (1C, s), 156.69 (1C, s), 119.77-125.59 (1C, m), 57.24 (1C, br. s.), 52.48 (1C, br. s.), 52.43 (1C, s), 39.15 (1C, s), 32.50-33.48 (2C, m), 25.30 (1C, d, J=9.60 Hz), 24.03 (1C, d, J=9.60 Hz). LC (Cond. OL1): $R_t$=1.49 min. LC/MS: Anal. Calcd. For [M+Na]$^+$ $C_{11}H_{17}F_2NNaO_4$: 288.10. Found: 288.03.

Cap-176

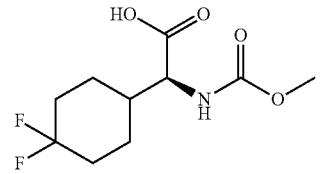 [SMILES: COC(=O)N[C@H](C(=O)O)C1CCC(F)(F)CC1]

(S)-2-(4,4-difluorocyclohexyl)-2-(methoxycarbonylamino)acetic acid

A solution of LiOH (0.379 g, 15.83 mmol) in water (25 mL) was added to a solution of carbamate Cap-176, step f (2.1 g, 7.92 mmol) in THF (75 mL) and the resulting mixture was stirred at ambient temperature for 4 h. THF was removed under vacuum and the remaining aqueous phase was acidified with 1N HCl solution (2 mL) and then extracted with EtOAc (2×50 mL). The combined organic layers were dried (MgSO$_4$), filtered and concentrated to give a white foam corresponding to Cap-176 (1.92 g). $^1$H NMR (400 MHz, DMSO-d$_6$) δ ppm 12.73 (1H, s), 7.50 (1H, d, J=8.78 Hz), 3.97 (1H, dd, J=8.53, 6.02 Hz), 3.54 (3H, s), 1.92-2.08 (2H, m), 1.57-1.90 (5H, m), 1.34-1.48 (1H, m), 1.27 (1H, qd, J=12.72, 3.26 Hz). $^{19}$F NMR (376 MHz, DMSO-d$_6$) δ ppm −89.62 (1F, d, J=232.35 Hz), −99.93 (1F, d, J=232.35 Hz). LC (Cond. OL2): R$_t$=0.76 min. LC/MS: Anal. Calcd. For [M−H]$^+$ C$_{10}$H$_{14}$F$_2$NO$_4$: 250.09. Found: 250.10.

Cap-177a and 177b

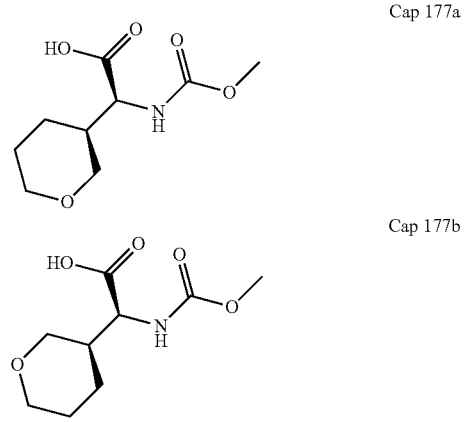

Cap 177a

Cap 177b

Cap-177a and 177b, Step a

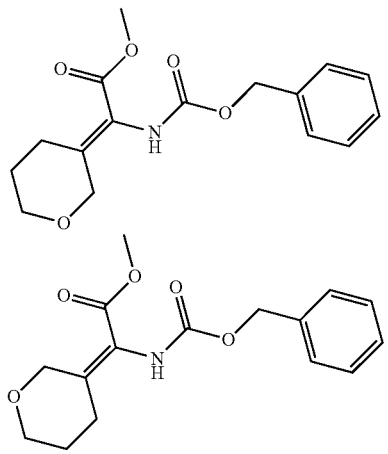

1,1,3,3-Tetramethylguanidine (0.985 mL, 7.85 mmol) was added to a stirred solution of methyl 2-(benzyloxycarbonylamino)-2-(dimethoxyphosphoryl)acetate (2.0 g, 6.0 mmol) in EtOAc (40 mL) and the mixture was stirred at rt under N$_2$ for 10 min. Then dihydro-2H-pyran-3(4H)-one [23462-75-1] (0.604 g, 6.04 mmol) was added and the mixture was stirred at rt for 16 h. The reaction mixture was then cooled in freezer for 10 min and neutralized with aq. citric acid (1.5 g in 20 mL water). The two phases were partitioned and the organic layer was washed with 0.25 N aq. HCl and brine, and then dried (MgSO$_4$) and concentrated to a colorless oil. The crude material was purified by flash silica chromatography (loading solvent: DCM, eluted with EtOAc/Hexanes, gradient from 20% to 30% EtOAc) to yield two isomeric products: The first eluted product was (Z)-methyl 2-(benzyloxycarbonylamino)-2-(2H-pyran-3(4H,5H,6H)-ylidene)acetate (490 mg) (white solid), and the second was (E)-methyl 2-(benzyloxycarbonylamino)-2-(2H-pyran-3(4H,5H,6H)-ylidene)acetate (433 mg) (white solid). LC-MS retention time 1.398 min (for Z-isomer) and 1.378 min (for E-isomer); m/z 304.08 (for Z-isomer) and 304.16 (for E-isomer) (MH−). LC data was recorded on a Shimadzu LC-10AS liquid chromatograph equipped with a PHENOMENEX® Luna 10 u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, chloroform-d) (for Z-isomer) δ ppm 7.30-7.44 (m, 5H), 6.18 (br. s., 1H), 5.10-5.17 (m, 2H), 4.22 (s, 2H), 3.78 (br. s., 3H), 2.93-3.02 (m, 2H), 1.80 (dt, J=11.7, 5.8 Hz, 2H), 1.62 (s, 2H). $^1$H NMR (400 MHz, chloroform-d) (for E-isomer) δ ppm 7.31-7.44 (m, 5H), 6.12 (br. s., 1H), 5.13-5.17 (m, 2H), 4.64 (br. s., 2H), 3.70-3.82 (m, 5H), 2.49 (t, J=6.5 Hz, 2H), 1.80 (br. s., 2H). (Note: the absolute regiochemistry was determined by $^1$H NMR shifts and coupling constants).

Cap-177a and 177b, Step b

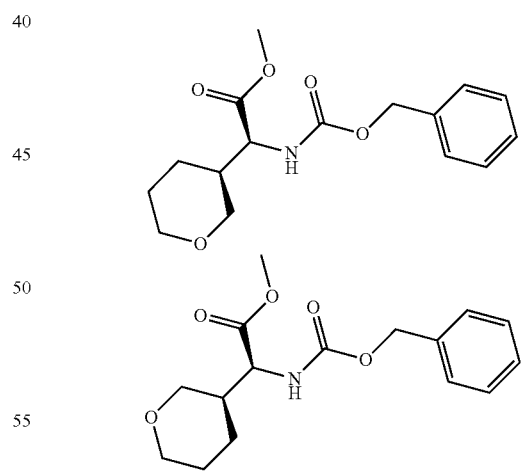

(−)-1,2-Bis((2S,5S)-2,5-dimethylphospholano)ethane(cyclooctadiene)-rhodium(I)tetrafluoroborate (28.2 mg, 0.051 mmol) was added to a stirred solution of (Z)-methyl 2-(benzyloxycarbonylamino)-2-(2H-pyran-3(4H,5H,6H)-ylidene) acetate (310 mg, 1.015 mmol) in MeOH (10 mL) and the mixture was vacuum flushed with N$_2$, followed by H$_2$, and then the reaction was stirred under H$_2$ (60 psi) at rt for 2d. The reaction mixture was concentrated and the residue was purified by flash silica chromatography (loading solvent: DCM, eluted with 20% EtOAc in hexanes) to yield (S)-methyl 2-(benzyloxycarbonylamino)-2-((S)-tetrahydro-2H-pyran-3-yl)acetate (204 mg) as clear colorless oil. LC-MS retention time 1.437 min; m/z 307.89 (MH+). LC data was recorded on a Shimadzu LC-10AS liquid chromatograph equipped with a PHENOMENEX® Luna 10 u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, chloroform-d) δ ppm 7.30-7.46 (m, 5H), 5.32 (d, J=8.8 Hz, 1H), 5.12 (s, 2H), 4.36 (dd, J=8.9, 5.6 Hz, 1H), 3.84-3.98 (m, 2H), 3.77 (s, 3H), 3.28-3.37 (m, 1H), 3.23 (dd, J=11.3, 10.5 Hz, 1H), 2.04-2.16 (m, 1H), 1.61-1.75 (m, 3H), 1.31-1.43 (m, 1H).

The other stereoisomer ((E)-methyl 2-(benzyloxycarbonylamino)-2-(2H-pyran-3(4H,5H,6H)-ylidene)acetate) (360 mg, 1.18 mmol) was reduced in a similar manner to yield (S)-methyl 2-(benzyloxycarbonylamino)-2-((R)-tetrahydro-2H-pyran-3-yl)acetate (214 mg) as clear colorless oil. LC-MS retention time 1.437 min; m/z 308.03 (MH+). LC data was recorded on a Shimadzu LC-10AS liquid chromatograph equipped with a PHENOMENEX® Luna 10 u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, chloroform-d) δ ppm 7.30-7.44 (m, 5H), 5.31 (d, J=9.0 Hz, 1H), 5.12 (s, 2H), 4.31 (dd, J=8.7, 6.9 Hz, 1H), 3.80-3.90 (m, 2H), 3.77 (s, 3H), 3.37 (td, J=10.8, 3.5 Hz, 1H), 3.28 (dd, J=11.3, 9.8 Hz, 1H), 1.97-2.10 (m, 1H), 1.81 (d, J=11.5 Hz, 1H), 1.61-1.72 (m, 2H), 1.33-1.46 (m, 1H).

30% EtOAc in hexanes) to yield product (S)-methyl 2-(methoxycarbonylamino)-2-((S)-tetrahydro-2H-pyran-3-yl)acetate (132 mg) as colorless oil. LC-MS retention time 0.92 min; m/z 231.97 (MH+). LC data was recorded on a Shimadzu LC-10AS liquid chromatograph equipped with a PHENOMENEX® Luna 10 u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, chloroform-d) δ ppm 5.24 (d, J=8.5 Hz, 1H), 4.34 (dd, J=8.9, 5.6 Hz, 1H), 3.84-3.97 (m, 2H), 3.77 (s, 3H), 3.70 (s, 3H), 3.29-3.38 (m, 1H), 3.23 (dd, J=11.2, 10.4 Hz, 1H), 2.03-2.14 (m, 1H), 1.56-1.75 (m, 3H), 1.32-1.43 (m, 1H).

Another diastereomer ((S)-methyl 2-(benzyloxycarbonylamino)-2-((R)-tetrahydro-2H-pyran-3-yl)acetate) was transformed in a similar manner to yield (S)-methyl 2-(methoxycarbonylamino)-2-((R)-tetrahydro-2H-pyran-3-yl)acetate as clear colorless oil. LC-MS retention time 0.99 min; m/z 231.90 (MH+). LC data was recorded on a Shimadzu LC-10AS liquid chromatograph equipped with a PHENOMENEX® Luna 10 u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, chloroform-d) δ ppm 5.25 (d, J=8.0 Hz, 1H), 4.29 (dd, J=8.4, 7.2 Hz, 1H), 3.82-3.90 (m, 2H), 3.77 (s, 3H), 3.70 (s, 3H), 3.37 (td, J=10.8, 3.3 Hz, 1H), 3.28 (t, J=10.5 Hz, 1H), 1.96-2.08 (m, 1H), 1.81 (dd, J=12.9, 1.6 Hz, 1H), 1.56-1.72 (m, 2H), 1.33-1.46 (m, 1H).

Cap-177a and 177b, Step c

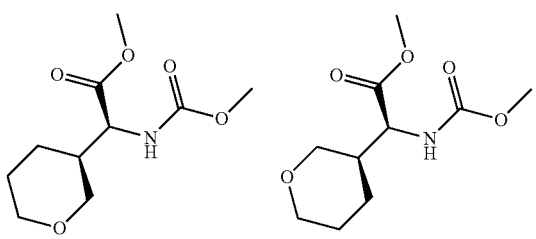 [SMILES: COC(=O)N[C@H](C(=O)OC)[C@@H]1CCCOC1 ; COC(=O)N[C@H](C(=O)OC)[C@H]1CCCOC1]

10% Pd/C (69.3 mg, 0.065 mmol) was added to a solution of (S)-methyl 2-(benzyloxycarbonylamino)-2-((S)-tetrahydro-2H-pyran-3-yl)acetate (200 mg, 0.651 mmol) and dimethyl dicarbonate [4525-33-1] (0.104 mL, 0.976 mmol) in MeOH (10 mL). The reaction mixture was vacuum flushed with N$_2$, followed by H$_2$, and then the reaction was stirred under H$_2$ (55 psi) at rt for 5 h. The reaction mixture was filtered through CELITE®/silica pad and the filtrate was concentrated to a colorless oil. The crude oil was purified by flash silica chromatography (loading solvent: DCM, eluted with Cap-177a and 177b, Step d

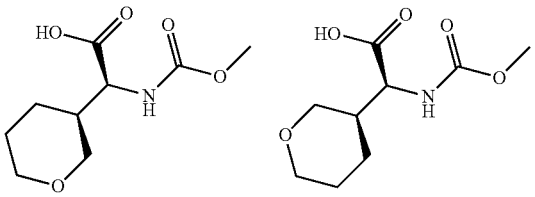

To a solution of (S)-methyl 2-(methoxycarbonylamino)-2-((S)-tetrahydro-2H-pyran-3-yl)acetate (126 mg, 0.545 mmol) in THF (4 mL) stirring at rt was added a solution of 1M LiOH (1.090 mL, 1.090 mmol) in water. The reaction was stirred at rt for 3 h, neutralized with 1M HCl (1.1 mL) and extracted with EtOAc (3×10 mL). The organics were dried, filtered and concentrated to yield (S)-2-(methoxycarbonylamino)-2-((S)-tetrahydro-2H-pyran-3-yl)acetic acid (Cap-177a) (125 mg) as a clear colorless oil. LC-MS retention time 0.44 min; m/z 218.00 (MH+). LC data was recorded on a Shimadzu LC-10AS liquid chromatograph equipped with a PHENOMENEX® Luna 10 u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, chloroform-d) δ ppm 5.28 (d, J=8.8 Hz, 1H), 4.38 (dd, J=8.7, 5.6 Hz, 1H), 3.96-4.04 (m, 1H), 3.91 (d, J=11.0 Hz, 1H), 3.71 (s, 3H), 3.33-3.41 (m, 1H), 3.24-3.32 (m, 1H), 2.10-2.24 (m, 1H), 1.74-1.83 (m, 1H), 1.63-1.71 (m, 2H), 1.35-1.49 (m, 1H).

Another diastereomer ((S)-methyl 2-(methoxycarbonylamino)-2-((R)-tetrahydro-2H-pyran-3-yl)acetate) was transformed in a similar manner to yield (S)-2-(methoxycarbonylamino)-2-((R)-tetrahydro-2H-pyran-3-yl)acetic acid (Cap-177b) as clear colorless oil. LC-MS retention time 0.41 min; m/z 217.93 (MH+). LC data was recorded on a Shimadzu LC-10AS liquid chromatograph equipped with a PHENOMENEX® Luna 10 u C18 3.0×50 mm column using a SPD-10AV UV-Vis detector at a detector wave length of 220 nM. The elution conditions employed a flow rate of 4 mL/min, a gradient of 100% Solvent A/0% Solvent B to 0% Solvent A/100% Solvent B, a gradient time of 3 min, a hold time of 1 min, and an analysis time of 4 min where Solvent A was 5% MeOH/95% H$_2$O/10 mM ammonium acetate and Solvent B was 5% H$_2$O/95% MeOH/10 mM ammonium acetate. MS data was determined using a MICROMASS® Platform for LC in electrospray mode. $^1$H NMR (400 MHz, chloroform-d) δ ppm 6.18 (br. s., 1H), 5.39 (d, J=8.5 Hz, 1H), 4.27-4.37 (m, 1H), 3.82-3.96 (m, 2H), 3.72 (s, 3H), 3.42 (td, J=10.8, 3.3 Hz, 1H), 3.35 (t, J=10.4 Hz, 1H), 2.01-2.18 (m, 1H), 1.90 (d, J=11.8 Hz, 1H), 1.59-1.76 (m, 2H), 1.40-1.54 (m, 1H).

Cap-178

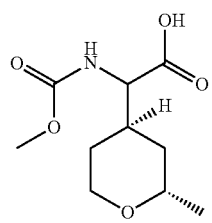 [SMILES: COC(=O)NC(C(=O)O)[C@@H]1CCO[C@@H](C)C1]

Cap-178, Step a

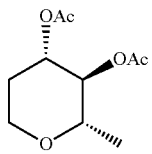

To a solution of (2S,3S,4S)-2-methyl-3,4-dihydro-2H-pyran-3,4-diyl diacetate (5 g, 23.34 mmol) in 20 mL of MeOH in a hydrogenation tank was added Pd/C (150 mg, 0.141 mmol). The resulting mixture was hydrogenated at 40 psi on Parr Shaker for 1 hour. The mixture was then filtered and the filtrate was concentrated to afford Cap-178, step a (5.0 g) as a clear oil, which solidified while standing. $^1$H NMR (500 MHz, CDCl$_3$) δ ppm 4.85-4.94 (1H, m), 4.69 (1H, t, J=9.46 Hz), 3.88-3.94 (1H, m), 3.44 (1H, td, J=12.21, 1.83 Hz), 3.36 (1H, dq, J=9.42, 6.12 Hz), 2.03-2.08 (1H, m), 2.02 (3H, s), 2.00 (3H, s), 1.70-1.80 (1H, m), 1.16 (3H, d, J=6.10 Hz).

Cap-178, Step b

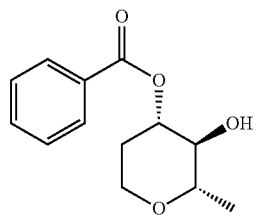 [SMILES: C[C@@H]1OCC[C@H](OC(=O)c2ccccc2)[C@H]1O]

To a solution of Cap-178, step a (5.0 g, 23 mmol) in 50 mL of MeOH was added several drops of sodium methoxide. After stirring at room temperature for 30 min, sodium methoxide (0.1 mL, 23.12 mmol) was added and the solution was stirred at room temperature overnight. The solvent was then removed under vacuum. The residue was diluted with benzene and concentrated to afford the corresponding diol as a yellow solid. The solid was dissolved in 50 mL of pyridine and to this solution at −35° C. was added benzoyl chloride (2.95 mL, 25.4 mmol) dropwise. The resulting mixture was stirred at −35° C. for 1 hour then at room temperature overnight. The mixture was diluted with Et$_2$O and washed with water. The aqueous layer was extracted with EtOAc (2×). The combined organic layers were dried with MgSO$_4$ and concentrated. The crude product was purified by flash chromatography (silica gel, 5%-15% EtOAc/Hex) to afford Cap-178, step b (4.5 g) as clear oil which slowly crystallized upon prolonged standing. LC/MS: Anal. Calcd. for [M+Na]$^+$ C$_{13}$H$_{16}$NaO$_4$ 259.09. Found 259.0. $^1$H NMR (500 MHz, CDCl$_3$) δ ppm 8.02-8.07 (2H, m), 7.55-7.61 (1H, m), 7.45 (2H, t, J=7.78 Hz), 5.01 (1H, ddd, J=11.44, 8.70, 5.49 Hz), 3.98 (1H, ddd, J=11.90, 4.88, 1.53 Hz), 3.54 (1H, td, J=12.36, 2.14 Hz), 3.41 (1H, t, J=9.00 Hz), 3.31-3.38 (1H, m), 2.13-2.19 (1H, m), 1.83-1.94 (1H, m), 1.36 (3H, d, J=5.80 Hz).

Cap-178, step c

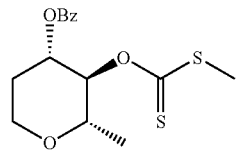

To a mixture of NaH (1.143 g, 28.6 mmol) (60% in mineral oil) in 6 mL of CS2 was added Cap-178, step b (4.5 g, 19 mmol) in 40 mL of CS$_2$ dropwise over 15 min. The resulting mixture was stirred at room temperature for 30 min. The mixture turned light orange with some solid. MeI (14.29 mL, 229 mmol) was then added dropwise over 20 min. The mixture was then stirred at room temperature overnight. The reaction was carefully quenched with saturated NH$_4$Cl solution. The mixture was extracted with EtOAc (3×). The combined organic layers were dried with MgSO$_4$ and concentrated. The crude product was purified by flash chromatography (silica gel, 6% EtOAc/Hex) to afford Cap-178, step c (3.13 g) as clear oil. LC/MS: Anal. Calcd. for [M+Na]$^+$ C$_{15}$H$_{18}$NaO$_4$S$_2$ 349.05. Found 349.11. $^1$H NMR (500 MHz, CDCl$_3$) δ ppm 7.94-8.00 (2H, m), 7.50-7.58 (1H, m), 7.41 (2H, t, J=7.78 Hz), 5.96 (1H, t, J=9.46 Hz), 5.28 (1H, ddd, J=11.37, 9.38, 5.49 Hz), 4.02 (1H, ddd, J=11.98, 4.96, 1.68 Hz), 3.54-3.68 (2H, m), 2.48 (3H, s), 2.31 (1H, dd), 1.88-1.99 (1H, m), 1.28 (3H, d).

Cap-178, Step d

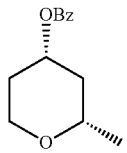

To a mixture of Cap-178, step c (3.13 g, 9.59 mmol) and AIBN (120 mg, 0.731 mmol) in 40 mL of benzene at 80° C. was added tri-n-butyltin hydride (10.24 mL, 38.4 mmol). The resulting mixture was stirred at reflux temperature for 20 min then cooled to room temperature. The mixture was diluted with diethyl ether and 100 mL of KF (10 g) aqueous solution was added and the mixture was stirred vigorously for 30 min. The two layers were then separated and the aqueous phase was extracted with EtOAc (2×). The organic layer was dried with MgSO$_4$ and concentrated. The crude product was purified by flash chromatography (silica gel, deactivated with 3% Et$_3$N in Hexanes and flushed with 3% Et$_3$N in Hexanes to remove tributyltin derivative and then eluted with 15% EtOAc/Hex) to afford Cap-178, step d (1.9 g) as clear oil. $^1$H NMR (500 MHz, CDCl$_3$) δ ppm 7.98-8.07 (2H, m), 7.52-7.58 (1H, m), 7.43 (2H, t, J=7.63 Hz), 5.08-5.17 (1H, m), 4.06 (1H, ddd, J=11.90, 4.88, 1.53 Hz), 3.50-3.59 (2H, m), 2.08-2.14 (1H, m), 1.99-2.06 (1H, m), 1.69-1.80 (1H, m), 1.41-1.49 (1H, m), 1.24 (3H, d, J=6.10 Hz).

Cap-178, Step e

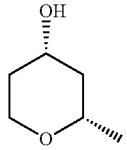

To a mixture of Cap-178, step d (1.9 g, 8.63 mmol) in 10 mL of MeOH was added sodium methoxide (2 mL, 4.00 mmol) (2 M in methanol). The resulting mixture was stirred at room temperature for 5 hours. The solvent was removed under vacuum. The mixture was neutralized with saturated NH$_4$Cl solution and extracted with EtOAc (3×). The organic layers were dried with MgSO$_4$ and concentrated to afford Cap-178, step e (0.8 g) as clear oil. The product was used in the next step without further purification. $^1$H NMR (400 MHz, CDCl$_3$) δ ppm 4.01 (1H, ddd, J=11.80, 5.02, 1.76 Hz), 3.73-3.83 (1H, m), 3.36-3.46 (2H, m), 1.92-2.00 (1H, m), 1.88 (1H, m), 1.43-1.56 (1H, m), 1.23 (3H, d), 1.15-1.29 (1H, m).

Cap-178, Step f

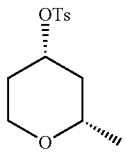

Tosyl-Cl (2.63 g, 13.77 mmol) was added to a solution of Cap-178, step e (0.8 g, 6.89 mmol) and pyridine (2.23 mL, 27.5 mmol) in 100 mL of CH$_2$Cl$_2$. The resulting mixture was stirred at room temperature for 3 days. 10 mL of water was then added into the reaction mixture and the mixture was stirred at room temperature for an hour. The two layers were separated and the organic phase was washed with water and 1 N HCl aq. solution. The organic phase was dried with MgSO$_4$ and concentrated to afford Cap-178, step f (1.75 g) as a light yellow solid. The product was used in the next step without further purification. Anal. Calcd. for [M+H]$^+$ C$_{13}$H$_{19}$O$_4$S 271.10. Found 270.90. $^1$H NMR (500 MHz, CDCl$_3$) δ ppm 7.79 (2H, d, J=8.24 Hz), 7.34 (2H, d, J=7.93 Hz), 4.53-4.62 (1H, m), 3.94 (1H, ddd, J=12.13, 4.96, 1.83 Hz), 3.29-3.41 (2H, m), 2.45 (3H, s), 1.90-1.97 (1H, m), 1.79-1.85 (1H, m), 1.64-1.75 (1H, m), 1.38-1.48 (1H, m), 1.17 (3H, d, J=6.10 Hz).

Cap-178, Step g

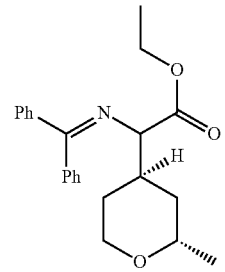 [SMILES: CCOC(=O)C(N=C(c1ccccc1)c1ccccc1)[C@@H]1CCO[C@@H](C)C1]

To a microwave tube was placed ethyl 2-(diphenylmethyleneamino)acetate (1.6 g, 5.92 mmol) and Cap-178, step f (1.6 g, 5.92 mmol). 10 mL of Toluene was added. The tube was sealed and LiHMDS (7.1 mL, 7.10 mmol) (1 N in toluene) was added dropwise under N$_2$. The resulting dark brown solution was heated at 100° C. under microwave radiation for 6 hours. To the mixture was then added water and the mixture was extracted with EtOAc (3×). The combined organic layers were washed with brine, dried with MgSO$_4$ and concentrated to afford a diastereomeric mixture of Cap-3, step g (3.1 g) as an orange oil. The crude mixture was submitted to the next step without separation. LC/MS: Anal. Calcd. for [M+H]$^+$ C$_{23}$H$_{28}$NO$_3$ 366.21. Found 366.3.

Cap-178, Step h

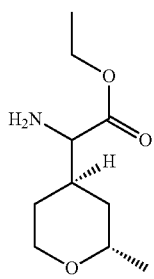

To a solution of the diastereomeric mixture of ethyl Cap-178, step g in 20 mL of THF was added HCl (30 ml, 60.0 mmol) (2 N aqueous). The resulting mixture was stirred at room temperature for 1 hour. The mixture was extracted with EtOAc and the aqueous layer was concentrated to afford an HCl salt of Cap-178, step h (1.9 g) as an orange oil. The salt was used in the next step without further purification. LC/MS: Anal. Calcd. for [M+H]$^+$ C$_{10}$H$_{20}$NO$_3$ 202.14. Found 202.1.

Cap-178, step i

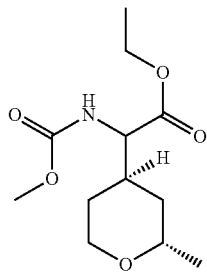 [SMILES: CCOC(=O)C(NC(=O)OC)[C@@H]1CCO[C@@H](C)C1]

A solution of 1.9 g Cap-178, step h (HCl salt), DiPEA (4.19 mL, 24.0 mmol) and methyl chloroformate (1.24 mL, 16.0 mmol) in 20 mL of CH$_2$Cl$_2$ was stirred at room temperature for 1 hour. The mixture was diluted with CH$_2$Cl$_2$ and washed with water. The organic layer was dried with Na$_2$SO$_4$ and concentrated. The crude product was purified by flash chromatography (silica gel, 0-20% EtOAc/Hex) to afford Cap-178, step i (1.1 g) as a yellow oil. Anal. Calcd. for [M+Na]$^+$ C$_{12}$H$_{21}$NNaO$_5$ 282.13. Found 282.14. $^1$H NMR (400 MHz, CDCl$_3$) δ ppm 5.16 (1H, br. s.), 4.43-4.58 (1H, m), 4.17-4.28 (2H, m), 3.89-4.03 (1H, m), 3.72-3.78 (2H, m), 3.67-3.72 (3H, m), 2.07-2.19 (1H, m), 1.35-1.77 (4H, m), 1.30 (3H, td, J=7.09, 2.89 Hz), 1.19 (3H, d, J=6.53 Hz).

Cap-178, Step j

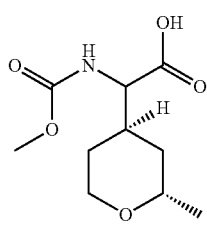 [SMILES: COC(=O)NC(C(=O)O)[C@@H]1CCO[C@@H](C)C1]

To a mixture of Cap-178, step i (1.1 g, 4.2 mmol) in 5 mL of THF and 2 mL of water was added LiOH (6.36 mL, 12.7 mmol) (2 N aq.). The resulting mixture was stirred at room temperature overnight. The mixture was then neutralized with 1 N HCl aq. and extracted with EtOAc (3×). The combined organic layers were dried with MgSO$_4$ and concentrated to afford Cap-178, step j (0.8 g) as a clear oil. LC/MS: Anal. Calcd. for [M+H]$^+$ C$_{10}$H$_{18}$NO$_5$ 232.12. Found 232.1. $^1$H NMR (400 MHz, CDCl$_3$) δ ppm 5.20 (1H, d, J=8.28 Hz), 4.54 (1H, t, J=8.16 Hz), 3.95-4.10 (1H, m), 3.66-3.85 (5H, m), 2.15-2.29 (1H, m), 1.41-1.85 (4H, m), 1.23 (3H, dd, J=6.53, 1.76 Hz).

Cap-178, Step k

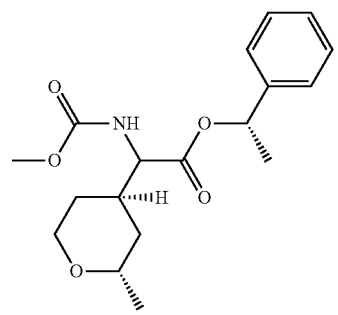 [SMILES: COC(=O)NC(C(=O)O[C@@H](C)c1ccccc1)[C@@H]1CCO[C@@H](C)C1]

To a solution of Cap-178, step j (240 mg, 1.04 mmol), (S)-1-phenylethanol (0.141 mL, 1.142 mmol) and EDC (219 mg, 1.14 mmol) in 10 mL of CH$_2$Cl$_2$ was added DMAP (13.95 mg, 0.114 mmol). The resulting solution was stirred at room temperature overnight and the solvent was removed under vacuum. The residue was taken up into EtOAc, washed with water, dried with MgSO$_4$ and concentrated. The crude product was purified by chromatography (silica gel, 0-15% EtOAc/Hexanes) to afford Cap-178, step k as a mixture of two diastereomers. The mixture was separated by chiral HPLC (CHIRALPAK® AS column, 21×250 mm, 10 um) eluting with 90% 0.1% diethylamine/Heptane-10% EtOH at 15 mL/min to afford Cap-178, step k stereoisomer 1 (eluted first) and Cap-178, step k stereoisomer 2 (eluted second) as white solids. The stereochemistry of the isomers was not assigned. Cap-178, step k stereoisomer 1 (130 mg): LC/MS: Anal. Calcd. for [M+Na]$^+$ C$_{18}$H$_{25}$NNaO$_5$ 358.16. Found 358.16. $^1$H NMR (500 MHz, CDCl$_3$) δ ppm 7.28-7.38 (5H, m), 5.94 (1H, q, J=6.71 Hz), 5.12 (1H, d, J=9.16 Hz), 4.55 (1H, t, J=9.00 Hz), 3.72-3.81 (1H, m), 3.67 (3H, s), 3.60-3.70 (2H, m), 1.98-2.08 (1H, m), 1.59 (3H, d, J=6.71 Hz), 1.38-1.47 (2H, m), 1.30 (2H, t, J=5.34 Hz), 0.93 (3H, d, J=6.41 Hz).

Cap-178, Stereoisomer 1

To a solution of Cap-178, step k stereoisomer 1 ((S)-2-(methoxycarbonylamino)-2-((2S,4R)-2-methyltetrahydro-2H-pyran-4-yl)acetic acid) (150 mg, 0.447 mmol) in 10 mL of EtOH was added Pd/C (20 mg, 0.188 mmol) and the mixture was hydrogenated on Parr shaker at 40 psi overnight. The mixture was then filtered and the filtrate was concentrated to afford Cap-178, stereoisomer 1 (100 mg) as a sticky white solid.

LC/MS: Anal. Calcd. for [M+H]$^+$ C$_{10}$H$_{18}$NO$_5$ 232.12. Found 232.1. $^1$H NMR (500 MHz, CDCl$_3$) δ ppm 5.14-5.27 (1H, m), 4.51 (1H, t, J=8.39 Hz), 3.90-4.07 (1H, m), 3.60-3.83 (5H, m), 2.06-2.27 (1H, m), 1.45-1.77 (4H, m), 1.21 (3H, d, J=6.41 Hz).

Cap-179 (Enantiomer-1&-2)

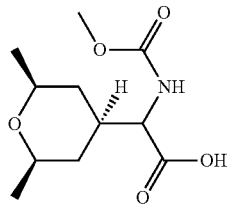 [SMILES: COC(=O)NC(C(=O)O)[C@H]1C[C@@H](C)O[C@@H](C)C1]

Cap-179, Step a

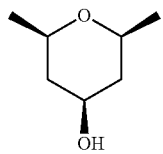

2,6-Dimethyl-4H-pyran-4-one (10 g, 81 mmol) was dissolved in ethanol (125 mL) and Pd/C (1 g, 0.94 mmol) was added. The mixture was hydrogenated in a Parr shaker under $H_2$ (0.325 g, 161 mmol) (70 psi) at room temperature for 12 hrs. The catalyst was filtered through a pad of CELITE® and washed with ethanol. The filtrate was concentrated in vacuum and the residue was purified via BIOTAGE® (2% to 25% EtOAc/Hex; 160 g column) Two fractions of clear oils were isolated. The first eluting one corresponded to (2R,6S)-2,6-dimethyldihydro-2H-pyran-4(3H)-one (1.8 g) while the second one corresponded to Cap-179, step a (1.8 g). (2R,6S)-2,6-Dimethyldihydro-2H-pyran-4(3H)-one data: $^1$H NMR (500 MHz, CDCl$_3$) δ ppm 3.69 (2H, ddd, J=11.29, 5.95, 2.29 Hz), 2.24-2.36 (2H, m), 2.08-2.23 (2H, m), 1.18-1.34 (6H, m); $^{13}$C NMR (126 MHz, CDCl$_3$) δ ppm 206.96 (1C, br. s.), 72.69 (2C, s), 48.70 (2C, s), 21.72 (2C, s). Cap-179, step a data: $^1$H NMR (500 MHz, CDCl$_3$) δ ppm 3.69-3.78 (1H, m), 3.36-3.47 (2H, m), 2.10 (1H, br. s.), 1.88 (2H, dd, J=12.05, 4.73 Hz), 1.19 (6H, d, J=6.10 Hz), 1.10 (2H, q, J=10.70 Hz); $^{13}$C NMR (126 MHz, CDCl$_3$) δ ppm 71.44 (2C, s), 67.92 (1C, s), 42.59 (2C, s), 21.71 (2C, s).

Cap-179, Step b

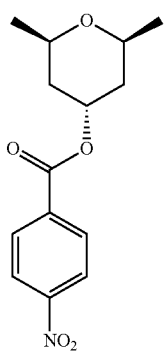 [SMILES: C[C@@H]1C[C@@H](OC(=O)c2ccc([N+](=O)[O-])cc2)C[C@H](C)O1]

DEAD (2.311 mL, 14.59 mmol) was added drop wise to a solution of Cap-179, step a (0.38 g, 2.92 mmol), 4-nitrobenzoic acid (2.195 g, 13.14 mmol) and Ph$_3$P (3.83 g, 14.59 mmol) in benzene (25 mL). Heat evolution was detected and the resulting amber solution was stirred at ambient temperature for 6 h. Solvent was removed under reduced pressure and the residue was purified via BIOTAGE® (0 to 15% EtOAc/Hex; 80 g column). A white solid corresponding to Cap-179, step b (0.77 g) was isolated. LC/MS: Anal. Calcd. for [M]$^+$ C$_{14}$H$_{17}$NO$_5$: 279.11. Found 279.12. $^1$H NMR (500 MHz, CDCl$_3$) δ ppm 8.27-8.32 (2H, m), 8.20-8.24 (2H, m), 5.45 (1H, quin, J=2.82 Hz), 3.92 (2H, dqd, J=11.90, 6.10, 6.10, 6.10, 1.53 Hz), 1.91 (2H, dd, J=14.80, 2.29 Hz), 1.57 (3H, dt, J=14.65, 3.05 Hz), 1.22 (6H, d, J=6.10 Hz).

Cap-179, Step c

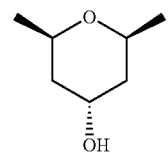

A solution LiOH (0.330 g, 13.8 mmol) in water (8 mL) was added to a solution of Cap-179, step b (0.77 g, 2.76 mmol) in THF (30 mL) and the resulting mixture was stirred at ambient temperature for 16 h. THF was removed under reduced pressure and the aqueous layer was diluted with more water (20 mL) and extracted with EtOAc (3×15 mL). The combined organic layers were dried (MgSO$_4$), filtered and concentrated under vacuum. An oily residue with a white solid was recovered. The mixture was triturated with hexanes and the solid was filtered off to yield a clear oil corresponding to Cap-179, step c (0.34 g). $^1$H NMR (500 MHz, CDCl$_3$) δ ppm 4.21 (1H, quin, J=2.82 Hz), 3.87-3.95 (2H, m), 1.72 (1H, br. s.), 1.63 (2H, dd, J=14.34, 2.14 Hz), 1.39-1.47 (2H, m), 1.17 (6H, d, J=6.41 Hz).

Cap-179, Step d

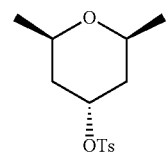

p-Tosyl chloride (3.98 g, 20.89 mmol) was added to a solution of Cap-179, step c (1.36 g, 10.5 mmol) and Pyridine (3.38 mL, 41.8 mmol) in CH$_2$Cl$_2$ (150 mL) at room temperature and stirred for 24 h and then concentrated to a yellow oil. The remaining residue was added to pyridine (20 mL) and water (30 mL) and the resulting mixture was stirred at ambient temperature for 1½ h. The mixture was extracted with Et$_2$O (75 mL) and the separated organic layer was the washed thoroughly with 1 N aq. HCl (4×50 mL). The organic layer was then dried (MgSO$_4$), filtered and concentrated. A white solid corresponding to Cap-179, step d (2.2 g) was isolated. LC/MS: Anal. Calcd. for [2M+H]$^+$ C$_{28}$H$_{41}$O$_8$S$_2$: 569.22. Found 569.3. $^1$H NMR (400 MHz, CDCl$_3$) δ ppm 7.80 (2H, d, J=8.28 Hz), 7.35 (2H, d, J=8.03 Hz), 4.89 (1H, quin, J=2.82

Hz), 3.77-3.88 (2H, m), 2.46 (3H, s), 1.77 (2H, dd, J=14.93, 2.89 Hz), 1.36 (2H, ddd, J=14.31, 11.54, 2.76 Hz), 1.13 (6H, d, J=6.27 Hz).

Cap-179, Step e

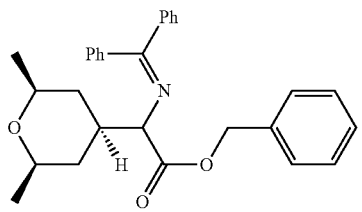 [SMILES: C[C@@H]1C[C@H](C(N=C(c2ccccc2)c2ccccc2)C(=O)OCc2ccccc2)C[C@H](C)O1]

LiHMDS (4.30 mL, 4.30 mmol) was added to a solution of Cap-179, step d (1.02 g, 3.59 mmol) and benzyl 2-(diphenyl-methyleneamino)acetate (1.181 g, 3.59 mmol) in Toluene (25 mL) at room temperature in a sealed microwave vial and the resulting mixture was then stirred for 5 h at 100° C. under microwave radiation. The reaction was quenched with water (10 mL), extracted with EtOAc, washed with water, dried over MgSO$_4$, filtrated, and concentrated in vacuum. The residue was purified via BIOTAGE® (0% to 6% EtOAc/Hex; 80 g column) and a yellow oil corresponding to Cap-179, step e (1.2 g) was isolated. Anal. Calcd. for $[2M+Na]^+$ $C_{58}H_{62}N_2NaO_6$: 905.45. Found 905.42. $^1$H NMR (400 MHz, CDCl$_3$) δ ppm 7.64-7.70 (4H, m), 7.29-7.44 (29H, m), 7.06 (4H, dd, J=7.65, 1.63 Hz), 5.18 (2H, d, J=2.01 Hz), 3.89 (2H, d, J=6.53 Hz), 3.79-3.87 (1H, m), 3.46 (5H, dquind, J=11.26, 5.87, 5.87, 5.87, 5.87, 1.88 Hz), 2.47 (2H, s), 2.35-2.46 (2H, m), 1.78 (1H, dd, J=14.81, 3.01 Hz), 1.62-1.65 (1H, m), 1.61 (2H, s), 1.36-1.43 (3H, m), 1.19 (7H, d, J=6.27 Hz), 1.14 (11H, dd, J=6.15, 2.89 Hz), 0.86-0.96 (3H, m).

Cap-179, Step f (Enantiomer-1 & Enantiomer-2)

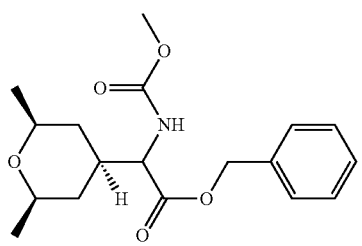 [SMILES: COC(=O)NC(C(=O)OCc1ccccc1)[C@H]1C[C@@H](C)O[C@@H](C)C1]

Cap-179, step e (2.08 g, 4.71 mmol) was dissolved in THF (100 mL) and treated with 2 N HCl (9.42 mL, 18.84 mmol). The resulting clear solution was stirred at ambient temperature for 4 h and then THF was removed under reduced pressure. The remaining aqueous layer was extracted with hexanes (3×20 ml) and after diluting with H$_2$O (20 mL), the aqueous phase was basified with 1 N NaOH to pH=10 and extracted with EtOAc (3×10 mL). The combined organic layers were dried (MgSO$_4$), filtered and concentrated under vacuum. The resulting residue was taken up in CH$_2$Cl$_2$ (100 mL) and charged with DIEA (2.468 mL, 14.13 mmol) and methyl chloroformate (0.401 mL, 5.18 mmol). The resulting solution was stirred at ambient temperature for 2 h. The reaction mixture was quenched with water (10 mL) and the organic layer was removed under reduced pressure. The aqueous layer was then extracted with EtOAc (3×10 mL) and the combined organic layers were dried (MgSO$_4$), filtered and concentrated. The residue was purified via BIOTAGE® (10% EtOAc/Hex; 25 g column). A clear colorless oil corresponding to Cap-179, step f (1.05 g) was recovered. LC/MS: Anal. Calcd. for $[M+H]^+$ $C_{18}H_{26}NO_5$: 336.18. Found 336.3. $^1$H NMR (500 MHz, CDCl$_3$) δ ppm 7.32-7.40 (5H, m), 5.26 (1H, d, J=8.24 Hz), 5.13-5.24 (2H, m), 4.36 (1H, dd, J=8.85, 4.88 Hz), 3.68 (3H, s), 3.32-3.46 (2H, m), 2.02-2.14 (1H, m), 1.52 (1H, d, J=12.82 Hz), 1.32 (1H, d, J=12.51 Hz), 1.11-1.18 (6H, m), 0.89-1.07 (2H, m).

A chiral SFC method was developed to separate the racemic mixture by using 12% methanol as the modifier on a CHIRALPAK® AD-H column (30×250 mm, 5 μm) (Temp=35° C., Pressure=150 bar, Wavelength=210 nm, Flow rate=70 mL/min for 8 min, Solvent A=CO$_2$, Solvent B=MeOH). The two separated isomers, Cap-179 step f (enantiomer-1) (first eluting) and Cap-179 step f (enantiomer-2) (second eluting), exhibited the same analytical data as the corresponding mixture (see above).

Cap-179 (Enantiomer-1 &-2)

Cap-179 step f (Enantiomer-1) (0.35 g, 1.044 mmol) was dissolved in MeOH (50 mL) in a Parr bottle and charged with Pd/C (0.111 g, 1.044 mmol). The suspension was then placed in a Parr shaker and the mixture was flushed with N$_2$ (3×), placed under 40 psi of H$_2$ (2.104 mg, 1.044 mmol) and shaken at room temperature for 2 h. The catalyst was filtered off through a pad of CELITE® and the solvent was removed under reduced pressure, to yield an amber solid corresponding to Cap-179 enantiomer-1 (0.25 g). $^1$H NMR (500 MHz, DMSO-d$_6$) δ ppm 12.74 (4H, br. s.), 7.35 (4H, d, J=6.10 Hz), 3.85 (4H, br. s.), 3.53 (3H, s), 3.35 (2H, ddd, J=15.95, 9.99, 6.10 Hz), 1.97 (1H, br. s.), 1.48 (2H, t, J=13.28 Hz), 1.06 (6H, d, J=6.10 Hz), 0.82-1.00 (2H, m)

Cap-179 enantiomer-2 was prepared similarly: $^1$H NMR (500 MHz, DMSO-d$_6$) δ ppm 12.50 (1H, br. s.), 7.31 (1H, br. s.), 3.84 (1H, t, J=7.32 Hz), 3.53 (3H, s), 3.29-3.41 (2H, m), 1.99 (1H, s), 1.48 (2H, t, J=14.34 Hz), 1.06 (6H, d, J=6.10 Hz), 0.95 (1H, q, J=12.21 Hz), 0.87 (1H, q, J=11.80 Hz). [Note: the minor variation in the $^1$H NMR profile of the enantiomers is likely a result of a difference in sample concentration.]

Cap-180 (Racemic Mixture)

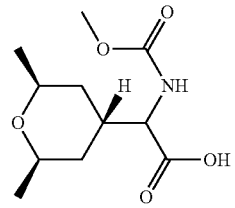 [SMILES: COC(=O)NC(C(=O)O)[C@@H]1C[C@@H](C)O[C@@H](C)C1]

Cap-180, Step a

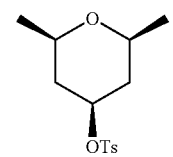

p-Tosyl-Cl (4.39 g, 23.0 mmol) was added to a solution of Cap-179, step a (1.50 g, 11.5 mmol) and pyridine (3.73 mL, 46.1 mmol) in $CH_2Cl_2$ (50 mL) at room temperature and stirred for 2 days. The reaction was diluted with $CH_2Cl_2$, washed with water, then 1 N HCl. The organic layer was dried ($MgSO_4$) and concentrated to a yellow oil which was purified via BIOTAGE® (5% to 20% EtOAc/Hex; 40 g column). A clear oil that solidified under vacuum and corresponding to Cap-180, step a (2.89 g) was isolated. LC/MS: Anal. Calcd. for $[2M+Na]^+$ $C_{28}H_{40}NaO_8S_2$: 591.21. Found 591.3. $^1$H NMR (500 MHz, $CDCl_3$) δ ppm 7.80 (2H, d, J=8.24 Hz), 7.35 (2H, d, J=7.93 Hz), 4.59 (1H, tt, J=11.37, 4.96 Hz), 3.36-3.46 (2H, m), 2.46 (3H, s), 1.91 (2H, dd, J=12.05, 5.04 Hz), 1.37 (2H, dt, J=12.67, 11.52 Hz), 1.19 (6H, d, J=6.10 Hz).

Cap-180, Step b

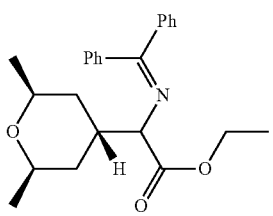 [SMILES: CCOC(=O)C(N=C(c1ccccc1)c1ccccc1)[C@@H]1C[C@@H](C)O[C@@H](C)C1]

LiHMDS 1 N (7.09 mL, 7.09 mmol) was added to a solution of Cap 180, step a (1.68 g, 5.91 mmol) and ethyl 2-(diphenylmethyleneamino)acetate (1.579 g, 5.91 mmol) in Toluene (30 mL) at room temperature and the resulting mixture was then stirred for 16 h at 85° C. The reaction was quenched with water (50 mL), extracted with EtOAc, washed with water, dried over $MgSO_4$, filtrated, and concentrated in vacuo. The residue was purified via BIOTAGE® (0% to 15% EtOAc/Hex; 40 g column). A clear yellowish oil corresponding to Cap-180, step b (racemic mixture; 0.64 g) was isolated. LC/MS: Anal. Calcd. for $[M+H]^+$ $C_{24}H_{30}NO_3$: 380.22. Found 380.03. $^1$H NMR (400 MHz, $CDCl_3$) δ ppm 7.64-7.70 (2H, m), 7.45-7.51 (3H, m), 7.38-7.44 (1H, m), 7.31-7.37 (2H, m), 7.13-7.19 (2H, m), 4.39 (1H, d, J=10.54 Hz), 4.16-4.26 (2H, m), 3.29-3.39 (1H, m), 2.93-3.03 (1H, m), 2.70 (1H, m, J=9.41, 4.14 Hz), 1.42-1.49 (2H, m), 1.31-1.37 (1H, m), 1.29 (4H, t, J=7.15 Hz), 1.04 (6H, dd, J=7.78, 6.27 Hz).

Cap-180, Step c

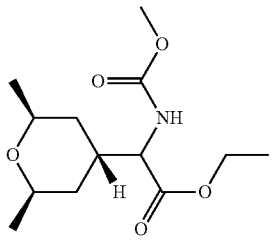 [SMILES: CCOC(=O)C(NC(=O)OC)[C@@H]1C[C@@H](C)O[C@@H](C)C1]

Cap 180, step b (0.36 g, 0.949 mmol) was dissolved in THF (10 mL) and treated with 2 N HCl (1.897 mL, 3.79 mmol). The resulting clear solution was stirred at ambient temperature for 20 h and THF was removed under reduced pressure. The remaining aqueous layer was extracted with hexanes (3×20 mL) and after diluting with $H_2O$ (20 mL), the aqueous phase was basified with 1 N NaOH to pH=10 and extracted with EtOAc (3×10 mL). The combined organic layers were dried ($MgSO_4$), filtered and concentrated under vacuum. The resulting residue was taken up in $CH_2Cl_2$ (10.00 mL) and charged with DIEA (0.497 mL, 2.85 mmol) and methyl chloroformate (0.081 mL, 1.044 mmol). The resulting solution was stirred at ambient temperature for 2 h and the reaction mixture was quenched with water (10 mL) and the organic layer was removed under reduced pressure. Aqueous layer was extracted with EtOAc (3×10 mL) and the combined organic layers were dried ($MgSO_4$), filtered and concentrated. An amber oil corresponding to Cap-180, step c (0.21 g) was recovered and it was used without further purification. LC/MS: Anal. Calcd. for $[M+H]^+$ $C_{13}H_{24}NO_5$: 273.17. Found 274.06. $^1$H NMR (400 MHz, $CDCl_3$) δ ppm 5.20 (1H, d, J=8.03 Hz), 4.59 (1H, t, J=10.16 Hz), 4.11-4.27 (3H, m), 3.69-3.82 (2H, m), 3.64 (3H, s), 1.95-2.07 (1H, m), 1.63 (1H, d, J=13.80 Hz), 1.41 (2H, dd, J=8.03, 4.02 Hz), 1.31-1.37 (1H, m), 1.26 (3H, t, J=7.15 Hz), 1.16 (1H, d, J=6.27 Hz), 1.12 (6H, dd, J=6.15, 3.89 Hz).

Cap-180 (Racemic Mixture)

Cap-180, step c (0.32 g, 1.2 mmol) was dissolved in THF (10 mL) and charged with LiOH (0.056 g, 2.342 mmol) in water (3.33 mL) at 0° C. The resulting solution was stirred at rt for 2 h. THF was removed under reduced pressure and the remaining residue was diluted with water (15 mL) and washed with $Et_2O$ (2×10 mL). The aqueous layer was then acidified with 1N HCl to pH ~2 and extracted with EtOAc (3×15 mL). The combined organic layers were dried ($MgSO_4$), filtered and concentrated under vacuum to yield Cap-180 (racemic mixture) (0.2 g) as a white foam. LC/MS: Anal. Calcd. for $[M+H]^+$ $C_{11}H_{20}NO_5$: 246.13. Found 246.00. $^1$H NMR (400 MHz, $CDCl_3$) δ ppm 5.14 (1H, d, J=9.03 Hz), 4.65 (1H, t, J=9.91 Hz), 3.63-3.89 (5H, m), 1.99-2.13 (1H, m), 1.56-1.73 (2H, m), 1.48-1.55 (1H, m), 1.35-1.48 (1H, m), 1.27 (1H, br. s.), 1.17 (6H, d, J=6.02 Hz).

Cap-181

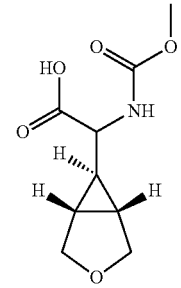

Cap-181, Step a

A solution of tert-Butyl diazoacetate (1.832 mL, 13.22 mmol) in 50 mL of $CH_2Cl_2$ was added into a mixture of 2,5-dihydrofuran (9.76 mL, 132 mmol), Rhodium(II) acetate dimer (0.058 g, 0.132 mmol) in 40 mL of $CH_2Cl_2$ dropwise by a syringe pump over 5 hours. The resulting mixture was then stirred at room temperature overnight. The solvent was removed under vacuum. The residue was purified by chromatography (silica gel, 0%-15% EtOAc/Hex) to afford Cap-181 step a (trans isomer) (720 mg) and Cap-181, step a (cis-isomer) (360 mg) as clear oil. Cap-181 step a (trans-isomer): ¹H NMR (500 MHz, CDCl₃) δ ppm 3.88 (2H, d, J=8.55 Hz), 3.70 (2H, d, J=8.55 Hz), 2.03-2.07 (2H, m), 1.47 (1H, t, J=3.20 Hz), 1.41 (9H, s); Cap-1, step a (cis-isomer): ¹H NMR (400 MHz, CDCl₃) δ ppm 4.06 (2H, d, J=8.53 Hz), 3.73 (2H, d, J=8.03 Hz), 1.81-1.86 (2H, m), 1.65-1.71 (1H, m), 1.43-1.47 (9H, m).

Cap-181, Step b

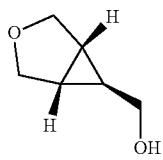

To a solution of (Cap-181, step a (trans isomer)) (700 mg, 3.80 mmol) in 15 mL of diethyl ether at −10° C. was added LiAlH4 (7.60 mL, 7.60 mmol) (1 M in THF) dropwise over 1 hour. The resulting mixture was stirred at −10° C. for 1 hour then at room temperature for 1 hour. The mixture was then cooled to −5° C. 10 mL of Rochelle's salt (Potassium sodium tartrate) aqueous solution was added dropwise to quench the reaction. The mixture was stirred at room temperature for 30 min and then extracted with EtOAc (3×). The combined organic layers were dried with MgSO₄ and concentrated to afford Cap-181, step b (380 mg) as light yellow oil. The product was used in the next step without purification. ¹H NMR (400 MHz, CDCl₃) δ ppm 3.85 (2H, d, J=8.28 Hz), 3.68 (2H, d, J=8.53 Hz), 3.45-3.55 (2H, m), 1.50-1.56 (2H, m), 1.02-1.11 (1H, m).

Cap-181, Step c

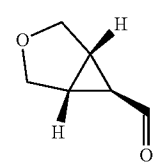

To a solution of DMSO (4.82 mL, 67.9 mmol) in CH₂Cl₂ (70 mL) was added dropwise oxalyl chloride (3.14 mL, 35.8 mmol) at −78° C. The resulting mixture was stirred at −78° C. for 15 min. A solution of Cap-181, step b (3.10 g, 27.2 mmol) in 35 mL of CH₂Cl₂ was added and the mixture was stirred at −78° C. for 1 hour. Et₃N (18.93 mL, 136 mmol) was then added dropwise. After 30 min, the cooling bath was removed and the reaction was quenched with cold 20% K₂HPO₄ aq. solution (10 mL) and water. The mixture was stirred at room temperature for 15 min and then diluted with Et₂O. The layers were separated. The aqueous layer was extracted with Et₂O (2×). The combined organic layers were washed with brine, dried with MgSO₄ and concentrated. The residue was purified by flash chromatography (silica gel, 100% CH₂Cl₂) to afford Cap-181, step c (2.71 g) as light yellow oil. ¹H NMR (500 MHz, CDCl₃) δ ppm 9.41 (1H, d, J=4.27 Hz), 3.96 (2H, d, J=8.85 Hz), 3.80 (2H, d, J=8.55 Hz), 2.27-2.33 (2H, m), 1.93 (1H, m).

Cap-181, Step d

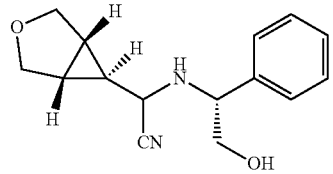 [SMILES: N#CC(N[C@@H](CO)c1ccccc1)[C@H]1[C@@H]2COC[C@@H]21]

To a mixture of Cap-181, step c (2.7 g, 24.08 mmol) in 50 mL of water at 0° C. was added sodium bisulfate (2.506 g, 24.08 mmol) and KCN (1.631 g, 25.04 mmol), followed by a solution of (R)-2-amino-2-phenylethanol (3.30 g, 24.08 mmol) in 18 mL of MeOH. The resulting mixture was stirred at room temperature for 2 hours and then heated to reflux overnight. The mixture was cooled to room temperature. 100 mL of EtOAc was added. After mixing for 15 min, the layers were separated. The aqueous layer was extracted with EtOAc (2×). The combined organic layers were washed with brine, dried with MgSO₄ and concentrated. The crude diastereomeric mixture was purified by reverse phase HPLC (Column: Water Sunfire 30×150 mm, acetonitrile/water/NH₄OAc) to afford a two diastereomers of Cap-181, step d. The absolute stereochemistry of each isomer was not determined Diastereomer 1 (later eluting fraction) (570 mg): LC/MS: Anal. Calcd. for [M+H]⁺ C₁₅H₁₉N₂O₂ 259.14. Found 259.2.

Cap-181, Step e

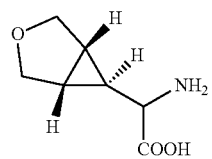 [SMILES: NC(C(=O)O)[C@H]1[C@@H]2COC[C@@H]21]

To a solution of Cap-181, step d (diastereomer 1) (570 mg, 2.207 mmol) in 20 mL of CH₂Cl₂ and 20 mL of MeOH at 0° C. was added lead tetraacetate (1174 mg, 2.65 mmol). The resulting orange mixture was stirred at 0° C. for 10 min. Water (20 mL) was then added into the mixture and the mixture was filtered off (CELITE®). The filtrate was concentrated and diluted with 25 mL of 6 N HCl aq. solution. The resulting mixture was refluxed for 4 hours. The mixture was filtered off and washed with CH₂Cl₂. The aqueous layer was concentrated to afford Cap-181, step e (HCl salt). The crude product was used in the next step without further purification. ¹H NMR (500 MHz, MeOD) δ ppm 3.87-3.91 (2H, m), 3.73 (2H, dd, J=8.70, 2.90 Hz), 3.55 (1H, d, J=10.07 Hz), 2.02-2.07 (1H, m), 1.94-1.99 (1H, m), 1.03-1.10 (1H, m).

Cap-181

To a mixture of the above crude Cap-181, step e in 1 N NaOH aq. solution (10 mL) was added sodium bicarbonate (371 mg, 4.42 mmol). Methyl chloroformate (0.342 mL, 4.42 mmol) was then added dropwise, and the resulting mixture was stirred at room temperature for 3 hours. The mixture was neutralized with 1 N HCl aq. Solution and extracted with EtOAc (3×). The combined organic layers were dried with MgSO$_4$ and concentrated to afford Cap-181 (100 mg, 21% over two steps) as light yellow oil. LC/MS: Anal. Calcd. for [M+H]$^+$ C$_9$H$_{14}$NO$_5$ 216.09. Found 216.1. $^1$H NMR (500 MHz, CDCl$_3$) δ ppm 5.29 (1H, br. s.), 3.53-4.02 (8H, m), 1.66-1.92 (2H, m), 1.08 (1H, br. s.).

Cap-182 (Racemic Mixture)

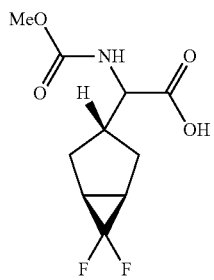

Cap-182, Step a

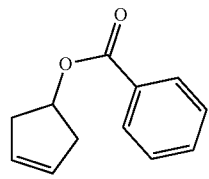 [SMILES: O=C(OC1CC=CC1)c1ccccc1]

A solution of cyclopent-3-enol (5 g, 59.4 mmol) and Et$_3$N (9.94 mL, 71.3 mmol) in 50 mL of CH$_2$Cl$_2$ was stirred at room temperature for 15 min. Benzoyl chloride (8.28 mL, 71.3 mmol) was then added dropwise and the mixture was stirred at room temperature overnight. The mixture was then washed with water, and the organic layer was dried with MgSO$_4$ and concentrated. The residue was purified by flash chromatography (silica gel, EtOAc/Hex 0-10%) to afford Cap-182, step a (9.25 g) as clear oil. $^1$H NMR (400 MHz, CDCl$_3$) δ ppm 8.01-8.07 (2H, m), 7.55 (1H, t, J=7.40 Hz), 7.43 (2H, t, J=7.65 Hz), 5.79 (2H, s), 5.64 (1H, tt, J=6.93, 2.60 Hz), 2.87 (2H, dd, J=16.56, 6.78 Hz), 2.52-2.63 (2H, m).

Cap-182, Step b

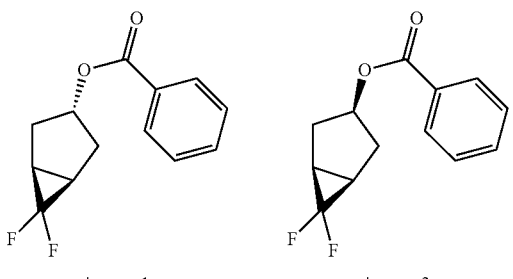

isomer 1        isomer 2

To a round bottom flask with a magnetic stirring bar was added sodium fluoride (5.02 mg, 0.120 mmol) and Cap-182, step a (2.25 g, 11.95 mmol). The flask was heated up to 100° C. and neat trimethylsilyl 2,2-difluoro-2-(fluorosulfonyl)acetate (5.89 mL, 29.9 mmol) was added slowly by syringe pump over 5 hours, and heated at 100° C. overnight. The mixture was then diluted with CH$_2$Cl$_2$, washed with water, sat. NaHCO$_3$ aq. solution and brine, dried with MgSO$_4$ and concentrated. The crude product was purified by flash chromatography (silica gel, 0-5% EtOAc/Hex) to afford Cap-182, step b (isomer 1) (750 mg) and Cap-182, step b (isomer 2) (480 mg) as clear oils. Relative stereochemical assignment was made by NOE study. Cap-182, step b (isomer 1): LC/MS: Anal. Calcd. for [M+H]$^+$ C$_{13}$H$_{13}$F$_2$O$_2$ 239.09. Found 239.2. $^1$H NMR (500 MHz, CDCl$_3$) δ ppm 7.99-8.04 (2H, m), 7.56 (1H, t, J=7.32 Hz), 7.43 (2H, t, J=7.63 Hz), 5.25-5.33 (1H, m), 2.50 (2H, dd, J=14.04, 6.71 Hz), 2.14-2.22 (2H, m), 2.08-2.14 (2H, m). Cap-182, step b (isomer 2): LC/MS: Anal. Calcd. for [M+H]$^+$ C$_{13}$H$_{13}$F$_2$O$_2$ 239.09. Found 239.2. $^1$H NMR (400 MHz, CDCl$_3$) δ ppm 7.98-8.08 (2H, m), 7.53-7.59 (1H, m), 7.41-7.48 (2H, m), 5.53-5.62 (1H, m), 2.59-2.70 (2H, m), 2.01-2.11 (4H, m).

Cap-182, Step c

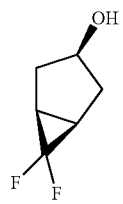

To a solution of Cap-182, step b (isomer 2) (480 mg, 2.015 mmol) in 4 mL of MeOH was added KOH (4 mL, 2.015 mmol) (10% aq.). The resulting mixture was stirred at room temperature overnight. The mixture was then extracted with CH$_2$Cl$_2$ (3×). The combined organic layers were dried with MgSO$_4$ and concentrated to afford Cap-182, step c (220 mg) as a light yellow solid. $^1$H NMR (500 MHz, CDCl$_3$) δ ppm 4.41-4.54 (1H, m), 2.38-2.50 (2H, m), 1.89-1.99 (2H, m), 1.81 (2H, dd, J=14.50, 5.04 Hz).

Cap-182, Step d

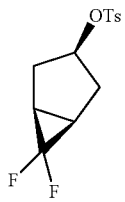

p-Tosyl-Cl (625 mg, 3.28 mmol) was added to a solution of Cap-182, step c (220 mg, 1.640 mmol) and pyridine (0.531 mL, 6.56 mmol) in 7 mL of CH$_2$Cl$_2$. The mixture was stirred at room temperature overnight and then diluted with CH$_2$Cl$_2$, washed with water and 1 N HCl aq. solution. The organic layer was dried (MgSO$_4$) and concentrated. The residue was purified by flash chromatography (silica gel, 0-15% EtOAc/Hexane) to afford Cap-182, step d (325 mg) as a clear oil.

LC/MS: Anal. Calcd. For [M+Na]+ $C_{13}H_{14}F_2NaO_3S$ 311.05. Found 311.2. $^1$H NMR (500 MHz, CDCl$_3$) δ ppm 7.76 (2H, d, J=8.24 Hz), 7.34 (2H, d, J=8.24 Hz), 4.99-5.08 (1H, m), 2.45 (3H, s), 2.31-2.41 (2H, m), 1.84-1.94 (4H, m).

Cap-182, Step e (Racemic Mixture)

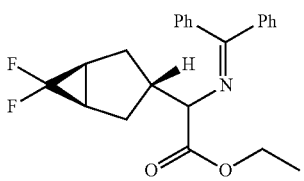 [SMILES: CCOC(=O)C(N=C(c1ccccc1)c1ccccc1)[C@@H]1C[C@@H]2[C@H](C1)C2(F)F]

To a microwave tube was added N-(diphenylmethylene) glycine ethyl ester (241 mg, 0.902 mmol) and Cap-182, step d (260 mg, 0.902 mmol) in 2 mL of toluene. The tube was sealed and LiHMDS (1.082 mL of 1 N in THF, 1.082 mmol) was added dropwise under N$_2$. The resulting dark brown solution was heated at 100° C. in microwave for 5 hours. The mixture was then quenched with water, and extracted with EtOAc (3×). The combined organic layers were washed with water, dried with MgSO$_4$ and concentrated. The crude product was purified by flash chromatography (silica gel, 0-5% EtOAc/Hex) to afford a racemic mixture of Cap-182, step e (240 mg) as light yellow oil. The mixture was submitted to the next step without separation. LC/MS: Anal. Calcd. for [M+H]+ $C_{23}H_{24}F_2NO_2$ 384.18. Found 384.35. $^1$H NMR (500 MHz, CDCl$_3$) δ ppm 7.63-7.70 (2H, m), 7.43-7.51 (3H, m), 7.38-7.43 (1H, m), 7.31-7.38 (2H, m), 7.13-7.22 (2H, m), 4.13-4.22 (2H, m), 3.95 (1H, d, J=6.41 Hz), 2.67-2.79 (1H, m), 2.07-2.16 (1H, m), 1.97-2.07 (2H, m), 1.90 (2H, m), 1.65-1.76 (1H, m), 1.25 (3H, t, J=7.17 Hz).

Cap-182, Step f (Racemic Mixture)

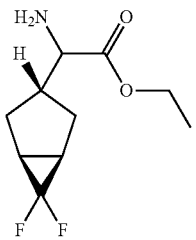

To a solution of Cap-182, step e (240 mg, 0.626 mmol) in 4 mL of THF was added HCl (1 mL, 2.0 mmol) (2 N aq.). The resulting mixture was stirred at room temperature for 2 hours. The mixture was then washed with EtOAc, neutralized with sat. NaHCO$_3$ aq. solution and then extracted with EtOAc (3×). The combined organic layers were dried with MgSO$_4$ and concentrated to afford Cap-182, step f (120 mg) as clear oil. LC/MS: Anal. Calcd. for [M+H]+ $C_{10}H_{16}F_2NO_2$ 220.11. Found 220.26. $^1$H NMR (500 MHz, CDCl$_3$) δ ppm 4.14-4.25 (2H, m), 3.26 (1H, d, J=6.71 Hz), 2.22-2.35 (1H, m), 1.90-2.11 (5H, m), 1.79-1.90 (1H, m), 1.22-1.34 (3H, m).

Cap-182, Step g (Racemic Mixture)

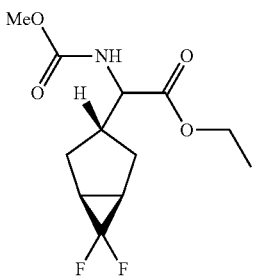

To a solution of Cap-182, step f (120 mg, 0.547 mmol) in 2 mL of CH$_2$Cl$_2$ was added methyl chloroformate (0.085 mL, 1.095 mmol). The resulting mixture was stirred at room temperature for 1 hour. The mixture was diluted with CH$_2$Cl$_2$ and washed with water. The organic layer was dried with Na$_2$SO$_4$ and concentrated to afford Cap-182, step g (150 mg) as a white solid. LC/MS: Anal. Calcd. for [M+H]+ $C_{12}H_{18}F_2NO_4$ 278.12. Found 278.2. $^1$H NMR (500 MHz, CDCl$_3$) δ ppm 5.23 (1H, d, J=8.24 Hz), 4.29 (1H, t, J=7.48 Hz), 4.15-4.23 (2H, m), 3.68 (3H, s), 2.37 (1H, br. s.), 2.02-2.10 (1H, m), 1.85-2.00 (4H, m), 1.75-1.84 (1H, m), 1.27 (3H, t, J=7.02 Hz).

Cap-182 (Racemic Mixture)

To a mixture of Cap-182, step g (150 mg, 0.541 mmol) in 2 mL of THF and 1 mL of water was added LiOH (0.811 mL, 1.623 mmol) (2 N aq.). The resulting mixture was stirred at room temperature overnight. The mixture was neutralized with 1 N HCl aq. solution and extracted with EtOAc (3×). The combined organic layers were dried with MgSO$_4$ and concentrated to afford Cap-182 (133 mg) as a white solid. LC/MS: Anal. Calcd. for [M+H]+ $C_{10}H_{14}F_2NO_4$ 250.09. Found 250.13. $^1$H NMR (500 MHz, CDCl$_3$) δ ppm 5.18-5.36 (1H, m), 4.28-4.44 (1H, m), 3.70 (3H, s), 2.37-2.56 (1H, m), 1.74-2.31 (6H, m).

Cap-183 (Racemic Mixture)

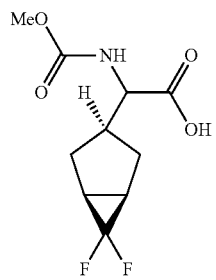 [SMILES: COC(=O)NC(C(=O)O)[C@H]1C[C@@H]2[C@H](C1)C2(F)F]

Cap-183 was synthesized from Cap-182, step b (isomer 1) according to the procedure described for the preparation of Cap-182. Anal. Calcd. for [M+H]+ $C_{10}H_{14}F_2NO_4$ 250.09. Found 249.86. $^1$H NMR (500 MHz, CDCl$_3$) δ ppm 5.15 (1H, d, J=8.24 Hz), 4.32 (1H, t, J=7.48 Hz), 3.69 (3H, s), 2.83-2.99 (1H, m), 1.96-2.26 (4H, m), 1.70 (1H, t, J=11.75 Hz), 1.59 (1H, t, J=12.05 Hz).

Cap-184 (Racemic Mixture)

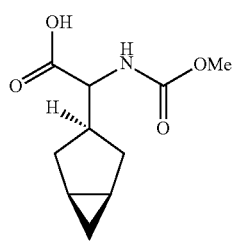 [SMILES: COC(=O)NC(C(=O)O)[C@@H]1C[C@@H]2C[C@@H]2C1]

Cap-184, Step a

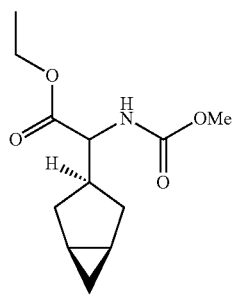 [SMILES: CCOC(=O)C(NC(=O)OC)[C@@H]1C[C@@H]2C[C@@H]2C1]

A mixture of ethyl 2-amino-2-((1R,3r,5S)-bicyclo[3.1.0] hexan-3-yl)acetate (prepared from commercially available (1R,3r,5S)-bicyclo[3.1.0]hexan-3-ol by employing the same procedures described for the preparation of Cap-182; 350 mg, 1.910 mmol), DiPEA (0.667 mL, 3.82 mmol), methyl chloroformate (0.296 mL, 3.82 mmol) in 5 mL of $CH_2Cl_2$ was stirred at room temperature for 1 hour. The mixture was then diluted with $CH_2Cl_2$ and washed with water. The organic layer was dried with $MgSO_4$ and concentrated to afford Cap-184 step a (461 mg) as yellow oil. LC/MS: Anal. Calcd. for $[M+H]^+$ $C_{12}H_{20}NO_4$ 242.14. Found 242.2. $^1$H NMR (500 MHz, $CDCl_3$) δ ppm 5.04 (1H, d, J=7.63 Hz), 4.09-4.20 (2H, m), 4.05 (1H, t, J=8.39 Hz), 3.63 (3H, s), 2.55-2.70 (1H, m), 1.96-2.09 (2H, m), 1.37-1.60 (4H, m), 1.24 (3H, t, J=7.17 Hz), 0.66-0.76 (1H, m), −0.03-0.06 (1H, m).

Cap-184 (Racemic Mixture)

To a mixture of ethyl ester Cap-184, step a (461 mg, 1.911 mmol) in 5 mL of THF and 2 mL of water was added LiOH (2.87 mL, 5.73 mmol) (2 N aq.). The resulting mixture was stirred at room temperature overnight. The mixture was then neutralized with 1 N HCl aqueous solution, and extracted with EtOAc (3×). The combined organic layers were dried with $MgSO_4$ and concentrated to afford Cap-184 (350 mg) as clear oil. LC/MS: Anal. Calcd. for $[2M+Na]^+ C_{20}H_{30}N_2NaO_8$ 449.19. Found 449.3. $^1$H NMR (500 MHz, $CDCl_3$) δ ppm 5.07 (1H, d, J=8.85 Hz), 4.13 (1H, t, J=8.24 Hz), 3.68 (3H, s), 2.64-2.79 (1H, m), 2.04-2.21 (2H, m), 1.23-1.49 (4H, m), 0.71-0.81 (1H, m), 0.03-0.12 (1H, m).

Cap-185 (Enantiomer-1 &-2)

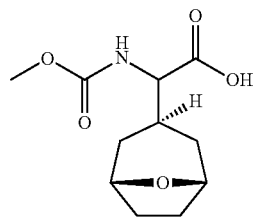

Cap-185, Step a

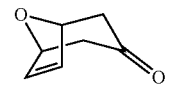

To a mixture of furan (1.075 mL, 14.69 mmol) and zinc (1.585 g, 24.24 mmol) in 1 mL of THF was added 1,1,3,3-tetrabromopropan-2-one (8.23 g, 22.03 mmol) and triethyl borate (5.25 mL, 30.8 mmol) in 4 mL of THF dropwise during 1 hour in dark. The resulting mixture was stirred at room temperature in dark for 17 hours. The resulting dark brown mixture was cooled to −15° C., and 6 mL of water was added. The mixture was warmed to 0° C. and stirred at this temperature for 30 min. The mixture was then filtered and washed with ether. The filtrate was diluted with water and extracted with ether (3×). The combined organic layers were dried with MgSO4 and concentrated to afford dark brown oil. The dark brown oil was dissolved in 6 mL of MeOH and the solution was added dropwise to a mixture of zinc (4.99 g, 76 mmol), copper (I) chloride (0.756 g, 7.64 mmol) and ammonium chloride (5.4 g, 101 mmol) in 20 mL of MeOH. The reaction temperature was maintained below 15° C. during addition. The mixture was then stirred at room temperature for 20 hours, filtered, and the filtrate was diluted with water and extracted with $CH_2Cl_2$ (3×). The combined organic layers were dried with $MgSO_4$ and concentrated. The crude product was purified by flash chromatography (silica gel, 0-14% EtOAc/Hex) to afford Cap-185, step a as a white solid (1.0 g) as a white solid, which turned yellow soon. $^1$H NMR (500 MHz, $CDCl_3$) δ ppm 6.24 (2H, s), 5.01 (2H, d, J=4.88 Hz), 2.73 (2H, dd, J=16.94, 5.04 Hz), 2.31 (2H, d, J=16.79 Hz).

Cap-185, Step b

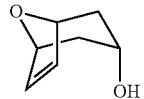

To a solution of Cap-185, step a (240 mg, 1.933 mmol) in 2 mL of THF at −78° C. was added L-selectride (3.87 mL, 3.87 mmol) (1 M in THF) dropwise over 100 min. The resulting mixture was stirred at −78° C. for 1 hour and then at room temperature overnight. The mixture was then cooled to 0° C., 4 mL of 20% NaOH aqueous solution was added, followed by 2 mL of H$_2$O$_2$ (30% water solution) dropwise. The resulting mixture was stirred for 1 hour and then neutralized with 6N HCl (~5 mL). The aqueous layer was saturated with NaCl and extracted with CH$_2$Cl$_2$ (3×). The combined organic layers were dried with MgSO$_4$ and concentrated. The crude product was purified by flash chromatography (silica gel, 0-40% EtOAc/Hex) to afford Cap-185, step b (180 mg) as clear oil. $^1$H NMR (400 MHz, CDCl$_3$) δ ppm 6.49 (2H, s), 4.76 (2H, d, J=4.27 Hz), 3.99 (1H, t, J=5.77 Hz), 2.29 (2H, ddd, J=15.18, 5.65, 4.02 Hz), 1.70-1.78 (2H, m).

Cap-185, Step c

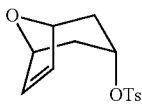 [SMILES: Cc1ccc(S(=O)(=O)OC2CC3C=CC(C2)O3)cc1]

p-Tosyl-Cl (544 mg, 2.85 mmol) was added to a solution of Cap-185, step b (180 mg, 1.427 mmol) and pyridine (0.462 mL, 5.71 mmol) in 5 mL of CH$_2$Cl$_2$ (5 mL) and the mixture was stirred at room temperature for 2 days. The reaction was diluted with CH$_2$Cl$_2$ and washed with 1 N aq. HCl. The aqueous layer was extracted with CH$_2$Cl$_2$ (2×). The combined organic layers were dried with MgSO$_4$ and concentrated. The crude product was purified by flash chromatography (silica gel, 0-15% EtOAc/Hex) to afford Cap-185, step c (210 mg) as a white solid. $^1$H NMR (500 MHz, CDCl$_3$) δ ppm 7.73 (2H, d, J=8.24 Hz), 7.32 (2H, d, J=8.24 Hz), 6.25 (2H, s), 4.76 (1H, t, J=5.65 Hz), 4.64 (2H, d, J=3.66 Hz), 2.44 (3H, s), 2.18 (2H, td, J=10.07, 5.49 Hz), 1.71 (2H, d, J=15.56 Hz).

Cap-185, Step d

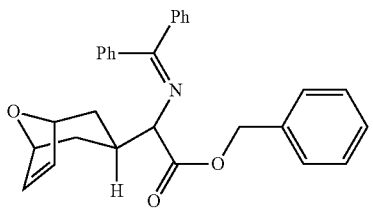 [SMILES: O=C(OCc1ccccc1)C(N=C(c1ccccc1)c1ccccc1)C1CC2C=CC(C1)O2]

A microwave tube was charged with benzyl 2-(diphenyl-methyleneamino)acetate (1.5 g, 4.57 mmol) and Cap-185, step c (1.28 g, 4.57 mmol) in 5 mL of toluene. The tube was sealed and LiHMDS (5.5 mL, 5.5 mmol) (1 N in toluene) was added dropwise under N$_2$. The resulting dark brown solution was heated at 100° C. in microwave for 5 hours. To the mixture was then added water and EtOAc. The layers were separated and the water phase was extracted with EtOAc (2×). The combined organic layers were concentrated to afford Cap-185, step d as a racemic mixture of. The crude mixture was submitted to the next step without purification or separation. LC/MS: Anal. Calcd. for [M+H]$^+$ C$_{29}$H$_{28}$NO$_3$ 438.21. Found 438.4.

Cap-185, Step e

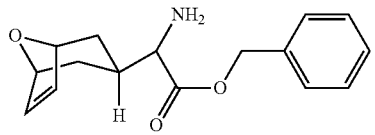 [SMILES: NC(C(=O)OCc1ccccc1)C1CC2C=CC(C1)O2]

To a solution of the racemic mixture of Cap-185, step d in 30 mL of THF was added HCl (20 mL) (2 N aq.). The resulting mixture was stirred at room temperature for 2 hours. After the reaction was done as judged by TLC, the two layers were separated. The aqueous layer was washed with EtOAc, neutralized with sat. NaHCO$_3$ aq. solution and then extracted with EtOAc (3×). The combined organic layers were dried with MgSO$_4$ and concentrated to afford Cap-185, step e. LC/MS: Anal. Calcd. for [M+H]$^+$ C$_{16}$H$_{20}$NO$_3$ 274.14. Found 274.12.

Cap-185, Step f

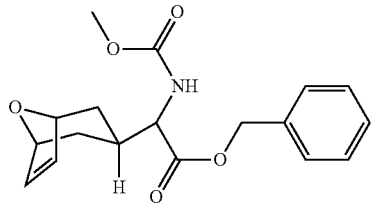 [SMILES: COC(=O)NC(C(=O)OCc1ccccc1)C1CC2C=CC(C1)O2]

A solution of the crude Cap-185, step e, DiPEA (1.24 mL, 7.1 mmol) and methyl chloroformate (0.55 mL, 7.1 mmol) in 5 mL of CH$_2$Cl$_2$ was stirred at room temperature for 1 hour. The mixture was then diluted with CH$_2$Cl$_2$ and washed with water. The organic layer was dried with Na$_2$SO$_4$ and concentrated. The crude product was purified by flash chromatography (silica gel, 0-40% EtOAc/Hex) to afford 700 mg of the racemic mixture. The mixture was then separated by chiral HPLC (CHIRALPAK® AD-H column, 30×250 mm, 5 um) eluting with 88% CO$_2$-12% EtOH at 70 mL/min to afford 240 mg of enantiomer-1 and 310 mg of enantiomer-2 of Cap-1, step f as white solids. Enantiomer-1: LC/MS: Anal. Calcd. for [M+H]$^+$ C$_{18}$H$_{22}$NO$_5$ 332.15. Found 332.3. $^1$H NMR (500 MHz, CDCl$_3$) δ ppm 7.30-7.40 (5H, m), 6.03-6.16 (2H, m), 5.09-5.26 (3H, m), 4.65-4.74 (2H, m), 4.33 (1H, dd, J=9.16, 4.88 Hz), 3.67 (3H, s), 2.27-2.38 (1H, m), 1.61-1.69 (1H, m), 1.45-1.56 (1H, m), 1.34 (1H, dd, J=13.43, 5.19 Hz), 1.07 (1H, dd, J=13.12, 5.19 Hz). Enantiomer-2: LC/MS: Anal. Calcd. for [M+H]$^+$ C$_{18}$H$_{22}$NO$_5$ 332.15. Found 332.06.

Cap-185 (Enantiomer-1 &-2)

To a hydrogenation bottle containing a solution Cap-185, step f (enantiomer-2) (300 mg, 0.905 mmol) in 10 mL of MeOH was added Pd/C (15 mg, 0.141 mmol) under a cover of nitrogen. The mixture was hydrogenated on a Parr shaker at 40 psi for 3 hours. The mixture was then filtered and the filtrate was concentrated to afford Cap-185 (enantiomer-2)

(200 mg) as a white solid. LC/MS: Anal. Calcd. for [M+H]+ $C_{11}H_{18}NO_5$ 244.12. Found 244.2. $^1$H NMR (500 MHz, $CDCl_3$) δ ppm 5.33 (1H, br. s.), 4.46 (2H, d), 4.28 (1H, br. s.), 3.68 (3H, s), 2.35 (1H, br. s.), 1.91-2.03 (2H, m), 1.56-1.80 (4H, m), 1.36-1.55 (2H, m). [Note: Cap-185 (enantiomer-1) can be obtained in a similar fashion.]

Cap-186

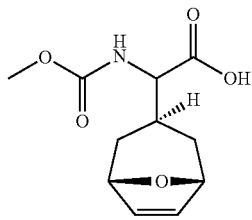

To a solution of the ester Cap-185, step f (enantiomer-2) (150 mg, 0.453 mmol) in 4 mL of MeOH was added NaOH (4 mL of 1 N in water, 4.00 mmol). The resulting mixture was stirred at room temperature for 3 hours. The methanol was then removed under vacuum, and the residue was neutralized with 1 N HCl solution and extracted with EtOAc (3×). The combined organic layers were dried with $MgSO_4$ and concentrated to afford Cap-186 that was contaminated with some benzyl alcohol (sticky white solid; 115 mg). LC/MS: Anal. Calcd. for [M+H]+ $C_{11}H_{16}NO_5$ 242.10. Found 242.1. $^1$H NMR (500 MHz, $CDCl_3$) δ ppm 6.10-6.19 (2H, m), 5.36 (1H, d, J=8.85 Hz), 4.75-4.84 (2H, m), 4.28 (1H, dd, J=8.55, 4.58 Hz), 3.68 (3H, s), 2.33-2.45 (1H, m), 1.60-1.72 (2H, m), 1.30-1.48 (2H, m).

Cap-187

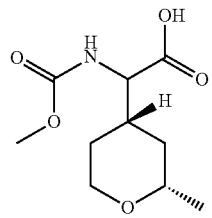 [SMILES: COC(=O)NC(C(=O)O)[C@H]1CCO[C@@H](C)C1]

Cap-187, Step a

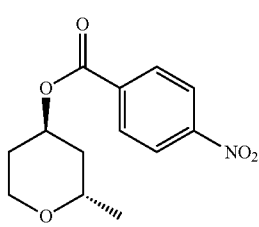 [SMILES: C[C@H]1C[C@H](OC(=O)c2ccc([N+](=O)[O-])cc2)CCO1]

To a solution of Cap-178, step e (2.2 g, 18.94 mmol), $PPh_3$ (24.84 g, 95 mmol) and 4-nitrobenzoic acid (14.24 g, 85 mmol) in 30 mL of benzene was added DEAD (42.9 mL, 95 mmol) dropwise. The resulting light orange solution was stirred at room temperature overnight. The solvent was then removed under vacuum and the residue was purified by flash chromatography (silica gel, 0-15% EtOAc/Hex) to afford Cap 187, step a (2.3 g) as a white solid. $^1$H NMR (500 MHz, $CDCl_3$) δ ppm 8.27-8.34 (2H, m), 8.20-8.26 (2H, m), 5.45 (1H, t, J=2.90 Hz), 3.83-3.96 (3H, m), 1.90-2.03 (2H, m), 1.80-1.88 (1H, m), 1.61-1.70 (1H, m), 1.21 (3H, d, J=6.10 Hz).

Cap-187, Step b

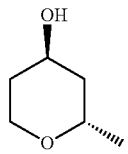

To a solution of Cap 187, step a (2.3 g, 8.67 mmol) in 10 mL of MeOH was added sodium methoxide (2.372 mL, 8.67 mmol) (25% in Methanol). The resulting mixture was stirred at room temperature for 3 hours. Water was added, and the mixture was extracted with EtOAc (5×). The combined organic layers were dried with MgSO4 and concentrated. The crude product was purified by flash chromatography (silica gel, 0-15% EtOAc/Hex, then 15-50% EtOAc/Hex) to afford Cap 187, step b (0.85 g) as clear oil. $^1$H NMR (500 MHz, $CDCl_3$) δ ppm 4.19-4.23 (1H, m), 3.82-3.91 (2H, m), 3.73-3.79 (1H, m), 1.79-1.88 (1H, m), 1.62-1.68 (1H, m), 1.46-1.58 (2H, m), 1.14 (3H, d, J=6.10 Hz).

Cap 187

The individual enantiomers of Cap-187 were synthesized from Cap 187, step b according to the procedure described for Cap-178. LC/MS: Anal. Calcd. for [M+H]+ $C_{10}H_{18}NO_5$ 232.12. Found 232.1. $^1$H NMR (400 MHz, $CDCl_3$) δ ppm 5.26 (1H, d, J=7.78 Hz), 4.32-4.43 (1H, m), 4.07 (1H, dd, J=11.54, 3.51 Hz), 3.72 (3H, s), 3.39-3.50 (2H, m), 2.08-2.23 (1H, m), 1.54-1.68 (1H, m), 1.38-1.52 (1H, m), 1.11-1.32 (5H, m).

Cap-188 (Four Stereoisomers)

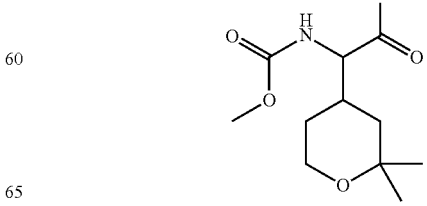

Cap-188, Step a

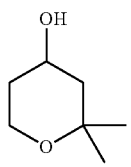

To a solution of 2,2-dimethyldihydro-2H-pyran-4(3H)-one (2 g, 15.60 mmol) in 50 mL of MeOH was slowly added sodium borohydride (0.649 g, 17.16 mmol). The resulting mixture was stirred at room temperature for 3 hours. To the mixture was then added 1 N HCl aqueous solution until it crosses into acidic pH range and then extracted with EtOAc (3×). The combined organic layers were dried with MgSO$_4$ and concentrated to afford Cap 188, step a (1.9 g) as clear oil. The product was used in the next step without purification. $^1$H NMR (400 MHz, CDCl$_3$) δ ppm 3.91-4.02 (1H, m), 3.79-3.86 (1H, m), 3.63 (1H, td, J=12.05, 2.51 Hz), 1.82-1.93 (2H, m), 1.40-1.53 (1H, m), 1.29-1.38 (1H, m), 1.27 (3H, s), 1.20 (3H, s).

Cap-188.1 & Cap 188.2, Step b

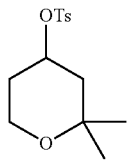

p-Tosyl-Cl (5.56 g, 29.2 mmol) was added to a solution of Cap 188, step a (1.9 g, 14.59 mmol) and pyridine (4.72 mL, 58.4 mmol) in 100 mL of CH$_2$Cl$_2$. The resulting mixture was stirred at room temperature for 3 days. To the reaction was added 10 mL of water, and the mixture was stirred at room temperature for an additional hour. The two layers were separated and the organic phase was washed with water and 1 N HCl aqueous solution. The organic phase was dried with MgSO$_4$ and concentrated to afford the mixture of two enantiomers as a light yellow solid. The mixture was then separated by chiral HPLC (CHIRALPAK® AD column, 21×250 mm, 10 um) eluting with 92% 0.1% diethylamine/Heptane-8% EtOH at 15 mL/min to afford Cap-188.1, step b (1.0 g) and Cap-188.2, step b (1.0 g). The absolute stereochemistry of the two enantiomers was not assigned. Cap-188.1, step b: LC/MS: Anal. Calcd. for [2M+Na]$^+$ C$_{28}$H$_{40}$NaO$_8$S$_2$ 591.21. Found 591.3. $^1$H NMR (500 MHz, CDCl$_3$) δ ppm 7.79 (2H, d, J=8.24 Hz), 7.34 (2H, d, J=8.24 Hz), 4.72-4.81 (1H, m), 3.78 (1H, dt, J=12.44, 4.16 Hz), 3.53-3.61 (1H, m), 2.45 (3H, s), 1.75-1.86 (2H, m), 1.61-1.71 (1H, m), 1.52-1.60 (1H, m), 1.22 (3H, s), 1.14 (3H, s). Cap-188.2, step b: LC/MS: Anal. Calcd. for [2M+Na]$^+$ C$_{28}$H$_{40}$NaO$_8$S$_2$ 591.21. Found 591.3;

Cap-188

The four stereoisomers of Cap-188 could be synthesized from Cap-188.1, step b and Cap-188.2, step b, according to the procedure described for the preparation of Cap-178. Cap-188 (Stereoisomer-1): LC/MS: Anal. Calcd. for [M+Na]$^+$ C$_{11}$H$_{19}$NNaO$_5$ 268.12. Found 268.23. $^1$H NMR (500 MHz, CDCl$_3$) δ ppm 5.32 (1H, d, J=8.55 Hz), 4.26-4.35 (1H, m), 3.57-3.82 (5H, m), 2.11-2.34 (1H, m), 1.25-1.58 (4H, m), 1.21 (6H, d, J=6.10 Hz). Cap-188 (Stereoisomer-2): LC/MS: Anal. Calcd. for [M+H]$^+$ C$_{11}$H$_{20}$NO$_5$ 246.13. Found 246.1. $^1$H NMR (500 MHz, CDCl$_3$) δ ppm 5.25 (1H, d, J=8.55 Hz), 4.33 (1H, dd, J=8.39, 5.04 Hz), 3.80 (1H, dd, J=11.90, 3.97 Hz), 3.62-3.76 (4H, m), 2.20-2.32 (1H, m), 1.52-1.63 (1H, m), 1.27-1.49 (3H, m), 1.22 (6H, d, J=14.04 Hz).

Cap-189

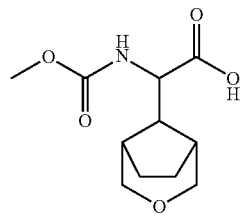 [SMILES: COC(=O)NC(C(=O)O)C1C2CCC1COC2]

Cap-189, Step a

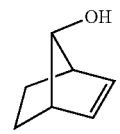

To a solution of phenylmagnesium bromide (113 mL, 340 mmol) (3 M in ether) in 100 mL of ether was added dropwise exo-2,3-epoxynorbornane (25 g, 227 mmol) in 50 mL of ether. After the initial exotherm, the mixture was heated to reflux overnight. The reaction was then cooled to room temperature and quenched carefully with water (~10 mL). The mixture was diluted with ether and washed with a 3 N HCl aqueous solution (~160 mL). The aqueous layer was extracted with ether (2×) and the combined organic layers were dried with MgSO$_4$ and concentrated. The crude product was purified by flash chromatography (silica gel, 0-18% EtOAc/Hex) to afford Cap-189, step a (11 g). $^1$H NMR (400 MHz, CDCl$_3$) δ ppm 6.03-6.11 (2H, m), 3.76 (1H, d, J=11.29 Hz), 2.72-2.81 (2H, m), 1.98 (1H, d, J=11.29 Hz), 1.67-1.76 (2H, m), 0.90-0.97 (2H, m).

Cap-189, Step b

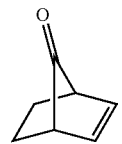

To a solution of oxalyl chloride (59.9 mL, 120 mmol) in 200 mL of CH$_2$Cl$_2$ at −78° C. was added DMSO (17.01 mL, 240 mmol) in 100 mL of CH$_2$Cl$_2$. The mixture was stirred for 10 min, and Cap-189, step a (11 g, 100 mmol) in 150 mL of CH$_2$Cl$_2$ was added followed by Et$_3$N (72.4 mL, 519 mmol) in 30 mL of CH$_2$Cl$_2$. The mixture was stirred at −78° C. for 30 min and then warmed to room temperature. Water (150 mL)

was added and the mixture was stirred at room temperature for 30 mins. The two layers were then separated, and the aqueous layer was extracted with CH₂Cl₂ (2×). The organic layers were combined, dried with MgSO₄ and concentrated. The crude product was purified by flash chromatography (silica gel, 0-5% EtOAc/Hex) to afford Cap-189, step b (5.3 g) as a light yellow oil. ¹H NMR (500 MHz, CDCl₃) δ ppm 6.50-6.55 (2H, m), 2.78-2.84 (2H, m), 1.92-1.99 (2H, m), 1.17-1.23 (2H, m).

Cap-189, Step c

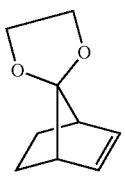

A mixture of Cap-189, step b (5.3 g, 49.0 mmol), p-toluenesulfonic acid monohydrate (1.492 g, 7.84 mmol) and ethylene glycol (4.10 mL, 73.5 mmol) in 100 mL of benzene was refluxed for 4 hours and then stirred at room temperature overnight. The reaction was partitioned between Et₂O and aqueous sat. NaHCO₃ solution and the two layers were separated. The organic layer was washed with brine, dried with MgSO₄ and concentrated. The crude product was purified by flash chromatography (silica gel, 0-6% EtOAc/Hex) to afford Cap-189, step c (5.2 g) as a clear oil. ¹H NMR (400 MHz, CDCl₃) δ ppm 6.20 (2H, t, J=2.13 Hz), 3.90-3.97 (2H, m), 3.81-3.89 (2H, m), 2.54 (2H, m), 1.89-1.99 (2H, m), 0.95-1.03 (2H, m).

Cap-189, Step d

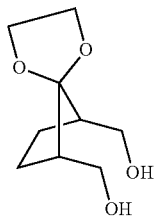 [SMILES: OCC1CCC(CO)C12OCCO2]

A solution of Cap-189, step c (5.2 g, 34.2 mmol) in 60 mL of MeOH and 50 mL of CH₂Cl₂ was cooled to −78° C. and treated with ozone gas until a light blue color was apparent. The reaction was then bubbled with N₂ to remove the excess ozone gas (blue color disappeared) and sodium borohydride (1.939 g, 51.3 mmol) was added into the reaction. The reaction was then warmed to 0° C. Acetone was added into the mixture to quench the excess sodium borohydride. The mixture was concentrated and the residue was purified by flash chromatography (silica gel, 100% EtOAc) to afford Cap-189, step d (5.0 g) as a clear oil. ¹H NMR (400 MHz, CDCl₃) δ ppm 3.99-4.09 (4H, m), 3.68 (4H, m), 2.17-2.29 (2H, m), 1.92-2.10 (2H, m), 1.77-1.88 (2H, m), 1.57-1.70 (2H, m).

Cap-189, Step e

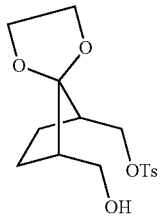 [SMILES: Cc1ccc(S(=O)(=O)OCC2CCC(CO)C23OCCO3)cc1]

To a solution of Cap-189, step d (1 g, 5.31 mmol) in 20 mL of CH₂Cl₂ was added silver oxide (3.8 g), p-Ts-Cl (1.215 g, 6.38 mmol) and KI (0.176 g, 1.063 mmol). The resulting solution was stirred at room temperature for 3 days. The mixture was then filtered and the filtrate was concentrated. The crude product was purified by flash chromatography (silica gel, 60% EtOAc/Hex) to afford Cap-189, step e (0.79 g) as clear oil. LC/MS: Anal. Calcd. for [M+Na]⁺ C₁₆H₂₂NaO₆S 365.10. Found 365.22. ¹H NMR (400 MHz, CDCl₃) δ ppm 7.80 (2H, d, J=8.28 Hz), 7.36 (2H, d, J=8.03 Hz), 4.11-4.17 (1H, m), 3.85-4.06 (5H, m), 3.64-3.71 (1H, m), 3.55-3.63 (1H, m), 2.47 (3H, s), 2.32-2.43 (1H, m), 2.15-2.27 (1H, m), 1.70-1.89 (2H, m), 1.52-1.66 (1H, m), 1.35-1.47 (1H, m).

Cap-189, Step f

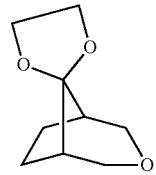 [SMILES: C1COC2(O1)C1CCC2COC1]

To a solution of Cap-189, step e (2.2 g, 6.43 mmol) in 40 mL of MeOH was added potassium carbonate (1.776 g, 12.85 mmol). The resulting mixture was stirred at room temperature overnight. The mixture was then diluted with water and EtOAc. The two layers were separated. The aqueous layer was extracted with EtOAc (2×). The combined organic layers were washed with brine, dried with MgSO₄ and concentrated. The crude product was purified by flash chromatography (silica gel, 0-15% EtOAc/Hex) to afford Cap-189, step f (0.89 g, 5.23 mmol, 81%) as clear oil. ¹H NMR (400 MHz, CDCl₃) δ ppm 3.89-4.02 (6H, m), 3.58 (2H, dd, J=10.79, 2.51 Hz), 1.69-1.89 (6H, m).

Cap-189, Step g

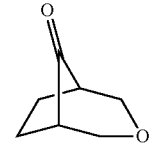

To the solution of Cap-189, step f (890 mg, 5.23 mmol) in 15 mL of THF was added HCl (15 mL, 45.0 mmol) (3 M aqueous). The resulting mixture was stirred at room temperature overnight. The mixture was then diluted with ether and the two layers were separated. The aqueous phase was extracted with Ether (2×) and the combined organic layers were dried with MgSO$_4$ and concentrated to afford Cap-189, step g (0.95 g, containing some residual solvents). The product was used in the next step without purification. $^1$H NMR (500 MHz, CDCl$_3$) δ ppm 3.95-4.00 (2H, m), 3.85 (2H, d, J=10.68 Hz), 2.21-2.28 (2H, m), 1.99-2.04 (2H, m), 1.90-1.96 (2H, m).

Cap-189, Step h (Enantiomer-1&-2)

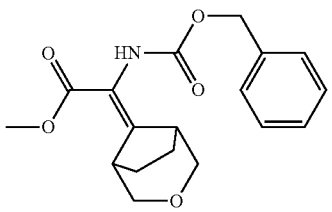 [SMILES: COC(=O)C(NC(=O)OCc1ccccc1)=C1C2CCC1COC2]

To a solution of (+/−)-benzyloxycarbonyl-α-phosphonoglycine trimethyl ester (1733 mg, 5.23 mmol) in 6 mL of THF at −20° C. was added 1,1,3,3-tetramethylguanidine (0.723 mL, 5.75 mmol). The resultant light yellow mixture was stirred at −20° C. for 1 hour, and Cap-189, step g (660 mg, 5.23 mmol) in 3 mL of THF was added and mixture was then stirred at room temperature for 3 days. The reaction mixture was then diluted with EtOAc, washed with a 0.1 N HCl aq. solution. The aqueous layer was extracted with EtOAc (2×) and the combined organic layers were dried with MgSO$_4$ and concentrated. The crude product was purified by flash chromatography (silica gel, 0-4% EtOAc/CH$_2$Cl$_2$) to afford 960 mg of the racemic mixture. The mixture was separated by chiral HPLC (CHIRALPAK® AD column, 21×250 mm, 10 um) eluting with 90% 0.1% diethylamine/Heptane-10% EtOH at 15 mL/min to afford Cap-189, step h (enantiomer-1; 300 mg) and Cap-189, step h (enantiomer-2; 310 mg) as white solids. Cap-189, step h (enantiomer-1): LC/MS: Anal. Calcd. for [M+H]$^+$ C$_{18}$H$_{22}$NO$_5$ 332.15. Found 332.2. $^1$H NMR (500 MHz, CDCl$_3$) δ ppm 7.29-7.41 (5H, m), 6.00 (1H, br. s.), 5.13 (2H, s), 3.63-3.87 (8H, m), 2.84 (1H, br. s.), 1.84-2.02 (2H, m), 1.63-1.84 (2H, m). Cap-189, step h (enantiomer-2): LC/MS: Anal. Calcd. for [M+H]$^+$ C$_{18}$H$_{22}$NO$_5$ 332.15. Found 332.2.

Cap-189, Step i

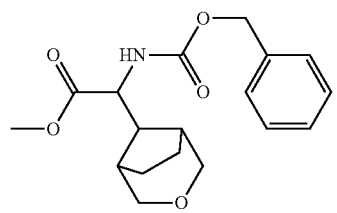 [SMILES: COC(=O)C(NC(=O)OCc1ccccc1)C1C2CCC1COC2]

N$_2$ was bubbled through a solution of Cap-189, step h (enantiomer-2; 290 mg, 0.875 mmol) in 10 mL of MeOH in a 500 mL hydrogenation bottle for 30 mins. To the solution was added (S,S)-Me-BPE-Rh (9.74 mg, 0.018 mmol), and the mixture was then hydrogenated at 60 psi for 6 days. The mixture was concentrated, and chiral analytical HPLC (CHIRALPAK® OJ column) indicated that there were a small amount of remaining starting material and one major product. The residue was then separated by chiral HPLC (CHIRALPAK® OJ column, 21×250 mm, 10 um) eluting with 70% 0.1% diethylamine/Heptane-30% EtOH at 15 mL/min to afford Cap-189, step i, (150 mg) as clear oil. LC/MS: Anal. Calcd. for [M+H]$^+$ C$_{18}$H$_{24}$NO$_5$ 334.17. Found 334.39. $^1$H NMR (500 MHz, CDCl$_3$) δ ppm 7.28-7.41 (5H, m), 5.12-5.18 (1H, m), 5.09 (2H, s), 4.05 (1H, t, J=10.07 Hz), 3.75 (3H, s), 3.60-3.72 (2H, m), 3.41-3.50 (2H, m), 2.10 (1H, br. s.), 1.72-1.99 (6H, m).

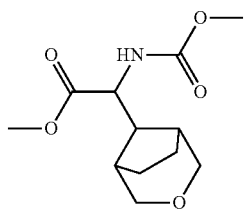

To a solution of Cap-189, step i (150 mg, 0.450 mmol) in 10 mL of MeOH in a hydrogenation bottle were added dimethyl dicarbonate (0.072 mL, 0.675 mmol) and 10% Pd/C (23.94 mg, 0.022 mmol) under a cover of nitrogen cover. The mixture was then hydrogenated on Parr-shaker at 45 psi overnight. The mixture was filtered and the filtrate was concentrated to afford Cap-189, step j (110 mg) as a clear oil. LC/MS: Anal. Calcd. for [M+H]$^+$ C$_{12}$H$_{20}$NO$_5$ 258.13. Found 258.19. $^1$H NMR (500 MHz, CDCl$_3$) δ ppm 5.08 (1H, d, J=9.16 Hz), 4.03 (1H, t, J=10.07 Hz), 3.75 (3H, s), 3.60-3.72 (5H, m), 3.46 (2H, t, J=10.38 Hz), 2.11 (1H, br. s.), 1.72-1.99 (6H, m).

Cap-189

To a mixture of Cap-189, step j (110 mg, 0.428 mmol) in 2 mL of THF and 1 mL of water was added LiOH (0.641 mL, 1.283 mmol) (2 N aq.). The resulting mixture was stirred at room temperature overnight. The mixture was neutralized with a 1 N HCl aq. solution and extracted with EtOAc (3×). The combined organic layers were dried with MgSO$_4$ and concentrated to afford Cap-189 (100 mg) as a white solid. LC/MS: Anal. Calcd. for [M+Na]$^+$ C$_{11}$H$_{17}$NNaO$_5$ 266.10. Found 266.21. $^1$H NMR (500 MHz, CDCl$_3$) δ ppm 5.10 (1H, d, J=9.16 Hz), 4.02 (1H, t, J=10.07 Hz), 3.62-3.78 (5H, m), 3.49 (2H, d, J=10.68 Hz), 2.07-2.22 (2H, m), 1.72-1.98 (6H, m).

Cap-190 (Diastereomeric Mixture)

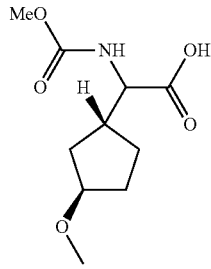

Cap-190, Step a

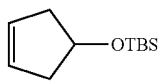 [SMILES: CC(C)(C)[Si](C)(C)OC1CC=CC1]

To a mixture of cyclopent-3-enol (2.93 g, 34.8 mmol) and imidazole (5.22 g, 77 mmol) in 30 mL of DMF at 0° C. was added t-butyldimethylchlorosilane (6.30 g, 41.8 mmol). The resulting colorless mixture was stirred at room temperature overnight. Hexanes and water were then added to the mixture and the two layers were separated. The aqueous layer was extracted with EtOAc (2×) and the combined organic layers were washed with brine, dried with MgSO$_4$ and concentrated. The crude product was purified by flash chromatography (silica gel, 2% EtOAc/Hex) to afford Cap-190, step a (6.3 g) as a clear oil. $^1$H NMR (500 MHz, CDCl$_3$) δ ppm 5.65 (2H, s), 4.49-4.56 (1H, m), 2.56 (2H, dd, J=15.26, 7.02 Hz), 2.27 (2H, dd, J=15.26, 3.36 Hz), 0.88 (9H, s), 0.06 (6H, s).

Cap-190, Step b

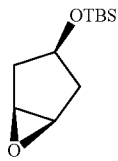 [SMILES: CC(C)(C)[Si](C)(C)O[C@@H]1C[C@@H]2O[C@@H]2C1]

To a solution of Cap-190, step a (2.3 g, 11.59 mmol) in 40 mL of CH$_2$Cl$_2$ at 0° C. was added m-CPBA (5.60 g, 16.23 mmol) in 5 portions. The reaction mixture was stirred at room temperature overnight. Hexanes and water were then added to the mixture and the two layers were separated. The organic layer was washed with 50 mL aq. 10% NaHSO$_3$ and brine, dried with MgSO$_4$ and concentrated. The crude product was purified by flash chromatography (silica gel, 3%-6% EtOAc/Hex) to afford Cap-190, step b (1.42 g) and its trans diastereomer (0.53 g) as clear oils. Cap-190, step b (cis): $^1$H NMR (400 MHz, CDCl$_3$) δ ppm 4.39-4.47 (1H, m), 3.47 (2H, s), 2.01-2.10 (2H, m), 1.93-2.00 (2H, m), 0.88 (9H, s), 0.04 (6H, s). Cap-190, step b (trans): $^1$H NMR (400 MHz, CDCl$_3$) δ ppm 4.04-4.14 (1H, m), 3.47 (2H, s), 2.41 (2H, dd, J=14.05, 7.28 Hz), 1.61 (2H, dd, J=14.18, 6.90 Hz), 0.87 (9H, s), 0.03 (6H, s).

Cap-190, Step c

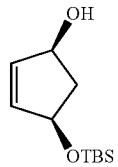

To a solution of (S)-1,2'-methylenedipyrrolidine (0.831 g, 5.39 mmol) in 15 mL of benzene at 0° C. was added dropwise n-butyllithium (4.90 mL, 4.90 mmol) (1 M in hexane). The solution turned bright yellow. The mixture was stirred at 0° C. for 30 min. Cap-190, step b (cis-isomer; 0.7 g, 3.27 mmol) in 10 mL of benzene was then added and the resulting mixture was stirred at 0° C. for 3 hours. EtOAc and sat. NH$_4$Cl aq. solution were added into the mixture, and the two layers were separated. The organic layer was washed with water and brine, dried with MgSO$_4$ and concentrated. The crude product was purified by flash chromatography (silica gel, 15% EtOAc/Hex) to afford Cap-190, step c (400 mg) as a light yellow oil. $^1$H NMR (500 MHz, CDCl$_3$) δ ppm 5.84-5.98 (2H, m), 4.53-4.69 (2H, m), 2.63-2.73 (1H, m), 1.51 (1H, dt, J=13.73, 4.43 Hz), 0.89 (9H, s), 0.08 (6H, s).

Cap-190, Step d

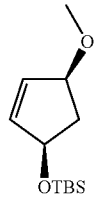

To a solution of Cap-190, step c (400 mg, 1.866 mmol), MeI (1.866 mL, 3.73 mmol) (2 M in t-butyl methyl ether) in 5 mL of THF at 0° C. was added NaH (112 mg, 2.80 mmol) (60% in mineral oil). The resulting mixture was allowed to warm up to room temperature and stirred at room temperature overnight. The reaction was then quenched with water and extracted with EtOAc (3×). The combined organic layers were washed with brine, dried with MgSO$_4$ and concentrated. The crude product was purified by flash chromatography (silica gel, 5% EtOAc/Hex) to afford Cap-190, step d (370 mg) as light yellow oil. $^1$H NMR (500 MHz, CDCl$_3$) δ ppm 5.92-5.96 (1H, m), 5.87-5.91 (1H, m), 4.64-4.69 (1H, m), 4.23-4.28 (1H, m), 3.32 (3H, s), 2.62-2.69 (1H, m), 1.54 (1H, dt, J=13.12, 5.49 Hz), 0.89 (9H, s), 0.07 (5H, d, J=1.83 Hz).

Cap-190, Step e

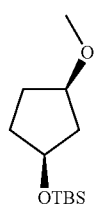

To a solution of Cap-190, step d (400 mg, 1.751 mmol) in 10 mL of EtOAc in a hydrogenation bottle was added platinum (IV) oxide (50 mg, 0.220 mmol). The resulting mixture was hydrogenated at 50 psi on Parr shaker for 2 hours. The mixture was then filtered through CELITE®, and the filtrate was concentrated to afford Cap-190, step e (400 mg) as a clear oil. LC/MS: Anal. Calcd. for [M+H]$^+$ C$_{12}$H$_{27}$O$_2$Si 231.18. Found 231.3. $^1$H NMR (500 MHz, CDCl$_3$) δ ppm 4.10-4.17 (1H, m), 3.65-3.74 (1H, m), 3.27 (3H, s), 1.43-1.80 (6H, m), 0.90 (9H, s), 0.09 (6H, s).

Cap-190, Step f

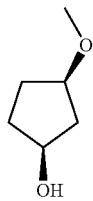

To a solution of Cap-190, step e (400 mg, 1.736 mmol) in 5 mL of THF was added TBAF (3.65 mL, 3.65 mmol) (1 N in THF). The color of the mixture turned brown after several min., and it was stirred at room temperature overnight. The volatile component was removed under vacuum, and the residue was purified by flash chromatography (silica gel, 0-25% EtOAc/Hex) to afford Cap-190, step f (105 mg) as light yellow oil. $^1$H NMR (500 MHz, CDCl$_3$) δ ppm 4.25 (1H, br. s.), 3.84-3.92 (1H, m), 3.29 (3H, s), 1.67-2.02 (6H, m).

Cap-190

Cap-190 was then synthesized from Cap-190, step f according to the procedure described for Cap-182. LC/MS: Anal. Calcd. for [M+Na]$^+$ C$_{10}$H$_{17}$NNaO$_5$ 254.10. Found 254.3. $^1$H NMR (500 MHz, CDCl$_3$) δ ppm 5.25 (1H, d, J=8.55 Hz), 4.27-4.41 (1H, m), 3.81-3.90 (1H, m), 3.69 (3H, s), 3.26 (3H, s), 2.46-2.58 (1H, m), 1.76-1.99 (3H, m), 1.64-1.73 (1H, m), 1.40-1.58 (1H, m), 1.22-1.38 (1H, m).

Cap-191 (Enantiomer-1)

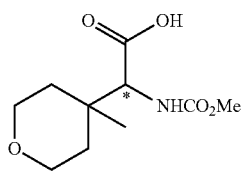

Cap-191, Step a

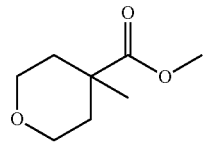

To a solution of diisopropylamine (3 ml, 21.05 mmol) in THF (3 ml) at −78° C. under nitrogen was added n-butyl lithium (2.5 M in hexanes; 8.5 ml, 21.25 mmol). The reaction was stirred at −78° C. for 10 min then brought up to 0° C. for 25 min. The reaction was cooled down again to −78° C., methyl tetrahydro-2H-pyran-4-carboxylate (3 g, 20.81 mmol) in THF (3 ml) was added. The reaction was stirred at −78° C. for 15 min then brought up to 0° C. for 30 min. The reaction was cooled down to −78° C., methyl iodide (1.301 ml, 20.81 mmol) was added. After the addition, the cold bath was removed and the reaction was allowed to slowly warm up to ~25° C. and stirred for 22 h. Ethyl acetate and aqueous HCl (0.1N) were added, and the organic layer was separated and washed with brine and dried (MgSO4), filtered, and concentrated in vacuo. The residue was loaded on a Thomson's silica gel cartridge eluting with 10% ethyl acetate/hexanes to afford a light yellow oil (2.83 g). $^1$H NMR (400 MHz, DMSO-d$_6$) δ ppm 3.73-3.66 (m, 2H), 3.66 (s, 3H), 3.40-3.30 (m, 2H), 1.95-1.93 (dm, 1H), 1.92-1.90 (dm, 1H), 1.43 (ddd, J=13.74, 9.72, 3.89, 2H), 1.18 (s, 3H).

Cap-191, Step b

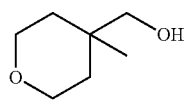

To a solution of Cap 191, step a (3 g, 18.96 mmol) in toluene (190 ml) at −78° C. under nitrogen was added diisobutylaluminum hydride (1.5M in toluene; 26.5 ml, 39.8 mmol) dropwise. The reaction was continued to stir at −78° C. for 1.5 h., and the bath was removed and was stirred for 18 h. The reaction was quenched with MeOH (20 mL). HCl (1M, 150 mL) was added and the mixture was extracted with EtOAc (4×40 mL). The combined organic phases were washed with brine, dried (MgSO$_4$), filtered, and concentrated in vacuo. The residue was purified with flash chromatography (silica gel; 40% ethyl acetate/hexanes) to afford a colorless oil (1.36 g). $^1$H NMR (400 MHz, CDCl$_3$) δ ppm 3.77 (dt, J=11.73, 4.55, 2H), 3.69-3.60 (m, 2H), 3.42 (s, 2H), 1.71-1.40 (bs, 1H) 1.59 (ddd, J=13.74, 9.72, 4.39, 2H), 1.35-1.31 (m, 1H), 1.31-1.27 (m, 1H), 1.06 (s, 3H).

Cap-191, Step c

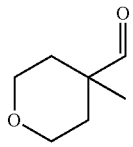

To a solution of DMSO (5.9 ml, 83 mmol) in CH$_2$Cl$_2$ (85 ml) at −78° C. under nitrogen was added oxalyl chloride (3.8 ml, 43.4 mmol) and stirred for 40 min. A solution of Cap 191, step b (4.25 g, 32.6 mmol) in CH$_2$Cl$_2$ (42.5 ml) was then added. The reaction was continued to be stirred at −78° C. under nitrogen for 2 h. The reaction was quenched with cold 20% K$_2$HPO$_4$ (aq) (10 mL) and water. The mixture was stirred at ~25° C. for 15 min, diluted with diethyl ether (50 mL) and the layers were separated. The aqueous layer was extracted with diethyl ether (2×50 mL). The combined organic layers were washed with brine, dried (MgSO$_4$), filtered, and concentrated in vacuo. The residue was taken up in CH$_2$Cl$_2$ (4 mL) and purified with flash chromatography (silica gel, eluting with CH$_2$Cl$_2$) to afford a colorless oil (2.1 g). $^1$H NMR (400 MHz, CDCl$_3$) δ ppm 9.49 (s. 1H), 3.80 (dt, J=11.98, 4.67, 2H), 3.53 (ddd, J=12.05, 9.41, 2.89, 2H), 1.98

(ddd, J=4.71, 3.20, 1.38, 1H), 1.94 (ddd, J=4.71, 3.20, 1.38, 1H), 1.53 (ddd, J=13.87, 9.60, 4.14, 2H), 1.12 (s, 3H).

Cap-191, Step d

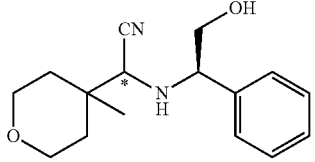 [SMILES: CC1(C(C#N)N[C@@H](CO)c2ccccc2)CCOCC1]

To a solution of Cap 191c (2.5 g, 19.51 mmol) in CHCl$_3$ (20 ml) under nitrogen at ~25° C. was added (R)-2-amino-2-phenylethanol (2.94 g, 21.46 mmol) and stirred for 5 h. The reaction was cooled to 0° C., trimethylsilyl cyanide (3.8 ml, 30.4 mmol) was added dropwise. The cold bath was removed and the reaction was allowed to stir at ~25° C. under nitrogen for 15.5 h. The reaction was treated with 3N HCl (20 mL) and water (20 mL), and the product was extracted with CHCl$_3$ (3×50 mL). The combined organic layers were dried (NaSO$_4$), filtered, and concentrated in vacuo. The residue was purified with flash chromatography (silica gel; 40% ethyl acetate/hexanes) to afford two diastereomers: Cap 191, step d1 (diastereomer 1) as a colorless oil which solidified into a white solid upon standing (3 g). $^1$H NMR (400 MHz, DMSO-d$_6$) δ ppm 7.42-7.26 (m, 5H), 5.21 (t, J=5.77, 1H), 3.87 (dd, J=8.53, 4.52, 1H), 3.61-3.53 (m, 1H), 3.53-3.37 (m, 5H), 3.10 (d, J=13.05, 1H), 2.65 (d, J=13.05, 1H), 1.64-1.55 (m, 1H), 1.55-1.46 (m, 1H), 1.46-1.39 (m, 1H), 1.31-1.23 (m, 1H), 1.11 (s, 3H). LC/MS: Anal. Calcd. for [M+H]$^+$ C$_{16}$H$_{23}$N$_2$O$_2$: 275.18. Found 275.20. Cap 191, step d2 (diastereomer 2) as a light yellow oil (0.5 g). $^1$H NMR (400 MHz, DMSO-d$_6$) δ ppm 7.44-7.21 (m, 5H), 4.82 (t, J=5.40, 1H), 3.82-3.73 (m, 1H), 3.73-3.61 (m, 3H), 3.61-3.37 (m, 5H), 2.71 (dd, J=9.29, 4.77, 1H), 1.72-1.55 (m, 2H), 1.48-1.37 (m, 1H), 1.35-1.25 (m, 1H), 1.10 (s, 3H). LC/MS: Anal. Calcd. for [M+H]$^+$ C$_{16}$H$_{23}$N$_2$O$_2$: 275.18. Found 275.20.

Cap-191, Step e

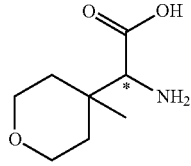

To a solution of Cap 191, step d2 (diastereomer 2) (0.4472 g, 1.630 mmol) in CH$_2$Cl$_2$ (11 ml) and MeOH (5.50 ml) at 0° C. under nitrogen was added lead tetraacetate (1.445 g, 3.26 mmol). The reaction was stirred for 1.5 h, the cold bath was removed and stirring was continued for 20 h. The reaction was treated with a phosphate buffer (pH=7; 6 mL) and stirred for 45 min. The reaction was filtered over CELITE®, washed with CH$_2$Cl$_2$ and the layers were separated. The aqueous layer was extracted with CH$_2$Cl$_2$ (3×25 mL), and the combined organic layers was washed with brine, dried (MgSO$_4$), filtered and concentrated in vacuo. The residue was purified with flash chromatography (silica gel; 15% ethyl acetate/hexanes) to afford the imine intermediate as a colorless oil (181.2 mg). $^1$H NMR (400 MHz, DMSO-d$_6$) δ ppm 8.55 (d, J=1.00, 1H), 7.89-7.81 (m, 2H), 7.61-7.46 (m, 3H), 4.80 (d, J=1.00, 1H), 3.74 (tt, J=11.80, 4.02, 2H), 3.62-3.46 (m, 2H), 1.79-1.62 (m, 2H), 1.46-1.30 (m, 2H), 1.15 (s, 3H).

The imine intermediate was taken up in 6N HCl (10 mL) and heated at 90° C. for 10 days. The reaction was removed from the heat, allowed to cool to room temperature and extracted with ethyl acetate (3×25 mL). The aqueous layer was concentrated in vacuo to afford an off-white solid. The solid was taken up in MeOH and loaded on a pre-conditioned MCX (6 g) cartridge, washed with MeOH followed by elution with 2N NH$_3$/MeOH solution and concentrated in vacuo to afford an off-white solid (79.8 mg). $^1$H NMR (400 MHz, DMSO-d$_6$) δ ppm 14.33-13.51 (bs, 1H), 8.30 (bs, 3H), 3.82-3.75 (m, 1H), 3.70 (dt, J=11.80, 4.02, 2H), 3.58-3.43 (m, 2H), 1.76-1.60 (m, 2H), 1.47-1.36 (m, 1H), 1.36-1.27 (m, 1H), 1.08 (s, 3H). LC/MS: Anal. Calcd. for [M+H]$^+$ C$_8$H$_{16}$NO$_3$: 174.11. Found 174.19.

Cap 191 (Enantiomer-1)

To a solution of Cap 191, step e (0.0669 g, 0.386 mmol) and sodium carbonate (0.020 g, 0.193 mmol) in sodium hydroxide (1M aq.; 0.4 ml, 0.40 mmol) at 0° C. was added methyl chloroformate (0.035 ml, 0.453 mmol) dropwise. The reaction was removed from the cold bath and allowed to stir at ~25° C. for 3 h. The reaction was washed with diethyl ether (3×20 mL). The aqueous layer was acidified with 12 N HCl (pH ~1-2), and extracted with ethyl acetate (2×20 mL). The combined organic layers were dried (MgSO4), filtered, and concentrated in vacuo to afford Cap 191 as a colorless film (66.8 mg). $^1$H NMR (400 MHz, DMSO-d$_6$) δ ppm 13.10-12.37 (bs, 1H), 7.37 (d, J=9.04, 1H), 4.02 (d, J=9.29, 1H), 3.72-3.57 (m, 2H), 3.56 (s, 3H), 3.54-3.44 (m, 2H), 1.65 (ddd, J=13.61, 9.72, 4.27, 1H), 1.53 (ddd, J=13.68, 9.66, 4.27, 1H), 1.41-1.31 (m, 1H), 1.31-1.22 (m, 1H), 1.00 (s, 3H). LC/MS: Anal. Calcd. for [M+Na]$^+$ C$_{10}$H$_{17}$NO$_5$Na: 254.10. Found 254.11.

Cap-192 (Enantiomer-2)

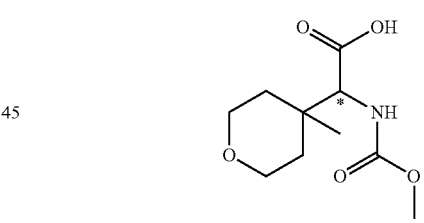

Cap 192 (enantiomer-2) was prepared from Cap 191, step d1 according to the procedure described for the preparation of its enantiomer Cap 191.

Biological Activity

An HCV Replicon assay was utilized in the present disclosure, and was prepared, conducted and validated as described in commonly owned PCT/US2006/022197 and in O'Boyle et al., *Antimicrob. Agents Chemother.*, 49(4):1346-1353 (April 2005). Assay methods incorporating luciferase reporters have also been used as described (Apath.com).

HCV-neo replicon cells and replicon cells containing mutations in the NS5A region were used to test the currently described family of compounds. The compounds were determined to have more than 10-fold less inhibitory activity on cells containing mutations than wild-type cells. Thus, the compounds of the present disclosure can be effective in inhibiting the function of the HCV NS5A protein and are understood to be as effective in combinations as previously described in application PCT/US2006/022197 and commonly owned WO 04/014852. Further, the compounds of the present disclosure can be effective against the HCV 1b genotype. It should also be understood that the compounds of the present disclosure can inhibit multiple genotypes of HCV. Table 2 shows the $EC_{50}$ (Effective 50% inhibitory concentration) values of representative compounds of the present disclosure against the HCV 1b genotype. In one embodiment compounds of the present disclosure are inhibitory versus 1a, 1b, 2a, 2b, 3a, 4a, and 5a genotypes. $EC_{50}$ values against HCV 1b are as follows: A (>10 μM); B (10 nM-10 μM); C (1.0 nM-9.999 nM); D (<1.0 nM). The compounds of the present disclosure may inhibit HCV by mechanisms in addition to or other than NS5A inhibition. In one embodiment the compounds of the present disclosure inhibit HCV replicon and in another embodiment the compounds of the present disclosure inhibit NS5A.

TABLE 2

| Example | 1b $EC_{50}$ (in μM or range) | Name |
|---|---|---|
| 1 | D | Methyl ((1S)-2-((2S)-2-(4-(5'-(2-((2S)-1-(N-(methoxycarbonyl)-L-alanyl)-2-pyrrolidinyl)-1H-imidazol-4-yl)-2,2'-bithiophen-5-yl)-1H-imidazol-2-yl)-1-pyrrolidinyl)-1-methyl-2-oxoethyl)carbamate |
| 2 | D | Methyl ((1S)-3-methoxy-1-(((2S)-2-(4-(5'-(2-((2S)-1-(N-(methoxycarbonyl)-O-methyl-L-homoseryl)-2-pyrrolidinyl)-1H-imidazol-4-yl)-2,2'-bithiophen-5-yl)-1H-imidazol-2-yl)-1-pyrrolidinyl)carbonyl)propyl) carbamate |
| 3 | B | Methyl ((1R)-1-(((2S)-2-(4-(5'-(2-((2S)-1-((2R)-2-((methoxycarbonyl)amino)-3-methylbutanoyl)-2-pyrrolidinyl)-1H-imidazol-4-yl)-2,2'-bithiophen-5-yl)-1H-imidazol-2-yl)-1-pyrrolidinyl)carbonyl)-2-methylpropyl)carbamate |
| 4 | D | Dimethyl (2,2'-bithiene-5,5'-diylbis(1H-imidazole-4,2-diyl(2S)-2,1-pyrrolidinediyl((1R)-2-oxo-1-phenyl-2,1-ethanediyl)))biscarbamate |
| 5 | D | (1R,1'R)-2,2'-(2,2'-Bithiene-5,5'-diylbis(1H-imidazole-4,2-diyl(2S)-2,1-pyrrolidinediyl))bis(N,N-dimethyl-2-oxo-1-phenylethanamine) |
| 6 | 0.000003 | Methyl ((1S)-1-(((2S)-2-(4-(5'-(2-((2S)-1-((2S)-2-((methoxycarbonyl)amino)-3-methylbutanoyl)-2-pyrrolidinyl)-1H-imidazol-4-yl)-2,2'-bithiophen-5-yl)-1H-imidazol-2-yl)-1-pyrrolidinyl)carbonyl)-2-methylpropyl)carbamate |
| 7 | D | Dimethyl (2,2'-bithiene-5,5'-diylbis(1H-imidazole-4,2-diyl(2S)-2,1-pyrrolidinediyl((1S)-1-cyclopropyl-2-oxo-2,1-ethanediyl)))biscarbamate |
| 8 | D | (1R,1'R)-2,2'-(5,5'-Bi-1,3-thiazole-2,2'-diylbis(1H-imidazole-4,2-diyl(2S)-2,1-pyrrolidinediyl))bis(N,N-dimethyl-2-oxo-1-phenylethanamine) |
| 9 | D | Dimethyl (5,5'-bi-1,3-thiazole-2,2'-diylbis(1H-imidazole-4,2-diyl(2S)-2,1-pyrrolidinediyl((1R)-2-oxo-1-phenyl-2,1-ethanediyl)))biscarbamate |
| 10 | C | Methyl ((1S)-1-(((2S)-2-(4-(2'-(2-((2S)-1-((2S)-2-((methoxycarbonyl)amino)-3-methylbutanoyl)-2-pyrrolidinyl)-1H-imidazol-4-yl)-5,5'-bi-1,3-thiazol-2-yl)-1H-imidazol-2-yl)-1-pyrrolidinyl)carbonyl)-2-methylpropyl)carbamate |
| 11 | 5.86 | Methyl ((1R)-1-(((2S)-2-(4-(2'-(2-((2S)-1-((2R)-2-((methoxycarbonyl)amino)-3-methylbutanoyl)-2-pyrrolidinyl)-1H-imidazol-4-yl)-5,5'-bi-1,3-thiazol-2-yl)-1H-imidazol-2-yl)-1-pyrrolidinyl)carbonyl)-2-methylpropyl)carbamate |
| 12 | B | Methyl ((1S,2R)-2-methoxy-1-(((2S)-2-(4-(2'-(2-((2S)-1-(N-(methoxycarbonyl)-O-methyl-L-threonyl)-2-pyrrolidinyl)-1H-imidazol-4-yl)-5,5'-bi-1,3-thiazol-2-yl)-1H-imidazol-2-yl)-1-pyrrolidinyl)carbonyl)propyl) carbamate |
| 13 | B | Methyl ((1S)-3-methoxy-1-(((2S)-2-(4-(2'-(2-((2S)-1-(N-(methoxycarbonyl)-O-methyl-L-homoseryl)-2-pyrrolidinyl)-1H-imidazol-4-yl)-5,5'-bi-1,3-thiazol-2-yl)-1H-imidazol-2-yl)-1-pyrrolidinyl)carbonyl)propyl) carbamate |
| 14 | D | Methyl ((1S)-1-(((2S)-2-(4-(5'-(2-((2S)-1-((2S)-2-((methoxycarbonyl)amino)-3-methylbutanoyl)-2-pyrrolidinyl)-1H-imidazol-4-yl)-2,2'-bi-1,3-thiazol-5-yl)-1H-imidazol-2-yl)-1-pyrrolidinyl)carbonyl)-2-methylpropyl)carbamate |

TABLE 2-continued

| Example | 1b EC$_{50}$ (in μM or range) | Name |
|---|---|---|
| 15 | 0.00238 | Methyl ((1S)-3-methoxy-1-(((2S)-2-(4-(5'-(2-((2S)-1-(N-(methoxycarbonyl)-O-methyl-L-homoseryl)-2-pyrrolidinyl)-1H-imidazol-4-yl)-2,2'-bi-1,3-thiazol-5-yl)-1H-imidazol-2-yl)-1-pyrrolidinyl)carbonyl)propyl)carbamate |
| 16 | D | Dimethyl (2,2'-bi-1,3-thiazole-5,5'-diylbis(1H-imidazole-4,2-diyl(2S)-2,1-pyrrolidinediyl((1R)-2-oxo-1-phenyl-2,1-ethanediyl)))biscarbamate |
| 17 | D | (1R,1'R)-2,2'-(2,2'-Bi-1,3-thiazole-5,5'-diylbis(1H-imidazole-4,2-diyl(2S)-2,1-pyrrolidinediyl))bis(N,N-dimethyl-2-oxo-1-phenylethanamine) |
| 18 | B | Methyl ((1R)-1-(((2S)-2-(4-(5'-(2-((2S)-1-((2R)-2-((methoxycarbonyl)amino)-3-methylbutanoyl)-2-pyrrolidinyl)-1H-imidazol-4-yl)-2,2'-bi-1,3-thiazol-5-yl)-1H-imidazol-2-yl)-1-pyrrolidinyl)carbonyl)-2-methylpropyl)carbamate |
| 19 | C | Methyl ((1S,2R)-2-methoxy-1-(((2S)-2-(4-(5'-(2-((2S)-1-(N-(methoxycarbonyl)-O-methyl-L-threonyl)-2-pyrrolidinyl)-1H-imidazol-4-yl)-2,2'-bi-1,3-thiazol-5-yl)-1H-imidazol-2-yl)-1-pyrrolidinyl)carbonyl)propyl)carbamate |
| 20 | C | Methyl ((1S)-2-((2S)-2-(4-(5'-(2-((2S)-1-(N-(methoxycarbonyl)-L-alanyl)-2-pyrrolidinyl)-1H-imidazol-4-yl)-2,2'-bi-1,3-thiazol-5-yl)-1H-imidazol-2-yl)-1-pyrrolidinyl)-1-methyl-2-oxoethyl)carbamate |
| 21 | D | Methyl ((1R)-2-((2S)-2-(4-(3-(2-(2-((2S)-1-((2R)-2-((methoxycarbonyl)amino)-2-phenylacetyl)-2-pyrrolidinyl)-1H-imidazol-4-yl)-1,3-oxazol-5-yl)phenyl)-1H-imidazol-2-yl)-1-pyrrolidinyl)-2-oxo-1-phenylethyl)carbamate |
| 22 | C | (1R)-2-((2S)-2-(4-(3-(2-(2-((2S)-1-((2R)-2-(Dimethylamino)-2-phenylacetyl)-2-pyrrolidinyl)-1H-imidazol-4-yl)-1,3-oxazol-5-yl)phenyl)-1H-imidazol-2-yl)-1-pyrrolidinyl)-N,N-dimethyl-2-oxo-1-phenylethanamine |
| 23 | C | Methyl ((1R)-2-((2S)-2-(4-(5-(3-(2-((1S)-1-(((2R)-2-((methoxycarbonyl)amino)-2-phenylacetyl)amino)ethyl)-1H-imidazol-4-yl)phenyl)-1,3-oxazol-2-yl)-1H-imidazol-2-yl)-1-pyrrolidinyl)-2-oxo-1-phenylethyl)carbamate |
| 24 | 0.001812 | (2R)-2-(dimethylamino)-N-((1S)-1-(4-(3-(2-(2-((2S)-1-((2R)-2-(dimethylamino)-2-phenylacetyl)-2-pyrrolidinyl)-1H-imidazol-4-yl)-1,3-oxazol-5-yl)phenyl)-1H-imidazol-2-yl)ethyl)-2-phenylacetamide |
| 25 | C | Methyl ((1R)-2-((2S)-2-(4-(4-(2-(2-((2S)-1-((2R)-2-((methoxycarbonyl)amino)-2-phenylacetyl)-2-pyrrolidinyl)-1H-imidazol-4-yl)-1,3-oxazol-5-yl)phenyl)-1H-imidazol-2-yl)-1-pyrrolidinyl)-2-oxo-1-phenylethyl)carbamate |
| 26 | C | (1R)-2-((2S)-2-(4-(4-(2-(2-((2S)-1-((2R)-2-(dimethylamino)-2-phenylacetyl)-2-pyrrolidinyl)-1H-imidazol-4-yl)-1,3-oxazol-5-yl)phenyl)-1H-imidazol-2-yl)-1-pyrrolidinyl)-N,N-dimethyl-2-oxo-1-phenylethanamine |
| 27 | 0.006714 | Benzyl (2S)-2-(4-(5-(4-(2-((2S)-1-((2R)-2-((methoxycarbonyl)amino)-2-phenylacetyl)-2-pyrrolidinyl)-1H-imidazol-4-yl)phenyl)-1,3-oxazol-2-yl)-1H-imidazol-2-yl)-1-pyrrolidinecarboxylate |
| 28 | C | Benzyl (2S)-2-(4-(5-(4-(2-((2S)-1-((2R)-2-((methoxycarbonyl)amino)-2-phenylacetyl)-2-pyrrolidinyl)-1H-imidazol-4-yl)phenyl)-1,3-oxazol-2-yl)-1H-imidazol-2-yl)-1-pyrrolidinecarboxylate |
| 29 | D | Dimethyl (1R,1'R)-2,2'-((2S,2'S)-2,2'-(5,5'-(buta-1,3-diyne-1,4-diyl)bis(1H-imidazole-5,2-diyl))bis(pyrrolidine-2,1-diyl))bis(2-oxo-1-phenylethane-2,1-diyl)dicarbamate |
| 30 | D | (2R,2'R)-1,1'-((2S,2'S)-2,2'-(5,5'-(Buta-1,3-diyne-1,4-diyl)bis(1H-imidazole-5,2-diyl))bis(pyrrolidine-2,1-diyl))bis(2-phenyl-2-(piperidin-1-yl)ethanone) |
| 31 | D | Dimethyl (2S,2'S)-1,1'-((2S,2'S)-2,2'-(5,5'-(buta-1,3-diyne-1,4-diyl)bis(1H-imidazole-5,2-diyl))bis(pyrrolidine-2,1-diyl))bis(3-methyl-1-oxobutane-2,1-diyl)dicarbamate |

TABLE 2-continued

| Example | 1b EC$_{50}$ (in μM or range) | Name |
|---|---|---|
| 32 | B | Dimethyl (2S,2'S)-1,1'-((2S,2'S)-2,2'-(5,5'-(buta-1,3-diyne-1,4-diyl)bis(1H-imidazole-5,2-diyl))bis(pyrrolidine-2,1-diyl))bis(1-oxopropane-2,1-diyl)dicarbamate |
| 33 | D | Methyl ((1S)-1-(((2S)-2-(4-(4'-((2-((2S)-1-((2S)-2-((methoxycarbonyl)amino)-3-methylbutanoyl)-2-pyrrolidinyl)-1H-imidazol-4-yl)ethynyl)-4-biphenylyl)-1H-imidazol-2-yl)-1-pyrrolidinyl)carbonyl)-2-methylpropyl)carbamate |
| 34 | C | Dimethyl (1,3-butadiyne-1,4-diylbis(1H-imidazole-4,2-diyl(1R,3S,5R)-2-azabicyclo[3.1.0]hexane-3,2-diyl((1S)-2-oxo-1-(tetrahydro-2H-pyran-4-yl)-2,1-ethanediyl)))biscarbamate |
| 35 | 0.00014 | (1R)-2-((2S)-2-(4-((E)-2-(4-((E)-2-(2-((2S)-1-((2R)-2-(Diethylamino)-2-phenylacetyl)-2-pyrrolidinyl)-1H-imidazol-5-yl)vinyl)phenyl)vinyl)-1H-imidazol-2-yl)-1-pyrrolidinyl)-N,N-diethyl-2-oxo-1-phenylethanamine |
| 36 | D | Dimethyl (1,4-phenylenebis((E)-2,1-ethenediyl-1H-imidazole-4,2-diyl(2S)-2,1-pyrrolidinediyl((1R)-2-oxo-1-phenyl-2,1-ethanediyl)))biscarbamate |
| 37 | D | Methyl ((1S)-2-((2S)-2-(4-((E)-2-(4-((E)-2-(2-((2S)-1-(N-(methoxycarbonyl)-L-alanyl)-2-pyrrolidinyl)-1H-imidazol-4-yl)vinyl)phenyl)vinyl)-1H-imidazol-2-yl)-1-pyrrolidinyl)-1-methyl-2-oxoethyl)carbamate |
| 38 | D | Methyl ((1S)-1-(((2S)-2-(4-((E)-2-(4-((E)-2-(2-((2S)-1-((2S)-2-((methoxycarbonyl)amino)-3-methylbutanoyl)-2-pyrrolidinyl)-1H-imidazol-4-yl)vinyl)phenyl)vinyl)-1H-imidazol-2-yl)-1-pyrrolidinyl)carbonyl)-2-methylpropyl)carbamate |
| 39 | D | Methyl ((1S,2R)-2-methoxy-1-(((2S)-2-(4-((E)-2-(4-((E)-2-(2-((2S)-1-(N-(methoxycarbonyl)-O-methyl-L-threonyl)-2-pyrrolidinyl)-1H-imidazol-4-yl)vinyl)phenyl)vinyl)-1H-imidazol-2-yl)-1-pyrrolidinyl)carbonyl)propyl)carbamate |
| 40 | D | (1R)-2-((2S)-2-(4-(2-(4-(2-(2-((2S)-1-((2R)-2-(Diethylamino)-2-phenylacetyl)-2-pyrrolidinyl)-1H-imidazol-5-yl)ethyl)phenyl)ethyl)-1H-imidazol-2-yl)-1-pyrrolidinyl)-N,N-diethyl-2-oxo-1-phenylethanamine |
| 41 | D | Dimethyl (1,4-phenylenebis(2,1-ethanediyl-1H-imidazole-4,2-diyl(2S)-2,1-pyrrolidinediyl((1R)-2-oxo-1-phenyl-2,1-ethanediyl)))biscarbamate |
| 42 | 0.274 | Methyl ((1S)-2-((2S)-2-(4-(2-(4-(2-(2-((2S)-1-(N-(methoxycarbonyl)-L-alanyl)-2-pyrrolidinyl)-1H-imidazol-4-yl)ethyl)phenyl)ethyl)-1H-imidazol-2-yl)-1-pyrrolidinyl)-1-methyl-2-oxoethyl)carbamate |
| 43 | C | Methyl ((1S)-1-(((2S)-2-(4-(2-(4-(2-(2-((2S)-1-((2S)-2-((methoxycarbonyl)amino)-3-methylbutanoyl)-2-pyrrolidinyl)-1H-imidazol-4-yl)ethyl)phenyl)ethyl)-1H-imidazol-2-yl)-1-pyrrolidinyl)carbonyl)-2-methylpropyl)carbamate |
| 44 | B | Methyl ((1S,2R)-2-methoxy-1-(((2S)-2-(4-(2-(4-(2-(2-((2S)-1-(N-(methoxycarbonyl)-O-methyl-L-threonyl)-2-pyrrolidinyl)-1H-imidazol-4-yl)ethyl)phenyl)ethyl)-1H-imidazol-2-yl)-1-pyrrolidinyl)carbonyl)propyl)carbamate |
| M1 | D | Methyl ((1R)-2-((2S)-2-(4-((2-((2S)-1-((2R)-2-((methoxycarbonyl)amino)-2-phenylacetyl)-2-pyrrolidinyl)-1H-imidazol-4-yl)ethynyl)phenyl)-1H-imidazol-2-yl)-1-pyrrolidinyl)-2-oxo-1-phenylethyl)carbamate |
| M2 | D | Methyl ((1R)-2-((2S)-2-(4-(2-(2-((2S)-1-((2R)-2-((methoxycarbonyl)amino)-2-phenylacetyl)-2-pyrrolidinyl)-1H-imidazol-4-yl)ethyl)phenyl)-1H-imidazol-2-yl)-1-pyrrolidinyl)-2-oxo-1-phenylethyl)carbamate |
| M3 | C | (1R)-2-((2S)-2-(4-(4-(2-(2-((2S)-1-((2R)-2-(Dimethylamino)-2-phenylacetyl)-2-pyrrolidinyl)-1H-imidazol-4-yl)ethyl)phenyl)-1H-imidazol-2-yl)-1-pyrrolidinyl)-N,N-dimethyl-2-oxo-1-phenylethanamine |
| M4 | D | Methyl ((1S)-1-(((2S)-2-(4-((4-((2-((2S)-1-((2S)-2-((methoxycarbonyl)amino)-3-methylbutanoyl)-2-pyrrolidinyl)-1H-imidazol-4-yl)ethynyl)phenyl)ethynyl)-1H-imidazol-2-yl)-1-pyrrolidinyl)carbonyl)-2-methylpropyl)carbamate |

TABLE 2-continued

| Example | 1b EC$_{50}$ (in μM or range) | Name |
|---|---|---|
| M5 | D | Methyl ((1S,2R)-2-methoxy-1-(((2S)-2-(4-((4-((2-((2S)-1-(N-(methoxycarbonyl)-O-methyl-L-threonyl)-2-pyrrolidinyl)-1H-imidazol-4-yl)ethynyl)phenyl)ethynyl)-1H-imidazol-2-yl)-1-pyrrolidinyl)carbonyl)propyl) carbamate |
| M6 | C | Methyl ((1S)-2-((2S)-2-(4-((4-((2-((2S)-1-(N-(methoxycarbonyl)-L-alanyl)-2-pyrrolidinyl)-1H-imidazol-4-yl)ethynyl)phenyl)ethynyl)-1H-imidazol-2-yl)-1-pyrrolidinyl)-1-methyl-2-oxoethyl)carbamate |
| M7 | D | Methyl ((1S)-3-methoxy-1-(((2S)-2-(4-((4-((2-((2S)-1-(N-(methoxycarbonyl)-O-methyl-L-homoseryl)-2-pyrrolidinyl)-1H-imidazol-4-yl)ethynyl)phenyl)ethynyl)-1H-imidazol-2-yl)-1-pyrrolidinyl)carbonyl)propyl) carbamate |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of Formula (I):

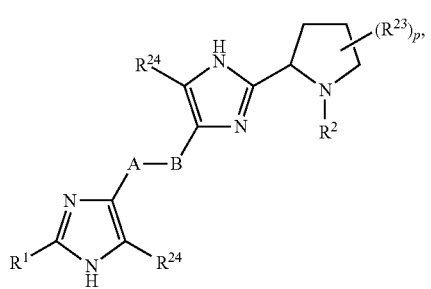

or a pharmaceutically acceptable salt thereof, wherein:

A-B is

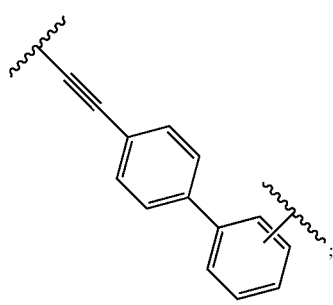

each R$^{24}$ is independently selected from hydrogen and halo;

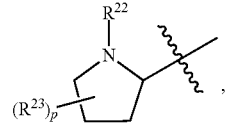

wherein p is 0 or 1;
R$^{20}$ is selected from hydrogen and alkyl;
R$^{21}$ is selected from hydrogen and alkyl;
R$^{22}$ is hydrogen or —C(O)R$^x$; and
R$^{23}$ is selected from hydrogen and alkyl, wherein the alkyl can optionally form a fused three- to six-membered ring with an adjacent carbon atom, wherein the three- to six-membered ring is optionally substituted with one or two alkyl groups;
R$^2$ is hydrogen or —C(O)R$^y$;
R$^x$ and R$^y$ are each independently selected from cycloalkyl, heteroaryl, heterocyclyl, alkoxy, and alkyl, said alkyl being substituted by one or more substituents independently selected from aryl, alkenyl, cycloalkyl, heterocyclyl, heteroaryl, —OR$^3$, —NR$^a$R$^b$, and —C(O)NR$^c$R$^d$,
wherein any said aryl and heteroaryl may optionally be substituted with one or more substituents independently selected from alkenyl, alkyl, haloalkyl, arylalkyl, heterocyclyl, heterocyclylalkyl, halogen, cyano, nitro, —C(O)OR$^4$, OR$^5$, —NR$^a$R$^b$, (NR$^a$R$^b$)alkyl, and (MeO)(HO)P(O)O—, and
wherein any said cycloalkyl and heterocyclyl may optionally be fused onto an aromatic ring and may optionally be substituted with one or more substituents independently selected from alkoxy, alkyl, hydroxyl, halogen, aryl, —NR$^a$R$^b$, oxo, and —C(O)OR$^4$;
R$^3$ is hydrogen, alkyl, or arylalkyl;
R$^4$ is selected from alkyl and arylalkyl;
R$^5$ is hydrogen, alkyl, or arylalkyl;
R$^a$ and R$^b$ are independently selected from hydrogen, alkyl, cycloalkyl, arylalkyl, heteroaryl, —C(O)R$^6$, —C(O)OR$^7$, —C(O)NR$^c$R$^d$, and (NR$^c$R$^d$)alkyl, or alternatively, R$^a$ and R$^b$, together with the nitrogen atom to which they are attached, form a five- or six-membered ring or bridged bicyclic ring structure, wherein said five- or six-membered ring or bridged bicyclic ring structure optionally may contain one or two additional heteroatoms independently selected from nitrogen, oxygen, and sulfur and may contain one, two, or three substituents independently selected from C$_1$ to C$_6$ alkyl, C$_1$ to C$_4$ haloalkyl, aryl, hydroxyl, C$_1$ to C$_6$ alkoxy, C$_1$ to C$_4$ haloalkoxy, and halogen;

$R^6$ is alkyl;
$R^7$ is alkyl, cycloalkyl, arylalkyl, or haloalkyl; and
$R^c$ and $R^d$ are independently selected from hydrogen, alkyl, arylalkyl, and cycloalkyl.

2. The compound according to claim 1, or a pharmaceutically acceptable salt thereof, wherein:
$R^1$ is

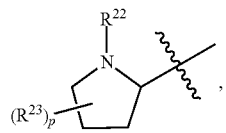

wherein $R^{22}$ is —C(O)$R^x$;
$R^2$ is —C(O)$R^y$; and
$R^x$ and $R^y$ are independently alkyl substituted by at least one —$NR^aR^b$, characterized by Formula (A):

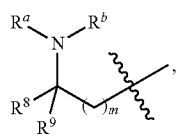

(A)

wherein:
m is 0 or 1;
$R^8$ is hydrogen or alkyl;
$R^9$ is selected from hydrogen, cycloalkyl, aryl, heteroaryl, heterocyclyl, and alkyl optionally substituted with a substituent selected from aryl, alkenyl, cycloalkyl, heterocyclyl, heteroaryl, heterobicyclyl, —$OR^3$, —C(O)$OR^4$, —$NR^aR^b$, and —C(O)$NR^cR^d$, wherein aryl and heteroaryl may optionally be substituted with one or more substituents independently selected from alkenyl, alkyl, haloalkyl, arylalkyl, heterocyclyl, heterocyclylalkyl, halogen, cyano, nitro, —C(O)$OR^4$, $OR^5$, —$NR^aR^b$, ($NR^aR^b$)alkyl, and (MeO)(HO)P(O)O—, and wherein cycloalkyl and heterocyclyl may optionally be fused onto an aromatic ring and may optionally be substituted with one or more substituents independently selected from alkoxy, alkyl, hydroxyl, halogen, aryl, —$NR^aR^b$, oxo, and —C(O)$OR^4$; and $R^3$, $R^4$, $R^5$, $R^a$, $R^b$, $R^c$, and $R^d$ are defined as in claim 1.

3. The compound of claim 2, or a pharmaceutically acceptable salt thereof,
wherein:
m is 0;
$R^8$ is hydrogen; and
$R^9$ is selected from hydrogen, cycloalkyl, aryl, and alkyl optionally substituted with one —$OR^3$ substituent.

4. A compound, or a pharmaceutically acceptable salt thereof, selected from the group consisting of:
Methyl ((1S)-1-(((2S)-2-(4-(4'-((2-((2S)-1-((2S)-2-((methoxycarbonyl)amino)-3-methylbutanoyl)-2-pyrrolidinyl)-1H-imidazol-4-yl)ethynyl)-4-biphenylyl)-1H-imidazol-2-yl)-1-pyrrolidinyl)carbonyl)-2-methylpropyl)carbamate;
and corresponding stereoisomers and tautomers thereof.

5. A composition comprising a compound of claim 1, or a pharmaceutically acceptable salt thereof, and a pharmaceutically acceptable carrier.

6. A method of treating an HCV infection in a patient, comprising administering to the patient a therapeutically effective amount of a compound of claim 1, or a pharmaceutically acceptable salt thereof.

* * * * *

UNITED STATES PATENT AND TRADEMARK OFFICE
CERTIFICATE OF CORRECTION

PATENT NO. : 8,618,153 B2
APPLICATION NO. : 13/611708
DATED : December 31, 2013
INVENTOR(S) : John A. Bender et al.

It is certified that error appears in the above-identified patent and that said Letters Patent is hereby corrected as shown below:

In the Specification:

Column 7, line 49, change "Imiqimod," to -- Imiquimod, --.

Column 7, line 50, change "5'-monophospate" to -- 5'-monophosphate --.

Column 8, line 40, change "Imiqimod," to -- Imiquimod, --.

Column 8, line 41, change "5'-monophospate" to -- 5'-monophosphate --.

In the Claims:

Claim 1:

Column 268, lines 20 to 25, change " [structure] " to " -- $R^1$ is [structure] --."

Signed and Sealed this
Thirty-first Day of March, 2015

Michelle K. Lee
*Director of the United States Patent and Trademark Office*